US011447809B2

(12) United States Patent
Liu et al.

(10) Patent No.: US 11,447,809 B2
(45) Date of Patent: Sep. 20, 2022

(54) EVOLUTION OF TRNA SYNTHETASES

(71) Applicant: President and Fellows of Harvard College, Cambridge, MA (US)

(72) Inventors: David R. Liu, Lexington, MA (US); David Irby Bryson, Jr., Dorchester, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 98 days.

(21) Appl. No.: 16/628,456

(22) PCT Filed: Jul. 3, 2018

(86) PCT No.: PCT/US2018/040692
§ 371 (c)(1),
(2) Date: Jan. 3, 2020

(87) PCT Pub. No.: WO2019/010164
PCT Pub. Date: Jan. 10, 2019

(65) Prior Publication Data
US 2022/0154237 A1 May 19, 2022

Related U.S. Application Data

(60) Provisional application No. 62/535,090, filed on Jul. 20, 2017, provisional application No. 62/529,320, filed on Jul. 6, 2017.

(51) Int. Cl.
*C12P 21/02* (2006.01)
*C12N 9/00* (2006.01)

(52) U.S. Cl.
CPC ................ *C12P 21/02* (2013.01); *C12N 9/93* (2013.01); *C12Y 601/01026* (2013.01)

(58) Field of Classification Search
None
See application file for complete search history.

(56) References Cited

U.S. PATENT DOCUMENTS

| | | | |
|---|---|---|---|
| 5,057,432 | A | 10/1991 | Wangersky et al. |
| 5,223,409 | A | 6/1993 | Ladner et al. |
| 5,658,727 | A | 8/1997 | Barbas et al. |
| 5,712,089 | A | 1/1998 | Borrebaeck et al. |
| 5,821,047 | A | 10/1998 | Garrard et al. |
| 5,880,275 | A | 3/1999 | Fischhoff et al. |
| 5,965,124 | A | 10/1999 | Feinberg et al. |
| 6,033,874 | A | 3/2000 | Baum et al. |
| 6,156,509 | A | 12/2000 | Schellenberger |
| 6,429,298 | B1 | 8/2002 | Ellington et al. |
| 6,713,063 | B1 | 3/2004 | Malvar et al. |
| 6,962,705 | B2 | 11/2005 | Malvar et al. |
| 6,969,731 | B1 | 11/2005 | Tang et al. |
| 7,064,249 | B2 | 6/2006 | Corbin et al. |
| 7,070,982 | B2 | 7/2006 | Malvar et al. |
| 9,023,594 | B2 | 5/2015 | Liu et al. |
| 9,228,207 | B2 | 1/2016 | Liu et al. |
| 9,267,127 | B2 | 2/2016 | Liu et al. |
| 9,340,799 | B2 | 5/2016 | Liu et al. |
| 9,340,800 | B2 | 5/2016 | Liu et al. |
| 9,359,599 | B2 | 6/2016 | Liu et al. |
| 9,394,537 | B2 | 7/2016 | Liu et al. |
| 9,526,784 | B2 | 12/2016 | Liu et al. |
| 9,567,589 | B2 | 2/2017 | Jin et al. |
| 9,737,604 | B2 | 8/2017 | Jin et al. |
| 9,766,216 | B2 | 9/2017 | Wada et al. |
| 9,771,574 | B2 | 9/2017 | Liu et al. |
| 10,179,911 | B2 | 1/2019 | Liu et al. |
| 10,227,581 | B2 | 3/2019 | Liu et al. |
| 10,336,997 | B2 | 7/2019 | Liu et al. |
| 10,392,674 | B2 | 8/2019 | Liu et al. |
| 10,597,679 | B2 | 3/2020 | Liu et al. |
| 10,612,011 | B2 | 4/2020 | Liu et al. |
| 10,682,410 | B2 | 6/2020 | Liu et al. |
| 10,920,208 | B2 | 2/2021 | Liu et al. |
| 2002/0132327 | A1 | 9/2002 | Hay et al. |
| 2003/0119764 | A1 | 6/2003 | Loeb et al. |
| 2003/0167533 | A1 | 9/2003 | Yadav et al. |
| 2003/0203480 | A1 | 10/2003 | Kovesdi et al. |
| 2005/0019753 | A1 | 1/2005 | Kukolj et al. |
| 2005/0100973 | A1 | 5/2005 | Steward et al. |
| 2006/0112447 | A1 | 5/2006 | Bogdanova et al. |
| 2006/0160222 | A1 | 7/2006 | Rozwadowski et al. |
| 2006/0166319 | A1 | 7/2006 | Chan et al. |
| 2008/0220502 | A1 | 9/2008 | Schellenberger et al. |
| 2009/0215110 | A1 | 8/2009 | Gibson et al. |
| 2009/0227463 | A1 | 9/2009 | Reif et al. |

(Continued)

FOREIGN PATENT DOCUMENTS

| | | | |
|---|---|---|---|
| EP | 0289479 | A2 | 11/1988 |
| EP | 3115457 | A1 | 1/2017 |

(Continued)

OTHER PUBLICATIONS

[No Author Listed] Genbank Submission. NCBI; Accession No. WP_010869888, version WP_010869888.1. tyrosine—tRNA ligase [Methanocaldococcus jannaschii]. Jun. 1, 2019.
Agarwal et al., Mode of VAMP substrate recognition and inhibition of *Clostridium botulinum* neurotoxin F. Nature Structural & Molecular Biology. 2009;16:789-94.
Amiram et al., Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Bade et al., Botulinum neurotoxin type D enables cytosolic delivery of enzymatically active cargo proteins to neurones via unfolded translocation intermediates. J Neurochem. Dec. 2004;91(6):1461-72.

(Continued)

*Primary Examiner* — Kagnew H Gebreyesus
(74) *Attorney, Agent, or Firm* — Wolf, Greenfield & Sacks, P.C.

(57) ABSTRACT

The disclosure provides amino acid sequence variants of orthogonal aminoacyl-tRNA synthetases (AARSs) having increased activity and selectivity compared to previous AARSs, and methods of producing the same.

8 Claims, 41 Drawing Sheets

Specification includes a Sequence Listing.

(56) References Cited

U.S. PATENT DOCUMENTS

| | | | |
|---|---|---|---|
| 2009/0300777 | A1 | 12/2009 | Nakayama |
| 2010/0297180 | A1 | 11/2010 | Shone |
| 2011/0177495 | A1 | 7/2011 | Liu et al. |
| 2012/0128649 | A1 | 5/2012 | Chaddock et al. |
| 2013/0059931 | A1 | 3/2013 | Petersen-Mahrt et al. |
| 2013/0117869 | A1 | 5/2013 | Duchateau et al. |
| 2013/0345064 | A1 | 12/2013 | Liu et al. |
| 2013/0345065 | A1 | 12/2013 | Liu et al. |
| 2014/0201858 | A1 | 7/2014 | Ostertag et al. |
| 2015/0056177 | A1 | 2/2015 | Liu et al. |
| 2015/0259721 | A1 | 9/2015 | Van Brunt et al. |
| 2015/0275202 | A1 | 10/2015 | Liu et al. |
| 2016/0002301 | A1 | 1/2016 | Je et al. |
| 2016/0201040 | A1 | 7/2016 | Liu et al. |
| 2016/0348096 | A1 | 12/2016 | Liu et al. |
| 2017/0009224 | A1 | 1/2017 | Liu et al. |
| 2017/0029844 | A1 | 2/2017 | Ball et al. |
| 2017/0044520 | A1 | 2/2017 | Liu et al. |
| 2017/0233708 | A1 | 8/2017 | Liu et al. |
| 2018/0057545 | A9 | 3/2018 | Liu et al. |
| 2018/0087046 | A1 | 3/2018 | Liu et al. |
| 2018/0237758 | A1 | 8/2018 | Liu et al. |
| 2019/0219575 | A1 | 7/2019 | Gray et al. |
| 2019/0256842 | A1 | 8/2019 | Liu et al. |
| 2019/0276816 | A1 | 9/2019 | Liu et al. |
| 2019/0276873 | A1 | 9/2019 | Dong et al. |
| 2020/0071722 | A1 | 3/2020 | Liu et al. |
| 2020/0216833 | A1 | 7/2020 | Liu et al. |
| 2020/0255868 | A1 | 8/2020 | Liu et al. |
| 2020/0277587 | A1 | 9/2020 | Liu et al. |
| 2020/0323984 | A1 | 10/2020 | Liu et al. |

FOREIGN PATENT DOCUMENTS

| | | | |
|---|---|---|---|
| JP | H0937764 | A | 2/1997 |
| JP | 2011-081011 | | 4/2011 |
| WO | 90/02809 | A1 | 3/1990 |
| WO | 91/17271 | A1 | 11/1991 |
| WO | 92/01047 | A1 | 1/1992 |
| WO | 92/09690 | A2 | 6/1992 |
| WO | 92/15679 | A1 | 9/1992 |
| WO | 92/18619 | A1 | 10/1992 |
| WO | 92/20791 | A1 | 11/1992 |
| WO | 93/01288 | A1 | 1/1993 |
| WO | 94/18316 | A2 | 8/1994 |
| WO | 96/04403 | A1 | 2/1996 |
| WO | 98/32845 | A1 | 7/1998 |
| WO | 00/71694 | A1 | 11/2000 |
| WO | 01/05950 | A2 | 1/2001 |
| WO | 01/61049 | A1 | 8/2001 |
| WO | 2005/081632 | A2 | 9/2005 |
| WO | 2007/066923 | A1 | 6/2007 |
| WO | 2008/005529 | A2 | 1/2008 |
| WO | 2009/082488 | A2 | 7/2009 |
| WO | 2009/108180 | A2 | 9/2009 |
| WO | 2010/028347 | A2 | 3/2010 |
| WO | WO 2010/028347 | A2 | 3/2010 |
| WO | 2011/039518 | A2 | 4/2011 |
| WO | WO 2011/147590 | A2 | 12/2011 |
| WO | WO 2011/066747 | A1 | 6/2012 |
| WO | WO 2012/088381 | A2 | 6/2012 |
| WO | WO 2012/138927 | A2 | 10/2012 |
| WO | WO 2013/047844 | | 4/2013 |
| WO | WO 2014/039585 | A2 | 3/2014 |
| WO | WO 2014/157820 | A1 | 10/2014 |
| WO | WO 2014/158593 | A1 | 10/2014 |
| WO | WO 2015/134121 | A2 | 9/2015 |
| WO | WO 2015/193897 | A1 | 12/2015 |
| WO | WO 2016/077052 | A9 | 5/2016 |
| WO | WO 2016/168631 | A1 | 10/2016 |
| WO | WO 2017/015559 | A2 | 1/2017 |
| WO | WO 2017/070632 | A2 | 4/2017 |
| WO | WO 2018/009903 | A2 | 1/2018 |
| WO | WO 2018/027078 | A1 | 2/2018 |
| WO | WO 2018/039438 | A1 | 3/2018 |
| WO | WO 2018/109447 | A1 | 6/2018 |
| WO | WO 2018/136939 | A1 | 7/2018 |
| WO | WO 2019/040935 | A1 | 2/2019 |
| WO | WO 2019/067815 | A2 | 4/2019 |

OTHER PUBLICATIONS

Binz et al., Clostridial neurotoxins: mechanism of SNARE cleavage and outlook on potential substrate specificity reengineering. Toxins. Apr. 2010;2(4):665-82. Epub Apr. 13, 2010.

Box et al., A multi-domain protein system based on the HC fragment of tetanus toxin for targeting DNA to neuronal cells. Journal of Drug Targeting. 2003;11(6):333-43. Epub Oct. 3, 2008.

Chaddock et al., Inhibition of vesicular secretion in both neuronal and nonneuronal cells by a retargeted endopeptidase derivative of Clostridium botulinum neurotoxin type A. Infect. Immun. May 2008;68(5):2587-93.

Chaineau et al., Multiple roles of the vesicular-SNARE TI-VAMP in post-Golgi and endosomal trafficking. FEBS Letters. Oct. 2009;583:3817-26.

Chen et al., Engineering botulinum neurotoxin to extend therapeutic intervention. PNAS. Jun. 2009;106(23):9180-4.

Chen et al., SNARE-mediated membrane fusion. Nat Rev Mol Cell Biol. Feb. 2001;2(2):98-106.

Chen et al., VAMP8 facilitates cellular proliferation and temozolomide resistance in human glioma cells. Neuro-Oncology. 2015;17(3):407-18. Epub Sep. 10, 2014.

Chin, Expanding and reprogramming the genetic code of cells and animals. Annu Rev Biochem. 2014;83:379-408. doi: 10.1146/annurev-biochem-060713-035737. Epub Feb. 10, 2014.

Craik et al., Proteases as therapeutics. Biochem J. Apr. 2011;435(1):16 pages.

Duggan et al., Inhibition of Release of Neurotransmitters from Rat Dorsal Root Ganglia by a Novel Conjugate of a Clostridium botulinum Toxin A Endopeptidase Fragment and Erythrina cristagalli Lectin. The Journal of Biological Chemistry. Sep. 2002;277(38):34846-52.

Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.

Feng et al., Exol: A new chemical inhibitor of the exocytic pathway. PNAS. May 2003;100(11):6469-74.

Foster et al., Re-engineering the target specificity of Clostridial neurotoxins—A route to novel therapeutics. Neurotoxicity Research. May 2006;9(2,3):101-7.

Foster et al., Targeted Secretion Inhibitors—Innovative Protein Therapeutics. Toxins. Dec. 2010;2:2795-815.

Fu et al., Promises and Pitfalls of Intracellular Delivery of Proteins. Bioconjugate Chemistry. Aug. 2014;25:1602-8.

Genbank Submission. NCBI; Accession No. WP_011033391, version WP_011033391.1. pyrrolysine—tRNA(Pyl) ligase [Methanosarcina mazei]. Polycarpo et al.; Nov. 29, 2019.

Genbank Submission. NCBI; Accession No. WP_011305865, version WP_011305865.1. pyrrolysine—tRNA(Pyl) ligase [Methanosarcina barkeri].Polycarpo et al.; Nov. 29, 2019.

Gill, Bacterial Toxins: a Table of Letal Amounts. Microbiological Reviews. Mar. 1982;46(1):86-94.

Goodnough et al., Development of a delivery vehicle for intracellular transport of botulinum neurotoxin antagonists. FEBS Lett. Feb. 27, 2002;513(2-3):163-8.

Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.

Guo et al., Polyspecific pyrrolysyl-tRNA synthetases from directed evolution. Proc Natl Acad Sci U S A. Nov. 25, 2014;111(47):16724-9. doi: 10.1073/pnas.1419737111. Epub Nov. 10, 2014.

Hedstrom et al., Converting trypsin to chymotrypsin: the role of surface loops. Science. Mar. 1992;255(5049):1249-53.

Hendricks et al., The S. cerevisiae Mag1 3-methyladenine DNA glycosylase modulates susceptibility to homologous recombination. DNA Repair (Amst). 2002;1(8):645-659.

(56) References Cited

OTHER PUBLICATIONS

Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.
Ho et al., Recombinant botulinum neurotoxin A heavy chainbased delivery vehicles for neuronal cell targeting. Protein Engineering, Design & Selection. 2011;24(3):247-53. Epub Nov. 4, 2010.
Jiang et al., PylSn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.
Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.
Köhler, A yeast-based growth assay for the analysis of site-specific proteases. Nucleic Acids Res. 2003;31(4):e16. 5 pages.
Lebeda et al., The Zinc-Dependent Protease Activity of the Botulinum Neurotoxins. Toxins. May 2010;2:978-97.
Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.
Liu et al., Adding new chemistries to the genetic code. Annu Rev Biochem. 2010;79:413-44. doi: 10.1146/annurev.biochem.052308.105824.
Marcet-Palacios et al., Vesicle-associated membrane protein 7 (VAMP-7) is essential for target cell killing in a natural killer cell line. Biochemical and Biophysical Research Communications. Feb. 2008;366(3):617-23.
Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.
O'Donoghue et al., Upgrading protein synthesis for synthetic biology. Nat Chem Biol. Oct. 2013;9(10):594-8. doi: 10.1038/nchembio.1339.
Pickett et al., Towards New Uses of Botulinum Toxin as a Novel Therapeutic Tool. Toxins. Jan. 2011;3:63-81.
Pogson et al., Engineering Next Generation Proteases. Curr Opin Biotechnol. Aug. 2009;20(4):390-7.
Rossetto et al., Botulinum neurotoxins: genetic, structural and mechanistic insights. Nature Review Microbiology. 2014;12:535-9. Epub Jun. 30, 2014.
Sikorra et al., Substrate Recognition Mechanism of VAMP/Synaptobrevin-cleaving Clostridial Neurotoxins. Journal of Biological Chemistry. 2008;283:21145-52. Epub May 29, 2008.
Somm et al., A botulinum toxin-drived targeted secretion inihibitor downregulates the GH/IGF1 axis. The Journal of Clinical Investigation. Sep. 2012;122(9):3295-306.
Steffen et al., MT1-MMP-Dependent Invasion Is Regulated by TI-VAMP/VAMP7. Current Biology. Jun. 2008;18:926-31.
Tsai et al., Targeting botulinum neurotoxin persistence by the ubiquitin-proteasome system. PNAS. Sep. 2010;107(38):16554-9.
Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.
Umehara et al., N-acetyl lysyl-tRNA synthetases evolved by a CedB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.
Varadarajan et al., Engineering of protease variants exhibiting high catalytic activity and exquisite substrate selectivity. PNAS. May 2005;102(19):6855-60.
Varadarajan et al., Highly active and selective endopeptidases with programmed substrate specificities. Nat Chem Biol. May 2008;4(5):290-4.
Wan et al., Pyrrolysyl-tRNA Synthetase: An Ordinary Enzyme but an Outstanding Genetic Code Expansion Tool. Biochim Biophys Acta. Jun. 2014 ; 1844(6): 1059-1070.
Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.
Williams et al., SNAP23, Syntaxin4, and vesicle-associated membrane protein 7 (VAMP7) mediate trafficking of membrane type 1-matrix metalloproteinase (MT1-MMP) during invadopodium formation and tumor cell invasion. MBoC. Jul. 2014;25:2061-70.
Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.
Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.
Yeh et al., Retargeted Clostridial neurotoxins as Novel Agents for Treating Chronic Diseases. Biochemistry. Nov. 2011;50:10419-21.
Yi et al., Engineering of TEV protease variants by yeast ER sequestration screening (YESS) of combinatorial libraries. PNAS. Apr. 2013;110(18):7229-34.
Extended European Search Report, dated Mar. 30, 2012, in connection with Application No. EP 09812363.
Extended European Search Report, dated May 26, 2017, in connection with Application No. EP 16 20 3684.
International Search Report and Written Opinion, dated Jun. 21, 2010, in connection with Application No. PCT/US2009/056194.
International Preliminary Report on Patentability, dated Mar. 17, 2011, in connection with Application No. PCT/US2009/056194.
Extended European Search Report, dated May 16, 2017, in connection with Application No. EP 17 16 0955.
Invitation to Pay Additional Fees, dated Aug. 30, 2012, in connection with Application No. PCT/US2011/066747.
International Search Report and Written Opinion, dated Oct. 30, 2012, in connection with Application No. PCT/US2011/066747.
International Preliminary Report on Patentability, dated Jul. 4, 2013, in connection with Application No. PCT/US2011/066747.
International Search Report and Written Opinion, dated Sep. 25, 2015, in connection with Application No. PCT/US2015/012022.
International Preliminary Report on Patentability, dated Aug. 4, 2016, in connection with Application No. PCT/US2015/012022.
Invitation to Pay Additional Fees, dated Jan. 12, 2017, in connection with Application No. PCT/US/2016/043559.
International Search Report and Written Opinion, dated Mar. 10, 2017, in connection with Application No. PCT/US/2016/043559.
International Preliminary Report on Patentability, dated Feb. 1, 2018, in connection with Application No. PCT/US/2016/043559.
International Search Report and Written Opinion, dated Jun. 10, 2016, in connection with Application No. PCT/US2015/057012.
International Preliminary Report on Patentability, dated May 4, 2017, in connection with Application No. PCT/US2015/057012.
International Search Report and Written Opinion, dated Aug. 11, 2016, in connection with Application No. PCT/US2016/027795.
International Preliminary Report on Patentability, dated Oct. 26, 2017, in connection with Application No. PCT/US2016/027795.
Invitation to Pay Additional Fees, dated Oct. 12, 2016, in connection with Application No. PCT/US2016/044546.
International Search Report and Written Opinion, dated Dec. 28, 2016, in connection with Application No. PCT/US2016/044546.
International Preliminary Report on Patentability, dated Feb. 8, 2018, in connection with Application No. PCT/US/2016/044546.
International Search Report and Written Opinion, dated Nov. 30, 2016, in connection with Application No. PCT/US2016/043513.
International Preliminary Report on Patentability, dated Feb. 1, 2018, in connection with Application No. PCT/US2016/043513.
Invitation to Pay Additional Fees, dated Apr. 5, 2018, in connection with Application No. PCT/US2018/14867.
International Search Report and Written Opinion, dated May 23, 2018, in connection with Application No. PCT/US2018/14867.
International Preliminary Report on Patentability, dated Aug. 1, 2019, in connection with Application No. PCT/US2018/14867.

(56) References Cited

OTHER PUBLICATIONS

Invitation to Pay Additional Fees, dated Sep. 12, 2018, in connection with Application No. PCT/US2018/040692.
International Search Report and Written Opinion, dated Nov. 15, 2018, in connection with Application No. PCT/US2018/040692.
International Preliminary Report on Patentability, dated Jan. 16, 2020, in connection with Application No. PCT/US2018/040692.
Invitation to Pay Additional Fees, dated Jan. 4, 2019, in connection with Application No. PCT/US2018/051557.
International Search Report and Written Opinion, dated Feb. 25, 2019, in connection with Application No. PCT/US2018/051557.
International Preliminary Report on Patentability, dated Apr. 2, 2020, in connection with Application No. PCT/US2018/051557.
International Search Report and Written Opinion, dated Nov. 21, 2018, in connection with Application No. PCT/US2018/044242.
International Search Report and Written Opinion, dated Sep. 4, 2019, in connection with Application No. PCT/US2019/037216.
Invitation to Pay Additional Fees, dated Nov. 19, 2018, in connection with Application No. PCT/US18/48134.
International Search Report and Written Opinion, dated Jan. 22, 2019, in connection with Application No. PCT/US18/48134.
International Preliminary Report on Patentability, dated Mar. 5, 2020, in connection with Application No. PCT/US18/48134.
[No Author Listed] NCBI Accession No. XP_015843220.1. C ->U editing enzyme APOBEC-1 [Peromyscus maniculatus bairdii], XP002793540.
[No Author Listed] NCBI Accession No. XP_021505673.1. C ->U editing enzyme APOBEC-1 [Meriones unguiculatus], XP002793541.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 22, 2003;100(15):8688-91. Epub Jul. 1, 2003.
Armstrong et al., Chapter 3. Vectors for Phage Display. In: Phage Display of Peptides and Proteins. Kay et al., eds. Academic Press. San Diego, CA. 1996:35-53.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pill. J Mol Biol. Feb. 17, 2006;356(2):266-73. Epub Dec. 9, 2005.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.
Bolusani et al., Evolution of variants of yeast site-specific recombinase F1p that utilize native genomic sequences as recombination target sites. Nucleic Acids Res. 2006;34(18):5259-69. Epub Sep. 26, 2006.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Caldwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Cattaneo et al., SEL1L affects human pancreatic cancer cell cycle and invasiveness through modulation of PTEN and genes related to cell-matrix interactions. Neoplasia. 2005;7(11):1030-1038.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Chen, Clinical uses of botulinum neurotoxins: current indications, limitations and future developments. Toxins (Basel). 2012;4(10):913-939.
Clackson et al., Making antibody fragments using phage display libraries. Nature. Aug. 15, 1991;352(6336):624-8.
Click et al., Filamentous phage infection: required interactions with the To1A protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in *Escherichia coli* K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.

(56) References Cited

OTHER PUBLICATIONS

Deribe, Mechanistic insights into the role of truncating PREX2 mutations in melanoma. Mol Cell Oncol. 2016;3(3):e1160174.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci U S A. May 2013;110(22):9007-12.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci U S A. Aug. 15, 1991;88(16):7160-4.
Durai et al., A bacterial one-hybrid selection system for interrogating zinc finger-DNA interactions. Comb Chem High Throughput Screen. May 2006;9(4):301-11.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fuchs et al., Targeting Recombinant Antibodies to the Surface of *Escherichia Coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guzman et al., Tight regulation, modulation, and high-level expression by vectors containing the arabinose PBAD promoter. J Bacteriol. 1995;177(14):4121-4130.
Harris et al., Measurement of enzyme activity. Methods Enzymol. 2009;463:57-71.
Hart et al., Directed Evolution To Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., *Escherichia coli* one- and two-hybrid systems for the analysis and identification of protein-protein interactions. Methods. Jan. 2000;20(1):80-94.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.
Husimi et al., Cellstat-a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein-DNA and protein-protein interactions. Proc Natl Acad Sci U S A. Jun. 20, 2000;97(13):7382-7.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Kim et al., DJ-1, a novel regulator of the tumor suppressor PTEN. Cancer Cell. 2005;7(3):263-273.
Kim et al., Increasing the genome-targeting scope and precision of base editing with engineered Cas9-cytidine deaminase fusions. Nature Biotechnology; Feb. 13, 2007; 35(4): 371-376.

(56) References Cited

OTHER PUBLICATIONS

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Komor et al., Programmable editing of a target base in genomic DNA without double-stranded DNA cleavage. Nature. May 19, 2016;533(7603):420-4. doi: 10.1038/nature17946. Epub Apr. 20, 2016.

Kozak et al., Structural features in eukaryotic mRNAs that modulate the initiation of translation. J Biol Chem. Oct. 25, 1991;266(30):19867-70.

Kuzmine et al., Binding of the priming nucleotide in the initiation of transcription by T7 RNA polymerase. J Biol Chem. Jan. 31, 2003;278(5):2819-23. Epub Nov. 9, 2002.

Laskowska et al., IbpA and IbpB, the new heat-shock proteins, bind to endogenous *Escherichia coli* proteins aggregated intracellularly by heat shock. Biochimie. 1996;78(2):117-22.

Latimer et al., Specificity of monoclonal antibodies produced against phosphorothioate and ribo modified DNAs. Mol Immunol. Oct. 1995;32(14-15):1057-64.

Leconte et al., A population-based experimental model for protein evolution: effects of mutation rate and selection stringency on evolutionary outcomes. Biochemistry. Feb. 26, 2013; 52(8): 1490-1499.

Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.

Lincoln et al., Self-sustained replication of an RNA enzyme. Science. Feb. 27, 2009;323(5918):1229-32. Epub Jan. 8, 2009.

Lindemann et al., Evolution of bacteriophage in continuous culture: a model system to test antiviral gene therapies for the emergence of phage escape mutants. J Virol. Jun. 2002;76(11):5784-92.

Lu, The destructive effect of botulinum neurotoxins on the SNARE protein: SNAP-25 and synaptic membrane fusion. PeerJ. 2015;3:e1065. Published Jun. 30, 2015.

Lutz et al., Creating multiple-crossover DNA libraries independent of sequence identity. Proc Natl Acad Sci U S A. Sep. 25, 2001;98(20):11248-53. Epub Sep. 18, 2001.

Maeder et al., Robust, synergistic regulation of human gene expression using TALE activators. Nat Methods. Mar. 2013;10(3):243-5. doi: 10.1038/nmeth.2366. Epub Feb. 10, 2013.

Makeyev et al., Evolutionary potential of an RNA virus. J Virol. Feb. 2004;78(4):2114-20.

Malmborg et al., Selective phage infection mediated by epitope expression on F pilus. J Mol Biol. Oct. 31, 1997;273(3):544-51.

Martin et al., Kinetic analysis of T7 RNA polymerase-promoter interactions with small synthetic promoters. Biochemistry. May 19, 1987;26(10):2690-6.

Masuyer et al., Engineered botulinum neurotoxins as new therapeutics. Annu Rev Pharmacol Toxicol. 2014;54:27-51.

Mccafferty et al., Phage antibodies: filamentous phage displaying antibody variable domains. Nature. Dec. 6, 1990;348(6301):552-4.

Mcconnell et al., Constrained peptide libraries as a tool for finding mimotopes. Gene. Dec. 30, 1994;151(1-2):115-8.

Mcnaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.

Mihai et al., PTEN inhibition improves wound healing in lung epithelia through changes in cellular mechanics that enhance migration. Am J Physiol Lung Cell Mol Physiol. 2012;302(3):L287-L299.

Miller et al., A TALE nuclease architecture for efficient genome editing. Nat Biotechnol. Feb. 2011;29(2):143-8. doi:10.1038/nbt.1755. Epub Dec. 22, 2010.

Milligan et al., Oligoribonucleotide synthesis using T7 RNA polymerase and synthetic DNA templates. Nucleic Acids Res. Nov. 11, 1987;15(21):8783-98.

Mills et al., An extracellular Darwinian experiment with a self-duplicating nucleic acid molecule. Proc Natl Acad Sci U S A. Jul. 1967;58(1):217-24.

Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.

Nelson et al., Filamentous phage DNA cloning vectors: a noninfective mutant with a nonpolar deletion in gene III. Virology. Jan. 30, 1981;108(2):338-50.

Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.

O'Maille et al., Structure-based combinatorial protein engineering (SCOPE). J Mol Biol. Aug. 23, 2002;321(4):677-91.

Oeemig et al., Solution structure of DnaE intein from Nostoc punctiforme: structural basis for the design of a new split intein suitable for site-specific chemical modification. FEBS Lett. May 6, 2009;583(9):1451-6.

Opperman et al., A model for a umuDC-dependent prokaryotic DNA damage checkpoint. Proc Natl Acad Sci U S A. Aug. 3, 1999;96(16):9218-23.

Ostendorf et al., Characterization of a dam mutant of Serratia marcescens and nucleotide sequence of the dam region. J Bacteriol. Jul. 1999;181(13):3880-5.

Ostermeier et al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Rakonjac et al., Filamentous phage are released from the bacterial membrane by a two-step mechanism involving a short C-terminal fragment of pIII. J Mol Biol. Jun. 25, 1999;289(5):1253-65.

Rakonjac et al., Filamentous phage infection-mediated gene expression: construction and propagation of the gIII deletion mutant helper phage R408d3. Gene. Oct. 1, 1997;198(1-2):99-103.

Rakonjac et al., Roles of pIII in filamentous phage assembly. J Mol Biol. Sep. 11, 1998;282(1):25-41.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rawlings et al., MEROPS: the database of proteolytic enzymes, their substrates and inhibitors. Nucleic Acids Res. Jan. 2014;42(Database issue):D503-9.

Rebar et al., Phage display methods for selecting zinc finger proteins with novel DNA-binding specificities. Methods Enzymol. 1996;267:129-49.

Reidhaar-Olson et al., Random mutagenesis of protein sequences using oligonucleotide cassettes. Methods Enzymol. 1991;208:564-86.

Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.

Riechmann et al., The C-terminal domain of To1A is the coreceptor for filamentous phage infection of *E. coli*. Cell. Jul. 25, 1997;90(2):351-60.

Ringquist et al., Translation initiation in *Escherichia coli*: sequences within the ribosome-binding site. Mol Microbiol. May 1992;6(9):1219-29.

Rosenberg et al., T7 Select® Phage Display System: A Powerful new protein display system based on bacteriophage T7. Innovations. 1996;6:1-6.

Santini et al., Efficient display of an HCV cDNA expression library as C-terminal fusion to the capsid protein D of bacteriophage lambda. J Mol Biol. Sep. 11, 1998;282(1):125-35.

(56) References Cited

OTHER PUBLICATIONS

Santoro et al., Directed evolution of the site specificity of Cre recombinase. Proc Natl Acad Sci U S A. Apr. 2, 2002;99(7):4185-90. Epub Mar. 19, 2002.
Schultz et al., Oligo-2'-fluoro-2'-deoxynucleotide N3'→P5' phosphoramidates: synthesis and properties. Nucleic Acids Res. Aug. 1, 1996;24(15):2966-73.
Scott et al., Searching for peptide ligands with an epitope library. Science. Jul. 27, 1990;249(4967):386-90.
Sices et al., A genetic screen for the isolation and characterization of site-specific proteases. Proc Natl Acad Sci U S A. Mar. 17, 1998;95(6):2828-33.
Sices et al., Rapid genetic selection of inhibitor-resistant protease mutants: clinically relevant and novel mutants of the HIV protease. AIDS Res Hum Retroviruses. Sep. 1, 2001;17(13):1249-55.
Sieber et al., Libraries of hybrid proteins from distantly related sequences. Nat Biotechnol. May 2001;19(5):456-60.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Smith, Filamentous fusion phage: novel expression vectors that display cloned antigens on the virion surface. Science. Jun. 14, 1985;228(4705):1315-7.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tsuji et al., Random multi-recombinant PCR for the construction of combinatorial protein libraries. Nucleic Acids Res. Oct. 15, 2001;29(20):E97.
Tzagoloff et al., The Initial Steps In Infection With Coliphage M13. Virology. Nov. 1964;24:372-80.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Continuous directed evolutions of proteins with improved soluble expression. Nature Chemical Biology. Nat Publishing Group. Aug. 20, 2018; 14(10):972-980.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Webb et al., Production of catalytically inactive BoNT/A1 holoprotein and comparison with BoNT/A1 subunit vaccines against toxin subtypes A1, A2, and A3. Vaccine. 2009;27(33):4490-4497.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yamamoto et al., Virological and immunological bases for HIV-1 vaccine design. Uirusu 2007;57(2):133-139. https://doi.org/10.2222/jsv.57.133.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
International Preliminary Report on Patentability, dated Dec. 24, 2020, in connection with Application No. PCT/US2019/037216.
Invitation to Pay Additional Fees, dated Oct. 13, 2020, in connection with Application No. PCT/US2020/042016.
International Search Report and Written Opinion, dated Dec. 10, 2020, in connection with Application No. PCT/US2020/042016.
Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Multiplex genome engineering using CRISPR/Cas systems. Science. 2013; 339: 819-23.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Ferretti et al., Complete genome sequence of an M1 strain of *Streptococcus pyogenes*. Proc Natl Acad Sci U S A. Apr. 10, 2001;98(8):4658-63. doi: 10.1073/pnas.071559398.
Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jankovic et al., Direct selection and phage display of a Gram-positive secretome. Genome Biology. Dec. 13, 2007; 8(266):1-15.
Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.
Mali et al., RNA-guided human genome engineering via Cas9. Science. 2013; 339:823-26.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46. doi: 10.1006/jmbi.1999.2605.
Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.
Ziemann et al., Gene name errors are widespread in the scientific literature. Genome Biol. Aug. 23, 2016;17(1):177. doi: 10.1186/s13059-016-1044-7.
*U.S. Appl. No. 17/123,632, filed Dec. 16, 2020, Liu et al.
*U.S. Appl. No. 17/251,276, filed Dec. 11, 2020, Liu et al.
PCT/US2019/037216, Dec. 24, 2020, International Preliminary Report on Patentability.

(56) References Cited

OTHER PUBLICATIONS

PCT/US2020/042016, Oct. 13, 2020, Invitation to Pay Additional Fees.
PCT/US2020/042016, Dec. 10, 2020, International Search Report and Written Opinion.
*U.S. Appl. No. 13/062,098, filed Apr. 4, 2011, Liu et al.
*U.S. Appl. No. 14/704,226, filed May 5, 2015, Liu et al.
*U.S. Appl. No. 15/713,403, filed Sep. 22, 2017, Liu et al.
*U.S. Appl. No. 13/996,208, filed Jun. 20, 2013, Liu et al.
*U.S. Appl. No. 15/188,627, filed Jun. 21, 2016, Liu et al.
*U.S. Appl. No. 16/410,767, filed May 13, 2019, Liu et al.
*U.S. Appl. No. 14/320,519, filed Jun. 30, 2014, Liu et al.
*U.S. Appl. No. 14/913,458, filed Feb. 22, 2016, Liu et al.
*U.S. Appl. No. 16/266,937, filed Feb. 4, 2019, Liu et al.
*U.S. Appl. No. 15/112,759, filed Jul. 20, 2016, Liu et al.
*U.S. Appl. No. 16/238,386, filed Jan. 2, 2019, Liu et al.
*U.S. Appl. No. 15/217,839, filed Jul. 22, 2016, Liu et al.
*U.S. Appl. No. 15/518,639, filed Apr. 12, 2017, Liu et al.
*U.S. Appl. No. 15/567,312, filed Oct. 17, 2017, Liu et al.
*U.S. Appl. No. 15/748,053, filed Jan. 26, 2018, Liu et al.
*U.S. Appl. No. 16/804,228, filed Feb. 28, 2020, Liu et al.
*U.S. Appl. No. 15/216,844, filed Jul. 22, 2016, Liu et al.
*U.S. Appl. No. 16/521,371, filed Jul. 24, 2019, Liu et al.
*U.S. Appl. No. 16/648,162, filed Mar. 17, 2020, Liu et al.
*U.S. Appl. No. 16/641,630, filed Feb. 24, 2020, Liu et al.
EP 09812363.1, Mar. 30, 2012, Extended European Search Report.
EP 16 20 3684, May 26, 2017, Extended European Search Report.
PCT/US2009/056194, Jun. 21, 2010, International Search Report and Written Opinion.
PCT/US2009/056194, Mar. 17, 2011, International Preliminary Report on Patentability.
EP 17 16 0955, May 16, 2017, Extended European Search Report.
PCT/US2011/066747, Aug. 30, 2012, Invitation to Pay Additional Fees.
PCT/US2011/066747, Oct. 30, 2012, International Search Report and Written Opinion.
PCT/US2011/066747, Jul. 4, 2013, International Preliminary Report on Patentability.
PCT/US2015/012022, Sep. 25, 2015, International Search Report and Written Opinion.
PCT/US2015/012022, Aug. 4, 2016, International Preliminary Report on Patentability.
PCT/US/2016/043559, Jan. 12, 2017, Invitation to Pay Additional Fees.
PCT/US/2016/043559, Mar. 10, 2017, International Search Report and Written Opinion.
PCT/US/2016/043559, Feb. 1, 2018, International Preliminary Report on Patentability.
PCT/US2015/057012, Jun. 10, 2016, International Search Report and Written Opinion.
PCT/US2015/057012, May 4, 2017, International Preliminary Report on Patentability.
PCT/US2016/027795, Aug. 11, 2016, International Search Report and Written Opinion.
PCT/US2016/027795, Oct. 26, 2017, International Preliminary Report on Patentability.
PCT/US2016/044546, Oct. 12, 2016, Invitation to Pay Additional Fees.
PCT/US2016/044546, Dec. 28, 2016, International Search Report and Written Opinion.
PCT/US2016/044546, Feb. 8, 2018, International Preliminary Report on Patentability.
PCT/US2016/043513, Nov. 30, 2016, International Search Report and Written Opinion.
PCT/US2016/043513, Feb. 1, 2018, International Preliminary Report on Patentability.
PCT/US2018/14867, Apr. 5, 2018, Invitation to Pay Additional Fees.
PCT/US2018/14867, May 23, 2018, International Search Report and Written Opinion.
PCT/US2018/14867, Aug. 1, 2019, International Preliminary Report on Patentability.
PCT/US2018/140692, Sep. 12, 2018, International Search Report and Written Opinion.
PCT/US2018/040692, Nov. 15, 2018, International Search Report and Written Opinion.
PCT/US2018/040692, Jan. 16, 2020, International Preliminary Report on Patentability.
PCT/US2018/051557, Jan. 4, 2019, Invitation to Pay Additional Fees.
PCT/US2018/051557, Feb. 25, 2019, International Search Report and Written Opinion.
PCT/US2018/051557, Apr. 2, 2020, International Preliminary Report on Patentability.
PCT/US2018/044242, Nov. 21, 2018, International Search Report and Written Opinion.
PCT/US2019/037216, Sep. 4, 2019, International Search Report and Written Opinion.
PCT/US18/481134, Nov. 19, 2018, Invitation to Pay Additional Fees.
PCT/US18/481134, Jan. 22, 2019, International Search Report and Written Opinion.
PCT/US18/481134, Mar. 5, 2020, International Preliminary Report on Patentability.

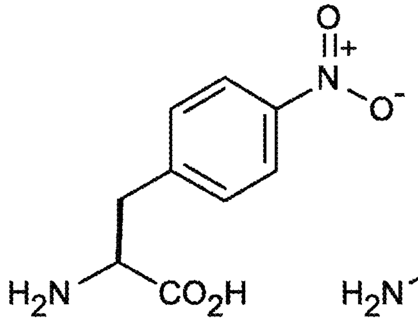
1
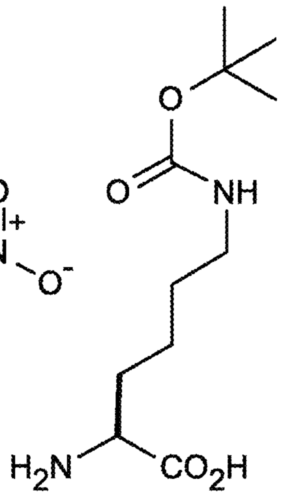
2
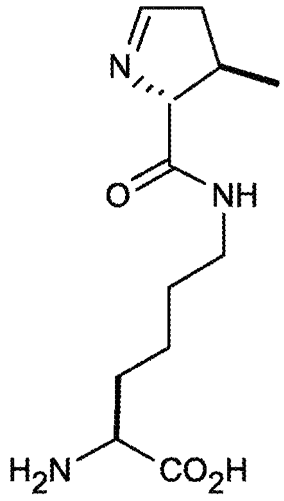
3
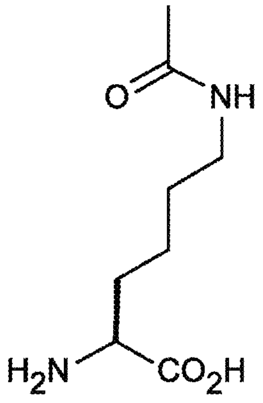
4
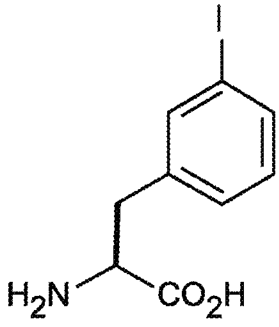
5
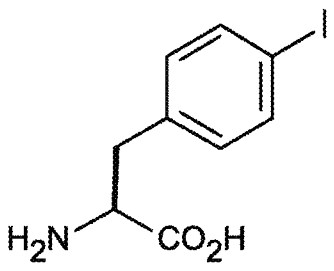
6
FIG. 3

```
M.barkeri_F        1 ---------------MDKKPLDVLISATGLWMSRTGTLHKIKHYEVSRSKIYIEMACGDHLVVNNSRSCRTARAFRHHKY
M.mazei            1 ---------------MDKKPLNTLISATGLWMSRTGTIHKIKHHEVSRSKIYIEMACGDHLVVNNSRSSRTARALRHHKY
chPylRS            1 ---------------MDKKPLDVLISATGLWMSRTGTLHKIKHYEVSRSKIYIEMACGDHLVVNNSRSCRTARAFRHHKY
chPylRS(IPYE)      1 ---------------MDKKPLDVLISATGLWMSRTGTLHKIKHYEISRSKIYIEMACGDHLVVNNSRSCRPARAFRYHKY
Split1             1 ---------------MDKKPLDVLISATGLWMSRTGTLHKIKHYEISRSKIYIEMACGDHLVVNNSRSCRPARAFRYHKY
Split2             1 ---------------MDKKPLDVLISATGLWMSRTGTLHKIKHYEISRSKIYIEMACGDHLVVNNSRSCRPARAFRYHKY
Split3             1 ---------------MDKKPLDVLISATGLWMSRTGTLHKIKHYEISRSKIYIEMACGDHLVVNNSRSCRPARAFRYHKY
Split4             1 ---------------MDKKPLDVLISATGLWMSRTGTLHKIKHYEISRSKIYIEMACGDHLVVNNSRSCRPARAFRYHKY
Split5             1 ---------------MDKKPLDVLISATGLWMSRTGTLHKIKHYEISRSKIYIEMACGDHLVVNNSRSCRPARAFRYHKY
Split6             1 ---------------MDKKPLDVLISATGLWMSRTGTLHKIKHYEISRSKIYIEMACGDHLVVNNSRSCRPARAFRYHKY
D.hafniense_PCP    1 --------------------------------------------------------------------------------
D.hafniense_Y51    1 MRGVSQASEEKKRYYRKNVDFFNLVEKIKLWPSRSGTLHGIKAMTRRGNTAEIVTHCNRRFIIYNSKHSRAARWLRNKLH
D.hafniense_DCB2   1 MRGVSQASEEKKRYYRKNVDFFNLVEKIKLWPSRSGTLHGIKAMTRRGNTAEIVTHCNRRFIIYNSKHSRAARWLRNKLH

M.barkeri_F       66 RKTCKRCRVSDEDINNFLTRSTEGKTSVKVKVVSAPK-VKKAMPKSVSRAPKPLENPVSAKASTDTSRSVPSP-------
M.mazei           66 RKTCKRCRVSDEDLNKFLTKANEDQTSVKVKVVSAPTRTKKAMPKSVARAPKPLENTEAAQKQPSGSKFSPAIPVSTQES
chPylRS           66 RKTCKRCRVSDEDINNFLTRSTEGKTSVKVKVVSAPK-VKKAMPKSVSRAPKPLENPVSAKASTDTSRSVPSP-------
chPylRS(IPYE)     66 RKTCKRCRVSDEDINNFLTRSTEGKTSVKVKVVSEPK-VKKAMPKSVSRAPKPLENPVSAKASTDTSRSVPSP-------
Split1            66 RKTCKRCRVSDEDINNFLTRSTEGKTSVKVKAVLSRK*----MPKSVSRAPKPLENPVSAKASTDTSRSVPSP-------
Split2            66 RKTCKRCRVSDEDINNFLTRSTEGKTSVKVKVVLSRK*----MPKSVSRAPKPLENPVSAKASTDTSRSVPSP-------
Split3            66 RKTCKRCRVSDEDINNFLTRSTEGKTSVKVKVVF*-------MPKSVSRAPKPLENPVSAKASTDTSRSVPSP-------
Split4            66 RKTCKRCRVSDEDINNFLTRSTEG*-----------------MPKSVSRAPKPLENPVSAKASTDTSRSVPSP-------
Split5            66 RKTCKRCRVSDEDINNFLTRSTEGKTSVKVKVVSERK*----MPKSVSRAPKPLENPVSAKASTDTSRSVPSP-------
Split6            66 RKTCKRCRVSDEDINNFLTRSTEGKTLC*-------------MPKSVSRAPKPLENPVSAKASTDTSRSVPSP-------
D.hafniense_PCP    1 --------------------------------------------------------------------------------
D.hafniense_Y51   81 FGVCPHCRIPEWKLQKYSSIVMSQHYGSHL*-------------------------------------------------
D.hafniense_DCB2  81 FGVCPHCRIPEWKLQKYSSIVMSQHYGSHL*-------------------------------------------------
```

Dh.PylSn

FIG. 16

```
M.barkeri_F        138 ---------------------------AKSTPNSPVPTSAPAPSLTRSQLDRVEALLSPED------KISLNIAKPFREL
M.mazei            146 VSVPASVSTSISSISTGATASALVKGNTNPITSMSAPVQASAPALTKSQTDRLEVLLNPKD------EISLNSGKPFREL
chPylRS            138 ---------------------------AKSTPNSPVPTSASAPALTKSQTDRLEVLLNPKD------EISLNSGKPFREL
chPylRS(IPYE)      138 ---------------------------AKSTPNSPVPTSASAPALTKSQTDRLEVLLNPKD------EISLNSGKPFREL
Split1             134 ---------------------------AKSTPNSPVPTSASAPALTKSQTDRLEVLLNPKD------EISLNSGKPFREL
Split2             134 ---------------------------AKSTPNSPVPTSASAPALTKSQTDRLEVLLNPKD------EISLNSGKPFREL
Split3             131 ---------------------------AKSTPNSPVPTSASAPALTKSQTDRLEVLLNPKD------EISLNSGKPFREL
Split4             121 ---------------------------AKSTPNSPVPTSASAPALTKSQTDRLEVLLNPKD------EISLNSGKPFREL
Split5             134 ---------------------------AKSTPNSPVPTSASAPALTKSQTDRLEVLLNPKD------EISLNSGKPFREL
Split6             125 ---------------------------AKSTPNSPVPTSASAPALTKSQTDRLEVLLNPKD------EISLNSGKPFREL
D.hafniense_PCP      1 ----------------------------MFLTRRDPPL---SSFWTKVQYQRLKELNASGEQLEMGFSDALSRDRAFQGI
D.hafniense_Y51    111 ----MDRIDHTDSKFVQAGETPVLPATFMFLTRRDPPL---SSFWTKVQYQRLKELNASGEQLEMGFSDALSRDRAFQGI
D.hafniense_DCB2   111 ----------------------------------------MSSFWTKVQYQRLKELNASGEQLEMGFSDALSRDRAFQGI
                          Dh.PylSc

M.barkeri_F        185 ESELVTRRKNDFQRLYTNDREDYLGKLERDITKFFVDRDFLEIKSPILIPAEYVERMGINNDTELSKQIFRVDKNLCLRP
M.mazei            220 ESELLSRRKKDLQQIYAEERENYLGKLEREITRFFVDRGFLEIKSPILIPLEYIERMGIDNDTELSKQIFRVDKNFCLRP
chPylRS            185 ESELLSRRKKDLQQIYAEERENYLGKLEREITRFFVDRGFLEIKSPILIPLEYIERMGIDNDTELSKQIFRVDKNFCLRP
chPylRS(IPYE)      185 ESELLSRRKKDLQQIYAEERENYLGKLEREITRFFVDRGFLEIKSPILIPLEYIERMGIDNDTELSKQIFRVDKNFCLRP
Split1             181 ESELLSRRKKDLQQIYAEERENYLGKLEREITRFFVDRGFLEIKSPILIPLEYIERMGIDNDTELSKQIFRVDKNFCLRP
Split2             181 ESELLSRRKKDLQQIYAEERENYLGKLEREITRFFVDRGFLEIKSPILIPLEYIERMGIDNDTELSKQIFRVDKNFCLRP
Split3             178 ESELLSRRKKDLQQIYAEERENYLGKLEREITRFFVDRGFLEIKSPILIPLEYIERMGIDNDTELSKQIFRVDKNFCLRP
Split4             168 ESELLSRRKKDLQQIYAEERENYLGKLEREITRFFVDRGFLEIKSPILIPLEYIERMGIDNDTELSKQIFRVDKNFCLRP
Split5             181 ESELLSRRKKDLQQIYAEERENYLGKLEREITRFFVDRGFLEIKSPILIPLEYIERMGIDNDTELSKQIFRVDKNFCLRP
Split6             172 ESELLSRRKKDLQQIYAEERENYLGKLEREITRFFVDRGFLEIKSPILIPLEYIERMGIDNDTELSKQIFRVDKNFCLRP
D.hafniense_PCP     50 EHQLMSQGKRHLEQLRTVKHRPALLELEEKLAKALHQQGFVQVVTPTIITKSALAKMTIGEDHPLFSQVFWLDGKKCLRP
D.hafniense_Y51    184 EHQLMSQGKRHLEQLRTVKHRPALLELEEGLAKALHQQGFVQVVTPTIITKSALAKMTIGEDHPLFSQVFWLDGKKCLRP
D.hafniense_DCB2   151 EHQLMSQGKRHLEQLRTVKHRPALLELEEGLAKALHQQGFVQVVTPTIITKSALAKMTIGEDHPLFSQVFWLDGKKCLRP
```

FIG. 16 (cont.)

```
M.barkeri_F         265 MLAPTLYNYLRKLDRILPDPIKIFEVGPCYRKESDGKEHLEEFTMVNFCQMGSGCTRE--NLESLIKEFLDYLE-IDFEI
M.mazei             300 MLAPNLYNYLRKLDRALPDPIKIFEIGPCYRKESDGKEHLEEFTMLNFCQMGSGCTRE--NLESIITDFLNHLG-IDFKI
chPylRS             265 MLAPNLYNYLRKLDRALPDPIKIFEIGPCYRKESDGKEHLEEFTMLNFCQMGSGCTRE--NLESIITDFLNHLG-IDFKI
chPylRS(IPYE)       265 MLAPNLYNYLRKLDRALPDPIKIFEIGPCYRKESDGKEHLEEFTMLNFCQMGSGCTRE--NLESIITDFLNHLG-IDFKI
Split1              261 MLAPNLYNYLRKLDRALPDPIKIFEIGPCYRKESDGKEHLEEFTMLNFCQMGSGCTRE--NLESIITDFLNHLG-IDFKI
Split2              261 MLAPNLYNYLRKLDRALPDPIKIFEIGPCYRKESDGKEHLEEFTMLNFCQMGSGCTRE--NLESIITDFLNHLG-IDFKI
Split3              258 MLAPNLYNYLRKLDRALPDPIKIFEIGPCYRKESDGKEHLEEFTMLNFCQMGSGCTRE--NLESIITDFLNHLG-IDFKI
Split4              248 MLAPNLYNYLRKLDRALPDPIKIFEIGPCYRKESDGKEHLEEFTMLNFCQMGSGCTRE--NLESIITDFLNHLG-IDFKI
Split5              261 MLAPNLYNYLRKLDRALPDPIKIFEIGPCYRKESDGKEHLEEFTMLNFCQMGSGCTRE--NLESIITDFLNHLG-IDFKI
Split6              252 MLAPNLYNYLRKLDRALPDPIKIFEIGPCYRKESDGKEHLEEFTMLNFCQMGSGCTRE--NLESIITDFLNHLG-IDFKI
D.hafniense_PCP     130 MLAPNLYTLWRELERLWDKPIRIFEIGTCYRKESQGAQHLNEFTMLNLTELGTPLEERHQRLEDMARWVLEAAGIREFEL
D.hafniense_Y51     264 MLAPNLYTLWRELERLWDKPIRIFEIGTCYRKESQGAQHLNEFTMLNLTELGTPLEERHQRLEDMARWVLEAAGIREFEL
D.hafniense_DCB2    231 MLAPNLYTLWRELERLWDKPIRIFEIGTCYRKESQGAQHLNEFTMLNLTELGTPLEERHQRLEDMARWVLEAAGIREFEL

M.barkeri_F         342 VGDSCMVYGDTLDIMHGDLELSSAVVGPVPLDREWGIDKPWIGAGFGLERLLKVMHGFKNIKRASRSESYYNGISTNL-
M.mazei             377 VGDSCMVYGDTLDVMHGDLELSSAVVGPIPLDREWGIDKPWIGAGFGLERLLKVKHDFKNIKRAARSESYYNGISTNL-
chPylRS             342 VGDSCMVYGDTLDVMHGDLELSSAVVGPIPLDREWGIDKPWIGAGFGLERLLKVKHDFKNIKRAARSESYYNGISTNL-
chPylRS(IPYE)       342 VGDSCMVYGDTLDVMHGDLELSSAVVGPIPLDREWGIDKPWIGAGFGLERLLKVKHDFKNIKRAARSESYYNGISTNL-
Split1              338 VGDSCMVYGDTLDVMHGDLELSSAVVGPIPLDREWGIDKPWIGAGFGLERLLKVKHDFKNIKRAARSESYYNGISTNL-
Split2              338 VGDSCMVYGDTLDVMHGDLELSSAVVGPIPLDREWGIDKPWIGAGFGLERLLKVKHDFKNIKRAARSESYYNGISTNL-
Split3              335 VGDSCMVYGDTLDVMHGDLELSSAVVGPIPLDREWGIDKPWIGAGFGLERLLKVKHDFKNIKRAARSESYYNGISTNL-
Split4              325 VGDSCMVYGDTLDVMHGDLELSSAVVGPIPLDREWGIDKPWIGAGFGLERLLKVKHDFKNIKRAARSESYYNGISTNL-
Split5              338 VGDSCMVYGDTLDVMHGDLELSSAVVGPIPLDREWGIDKPWIGAGFGLERLLKVKHDFKNIKRAARSESYYNGISTNL-
Split6              329 VGDSCMVYGDTLDVMHGDLELSSAVVGPIPLDREWGIDKPWIGAGFGLERLLKVKHDFKNIKRAARSESYYNGISTNL-
D.hafniense_PCP     210 VTESSVVYGDTVDVMKGDLELASGAMGPHFLDEKWEIFDPWVGLGFGLERLLMIREGTQHVQSMARSLSYLDGVRLNIN
D.hafniense_Y51     344 VTESSVVYGDTVDVMKGDLELASGAMGPHFLDEKWEIVDPWVGLGFGLERLLMIREGTQHVQSMARSLSYLDGVRLNIN
D.hafniense_DCB2    311 VTESSVVYGDTVDVMKGDLELASGAMGPHFLDEKWEIVDPWVGLGFGLERLLMIREGTQHVQSMARSLSYLDGVRLNIN
```

FIG. 16 (cont.)

| Non-continuous negative selection | Enrichment Factor (pfu in *p*-IF / pfu in *p*-NF) | Clonal phage isolate | Mutations |
|---|---|---|---|
| Stringent | 267 | Iodo.1 | S107P |
| | | Iodo.2 | ***RBS mutation*** |
| | | Iodo.3 | ***RBS mutation*** |
| | | Iodo.4 | ***RBS mutation*** |
| Less stringent | 233 | Iodo.5 | L69F, V235I |
| | | Iodo.6 | ***RBS mutation*** |
| | | Iodo.7 | G163C, N211K |
| | | Iodo.8 | S207A |

FIG. 22B

SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
caagcctcag cgaccgaata 20

<210> SEQ ID NO 2
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 2
ggaaaccgag gaaacgcaa 19

<210> SEQ ID NO 3
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 3

Met Glu Gln Lys Leu Ile Ser Glu Glu Asp Leu
1 5 10

<210> SEQ ID NO 4
<211> LENGTH: 8
<212> TYPE: PRT

<213> ORGANISM: Artificial Sequence
<220> FEATURE:
<223> OTHER INFORMATION: Synthetic Polypeptide

<400> SEQUENCE: 4

Gly Ser His His His His His His
1 5

<210> SEQ ID NO 5
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 5
atggataaga agccgctgga tgttctgatc tctgcgaccg gtctgtggat gtcccgtacc 60
ggcacgctgc acaagatcaa gcactatgag gtttctcgtt ctaaaatcta catcgaaatg 120
gcgtgtggtg accatctggt tgtgaacaac tctcgttctt gtcgtaccgc acgtgcattc 180
cgtcatcata aataccgtaa aacctgcaaa cgttgtcgtg tttctgacga agatatcaac 240
aacttcctga cccgttctac cgaaggcaaa acctctgtta aagttaaagt tgtttctgcg 300
ccgaaagtga aaaaagcgat gccgaaatct gtttctcgtg cgccgaaacc gctggaaaat 360
ccggtttctg cgaaagcgtc taccgacacc tctcgttctg ttccgtctcc ggcgaaatct 420
accccgaact ctccggttcc gacctctgca agtgcccccg cacttacgaa gagccagact 480
gacaggcttg aagtcctgtt aaacccaaaa gatgagattt ccctgaattc cggcaagcct 540
ttcagggagc ttgagtccga attgctctct cgcagaaaaa aagacctgca gcagatctac 600
gcggaagaaa gggagaatta tctggggaaa ctcgagcgtg aaattaccag gttctttgtg 660
gacaggggtt ttctggaaat aaaatccccg atcctgatcc ctcttgagta tatcgaaagg 720
atgggcattg ataatgatac cgaactttca aaacagatct tcagggttga caagaacttc 780
tgcctgagac ccatgcttgc tccaaacctt tacaactacc tgcgcaagct tgacagggcc 840
ctgcctgatc caataaaaat ttttgaaata ggcccatgct acagaaaaga gtccgacggc 900
aaagaacacc tcgaagagtt taccatgctg aacttctgcc agatgggatc gggatgcaca 960
cgggaaaatc ttgaaagcat aattacggac ttcctgaacc acctgggaat tgatttcaag 1020
atcgtaggcg attcctgcat ggtctatggg gataccettg atgtaatgca cggagacctg 1080
gaactttcct ctgcagtagt cggacccata ccgcttgacc gggaatgggg tattgataaa 1140
ccctggatag gggcaggttt cggactcgaa cgccttctaa aggttaaaca cgactttaaa 1200
aatatcaaga gagctgcaag gtccgagtct tactataacg ggatttctac caacctgtaa 1260

<210> SEQ ID NO 6
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 6
atggataaga agccgctgga tgttctgatc tctgcgaccg gtctgtggat gtcccgtacc 60
ggcacgctgc acaagatcaa gcactatgag gtttctcgtt ctaaaatcta catcgaaatg 120
gcgtgtggtg accatctggt tgtgaacaac tctcgttctt gtcgtaccgc acgtgcattc 180
cgtcatcata aataccgtaa aacctgcaaa cgttgtcgtg tttctgacga agatatcaac 240

```
aacttcctga cccgttctac cgaaggcaaa acctctgtta aagttaaagt tgtttctgcg    300

ccgaaagtga aaaaagcgat gccgaaatct gtttctcgtg cgccgaaacc gctggaaaat    360

ccggtttctg cgaaagcgtc taccgacacc tctcgttctg ttccgtctcc ggcgaaatct    420

accccgaact ctccggttcc gacctctgcg ccggcgccgt ctctgacccg ttctcagctg    480

gatcgtgttg aagcgctgct gtctccggaa gataaaatct ctctgaacat cgcgaaaccg    540

ttccgtgaac tggaatctga actggttacc cgtcgtaaaa acgatttcca gcgtctgtac    600

accaacgatc gtgaagacta cctgggtaaa ctggaacgtg acatcaccaa attcttcgtt    660

gaccgtgatt tcctggaaat caaatctccg atcctgatcc cggcggaata cgttgaacgt    720

atgggtatca acaacgatac cgaactgtct aaacagatct tccgtgttga taaaaacctg    780

tgcctgcgtc cgatgctggc gccgaccctg tacaactatc tgcgtaaact ggatcgtatc    840

ctgccggacc cgatcaaaat cttcgaagtt ggtccgtgct accgtaaaga atctgacggt    900

aaagaacacc tggaagagtt caccatggtg aacttctgcc agatgggttc tggttgcacc    960

cgtgagaacc tggaatctct gatcaaagaa tttctggact acctggaaat cgacttcgaa   1020

atcgttggtg actcctgcat ggtgtacggt gataccctgg acatcatgca cggtgacctg   1080

gaactgtctt ctgcggttgt tggtccggtt ccgctggatc gtgaatgggg tatcgacaaa   1140

ccgtggatcg gtgcgggttt cggtctggaa cgtctgctga aagttatgca cggtttcaaa   1200

aacatcaaac gtgcgtctcg ttctgaatct tactacaacg gtatctctac caacctgtaa   1260
```

<210> SEQ ID NO 7
<211> LENGTH: 1365
<212> TYPE: DNA
<213> ORGANISM: Artificial Sequence
<220> FEATURE:
<223> OTHER INFORMATION: Synthetic Polynucleotide

<400> SEQUENCE: 7

```
atggataaaa aaccactaaa cactctgata tctgcaaccg ggctctggat gtccaggacc     60

ggaacaattc ataaaataaa acaccacgaa gtctctcgaa gcaaaatcta tattgaaatg    120

gcatgcggag accaccttgt tgtaaacaac tccaggagca gcaggactgc aagagcgctc    180

aggcaccaca aatacaggaa gacctgcaaa cgctgcaggg tttcggatga ggatctcaat    240

aagttcctca caaaggcaaa cgaagaccag acaagcgtaa aagtcaaggt cgtttctgcc    300

cctaccagaa cgaaaaaggc aatgccaaaa tccgttgcga gagccccgaa acctcttgag    360

aatacagaag cggcacaggc tcaaccttct ggatctaaat tttcacctgc gataccggtt    420

tccacccaag agtcagtttc tgtcccggca tctgtttcaa catcaatatc aagcatttct    480

acaggagcaa ctgcatccgc actggtaaaa gggaatacga atcccattac atccatgtct    540

gcccctgttc aggcaagtgc ccccgcactt acgaagagcc agactgacag gcttgaagtc    600

ctgttaaacc caaaagatga gatttccctg aattccggca agcctttcag ggagcttgag    660

tccgaattgc tctctcgcag aaaaaaagac ctgcagcaga tctacgcgga agaaagggag    720

aattatctgg ggaaactcga gcgtgaaatt accaggttct ttgtggacag gggttttctg    780

gaaataaaat ccccgatcct gatccctctt gagtatatcg aaaggatggg cattgataat    840

gataccgaac tttcaaaaca gatcttcagg gttgacaaga acttctgcct gagacccatg    900

cttgctccaa acctttacaa ctacctgcgc aagcttgaca gggccctgcc tgatccaata    960

aaaatttttg aaataggccc atgctacaga aaagagtccg acggcaaaga acacctcgaa   1020

gagtttacca tgctgaactt ctgccagatg ggatcgggat gcacacggga aaatcttgaa   1080
```

agcataatta cggacttcct gaaccacctg ggaattgatt tcaagatcgt aggcgattcc 1140
tgcatggtct atggggatac ccttgatgta atgcacggag acctggaact ttcctctgca 1200
gtagtcggac ccataccgct tgaccgggaa tggggtattg ataaaccctg gataggggca 1260
ggtttcgggc tcgaacgcct tctaaaggtt aaacacgact ttaaaaatat caagagagct 1320
gcaaggtccg agtcttacta taacgggatt tctaccaacc tgtaa 1365

<210> SEQ ID NO 8
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 8
atggataaga agccgctgga tgttctgatc tctgcgaccg gtctgtggat gtcccgtacc 60
ggcacgctgc acaagatcaa gcactatgag gtttctcgtt ctaaaatcta catcgaaatg 120
gcgtgtggtg accatctggt tgtgaacaac tctcgttctt gtcgtaccgc acgtgcattc 180
cgtcatcata aataccgtaa aacctgcaaa cgttgtcgtg tttctggtga agatatcaac 240
aacttcctga cccgttctac cgaaggcaaa acctctgtta aagttaaagt tgtttctgcg 300
ccgaaagtga aaaaagcgat gccgaaatct gtttctcgtg cgccgaaacc gctggaaaat 360
ccggtttctg cgaaagcgtc taccgacacc tctcgttctg ttccgtctcc ggcgaaatct 420
accccgaact ctccggttcc gacctctgca agtgcccccg cacttacgaa gagccagact 480
gacaggcttg aagtcctgtt aaacccaaaa gatgagattt ccctgaattc cggcaagcct 540
ttcagggagc ttgagtccga attgctctct cgcagaaaaa aagacctgca gcagatctac 600
gcggaagaaa gggagaatta tctggggaaa ctcgagcgtg aaattaccag gttctttgtg 660
gacaggggtt ttctggaaat aaaatccccg atcctgatcc ctcttgagta tatcgaaagg 720
atgggcattg ataatgatac cgaactttca aaacagatct tcagggttga caagaacttc 780
tgcctgagac ccatgatggc tccaaacatt tttaactacg ctcgcaagct tgacagggcc 840
ctgcctgatc caataaaaat ttttgaaata ggcccatgct acagaaaaga gtccgacggc 900
aaagaacacc tcgaagagtt taccatgctg aacttctttc agatgggatc gggatgcaca 960
cgggaaaatc ttgaaagcat aattacggac ttcctgaacc acctgggaat tgatttcaag 1020
atcgtaggcg attcctgcat ggtctatggg gatacccttg atgtaatgca cggagacctg 1080
gaactttcct ctgcagtagt cggacccata ccgcttgacc gggaatgggg tattgataaa 1140
ccctggatag gggcaggttt cggactcgaa cgccttctaa aggttaaaca cgactttaaa 1200
aatatcaaga gagctgcaag gtccgagtct tactataacg ggatttctac caacctgtaa 1260

<210> SEQ ID NO 9
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 9
atggataaga agccgctgga tgttctgatc tctgcgaccg gtctgtggat gtcccgtacc 60
ggcacgctgc acaagatcaa gcactatgag gtttctcgtt ctaaaatcta catcgaaatg 120
gcgtgtggtg accatctggt tgtgaacaac tctcgttctt gtcgtaccgc acgtgcattc 180

-continued

```
cgtcatcata aataccgtaa aacctgcaaa cgttgtcgtg tttctggtga agatatcaac    240

aacttcctga cccgttctac cgaaggcaaa acctctgtta aagttaaagt tgtttctgcg    300

ccgaaagtga aaaaagcgat gccgaaatct gtttctcgtg cgccgaaacc gctggaaaat    360

ccggtttctg cgaaagcgtc taccgacacc tctcgttctg ttccgtctcc ggcgaaatct    420

accccgaact ctccggttcc gacctctgcg ccggcgccgt ctctgacccg ttctcagctg    480

gatcgtgttg aagcgctgct gtctccggaa gataaaatct ctctgaacat cgcgaaaccg    540

ttccgtgaac tggaatctga actggttacc cgtcgtaaaa acgatttcca gcgtctgtac    600

accaacgatc gtgaagacta cctgggtaaa ctggaacgtg acatcaccaa attcttcgtt    660

gaccgtgatt tcctggaaat caaatctccg atcctgatcc cggcggaata cgttgaacgt    720

atgggtatca acaacgatac cgaactgtct aaacagatct tccgtgttga taaaaacctg    780

tgcctgcgtc cgatgatggc gccgaccatt tttaactatg ctcgtaaact ggatcgtatc    840

ctgccggacc cgatcaaaat cttcgaagtt ggtccgtgct accgtaaaga atctgacggt    900

aaagaacacc tggaagagtt caccatggtg aacttctttc agatgggttc tggttgcacc    960

cgtgagaacc tggaatctct gatcaaagaa tttctggact acctggaaat cgacttcgaa   1020

atcgttggtg actcctgcat ggtgtacggt gataccctgg acatcatgca cggtgacctg   1080

gaactgtctt ctgcggttgt tggtccggtt ccgctggatc gtgaatgggg tatcgacaaa   1140

ccgtggatcg gtgcgggttt cggtctggaa cgtctgctga aagttatgca cggtttcaaa   1200

aacatcaaac gtgcgtctcg ttctgaatct tactacaacg gtatctctac caacctgtaa   1260
```

<210> SEQ ID NO 10
<211> LENGTH: 1365
<212> TYPE: DNA
<213> ORGANISM: Artificial Sequence
<220> FEATURE:
<223> OTHER INFORMATION: Synthetic Polynucleotide

<400> SEQUENCE: 10

```
atggataaaa aaccactaaa cactctgata tctgcaaccg ggctctggat gtccaggacc     60

ggaacaattc ataaaataaa acaccacgaa gtctctcgaa gcaaaatcta tattgaaatg    120

gcatgcggag accaccttgt tgtaaacaac tccaggagca gcaggactgc aagagcgctc    180

aggcaccaca aatacaggaa gacctgcaaa cgctgcaggg tttcgggtga ggatctcaat    240

aagttcctca caaaggcaaa cgaagaccag acaagcgtaa aagtcaaggt cgtttctgcc    300

cctaccagaa cgaaaaaggc aatgccaaaa tccgttgcga gagccccgaa acctcttgag    360

aatacagaag cggcacaggc tcaaccttct ggatctaaat tttcacctgc gataccggtt    420

tccacccaag agtcagtttc tgtcccggca tctgtttcaa catcaatatc aagcatttct    480

acaggagcaa ctgcatccgc actggtaaaa gggaatacga atcccattac atccatgtct    540

gcccctgttc aggcaagtgc ccccgcactt acgaagagcc agactgacag gcttgaagtc    600

ctgttaaacc caaaagatga gatttccctg aattccggca agcctttcag ggagcttgag    660

tccgaattgc tctctcgcag aaaaaaagac ctgcagcaga tctacgcgga agaaagggag    720

aattatctgg ggaaactcga gcgtgaaatt accaggttct ttgtggacag ggttttctg     780

gaaataaaat ccccgatcct gatccctctt gagtatatcg aaaggatggg cattgataat    840

gataccgaac tttcaaaaca gatcttcagg gttgacaaga acttctgcct gagacccatg    900

atggctccaa acatttttaa ctacgctcgc aagcttgaca gggccctgcc tgatccaata    960

aaaatttttg aaataggccc atgctacaga aaagagtccg acggcaaaga acacctcgaa   1020
```

```
gagtttacca tgctgaactt ctttcagatg ggatcgggat gcacacggga aaatcttgaa   1080

agcataatta cggacttcct gaaccacctg ggaattgatt tcaagatcgt aggcgattcc   1140

tgcatggtct atggggatac ccttgatgta atgcacggag acctggaact ttcctctgca   1200

gtagtcggac ccataccgct tgaccgggaa tggggtattg ataaaccctg gatagggggca   1260

ggtttcgggc tcgaacgcct tctaaaggtt aaacacgact ttaaaaatat caagagagct   1320

gcaaggtccg agtcttacta taacgggatt tctaccaacc tgtaa                   1365


<210> SEQ ID NO 11
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 11

atggataaga agccgctgga tgttctgatc tctgcgaccg gtctgtggat gtcccgtacc     60

ggcacgctgc acaagatcaa gcactatgag gtttctcgtt ctaaaatcta catcgaaatg    120

gcgtgtggtg accatctggt tgtgaacaac tctcgttctt gtcgtaccgc acgtgcattc    180

cgtcatcata aataccgtaa aacctgcaaa cgttgtcgtg tttctgacga agatatcaac    240

aacttcctga cccgttctac cgaaggcaaa acctctgtta aagttaaagt tgtttctgcg    300

ccgaaagtga aaaaagcgat gccgaaatct gtttctcgtg cgccgaaacc gctggaaaat    360

ccggtttctg cgaaagcgtc taccgacacc tctcgttctg ttccgtctcc ggcgaaatct    420

accccgaact ctccggttcc gacctctgca agtgcccccg cacttacgaa gagccagact    480

gacaggcttg aagtcctgtt aaacccaaaa gatgagattt ccctgaattc cggcaagcct    540

ttcagggagc ttgagtccga attgctctct cgcagaaaaa aagacctgca gcagatctac    600

gcggaagaaa gggagaatta tctggggaaa ctcgagcgtg aaattaccag gttctttgtg    660

gacaggggtt ttctggaaat aaaatccccg atcctgatcc ctcttgagta tatcgaaagg    720

atgggcattg ataatgatac cgaactttca aaacagatct tcagggttga caagaacttc    780

tgcctgagac ccatgcttgc tccaaacctt tacaactacc tgcgcaagct tgacagggcc    840

ctgcctgatc caataaaaat ttttgaaata ggcccatgct acagaaaaga gtccgacggc    900

aaagaacacc tcgaagagtt taccatgctg tcgttcattc agatgggatc gggatgtaca    960

cgggaaaatc ttgaaagcat aattacggac ttcctgaacc acctgggaat tgatttcaag   1020

atcgtaggcg attcctgcat ggtctatggg gatacccttg atgtaatgca cggagacctg   1080

gaactttcct ctgcagtagt cggacccata ccgcttgacc gggaatgggg tattgataaa   1140

ccctggatag gggcaggttt cgggctcgaa cgccttctaa aggttaaaca cgactttaaa   1200

aatatcaaga gagctgcaag gtccgagtct tactataacg ggatttctac caacctgtaa   1260


<210> SEQ ID NO 12
<211> LENGTH: 1259
<212> TYPE: DNA
<213> ORGANISM: Artificial Sequence
<220> FEATURE:
<223> OTHER INFORMATION: Synthetic Polynucleotide

<400> SEQUENCE: 12

atggataaga agccgctgga tgttctgatc tctgcgaccg gtctgtggat gtcccgtacc     60

ggcacgctgc acaagatcaa gcactatgag atttctcgtt ctaaaatcta catcgaaatg    120
```

-continued

```
gcgtgtggtg accatctggt tgtgaacaac tctcgttctt gtcgtcccgc acgtgcattc    180

cgttatcata aataccgtaa aacctgcaaa cgttgtcgtg tttctgacga agatatcaac    240

aacttcctga cccgttctac cgaaggcaaa acctctgtta aagttaaagc tgttctgagc    300

cgaaagtgaa aaaagcgatg ccgaaatctg tttctcgtgc gccgaaaccg ctggaaaatc    360

cggtttctgc gaaagcgtct accgacacct ctcgttctgt tccgtctccg gcgaaatcta    420

ccccgaactc tccggttccg acctctgcaa gtgcccccgc acttacgaag agccagactg    480

acaggcttga agtcctgtta aacccaaaag atgagatttc cctgaattcc ggcaagcctt    540

tcagggagct tgagtccgaa ttgctctctc gcagaaaaaa agacctgcag cagatctacg    600

cggaagaaag ggagaattat ctggggaaac tcgagcgtga aattaccagg ttctttgtgg    660

acaggggttt tctggaaata aaatccccga tcctgatccc tcttgagtat atcgaaagga    720

tgggcattga taatgatacc gaactttcaa aacagatctt cagggttgac aagaacttct    780

gcctgagacc catgcttgct ccaaaccttt acaactacct gcgcaagctt gacagggccc    840

tgcctgatcc aataaaaatt tttgaaatag gcccatgcta cagaaaagag tccgacggca    900

aagaacacct cgaagagttt accatgctga acttctgcca gatgggatcg ggatgcacac    960

gggaaaatct tgaaagcata attacggact tcctgaacca cctgggaatt gatttcaaga   1020

tcgtaggcga ttcctgcatg gtctatgggg ataccttga tgtaatgcac ggagacctgg   1080

aactttcctc tgcagtagtc ggacccatac cgcttgaccg ggaatggggt attgataaac   1140

cctggatagg ggcaggtttc gggctcgaac gccttctaaa ggttaaacac gactttaaaa   1200

atatcaagag agctgcaagg tccgagtctt actataacgg gatttctacc aacctgtaa    1259
```

```
<210> SEQ ID NO 13
<211> LENGTH: 1259
<212> TYPE: DNA
<213> ORGANISM: Artificial Sequence
<220> FEATURE:
<223> OTHER INFORMATION: Synthetic Polynucleotide

<400> SEQUENCE: 13

atggataaga agccgctgga tgttctgatc tctgcgaccg gtctgtggat gtcccgtacc     60

ggcacgctgc acaagatcaa gcactatgag atttctcgtt ctaaaatcta catcgaaatg    120

gcgtgtggtg accatctggt tgtgaacaac tctcgttctt gtcgtcccgc acgtgcattc    180

cgttatcata aataccgtaa aacctgcaaa cgttgtcgtg tttctgacga agatatcaac    240

aacttcctga cccgttctac cgaaggcaaa acctctgtta aagttaaagt tgttctgagc    300

cgaaagtgaa aaaagcgatg ccgaaatctg tttctcgtgc gccgaaaccg ctggaaaatc    360

cggtttctgc gaaagcgtct accgacacct ctcgttctgt tccgtctccg gcgaaatcta    420

ccccgaactc tccggttccg acctctgcaa gtgcccccgc acttacgaag agccagactg    480

acaggcttga agtcctgtta aacccaaaag atgagatttc cctgaattcc ggcaagcctt    540

tcagggagct tgagtccgaa ttgctctctc gcagaaaaaa agacctgcag cagatctacg    600

cggaagaaag ggagaattat ctggggaaac tcgagcgtga aattaccagg ttctttgtgg    660

acaggggttt tctggaaata aaatccccga tcctgatccc tcttgagtat atcgaaagga    720

tgggcattga taatgatacc gaactttcaa aacagatctt cagggttgac aagaacttct    780

gcctgagacc catgcttgct ccaaaccttt acaactacct gcgcaagctt gacagggccc    840

tgcctgatcc aataaaaatt tttgaaatag gcccatgcta cagaaaagag tccgacggca    900

aagaacacct cgaagagttt accatgctga acttctgcca gatgggatcg ggatgcacac    960
```

```
gggaaaatct tgaaagcata attacggact tcctgaacca cctgggaatt gatttcaaga   1020

tcgtaggcga ttcctgcatg gtctatgggg ataccettga tgtaatgcac ggagacctgg   1080

aactttcctc tgcagtagtc ggacccatac cgcttgaccg ggaatggggt attgataaac   1140

cctggatagg ggcaggtttc gggctcgaac gccttctaaa ggttaaacac gactttaaaa   1200

atatcaagag agctgcaagg tccgagtctt actataacgg gatttctacc aacctgtaa    1259
```

<210> SEQ ID NO 14
<211> LENGTH: 1261
<212> TYPE: DNA
<213> ORGANISM: Artificial Sequence
<220> FEATURE:
<223> OTHER INFORMATION: Synthetic Polynucleotide

<400> SEQUENCE: 14

```
atggataaga agccgctgga tgttctgatc tctgcgaccg gtctgtggat gtcccgtacc     60

ggcacgctgc acaagatcaa gcactatgag atttctcgtt ctaaaatcta catcgaaatg    120

gcgtgtggtg accatctggt tgtgaacaac tctcgttctt gtcgtcccgc acgtgcattc    180

cgttatcata aataccgtaa aacctgcaaa cgttgtcgtg tttctgacga agatatcaac    240

aacttcctga cccgttctac cgaaggcaaa acctctgtta aagttaaagt tgttttctga    300

gccgaaagtg aaaaaagcga tgccgaaatc tgtttctcgt gcgccgaaac cgctggaaaa    360

tccggtttct gcgaaagcgt ctaccgacac ctctcgttct gttccgtctc cggcgaaatc    420

taccccgaac tctccggttc cgacctctgc aagtgccccc gcacttacga agagccagac    480

tgacaggctt gaagtcctgt taaacccaaa agatgagatt tccctgaatt ccggcaagcc    540

tttcagggag cttgagtccg aattgctctc tcgcagaaaa aaagacctgc agcagatcta    600

cgcggaagaa agggagaatt atctggggaa actcgagcgt gaaattacca ggttctttgt    660

ggacaggggt tttctggaaa taaaatcccc gatcctgatc cctcttgagt atatcgaaag    720

gatgggcatt gataatgata ccgaactttc aaaacagatc ttcagggttg acaagaactt    780

ctgcctgaga cccatgcttg ctccaaacct ttacaactac ctgcgcaagc ttgacagggc    840

cctgcctgat ccaataaaaa tttttgaaat aggcccatgc tacagaaaag agtccgacgg    900

caaagaacac ctcgaagagt ttaccatgct gaacttctgc cagatgggat cgggatgcac    960

acgggaaaat cttgaaagca taattacgga cttcctgaac cacctgggaa ttgatttcaa   1020

gatcgtaggc gattcctgca tggtctatgg ggataccctt gatgtaatgc acggagacct   1080

ggaactttcc tctgcagtag tcggacccat accgcttgac cgggaatggg gtattgataa   1140

accctggata ggggcaggtt tcgggctcga acgccttcta aaggttaaac acgactttaa   1200

aaatatcaag agagctgcaa ggtccgagtc ttactataac gggatttcta ccaacctgta   1260

a                                                                   1261
```

<210> SEQ ID NO 15
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 15

```
atggataaga agccgctgga tgttctgatc tctgcgaccg gtctgtggat gtcccgtacc     60

ggcacgctgc acaagatcaa gcactatgag atttctcgtt ctaaaatcta catcgaaatg    120
```

-continued

```
gcgtgtggtg accatctggt tgtgaacaac tctcgttctt gtcgtcccgc acgtgcattc    180
cgttatcata aataccgtaa aacctgcaaa cgttgtcgtg tttctgacga agatatcaac    240
aacttcctga cccgttctac cgaaggctaa acctctgtta aagttaaagt tgtttctgag    300
ccgaaagtga aaaaagcgat gccgaaatct gtttctcgtg cgccgaaacc gctggaaaat    360
ccggtttctg cgaaagcgtc taccgacacc tctcgttctg ttccgtctcc ggcgaaatct    420
accccgaact ctccggttcc gacctctgca agtgcccccg cacttacgaa gagccagact    480
gacaggcttg aagtcctgtt aaacccaaaa gatgagattt ccctgaattc cggcaagcct    540
ttcagggagc ttgagtccga attgctctct cgcagaaaaa aagacctgca gcagatctac    600
gcggaagaaa gggagaatta tctggggaaa ctcgagcgtg aaattaccag gttctttgtg    660
gacaggggtt ttctggaaat aaaatccccg atcctgatcc ctcttgagta tatcgaaagg    720
atgggcattg ataatgatac cgaactttca aaacagatct tcagggttga caagaacttc    780
tgcctgagac ccatgcttgc tccaaacctt tacaactacc tgcgcaagct tgacagggcc    840
ctgcctgatc caataaaaat ttttgaaata ggcccatgct acagaaaaga gtccgacggc    900
aaagaacacc tcgaagagtt taccatgctg aacttctgcc agatgggatc gggatgcaca    960
cgggaaaatc ttgaaagcat aattacggac ttcctgaacc acctgggaat tgatttcaag   1020
atcgtaggcg attcctgcat ggtctatggg gatacccttg atgtaatgca cggagacctg   1080
gaactttcct ctgcagtagt cggacccata ccgcttgacc gggaatgggg tattgataaa   1140
ccctggatag gggcaggttt cgggctcgaa cgccttctaa aggttaaaca cgactttaaa   1200
aatatcaaga gagctgcaag gtccgagtct tactataacg ggatttctac caacctgtaa   1260
```

```
<210> SEQ ID NO 16
<211> LENGTH: 1259
<212> TYPE: DNA
<213> ORGANISM: Artificial Sequence
<220> FEATURE:
<223> OTHER INFORMATION: Synthetic Polynucleotide

<400> SEQUENCE: 16

atggataaga agccgctgga tgttctgatc tctgcgaccg gtctgtggat gtcccgtacc     60
ggcacgctgc acaagatcaa gcactatgag atttctcgtt ctaaaatcta catcgaaatg    120
gcgtgtggtg accatctggt tgtgaacaac tctcgttctt gtcgtcccgc acgtgcattc    180
cgttatcata aataccgtaa aacctgcaaa cgttgtcgtg tttctgacga agatatcaac    240
aacttcctga cccgttctac cgaaggcaaa acctctgtta aagttaaagt tgtttctgag    300
cgaaagtgaa aaaagcgatg ccgaaatctg tttctcgtgc gccgaaaccg ctggaaaatc    360
cggtttctgc gaaagcgtct accgacacct ctcgttctgt tccgtctccg gcgaaatcta    420
ccccgaactc tccggttccg acctctgcaa gtgcccccgc acttacgaag agccagactg    480
acaggcttga agtcctgtta aacccaaaag atgagatttc cctgaattcc ggcaagcctt    540
tcagggagct tgagtccgaa ttgctctctc gcagaaaaaa agacctgcag cagatctacg    600
cggaagaaag ggagaattat ctggggaaac tcgagcgtga aattaccagg ttctttgtgg    660
acaggggttt tctggaaata aaatccccga tcctgatccc tcttgagtat atcgaaagga    720
tgggcattga taatgatacc gaactttcaa aacagatctt cagggttgac aagaacttct    780
gcctgagacc catgcttgct ccaaaccttt acaactacct gcgcaagctt gacagggccc    840
tgcctgatcc aataaaaatt tttgaaatag gcccatgcta cagaaaagag tccgacggca    900
aagaacacct cgaagagttt accatgctga acttctgcca gatgggatcg ggatgcacac    960
```

```
gggaaaatct tgaaagcata attacggact tcctgaacca cctgggaatt gatttcaaga   1020
tcgtaggcga ttcctgcatg gtctatgggg atacccttga tgtaatgcac ggagacctgg   1080
aactttcctc tgcagtagtc ggacccatac cgcttgaccg ggaatggggt attgataaac   1140
cctggatagg ggcaggtttc gggctcgaac gccttctaaa ggttaaacac gactttaaaa   1200
atatcaagag agctgcaagg tccgagtctt actataacgg gatttctacc aacctgtaa    1259
```

<210> SEQ ID NO 17
<211> LENGTH: 1261
<212> TYPE: DNA
<213> ORGANISM: Artificial Sequence
<220> FEATURE:
<223> OTHER INFORMATION: Synthetic Polynucleotide

<400> SEQUENCE: 17

```
atggataaga agccgctgga tgttctgatc tctgcgaccg gtctgtggat gtcccgtacc     60
ggcacgctgc acaagatcaa gcactatgag atttctcgtt ctaaaatcta catcgaaatg    120
gcgtgtggtg accatctggt tgtgaacaac tctcgttctt gtcgtcccgc acgtgcattc    180
cgttatcata aataccgtaa aacctgcaaa cgttgtcgtg tttctgacga agatatcaac    240
aacttcctga cccgttctac cgaaggcaaa accctctgtt aaagttaaag ttgtttctga    300
gccgaaagtg aaaaaagcga tgccgaaatc tgtttctcgt gcgccgaaac cgctggaaaa    360
tccggtttct gcgaaagcgt ctaccgacac ctctcgttct gttccgtctc cggcgaaatc    420
taccccgaac tctccggttc cgacctctgc aagtgccccc gcacttacga agagccagac    480
tgacaggctt gaagtcctgt taaacccaaa agatgagatt tccctgaatt ccggcaagcc    540
tttcagggag cttgagtccg aattgctctc tcgcagaaaa aaagacctgc agcagatcta    600
cgcggaagaa agggagaatt atctggggaa actcgagcgt gaaattacca ggttctttgt    660
ggacaggggt tttctggaaa taaaatcccc gatcctgatc cctcttgagt atatcgaaag    720
gatgggcatt gataatgata ccgaactttc aaaacagatc ttcagggttg acaagaactt    780
ctgcctgaga cccatgcttg ctccaaacct ttacaactac ctgcgcaagc ttgacagggc    840
cctgcctgat ccaataaaaa tttttgaaat aggcccatgc tacagaaaag agtccgacgg    900
caaagaacac ctcgaagagt ttaccatgct gaacttctgc cagatgggat cgggatgcac    960
acgggaaaat cttgaaagca taattacgga cttcctgaac cacctgggaa ttgatttcaa   1020
gatcgtaggc gattcctgca tggtctatgg ggataccctt gatgtaatgc acggagacct   1080
ggaactttcc tctgcagtag tcggacccat accgcttgac cgggaatggg gtattgataa   1140
accctggata ggggcaggtt tcgggctcga acgccttcta aaggttaaac acgactttaa   1200
aaatatcaag agagctgcaa ggtccgagtc ttactataac gggatttcta ccaacctgta   1260
a                                                                   1261
```

<210> SEQ ID NO 18
<211> LENGTH: 921
<212> TYPE: DNA
<213> ORGANISM: Artificial Sequence
<220> FEATURE:
<223> OTHER INFORMATION: Synthetic Polynucleotide

<400> SEQUENCE: 18

```
atggacgaat ttgaaatgat aaagagaaac acatctgaaa ttatcagcga ggaagagtta     60
agagaggttt taaaaaaaga tgaaaaatct gctctgatag gttttgaacc aagtggtaaa    120
```

```
atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagttc gttccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tcctcttaat    480

tatgagggcg ttgatgttgc agttggaggg atggagcaga gaaaaaatac catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatgcgctt aaaaaatgct gtagctgaag aacttataaa gattttagag    900

ccaattagaa agagattata a                                              921
```

<210> SEQ ID NO 19
<211> LENGTH: 921
<212> TYPE: DNA
<213> ORGANISM: Artificial Sequence
<220> FEATURE:
<223> OTHER INFORMATION: Synthetic Polynucleotide

<400> SEQUENCE: 19

```
atggacgaat ttgaaatgat aaagagaaac acatctgaaa ttatcagcga ggaagagtta     60

agagaggttt taaaaaaaga tgaaaaatct gctctgatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagttc gttccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tcctcttcat    480

tatgagggcg ttgatgttgc agttggaggg atggagcaga gaaaaaatac catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatgcgctt aaaaaatgct gtagctgaag aacttataaa gattttagag    900

ccaattagaa agagattata a                                              921
```

<210> SEQ ID NO 20
<211> LENGTH: 419
<212> TYPE: PRT
<213> ORGANISM: Artificial Sequence
<220> FEATURE:
<223> OTHER INFORMATION: Synthetic Polypeptide -continued

<400> SEQUENCE: 20

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400
```

```
Asn Ile Lys Arg Ala Ser Arg Ser Glu Ser Tyr Tyr Asn Gly Ile Ser
                405                 410                 415

Thr Asn Leu


<210> SEQ ID NO 21
<211> LENGTH: 454
<212> TYPE: PRT
<213> ORGANISM: Artificial Sequence
<220> FEATURE:
<223> OTHER INFORMATION: Synthetic Polypeptide

<400> SEQUENCE: 21

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335
```

-continued

```
Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450


<210> SEQ ID NO 22
<211> LENGTH: 306
<212> TYPE: PRT
<213> ORGANISM: Artificial Sequence
<220> FEATURE:
<223> OTHER INFORMATION: Synthetic Polypeptide

<400> SEQUENCE: 22

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu Asn
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

```
Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 23
<211> LENGTH: 306
<212> TYPE: PRT
<213> ORGANISM: Artificial Sequence
<220> FEATURE:
<223> OTHER INFORMATION: Synthetic Polypeptide

<400> SEQUENCE: 23

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285
```

```
Asn Ala Val Ala Glu Glu Leu Ile Lys Ile Leu Glu Pro Ile Arg Lys
    290                 295                 300

Arg Leu
305


<210> SEQ ID NO 24
<211> LENGTH: 305
<212> TYPE: PRT
<213> ORGANISM: Artificial Sequence
<220> FEATURE:
<223> OTHER INFORMATION: Synthetic Polypeptide

<400> SEQUENCE: 24

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg
305


<210> SEQ ID NO 25
<211> LENGTH: 1260
```

<212> TYPE: DNA
<213> ORGANISM: Artificial Sequence
<220> FEATURE:
<223> OTHER INFORMATION: Synthetic Polynucleotide

<400> SEQUENCE: 25
atggataaga agccgctgga tgttctgatc tctgcgaccg gtctgtggat gtcccgtacc 60
ggcacgctgc acaagatcaa gcactatgag atttctcgtt ctaaaatcta catcgaaatg 120
gcgtgtggtg accatctggt tgtgaacaac tctcgttctt gtcgtcccgc acgtgcattc 180
cgttatcata aataccgtaa aacctgcaaa cgttgtcgtg tttctgacga agatatcaac 240
aacttcctga cccgttctac cgaaggcaaa acctctgtta aagttaaagt tgtttctgag 300
ccgaaagtga aaaaagcgat gccgaaatct gtttctcgtg cgccgaaacc gctggaaaat 360
ccggtttctg cgaaagcgtc taccgacacc tctcgttctg ttccgtctcc ggcgaaatct 420
accccgaact ctccggttcc gacctctgca agtgcccccg cacttacgaa gagccagact 480
gacaggcttg aagtcctgtt aaacccaaaa gatgagattt ccctgaattc cggcaagcct 540
ttcagggagc ttgagtccga attgctctct cgcagaaaaa aagacctgca gcagatctac 600
gcggaagaaa gggagaatta tctggggaaa ctcgagcgtg aaattaccag gttctttgtg 660
gacaggggtt ttctggaaat aaaatccccg atcctgatcc ctcttgagta tatcgaaagg 720
atgggcattg ataatgatac cgaactttca aaacagatct tcagggttga caagaacttc 780
tgcctgagac ccatgcttgc tccaaacctt tacaactacc tgcgcaagct tgacagggcc 840
ctgcctgatc caataaaaat ttttgaaata ggcccatgct acagaaaaga gtccgacggc 900
aaagaacacc tcgaagagtt taccatgctg aacttctgcc agatgggatc gggatgcaca 960
cgggaaaatc ttgaaagcat aattacggac ttcctgaacc acctgggaat tgatttcaag 1020
atcgtaggcg attcctgcat ggtctatggg gataccettg atgtaatgca cggagacctg 1080
gaactttcct ctgcagtagt cggacccata ccgcttgacc gggaatgggg tattgataaa 1140
ccctggatag gggcaggttt cggactcgaa cgccttctaa aggttaaaca cgactttaaa 1200
aatatcaaga gagctgcaag gtccgagtct tactataacg ggatttctac caacctgtaa 1260

<210> SEQ ID NO 26
<211> LENGTH: 419
<212> TYPE: PRT
<213> ORGANISM: Artificial Sequence
<220> FEATURE:
<223> OTHER INFORMATION: Synthetic Polypeptide

<400> SEQUENCE: 26

Met Asp Lys Lys Pro Leu Asp Val Leu Ile Ser Ala Thr Gly Leu Trp
1 5 10 15

Met Ser Arg Thr Gly Thr Leu His Lys Ile Lys His Tyr Glu Ile Ser
20 25 30

Arg Ser Lys Ile Tyr Ile Glu Met Ala Cys Gly Asp His Leu Val Val
35 40 45

Asn Asn Ser Arg Ser Cys Arg Pro Ala Arg Ala Phe Arg Tyr His Lys
50 55 60

Tyr Arg Lys Thr Cys Lys Arg Cys Arg Val Ser Asp Glu Asp Ile Asn
65 70 75 80

Asn Phe Leu Thr Arg Ser Thr Glu Gly Lys Thr Ser Val Lys Val Lys
85 90 95

Val Val Ser Glu Pro Lys Val Lys Lys Ala Met Pro Lys Ser Val Ser
100 105 110

```
Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Ser Ala Pro Ala Leu Thr Lys Ser Gln Thr
145                 150                 155                 160

Asp Arg Leu Glu Val Leu Leu Asn Pro Lys Asp Glu Ile Ser Leu Asn
                165                 170                 175

Ser Gly Lys Pro Phe Arg Glu Leu Glu Ser Glu Leu Leu Ser Arg Arg
            180                 185                 190

Lys Lys Asp Leu Gln Gln Ile Tyr Ala Glu Glu Arg Glu Asn Tyr Leu
        195                 200                 205

Gly Lys Leu Glu Arg Glu Ile Thr Arg Phe Phe Val Asp Arg Gly Phe
    210                 215                 220

Leu Glu Ile Lys Ser Pro Ile Leu Ile Pro Leu Glu Tyr Ile Glu Arg
225                 230                 235                 240

Met Gly Ile Asp Asn Asp Thr Glu Leu Ser Lys Gln Ile Phe Arg Val
                245                 250                 255

Asp Lys Asn Phe Cys Leu Arg Pro Met Leu Ala Pro Asn Leu Tyr Asn
            260                 265                 270

Tyr Leu Arg Lys Leu Asp Arg Ala Leu Pro Asp Pro Ile Lys Ile Phe
        275                 280                 285

Glu Ile Gly Pro Cys Tyr Arg Lys Glu Ser Asp Gly Lys Glu His Leu
    290                 295                 300

Glu Glu Phe Thr Met Leu Asn Phe Cys Gln Met Gly Ser Gly Cys Thr
305                 310                 315                 320

Arg Glu Asn Leu Glu Ser Ile Ile Thr Asp Phe Leu Asn His Leu Gly
                325                 330                 335

Ile Asp Phe Lys Ile Val Gly Asp Ser Cys Met Val Tyr Gly Asp Thr
            340                 345                 350

Leu Asp Val Met His Gly Asp Leu Glu Leu Ser Ser Ala Val Val Gly
        355                 360                 365

Pro Ile Pro Leu Asp Arg Glu Trp Gly Ile Asp Lys Pro Trp Ile Gly
    370                 375                 380

Ala Gly Phe Gly Leu Glu Arg Leu Leu Lys Val Lys His Asp Phe Lys
385                 390                 395                 400

Asn Ile Lys Arg Ala Ala Arg Ser Glu Ser Tyr Tyr Asn Gly Ile Ser
                405                 410                 415

Thr Asn Leu
```

<210> SEQ ID NO 27
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 27

```
atggataaga agccgctgga tgttctgatc tctgcgaccg gtctgtggat gtcccgtacc      60

ggcacgctgc acaagatcaa gcactatgag atttctcgtt ctaaaatcta catcgaaatg     120

gcgtgtggtg accatctggt tgtgaacaac tctcgttctt gtcgtcccgc acgtgcattc     180

cgttatcata aataccgtaa aacctgcaaa cgttgtcgtg tttctgacga agatatcaac     240

aacttcctga cccgttctac cgaaggcaaa acctctgtta aagttaaagt tgtttctgag     300
```

```
ccgaaagtga aaaaagcgat gccgaaatct gtttctcgtg cgccgaaacc gctggaaaat    360

ccggtttctg cgaaagcgtc taccgacacc tctcgttctg ttccgtctcc ggcgaaatct    420

accccgaact ctccggttcc gacctctgcg ccggcgccgt ctctgacccg ttctcagctg    480

gatcgtgttg aagcgctgct gtctccggaa gataaaatct ctctgaacat cgcgaaaccg    540

ttccgtgaac tggaatctga actggttacc cgtcgtaaaa acgatttcca gcgtctgtac    600

accaacgatc gtgaagacta cctgggtaaa ctggaacgtg acatcaccaa attcttcgtt    660

gaccgtgatt tcctggaaat caaatctccg atcctgatcc cggcggaata cgttgaacgt    720

atgggtatca acaacgatac cgaactgtct aaacagatct tccgtgttga taaaaacctg    780

tgcctgcgtc cgatgctggc gccgaccctg tacaactatc tgcgtaaact ggatcgtatc    840

ctgccggacc cgatcaaaat cttcgaagtt ggtccgtgct accgtaaaga atctgacggt    900

aaagaacacc tggaagagtt caccatggtg aacttctgcc agatgggttc tggttgcacc    960

cgtgagaacc tggaatctct gatcaaagaa tttctggact acctggaaat cgacttcgaa   1020

atcgttggtg actcctgcat ggtgtacggt gataccctgg acatcatgca cggtgacctg   1080

gaactgtctt ctgcggttgt tggtccggtt ccgctggatc gtgaatgggg tatcgacaaa   1140

ccgtggatcg gtgcgggttt cggtctggaa cgtctgctga aagttatgca cggtttcaaa   1200

aacatcaaac gtgcgtctcg ttctgaatct tactacaacg gtatctctac caacctgtaa   1260
```

```
<210> SEQ ID NO 28
<211> LENGTH: 419
<212> TYPE: PRT
<213> ORGANISM: Artificial Sequence
<220> FEATURE:
<223> OTHER INFORMATION: Synthetic Polypeptide

<400> SEQUENCE: 28

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Ile Ser
            20                  25                  30

Arg Ser Lys Ile Tyr Ile Glu Met Ala Cys Gly Asp His Leu Val Val
        35                  40                  45

Asn Asn Ser Arg Ser Cys Arg Pro Ala Arg Ala Phe Arg Tyr His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Glu Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190
```

-continued

```
Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu
```

<210> SEQ ID NO 29
<211> LENGTH: 1365
<212> TYPE: DNA
<213> ORGANISM: Artificial Sequence
<220> FEATURE:
<223> OTHER INFORMATION: Synthetic Polynucleotide

<400> SEQUENCE: 29

```
atggataaaa aaccactaaa cactctgata tctgcaaccg ggctctggat gtccaggacc     60

ggaacaattc ataaaataaa acaccacgaa atttctcgaa gcaaaatcta tattgaaatg    120

gcatgcggag accaccttgt tgtaaacaac tccaggagca gcaggcccgc aagagcgctc    180

aggtatcaca aatacaggaa gacctgcaaa cgctgcaggg tttcggatga ggatctcaat    240

aagttcctca caaaggcaaa cgaagaccag acaagcgtaa aagtcaaggt cgtttctgag    300

cctaccagaa cgaaaaaggc aatgccaaaa tccgttgcga gagccccgaa acctcttgag    360

aatacagaag cggcacaggc tcaaccttct ggatctaaat tttcacctgc gataccggtt    420

tccacccaag agtcagtttc tgtcccggca tctgtttcaa catcaatatc aagcatttct    480

acaggagcaa ctgcatccgc actggtaaaa gggaatacga atcccattac atccatgtct    540

gcccctgttc aggcaagtgc ccccgcactt acgaagagcc agactgacag gcttgaagtc    600

ctgttaaacc caaaagatga gatttccctg aattccggca agcctttcag ggagcttgag    660

tccgaattgc tctctcgcag aaaaaaagac ctgcagcaga tctacgcgga agaaagggag    720

aattatctgg ggaaactcga gcgtgaaatt accaggttct ttgtggacag gggttttctg    780
```

```
gaaataaaat ccccgatcct gatccctctt gagtatatcg aaaggatggg cattgataat    840

gataccgaac tttcaaaaca gatcttcagg gttgacaaga acttctgcct gagacccatg    900

cttgctccaa acctttacaa ctacctgcgc aagcttgaca gggccctgcc tgatccaata    960

aaaatttttg aaataggccc atgctacaga aaagagtccg acggcaaaga acacctcgaa   1020

gagtttacca tgctgaactt ctgccagatg ggatcgggat gcacacggga aaatcttgaa   1080

agcataatta cggacttcct gaaccacctg ggaattgatt tcaagatcgt aggcgattcc   1140

tgcatggtct atggggatac ccttgatgta atgcacggag acctggaact ttcctctgca   1200

gtagtcggac ccataccgct tgaccgggaa tggggtattg ataaaccctg gataggggca   1260

ggtttcgggc tcgaacgcct tctaaaggtt aaacacgact ttaaaaatat caagagagct   1320

gcaaggtccg agtcttacta taacgggatt tctaccaacc tgtaa                   1365
```

<210> SEQ ID NO 30
<211> LENGTH: 454
<212> TYPE: PRT
<213> ORGANISM: Artificial Sequence
<220> FEATURE:
<223> OTHER INFORMATION: Synthetic Polypeptide

<400> SEQUENCE: 30

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Ile Ser
            20                  25                  30

Arg Ser Lys Ile Tyr Ile Glu Met Ala Cys Gly Asp His Leu Val Val
        35                  40                  45

Asn Asn Ser Arg Ser Ser Arg Pro Ala Arg Ala Leu Arg Tyr His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Glu Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255
```

-continued

```
Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450


<210> SEQ ID NO 31
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 31

atggataaga agccgctgga tgttctgatc tctgcgaccg gtctgtggat gtcccgtacc      60

ggcacgctgc acaagatcaa gcactatgag atttctcgtt ctaaaatcta catcgaaatg     120

gcgtgtggtg accatctggt tgtgaacaac tctcgttctt gtcgtcccgc acgtgcattc     180

cgttatcata aataccgtaa aacctgcaaa cgttgtcgtg tttctggtga agatatcaac     240

aacttcctga cccgttctac cgaaggcaaa acctctgtta aagttaaagt tgtttctgag     300

ccgaaagtga aaaaagcgat gccgaaatct gtttctcgtg cgccgaaacc gctggaaaat     360

ccggtttctg cgaaagcgtc taccgacacc tctcgttctg ttccgtctcc ggcgaaatct     420

accccgaact ctccggttcc gacctctgca agtgcccccg cacttacgaa gagccagact     480

gacaggcttg aagtcctgtt aaacccaaaa gatgagattt ccctgaattc cggcaagcct     540

ttcagggagc ttgagtccga attgctctct cgcagaaaaa aagacctgca gcagatctac     600

gcggaagaaa gggagaatta tctggggaaa ctcgagcgtg aaattaccag gttctttgtg     660

gacaggggtt ttctggaaat aaaatccccg atcctgatcc ctcttgagta tatcgaaagg     720

atgggcattg ataatgatac cgaactttca aaacagatct tcagggttga caagaacttc     780

tgcctgagac ccatgatggc tccaaacatt tttaactacg ctcgcaagct tgacagggcc     840

ctgcctgatc caataaaaat ttttgaaata ggcccatgct acagaaaaga gtccgacggc     900
```

-continued

```
aaagaacacc tcgaagagtt taccatgctg aacttctttc agatgggatc gggatgcaca    960

cgggaaaatc ttgaaagcat aattacggac ttcctgaacc acctgggaat tgatttcaag   1020

atcgtaggcg attcctgcat ggtctatggg gatacccttg atgtaatgca cggagacctg   1080

gaactttcct ctgcagtagt cggacccata ccgcttgacc gggaatgggg tattgataaa   1140

ccctggatag gggcaggttt cggactcgaa cgccttctaa aggttaaaca cgactttaaa   1200

aatatcaaga gagctgcaag gtccgagtct tactataacg ggatttctac caacctgtaa   1260
```

```
<210> SEQ ID NO 32
<211> LENGTH: 419
<212> TYPE: PRT
<213> ORGANISM: Artificial Sequence
<220> FEATURE:
<223> OTHER INFORMATION: Synthetic Polypeptide

<400> SEQUENCE: 32

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Ile Ser
            20                  25                  30

Arg Ser Lys Ile Tyr Ile Glu Met Ala Cys Gly Asp His Leu Val Val
        35                  40                  45

Asn Asn Ser Arg Ser Cys Arg Pro Ala Arg Ala Phe Arg Tyr His Lys
    50                  55                  60

Tyr Arg Lys Thr Cys Lys Arg Cys Arg Val Ser Gly Glu Asp Ile Asn
65                  70                  75                  80

Asn Phe Leu Thr Arg Ser Thr Glu Gly Lys Thr Ser Val Lys Val Lys
                85                  90                  95

Val Val Ser Glu Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Ser Ala Pro Ala Leu Thr Lys Ser Gln Thr
145                 150                 155                 160

Asp Arg Leu Glu Val Leu Leu Asn Pro Lys Asp Glu Ile Ser Leu Asn
                165                 170                 175

Ser Gly Lys Pro Phe Arg Glu Leu Glu Ser Glu Leu Leu Ser Arg Arg
            180                 185                 190

Lys Lys Asp Leu Gln Gln Ile Tyr Ala Glu Glu Arg Glu Asn Tyr Leu
        195                 200                 205

Gly Lys Leu Glu Arg Glu Ile Thr Arg Phe Phe Val Asp Arg Gly Phe
    210                 215                 220

Leu Glu Ile Lys Ser Pro Ile Leu Ile Pro Leu Glu Tyr Ile Glu Arg
225                 230                 235                 240

Met Gly Ile Asp Asn Asp Thr Glu Leu Ser Lys Gln Ile Phe Arg Val
                245                 250                 255

Asp Lys Asn Phe Cys Leu Arg Pro Met Met Ala Pro Asn Ile Phe Asn
            260                 265                 270

Tyr Ala Arg Lys Leu Asp Arg Ala Leu Pro Asp Pro Ile Lys Ile Phe
        275                 280                 285

Glu Ile Gly Pro Cys Tyr Arg Lys Glu Ser Asp Gly Lys Glu His Leu
    290                 295                 300
```

Glu Glu Phe Thr Met Leu Asn Phe Phe Gln Met Gly Ser Gly Cys Thr
305 310 315 320

Arg Glu Asn Leu Glu Ser Ile Ile Thr Asp Phe Leu Asn His Leu Gly
325 330 335

Ile Asp Phe Lys Ile Val Gly Asp Ser Cys Met Val Tyr Gly Asp Thr
340 345 350

Leu Asp Val Met His Gly Asp Leu Glu Leu Ser Ser Ala Val Val Gly
355 360 365

Pro Ile Pro Leu Asp Arg Glu Trp Gly Ile Asp Lys Pro Trp Ile Gly
370 375 380

Ala Gly Phe Gly Leu Glu Arg Leu Leu Lys Val Lys His Asp Phe Lys
385 390 395 400

Asn Ile Lys Arg Ala Ala Arg Ser Glu Ser Tyr Tyr Asn Gly Ile Ser
405 410 415

Thr Asn Leu

<210> SEQ ID NO 33
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 33
atggataaga agccgctgga tgttctgatc tctgcgaccg gtctgtggat gtcccgtacc 60
ggcacgctgc acaagatcaa gcactatgag atttctcgtt ctaaaatcta catcgaaatg 120
gcgtgtggtg accatctggt tgtgaacaac tctcgttctt gtcgtcccgc acgtgcattc 180
cgttatcata aataccgtaa aacctgcaaa cgttgtcgtg tttctggtga agatatcaac 240
aacttcctga cccgttctac cgaaggcaaa acctctgtta aagttaaagt tgtttctgag 300
ccgaaagtga aaaaagcgat gccgaaatct gtttctcgtg cgccgaaacc gctggaaaat 360
ccggtttctg cgaaagcgtc taccgacacc tctcgttctg ttccgtctcc ggcgaaatct 420
accccgaact ctccggttcc gacctctgcg ccggcgccgt ctctgacccg ttctcagctg 480
gatcgtgttg aagcgctgct gtctccggaa gataaaatct ctctgaacat cgcgaaaccg 540
ttccgtgaac tggaatctga actggttacc cgtcgtaaaa acgatttcca gcgtctgtac 600
accaacgatc gtgaagacta cctgggtaaa ctggaacgtg acatcaccaa attcttcgtt 660
gaccgtgatt tcctggaaat caaatctccg atcctgatcc cggcggaata cgttgaacgt 720
atgggtatca acaacgatac cgaactgtct aaacagatct tccgtgttga taaaaacctg 780
tgcctgcgtc cgatgatggc gccgaccatt tttaactatg ctcgtaaact ggatcgtatc 840
ctgccggacc cgatcaaaat cttcgaagtt ggtccgtgct accgtaaaga atctgacggt 900
aaagaacacc tggaagagtt caccatggtg aacttctttc agatgggttc tggttgcacc 960
cgtgagaacc tggaatctct gatcaaagaa tttctggact acctggaaat cgacttcgaa 1020
atcgttggtg actcctgcat ggtgtacggt gataccctgg acatcatgca cggtgacctg 1080
gaactgtctt ctgcggttgt tggtccggtt ccgctggatc gtgaatgggg tatcgacaaa 1140
ccgtggatcg gtgcgggttt cggtctggaa cgtctgctga aagttatgca cggtttcaaa 1200
aacatcaaac gtgcgtctcg ttctgaatct tactacaacg gtatctctac caacctgtaa 1260

<210> SEQ ID NO 34
<211> LENGTH: 419
<212> TYPE: PRT

```
<213> ORGANISM: Artificial Sequence
<220> FEATURE:
<223> OTHER INFORMATION: Synthetic Polypeptide

<400> SEQUENCE: 34

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Ile Ser
            20                  25                  30

Arg Ser Lys Ile Tyr Ile Glu Met Ala Cys Gly Asp His Leu Val Val
        35                  40                  45

Asn Asn Ser Arg Ser Cys Arg Pro Ala Arg Ala Phe Arg Tyr His Lys
    50                  55                  60

Tyr Arg Lys Thr Cys Lys Arg Cys Arg Val Ser Gly Glu Asp Ile Asn
65                  70                  75                  80

Asn Phe Leu Thr Arg Ser Thr Glu Gly Lys Thr Ser Val Lys Val Lys
                85                  90                  95

Val Val Ser Glu Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Met Ala Pro Thr Ile Phe Asn
            260                 265                 270

Tyr Ala Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Phe Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380
```

Ala Gly Phe Gly Leu Glu Arg Leu Leu Lys Val Met His Gly Phe Lys
385 390 395 400

Asn Ile Lys Arg Ala Ser Arg Ser Glu Ser Tyr Tyr Asn Gly Ile Ser
405 410 415

Thr Asn Leu

<210> SEQ ID NO 35
<211> LENGTH: 1365
<212> TYPE: DNA
<213> ORGANISM: Artificial Sequence
<220> FEATURE:
<223> OTHER INFORMATION: Synthetic Polynucleotide

<400> SEQUENCE: 35
atggataaaa aaccactaaa cactctgata tctgcaaccg ggctctggat gtccaggacc 60
ggaacaattc ataaaataaa acaccacgaa atttctcgaa gcaaaatcta tattgaaatg 120
gcatgcggag accaccttgt tgtaaacaac tccaggagca gcaggcccgc aagagcgctc 180
aggtatcaca aatacaggaa gacctgcaaa cgctgcaggg tttcgggtga ggatctcaat 240
aagttcctca caaaggcaaa cgaagaccag acaagcgtaa aagtcaaggt cgtttctgag 300
cctaccagaa cgaaaaaggc aatgccaaaa tccgttgcga gagccccgaa acctcttgag 360
aatacagaag cggcacaggc tcaaccttct ggatctaaat tttcacctgc gataccggtt 420
tccacccaag agtcagtttc tgtcccggca tctgtttcaa catcaatatc aagcatttct 480
acaggagcaa ctgcatccgc actggtaaaa gggaatacga atcccattac atccatgtct 540
gcccctgttc aggcaagtgc ccccgcactt acgaagagcc agactgacag gcttgaagtc 600
ctgttaaacc caaaagatga gatttccctg aattccggca agcctttcag ggagcttgag 660
tccgaattgc tctctcgcag aaaaaaagac ctgcagcaga tctacgcgga agaaagggag 720
aattatctgg ggaaactcga gcgtgaaatt accaggttct ttgtggacag ggttttctg 780 gaaataaaat ccccgatcct gatccctctt gagtatatcg aaaggatggg cattgataat 840
gataccgaac tttcaaaaca gatcttcagg gttgacaaga acttctgcct gagacccatg 900
atggctccaa acatttttaa ctacgctcgc aagcttgaca gggccctgcc tgatccaata 960
aaaatttttg aaataggccc atgctacaga aaagagtccg acggcaaaga acacctcgaa 1020
gagtttacca tgctgaactt ctttcagatg ggatcgggat gcacacggga aaatcttgaa 1080
agcataatta cggacttcct gaaccacctg ggaattgatt tcaagatcgt aggcgattcc 1140
tgcatggtct atggggatac ccttgatgta atgcacggag acctggaact ttcctctgca 1200
gtagtcggac ccataccgct tgaccgggaa tggggtattg ataaaccctg gataggggca 1260
ggtttcgggc tcgaacgcct tctaaaggtt aaacacgact ttaaaaatat caagagagct 1320
gcaaggtccg agtcttacta taacgggatt tctaccaacc tgtaa 1365

<210> SEQ ID NO 36
<211> LENGTH: 454
<212> TYPE: PRT
<213> ORGANISM: Artificial Sequence
<220> FEATURE:
<223> OTHER INFORMATION: Synthetic Polypeptide

<400> SEQUENCE: 36

Met Asp Lys Lys Pro Leu Asn Thr Leu Ile Ser Ala Thr Gly Leu Trp
1 5 10 15

-continued

```
Met Ser Arg Thr Gly Thr Ile His Lys Ile Lys His His Glu Ile Ser
            20                  25                  30

Arg Ser Lys Ile Tyr Ile Glu Met Ala Cys Gly Asp His Leu Val Val
        35                  40                  45

Asn Asn Ser Arg Ser Ser Arg Pro Ala Arg Ala Leu Arg Tyr His Lys
    50                  55                  60

Tyr Arg Lys Thr Cys Lys Arg Cys Arg Val Ser Gly Glu Asp Leu Asn
65                  70                  75                  80

Lys Phe Leu Thr Lys Ala Asn Glu Asp Gln Thr Ser Val Lys Val Lys
                85                  90                  95

Val Val Ser Glu Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Met Ala Pro Asn
    290                 295                 300

Ile Phe Asn Tyr Ala Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Phe Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430
```

```
Asp Phe Lys Asn Ile Lys Arg Ala Ala Arg Ser Glu Ser Tyr Tyr Asn
        435                 440                 445

Gly Ile Ser Thr Asn Leu
    450
```

<210> SEQ ID NO 37
<211> LENGTH: 1260
<212> TYPE: DNA
<213> ORGANISM: Artificial Sequence
<220> FEATURE:
<223> OTHER INFORMATION: Synthetic Polynucleotide

<400> SEQUENCE: 37

```
atggataaga agccgctgga tgttctgatc tctgcgaccg gtctgtggat gtcccgtacc     60

ggcacgctgc acaagatcaa gcactatgag atttctcgtt ctaaaatcta catcgaaatg    120

gcgtgtggtg accatctggt tgtgaacaac tctcgttctt gtcgtcccgc acgtgcattc    180

cgttatcata aataccgtaa aacctgcaaa cgttgtcgtg tttctgacga agatatcaac    240

aacttcctga cccgttctac cgaaggcaaa acctctgtta aagttaaagt tgtttctgag    300

ccgaaagtga aaaaagcgat gccgaaatct gtttctcgtg cgccgaaacc gctggaaaat    360

ccggtttctg cgaaagcgtc taccgacacc tctcgttctg ttccgtctcc ggcgaaatct    420

accccgaact ctccggttcc gacctctgca agtgcccccg cacttacgaa gagccagact    480

gacaggcttg aagtcctgtt aaacccaaaa gatgagattt ccctgaattc cggcaagcct    540

ttcagggagc ttgagtccga attgctctct cgcagaaaaa aagacctgca gcagatctac    600

gcggaagaaa gggagaatta tctggggaaa ctcgagcgtg aaattaccag gttctttgtg    660

gacaggggtt ttctggaaat aaaatccccg atcctgatcc ctcttgagta tatcgaaagg    720

atgggcattg ataatgatac cgaactttca aaacagatct tcagggttga caagaacttc    780

tgcctgagac ccatgcttgc tccaaacctt tacaactacc tgcgcaagct tgacagggcc    840

ctgcctgatc caataaaaat ttttgaaata ggcccatgct acagaaaaga gtccgacggc    900

aaagaacacc tcgaagagtt taccatgctg tcgttcattc agatgggatc gggatgtaca    960

cgggaaaatc ttgaaagcat aattacggac ttcctgaacc acctgggaat tgatttcaag   1020

atcgtaggcg attcctgcat ggtctatggg gataccctg atgtaatgca cggagacctg    1080

gaactttcct ctgcagtagt cggacccata ccgcttgacc gggaatgggg tattgataaa   1140

ccctggatag gggcaggttt cgggctcgaa cgccttctaa aggttaaaca cgactttaaa   1200

aatatcaaga gagctgcaag gtccgagtct tactataacg ggatttctac caacctgtaa   1260
```

<210> SEQ ID NO 38
<211> LENGTH: 419
<212> TYPE: PRT
<213> ORGANISM: Artificial Sequence
<220> FEATURE:
<223> OTHER INFORMATION: Synthetic Polypeptide

<400> SEQUENCE: 38

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Ile Ser
            20                  25                  30

Arg Ser Lys Ile Tyr Ile Glu Met Ala Cys Gly Asp His Leu Val Val
        35                  40                  45

Asn Asn Ser Arg Ser Cys Arg Pro Ala Arg Ala Phe Arg Tyr His Lys
    50                  55                  60
```

```
Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Glu Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Ser Ala Pro Ala Leu Thr Lys Ser Gln Thr
145                 150                 155                 160

Asp Arg Leu Glu Val Leu Leu Asn Pro Lys Asp Glu Ile Ser Leu Asn
                165                 170                 175

Ser Gly Lys Pro Phe Arg Glu Leu Glu Ser Glu Leu Leu Ser Arg Arg
            180                 185                 190

Lys Lys Asp Leu Gln Gln Ile Tyr Ala Glu Glu Arg Glu Asn Tyr Leu
        195                 200                 205

Gly Lys Leu Glu Arg Glu Ile Thr Arg Phe Phe Val Asp Arg Gly Phe
    210                 215                 220

Leu Glu Ile Lys Ser Pro Ile Leu Ile Pro Leu Glu Tyr Ile Glu Arg
225                 230                 235                 240

Met Gly Ile Asp Asn Asp Thr Glu Leu Ser Lys Gln Ile Phe Arg Val
                245                 250                 255

Asp Lys Asn Phe Cys Leu Arg Pro Met Leu Ala Pro Asn Leu Tyr Asn
            260                 265                 270

Tyr Leu Arg Lys Leu Asp Arg Ala Leu Pro Asp Pro Ile Lys Ile Phe
        275                 280                 285

Glu Ile Gly Pro Cys Tyr Arg Lys Glu Ser Asp Gly Lys Glu His Leu
    290                 295                 300

Glu Glu Phe Thr Met Leu Ser Phe Ile Gln Met Gly Ser Gly Cys Thr
305                 310                 315                 320

Arg Glu Asn Leu Glu Ser Ile Ile Thr Asp Phe Leu Asn His Leu Gly
                325                 330                 335

Ile Asp Phe Lys Ile Val Gly Asp Ser Cys Met Val Tyr Gly Asp Thr
            340                 345                 350

Leu Asp Val Met His Gly Asp Leu Glu Leu Ser Ser Ala Val Val Gly
        355                 360                 365

Pro Ile Pro Leu Asp Arg Glu Trp Gly Ile Asp Lys Pro Trp Ile Gly
    370                 375                 380

Ala Gly Phe Gly Leu Glu Arg Leu Leu Lys Val Lys His Asp Phe Lys
385                 390                 395                 400

Asn Ile Lys Arg Ala Ala Arg Ser Glu Ser Tyr Tyr Asn Gly Ile Ser
                405                 410                 415

Thr Asn Leu
```

<210> SEQ ID NO 39
<211> LENGTH: 306
<212> TYPE: PRT
<213> ORGANISM: Artificial Sequence
<220> FEATURE:
<223> OTHER INFORMATION: Synthetic Polypeptide

<400> SEQUENCE: 39

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Leu
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Leu Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Ser Phe Gln Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Pro Leu Asn
145 150 155 160

Tyr Glu Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Arg Leu Lys
275 280 285

Asn Ala Val Ala Glu Glu Leu Ile Lys Ile Leu Glu Pro Ile Arg Lys
290 295 300

Arg Leu
305

<210> SEQ ID NO 40
<211> LENGTH: 306
<212> TYPE: PRT
<213> ORGANISM: Artificial Sequence
<220> FEATURE:
<223> OTHER INFORMATION: Synthetic Polypeptide

<400> SEQUENCE: 40

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Leu
20 25 30

-continued

```
Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

EVOLUTION OF TRNA SYNTHETASES

RELATED APPLICATIONS

This application is a national stage filing under 35 U.S.C. § 371 of international PCT application, PCT/US2018/040692, filed Jul. 3, 2018, which claims priority under 35 U.S.C. § 119(e) to U.S. provisional patent applications, U.S. Ser. No. 62/535,090, filed Jul. 20, 2017, entitled "EVOLUTION OF TRNA SYNTHETASES", and U.S. Ser. No. 62/529,320, filed Jul. 6, 2017, entitled "EVOLUTION OF TRNA SYNTHETASES", the entire contents of each of which are incorporated herein by reference.

FEDERALLY SPONSORED RESEARCH

This invention was made with government support under grant numbers N66001-12-C-4207, awarded by the Defense Advanced Research Projects Agency; EB022376, GM118062, AI119813, GM022854 and GM106621, awarded by the National Institutes of Health; and FG02-98ER2031, awarded by the Department of Energy. The government has certain rights in the invention.

BACKGROUND OF THE INVENTION

The directed evolution of orthogonal aminoacyl-tRNA synthetases (AARSs) enables genetic code expansion through the site-specific installation of non-canonical amino acids into proteins. Traditional laboratory evolution techniques typically produce AARSs with greatly reduced activity (often ~1,000-fold lower) and poor amino acid selectivity compared to their wild-type counterparts, limiting their utility.

Although researchers have evolved many AARSs to incorporate non-canonical amino acids (ncAAs) into proteins, several outstanding challenges limit their utility and generality. Laboratory evolution of AARSs with altered amino acid specificity typically relies on three to five rounds of sequential positive and negative selections from an AARS library containing either partially or fully randomized residues in the amino acid-binding pocket. The limited number of rounds of selection typically conducted in AARS evolution campaigns reflects the effort required to complete each round of evolution, which is on the order of one week or longer. A consequence of conducting relatively few rounds of selection on libraries that focus mutagenesis on and around the amino acid-binding pocket is that laboratory-evolved AARSs routinely emerge with suboptimal properties, including ~1,000-fold reduced activity ($k_{cat}/K_M$) compared to their wild-type counterparts, and modest selectivity for the target ncAA over endogenous amino acids that can require compensation with high concentrations of ncAA and expression in minimal media, lowering protein yields. The modest enzymatic efficiency and selectivity of many laboratory-evolved AARSs are longstanding challenges that limit the production and purity of expressed proteins containing ncAAs.

SUMMARY OF THE INVENTION

In some aspects, the disclosure relates to evolved AARSs that increase the utility of orthogonal translation systems and establish the capability of rapidly and continuously evolving orthogonal AARSs with high activity and amino acid specificity. The disclosure is based, in part, on the discovery that positive and negative phage-assisted continuous evolution (PACE) selections produce highly active and selective orthogonal AARSs through hundreds of generations on rapid time scales. For example, as described in the Examples section, continuous evolution of a pyrrolysyl-tRNA synthetase (PylRS), in some embodiments, improved enzymatic efficiency ($k_{cat}/K_M^{tRNA}$) up to 45-fold compared to the wild-type enzyme.

In some aspects, the disclosure relates to the discovery that PACE unexpectedly generated highly active, split-PylRS variants produced as two mutually dependent polypeptide fragments, recapitulating natural PylRS homologs. It was observed that simultaneous positive and negative selection PACE over 48 h greatly improved the selectivity of a promiscuous tyrosyl-tRNA synthetase variant for site-specific incorporation of p-iodo-1-phenylalanine, rejecting p-nitro-1-phenylalanine.

Accordingly, in some aspects, the disclosure provides pyrrolysyl-tRNA synthetase (PylRS) protein variants. In some embodiments, a PylRS protein variant described herein comprises a nucleic acid sequence or an amino acid sequence that is at least 90% identical to a *Methanosarcina* PylRS or a fragment thereof (e.g., the N-terminal domain of a *Methanosarcina* PylRS or the C-terminal domain of a *Methanosarcina* PylRS), for example *M. bakeri* PylRS (e.g., SEQ ID NO: 6) or *M. mazei* PylRS (e.g., SEQ ID NO: 7).

In some aspects, the disclosure provides tyrosyl-tRNA synthetase (TyrRS) proteins variant capable of incorporating a p-iodo-1-phenylalanine into a protein. In some embodiments, a TyrRS protein variant described herein comprises a nucleic acid sequence or an amino acid sequence that is at least 90% identical to a *Methanocaldococcus jannaschii* (*M. jannaschii*) TyrRS (MjTyrRS), for example SEQ ID NO: 24.

In some embodiments, a PylRS comprises an amino acid sequence that is at least 90% identical to the amino acid sequence of a wild-type *M. bakeri* or *M. mazei* PylRS (e.g., the amino acid sequence set forth in SEQ ID NO: 20 or 21), or a fragment thereof (e.g., amino acids 1-149 of SEQ ID NO: 20 or amino acids 185-454 of SEQ ID NO: 21).

In some aspects, the disclosure provides a pyrrolysyl-tRNA synthetase (PylRS) protein variant having an N-terminal domain amino acid substitution present in at least one of the following positions: V31, T56, H62, or A100 (e.g., relative to SEQ ID NO: 20 or 21). In some embodiments, the amino acid substitution is V31I, T56P, H62Y, or A100E.

In some aspects, the disclosure provides a chimeric pyrrolysyl-tRNA synthetase (PylRS) protein variant comprising: a first portion comprising amino acid residues 1-149 of *Methanosarcina barkeri* PylRS (SEQ ID NO: 20); and a second portion comprising amino acid residues 185-454 of *Methanosarcina mazei* PylRS (SEQ ID NO: 21), wherein the first portion or the second portion comprises at least one of the amino acid substitutions set forth in Tables 2-6.

In some embodiments, the chimeric protein variant comprises an amino acid substitution in at least one of the following positions: V31, T56, H62, or A100. In some embodiments, the amino acid substitution is V31I, T56P, H62Y, A100E, or any combination thereof.

In some aspects, the disclosure provides a tyrosyl-tRNA synthetase (TyrRS) protein variant having an amino acid substitution present in at least one of the following positions: L69 or V235. In some embodiments, the amino acid substitution is L69F, V235I, or L69F and V235I.

In some aspects, the disclosure provides an isolated nucleic acid comprising a sequence represented by any one of SEQ ID NO: 5-19. In some aspects, the disclosure provides a protein encoded by an isolated nucleic acid comprising a sequence represented by any one of SEQ ID NO: 5-19.

In some aspects, the disclosure relates to a host cell comprising a tRNA synthetase protein variant as described by the disclosure. In some aspects, the disclosure relates to an isolated nucleic acid as described by the disclosure. In some embodiments, the tRNA synthetase protein variant is orthogonal to the host cell (e.g., not expressed naturally in the host cell). In some embodiments, a host cell is a bacterial cell. In some embodiments, a bacterial cell is an *E. coli* cell.

In some aspects, the disclosure relates to a selection system comprising: a first container housing a selection phagemid as described by the disclosure; a second container housing a positive selection system as described by the disclosure; and, optionally, a third container housing negative selection system as described by the disclosure.

In some embodiments, a selection system further comprises a container housing one or more bacterial cells. In some embodiments, the bacterial cells are *E. coli* cells.

In some aspects, the disclosure relates to methods of using tRNA synthetase protein variants described by the disclosure. In some embodiments, the disclosure relates to methods for aminoacylation of a tRNA, the methods comprising, contacting a tRNA encoding an amber codon with a tRNA synthetase protein variant as described by the disclosure in the presence of a non-canonical amino acid.

In some embodiments, a non-canonical amino acid is a pyrolysine or a p-iodo-L-phenylalanine. In some embodiments, the tRNA is contacted with the tRNA synthetase inside a cell.

In some aspects, the disclosure relates to methods for incorporating a non-canonical amino acid into a peptide, the method comprising expressing in a cell: (i) an mRNA transcript, wherein the transcript comprises an amber codon at a position in which a non-canonical amino acid (ncAA) is to be translated; (ii) a tRNA capable of incorporating the ncAA; (iii) a tRNA synthetase protein variant as described herein, wherein (i), (ii), and (iii) are expressed in the presence of the ncAA.

In some embodiments, the non-canonical amino acid is a pyrolysine or a p-iodo-L-phenylalanine. In some embodiments, the tRNA synthetase is orthogonal to the cell. In some embodiments, the cell is an *E. coli* cell.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims

BRIEF DESCRIPTION OF DRAWINGS

FIG. 2A shows strategies for linking AARS activity to the expression of gene III, which encodes the pIII protein required for phage to be infectious. In strategy 1, AARS-catalyzed aminoacylation of an amber suppressor tRNA enables translation of full-length T7 RNAP from a transcript containing a premature amber stop codon. T7 RNAP subsequently drives expression of gene III from the T7 promoter ($P_{T7}$). In strategy 2, amber suppressor tRNA aminoacylation permits full-length translation of pIII from gene III mRNA containing a premature stop codon. FIG. 2B shows host-cell plasmids used to implement both selection strategies. The accessory plasmid (AP) encodes gene III and the amber suppressor tRNA. The complementary plasmid (CP) encodes T7 RNAP controlled by the phage-shock promoter ($P_{psp}$), which is induced only upon phage infection. The mutagenesis plasmid (MP) increases the rate of evolution during PACE through arabinose-induced production of mutagenic proteins. The selection phage (SP) encodes all phage genes except gene III, which is replaced by the evolving AARS gene. FIG. 2C shows a diagram of PACE with selection strategy 1 plasmids shown. SPs capable of catalyzing aminoacylation of the amber suppressor tRNA result in production of pIII protein from gene III of the AP in host *E. coli.* Under continuous dilution in the fixed-volume vessel (the "lagoon"), phage that are capable of triggering the production of pIII propagate faster than the rate of dilution, resulting in the continuous enrichment of SPs encoding active AARS variants.

FIG. 3 shows Non-canonical amino acids in this study. (1) p-nitro-L-phenylalanine, (2) Nε-(tert-butoxycarbonyl)-L-lysine, (3) L-pyrrolysine, (4) Nε-acetyl-L-lysine, (5) 3-iodo-L-phenylalanine, and (6) p-iodo-L-phenylalanine.

FIG. 4A shows a luciferase reporter assay for optimizing the position and number of TAG stop codons in T7 RNAP. The orthogonal AARS (inducible with IPTG) charges the ncAA onto the amber suppressor tRNA, enabling translation of full-length T7 RNAP (inducible with anhydrotetracycline, ATc). Production of T7 RNAP results in subsequent expression of the luciferase reporter gene, luxAB. FIG. 4B shows using p-NFRS to site-specifically incorporate p-NF at two positions (Ser12TAG+Ser203TAG) in T7 RNAP provided optimal reporter signal that was dependent on orthogonal AARS activity (+IPTG, +ncAA) and on expression of T7 RNAP (+ATc). FIG. 4C shows using chPylRS, reporter signal resulting from site-specific incorporation of BocK into T7 RNAP(Ser12TAG+Ser203TAG) suggests broad ncAA-tolerance at both sites of ncAA installation. Each value and error bar in b and c reflects the mean and s.d. of at least three independent biological replicates.

FIG. 6A shows that, in lagoon 1 (L1) supplemented with 1 mM p-NF, SP-p-NFRS propagates for 48 h of PACE using the selection based on amber suppression of two stop codons in T7 RNAP. SP-Kan, which lacks AARS activity, however, rapidly washed out of lagoon 2 (L2) by the first time point (16 h) under identical conditions. FIG. 6B shows phage were propagated for 30 h of PACE in the presence of 1 mM p-NF starting from a 1:1 mixture of SP-p-NFRS and SP-MBP-TEV using the selection based on amber suppression of a single stop codon in gene III. Activity-dependent phage titers and PCR analysis of phage taken from each time point sampled during PACE confirmed that SP-p-NFRS propagated exclusively while SP-MBP-TEV rapidly washed out.

FIG. 7A shows p-NFRS was challenged to aminoacylate the amber suppressor tRNA in the absence of its cognate ncAA substrate, p-NF, over 48 h of positive selection PACE conducted in two separate lagoons (L1 and L2). Enhanced mutagenesis from the MP was supplied in L2 only. Phage titers of L2 (green) rapidly increased after 16 h, while titers in L1 (magenta) were relatively stable throughout the evolution. FIG. 7B shows mutations in PACE-evolved clones and the relative amino acid substrate specificities of clones from L2. Relative aminoacylation activity was compared in the PACE host strain, S1030, by measuring luminescence signal resulting from amber suppression of a premature stop codon at position 361 of a luciferase gene (luxAB). More coding mutations were obtained in phage isolates from L2, in which the MP provided enhanced mutagenesis, and every characterized L2 mutant emerged from PACE with increased activity on endogenous amino acids (no ncAA) compared to the progenitor enzyme, p-NFRS. Each value and error bar in b reflects the mean and s.d. of at least three independent biological replicates.

FIG. 8A shows PACE was performed in three segments designed to gradually increase selection stringency. The first two segments (Pyl-1 and Pyl-2) used the selection requiring amber suppression of two stop codons in T7 RNAP, and the final segment (Pyl-3) used the selection requiring direct amber suppression of stop codons in gene III. The number of stop codons in the gene required for each selection and the concentration of BocK substrate are shown above the phage titer graph. Dotted lines (black) indicate transfer of evolved phage from the end of each PACE segment into the subsequent segment. Triangles indicate convergence toward the specified mutations. FIGS. 8B-8C show the relative expression of luciferase containing BocK at position 361 resulting from aminoacylation by progenitor enzyme, chPylRS, compared to evolved variants from the end of PACE segment Pyl-1 (FIG. 8B) or compared to variants containing only the consensus mutations from the end of each PACE segment (FIG. 8C). Labels correspond to PACE segments in FIG. 8A. FIG. 8D shows the relative efficiency of multisite, BocK incorporation into sfGFP resulting from aminoacylation by chPylRS variants with or without beneficial mutations discovered in PACE (V31I, T56P, H62Y, and A100E; IPYE). FIG. 8E shows the relative efficiency of AcK incorporation at position 2 of sfGFP resulting from aminoacylation by AcK3RS variants with or without transplanted mutations from PACE. Each value and error bar in b-e reflects the mean and s.d. of at least three independent biological replicates.

FIG. 9A shows contributions toward improved activity from consensus mutations in chPylRS generated during PACE segments Pyl-1 and Pyl-2. FIGS. 9C-9D show transplantation of the activity-enhancing PACE mutations V31I, T56P, H62Y, and A100E (IPYE) into *M. barkeri* (Mb) or *M. Mazei* (Mm) PylRS greatly improved the expression levels of luciferase containing the ncAA BocK at position 361 (FIG. 9B) and the expression levels of sfGFP containing a BocK at position 2 (FIG. 9C) or position 151 (FIG. 9D). FIGS. 9E-9F show transplantation of the 'IPYE' mutations into multiple variants of AcK3RS (FIG. 9E) or into the chimeric IFRS (FIG. 9F) improved expression of luciferase containing the ncAA residue at position 361. Each value and error bar in b-e reflects the mean and s.d. of at least three independent biological replicates.

FIGS. 12A-12B show the relative expression sfGFP containing three premature stop codons at positions 39, 135, and 151 (sfGFP(3×TAG)) was compared in the presence or absence of 1 mM BocK for the six, split proteins containing the 'IPYE' tetramutation (FIG. 12A) or with variants lacking the tetramutation (FIG. 12B). FIG. 12C shows the relative expression of sfGFP(Asn39TAG) in the presence of the unsplit chPylRS(IPYE) was compared to expression in the presence of the N-terminal fragments of split2 (NTerm.S2), split3 (NTerm.S3), or split6 (NTerm.S6) or the C-terminal fragment (CTerm) that would result from reinitiation at Met-107. Each value and error bar reflects the mean and s.d. of four independent biological replicates.

FIG. 14A shows the chPylRS variants were N-terminally tagged with c-Myc and C-terminally tagged with 6×His to enable two-color detection of the expressed proteins in order to characterize translation of stop codon-containing mutants that arose during PACE. FIG. 14B shows Western blot analysis of the protein lysates expressed in BL21 star DE3 cells indicated that the full-length variants chPylRS and PylRS(IPYE) were expressed with the N- and C-termini intact, but the presence of an internal start site also promotes alternative expression of the truncated, C-terminal fragment. Each of the split variants (split2, split3, and split 6) are expressed as two, distinct N- and C-terminal fragments indicating termination of translation at the premature stop codon and reinitiation at an internal start site.

FIG. 16 shows alignment of PylRS sequences from multiple organisms and from PACE variants. Activity enhancing mutations from PACE and premature stop codons (*) that emerged in each of the split variants are shown. Note that the activity-enhancing A100E mutation became A100S in Split1 and Split 2 due to the frameshift. Split3, Split4, and Split6 each lack the A100E mutations because they terminate earlier in the sequence. Arrows denote the PylSn and PylSc gene products of the *D. hafniense* strains.

FIG. 17A shows strategy for linking undesired aminoacylation to gene III-neg expression, which encodes the pIII-neg protein. When undesired aminoacylation occurs in the negative selection, pIII-neg is produced, impeding progeny phage infectivity. In the absence of undesired aminoacylation, only pIII is produced, resulting in infectious phage progeny. Negative-selection stringency is modulated by ATc concentration. FIG. 17B shows host-cell plasmids used to implement the negative selection. FIG. 17C shows a diagram of dual-selection PACE using simultaneous positive and negative selections. Evolving phage are continuously cross-seeded between positive and negative selection lagoons at a 50-fold dilution. FIG. 17D shows the relative site-specific incorporation efficiency of either endogenous amino acids (no ncAA), p¬-NF, or p-IF at position 39 of sfGFP resulting from aminoacylation by p-NFRS, p-IFRS, or evolved variants from PACE (Iodo.1, Iodo.5, Iodo.7, and Iodo.8). FIG. 17E shows the predicted position of mutations evolved during dual-selection PACE. The shown crystal structure is the p-NFRS protein sequence aligned to pdb:2AG636, which is the crystal structure of an AARS that has the identical protein sequence of p-IFRS and is bound to the ncAA substrate, p-bromo-L-phenylalanine. The shaded spheres in the crystal structure correspond to the mutations in the table to the left. Active-site residues within a 5 Å radius around the ncAA substrate are colored gray. Each value and error bar in d reflects the mean and s.d. of at least three independent biological replicates.

FIG. 18A shows a diagram of PACE negative selection plasmids. PACE host cells (S1030) are cotransformed with the negative-selection accessory plasmid (AP−) and a negative-selection complementary plasmid (CP−). When an SP infects the negative selection host, production of pIII protein from gene III is induced from the phage shock promoter (Ppsp) of the AP−. If the AARS encoded by the SP can catalyze aminoacylation under the conditions of the negative selection (e.g., in the absence of ncAA), full-length T7 RNAP is produced from the AP− through amber suppression of amber stop codons at position 12 and 203 of the T7 RNAP gene. When full-length T7 RNAP is produced, expression of gene III-neg is induced from the T7 promoter (PT7) of the CP− resulting in production of the dominant-negative pIII-neg protein. The infectivity of progeny phage decreases with the amount of pIII-neg in the host cell. Expression levels of the T7 RNAP gene on the AP− are also controlled by an ATc-inducible promoter (Ptet), allowing the negative selection to be turned on or off during PACE. FIG. 18B shows a diagram of inputs and outputs of the AND logic gate created by the PACE negative selection. The dominant-negative pIII-neg protein is produced only in the presence of both aminoacylation activity and ATc. In the absence of either negative-selection input, progeny phage are infectious and carry forward the encoded AARS into the subsequent round of evolution in PACE.

FIG. 19A shows mock PACE experiments were performed in parallel to demonstrate that the negative selection is dependent on both aminoacylation activity and the concentration of ATc. In lagoon 1 (L1), SP-p-NFRS was propagated in the absence of substrate amino acid (−p-NF) to determine the maximum concentration of ATc that could be tolerated without decreasing the rate of phage propagation when aminoacylation does not occur. In lagoon 2 (L2), SP-p-NFRS and SP-MBP-TEV were both propagated in the presence of the p-NFRS substrate (+p-NF) to determine the minimum concentration of ATc that would support negative selection when aminoacylation does occur. FIG. 19B shows activity-dependent titers were measured to detect the relative amount of active SP-p-NFRS present in the lagoons at each sampled time point of PACE. In L1, the maximum concentration of ATc (broken gray line) that did not affect phage propagation was 30 ng/mL. In L2 (magenta line), the minimum concentration of ATc that induced negative selection against aminoacylation was 10 ng/mL. FIG. 19C shows PCR analysis of phage from each sampled time point of L2 confirms that the inactive SP-MBP-TEV was selectively enriched from a 1000:1 excess of SP-p-NFRS at time points that correspond to ATc concentrations between 10 and 30 ng/mL (16-40 h of PACE).

FIG. 20B shows a peak corresponding to incorporation of p-NF into sfGFP was observed at 27,918.09 Da (calculated: 27,918.31 Da). FIGS. 20B-20C show peaks corresponding to incorporation of Phe were found at 27,873.01 Da and 27873.09 Da, respectively, (calculated: 27,873.32 Da) from expression in the presence or absence of 1 mM p-NF. FIG>20C shows a peak corresponding to incorporation of p-IF into sfGFP was found at 27,999.04 Da (calculated: 27,999.22 Da). Minor peaks in each spectrum correspond to an unclipped N-terminal methionine (calculated mass+131.19 Da).

FIG. 21A shows a diagram of chemostats and lagoons during dual-selection PACE. DRM media supplemented with 4 mM p-NF was pumped into the negative selection lagoon and DRM media supplemented with 1 mM p-IF was pumped into the positive selection lagoon. Host cell cultures from each chemostat were pumped through the corresponding lagoons that were supplemented with required inducers (ATc and arabinose). The opposing lagoons were coupled such that material was continuously exchanged ('cross-seeded') between each lagoon at a 50-fold slower flow rate (gray arrows) with respect to the flow rate from the chemostats through each lagoon (black arrows). FIG. 21B shows a plot of phage titers measured from samples taken at the indicated time points from each lagoon during PACE. Positive selection was conducted exclusively for the first 24 h of the experiment, and dual-selection began at the 24-h time point by cross-seeding phage between the opposing lagoons. The flow rate from the chemostats through the lagoons (broken gray line) was doubled after the two lagoons were coupled, and the flow rate of cross-seeded material was adjusted to maintain 50-fold dilution into the opposing selections.

FIGS. 22A-22B show non-continuous counterselections to isolate p-IF-selective evolved AARS variants after dual-selection PACE. FIG. 22A shows two counterselections were performed in parallel without enhanced mutagenesis (no MP) on the evolved pool of SP sampled from the negative-selection lagoon at the end of dual-selection PACE. Negative selections were performed in batch culture to non-continuously propagate phage lacking unwanted AARS activity on canonical amino acids and p-NF. The stringent negative selection (left) was performed in host cells containing an AP−:CP− pair in which the ATc-inducible promoter driving expression of T7 RNAP(Ser12TAG, Ser203TAG) on AP− (FIG. 18) was replaced with the strong, PproD constitutive-promoter1. A less stringent negative selection was performed (right) using an AP−:CP− pair in which the weaker PproA constitutive-promoter1 was upstream of T7 RNAP(Ser12TAG, Ser203TAG). SPs that propagated overnight in the non-continuous negative selection were isolated and used to infect positive-selection host cells to conduct activity-dependent plaque assays in the presence of p-NF or p-IF. Plaques that formed in the presence of the desired amino acid, p-IF, were isolated and subjected to DNA sequencing. FIG. 22B shows data from parallel counterselections. The enrichment factor reports the number of activity-dependent plaques that formed in 1 mM p-IF divided by the number of plaques that formed in 1 mM p-NF. Mutants marked "RBS mutation" indicate that the ribosome-binding site (RBS) driving translation of the AARS was mutated; these clones were not further characterized.

DEFINITIONS

Figure 1:
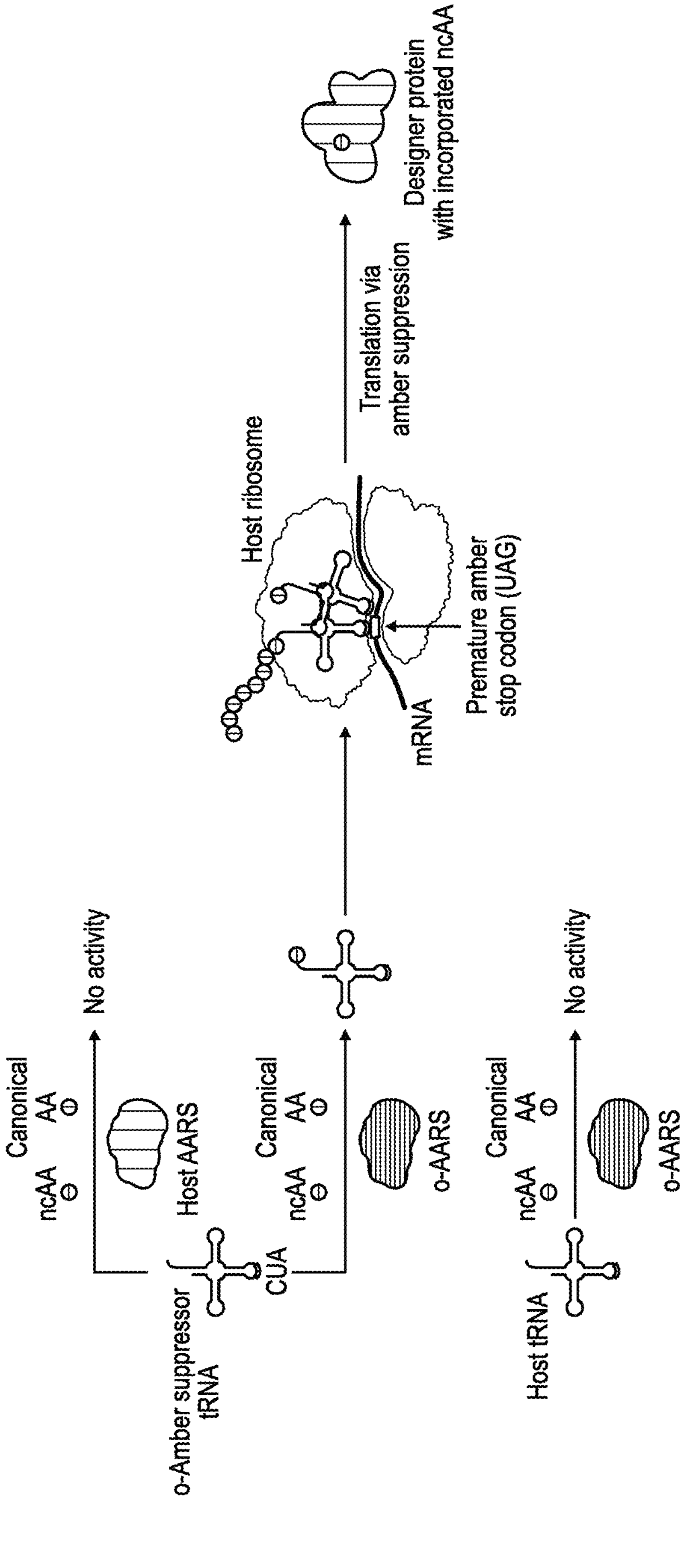
FIG. 1 shows an overview of orthogonal translation in biological systems. The orthogonal amber suppressor tRNA is not recognized by any of the cell's endogenous AARS enzymes, but is selectively aminoacylated by the orthogonal AARS with the desired ncAA. The charged amber suppressor tRNA decodes 'UAG' stop codons during translation of the protein of interest, enabling site-specific incorporation of the ncAA into proteins made by the cell.

The term "phage-assisted continuous evolution (PACE)," as used herein, refers to continuous evolution that employs phage as viral vectors. The general concept of PACE technology has been described, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; U.S. Application, U.S. Pat. No. 9,023,594, issued May 5, 2015, International PCT Application, PCT/US2015/012022, filed Jan. 20, 2015, published as WO 2015/134121 on Sep. 11, 2015, and International PCT Application, PCT/US2016/027795, filed Apr. 15, 2016, published as WO 2016/168631 on Oct. 20, 2016, the entire contents of each of which are incorporated herein by reference.

The term "continuous evolution," as used herein, refers to an evolution process, in which a population of nucleic acids encoding a gene to be evolved is subjected to multiple rounds of (a) replication, (b) mutation, and (c) selection to produce a desired evolved version of the gene to be evolved that is different from the original version of the gene, for example, in that a gene product, such as, e.g., an RNA or protein encoded by the gene, exhibits a new activity not present in the original version of the gene product, or in that an activity of a gene product encoded by the original gene to be evolved is modulated (increased or decreased). The multiple rounds can be performed without investigator intervention, and the steps (a)-(c) can be carried out simultaneously. Typically, the evolution procedure is carried out in vitro, for example, using cells in culture as host cells. In general, a continuous evolution process provided herein relies on a system in which a gene encoding a gene product of interest is provided in a nucleic acid vector that undergoes a life-cycle including replication in a host cell and transfer to another host cell, wherein a critical component of the life-cycle is deactivated and reactivation of the component is dependent upon an activity of the gene to be evolved that is a result of a mutation in the nucleic acid vector.

The term "vector," as used herein, refers to a nucleic acid that can be modified to encode a gene of interest and that is able to enter into a host cell, mutate and replicate within the host cell, and then transfer a replicated form of the vector into another host cell. Exemplary suitable vectors include viral vectors, such as retroviral vectors or bacteriophages, and conjugative plasmids. Additional suitable vectors will be apparent to those of skill in the art based on the instant disclosure.

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, P1, P2, P4, Phi X174, N4, Φ6, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications*. CRC Press; 1st edition (December 2004), ISBN: 0849313368; Martha R. J. Clokie and Andrew M. Kropinski: *Bacteriophages: Methods and Protocols, Volume 1: Isolation, Characterization, and Interactions* (*Methods in Molecular Biology*) Humana Press; 1st edition (December, 2008), ISBN: 1588296822; Martha R. J. Clokie and Andrew M. Kropinski: *Bacteriophages: Methods and Protocols, Volume 2: Molecular and Applied Aspects* (*Methods in Molecular Biology*) Humana Press; 1st edition (December 2008), ISBN: 1603275649; all of which are incorporated herein in their entirety by reference for disclosure of suitable phages and host cells as well as methods and protocols for isolation, culture, and manipulation of such phages).

The term "accessory plasmid," as used herein, refers to a plasmid comprising a gene required for the generation of infectious viral particles under the control of a conditional promoter. In the context of continuous evolution of genes, transcription from the conditional promoter of the accessory plasmid is typically activated, directly or indirectly, by a function of the gene to be evolved. Accordingly, the accessory plasmid serves the function of conveying a competitive advantage to those viral vectors in a given population of viral vectors that carry a version of the gene to be evolved able to activate the conditional promoter or able to activate the conditional promoter more strongly than other versions of the gene to be evolved. In some embodiments, only viral vectors carrying an "activating" version of the gene to be evolved will be able to induce expression of the gene required to generate infectious viral particles in the host cell, and, thus, allow for packaging and propagation of the viral genome in the flow of host cells. Vectors carrying non-activating versions of the gene to be evolved, on the other hand, will not induce expression of the gene required to generate infectious viral vectors, and, thus, will not be packaged into viral particles that can infect fresh host cells.

The term "helper phage," as used herein, interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes for the generation of infectious phage particles. Helper phages are useful to allow modified phages that lack a gene for the generation of infectious phage particles to complete the phage life cycle in a host cell. Typically, a helper phage will comprise the genes for the generation of infectious phage particles that are lacking in the phage genome, thus complementing the phage genome. In the continuous evolution context, the helper phage typically complements the selection phage, but both lack a phage gene required for the production of infectious phage particles.

The term "selection phage," as used herein interchangeably with the term "selection plasmid," refers to a modified phage that comprises a nucleic acid sequence encoding a tRNA synthetase to be evolved, and lacks a full-length gene encoding a protein required for the generation of infectious phage particles. For example, some M13 selection phages provided herein comprise a nucleic acid sequence encoding a gene to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a tRNA synthetase protein to be evolved, e.g., under the control of an M13 promoter, and lack all or part of a gene encoding a protein required for the generation of infective phage particles, e.g., the gIII gene encoding the pIII protein.

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene. In some embodiments, the gene is a GATC methylase gene, for example, a deoxyadenosine methylase (dam methylase) gene. In some embodiments, the gene is involved in binding of hemimethylated GATC sequences, for example, a seqA gene. In some embodiments, the gene is involved with repression of mutagenic nucleobase export, for example emrR. Mutagenesis plasmids (also referred to as mutagenesis constructs) are described, for example by International Patent Application, PCT/US2016/027795, filed Apr. 16, 2016, published as WO2016/168631 on Oct. 20, 2016, the entire contents of which are incorporated herein by reference.

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, 0(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

The term "protein," as used herein, refers to a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain; see, for example, cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "evolved synthetase protein," as used herein, refers to a tRNA synthetase protein variant that is expressed by a gene of interest (e.g., a gene encoding a wild-type synthetase protein, such as a wild-type pyrrolysyl-tRNA synthetase) that has been subjected to continuous evolution, such as PACE or SE-PACE. Examples of evolved synthetase proteins include but are not limited to evolved aminoacyl-tRNA synthetases (AARSs), such as evolved pyrrolysyl-tRNA synthetase (PylRS) proteins and evolved tyrosyl-tRNA synthetase (TyrRS) proteins.

The term "wild-type pyrrolysyl-tRNA synthetase (PylRS)" refers to the amino acid sequence of a pyrrolysyl-tRNA synthetase (PylRS) protein as it naturally occurs in the genome of the host from which it is derived. Examples of a wild-type PylRS proteins include *Methanosarcina barkeri* PylRS (MbPylRS), which is represented by the amino acid sequence set forth in SEQ ID NO: 20 or the amino acid sequence of NCBI Accession Number WP_011305865.1, or *Methanosarcina mazei* PylRS (MmPylRS), which is represented by the amino acid sequence set forth in SEQ ID NO: 21 or the amino acid sequence of NCBI Accession Number WP_011033391.1.

The term "wild-type tyrosyl-tRNA synthetase (TyrRS)" refers to the amino acid sequence of a tyrosyl-tRNA synthetase (TyrRS) protein as it naturally occurs in the genome of the host from which it is derived. Examples of a wild-type TyrRS proteins include *M. jannaschii* TyrRS (MjTyrRS), which is represented by the amino acid sequence set forth in SEQ ID NO: 24 or the amino acid sequence of NCBI Accession Number WP_010869888.1.

The term "pyrrolysyl-tRNA synthetase (PylRS) protein variant" refers to a PylRS protein having one or more amino acid variations introduced into the amino acid sequence, e.g., as a result of application of the PACE method, as compared to the amino acid sequence of a naturally-occurring or wild-type PylRS protein. Amino acid sequence variations may include one or more mutated residues within the amino acid sequence of the PylRS protein variant, e.g., as a result of a change in the nucleotide sequence encoding the protein that results in a change in the codon at any particular position in the coding sequence, the deletion of one or more amino acids (e.g., a truncated protein), the insertion of one or more amino acids, or any combination of the foregoing. In some embodiments, the N- or C-terminal domain of a PylRS variant is a variant of a naturally-occurring PylRS from an organism, that does not occur in nature. In some embodiments, a PylRS variant or PylRS N- or C-terminal domain variant is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring PylRS (or corresponding PylRS domain) from an organism.

The term "tyrosyl-tRNA synthetase (TyrRS) protein variant" refers to a TyrRS protein having one or more amino acid variations introduced into the amino acid sequence, e.g., as a result of application of the PACE method, as compared to the amino acid sequence of a naturally-occurring or wild-type TyrRS protein. Amino acid sequence variations may include one or more mutated residues within the amino acid sequence of the TyrRS protein variant, e.g., as a result of a change in the nucleotide sequence encoding the protein that results in a change in the codon at any particular position in the coding sequence, the deletion of one or more amino acids (e.g., a truncated protein), the insertion of one or more amino acids, or any combination of the foregoing. In some embodiments, a TyrRS variant is a variant of a naturally-occurring TyrRS from an organism, or a variant of an evolved TyrRS that does not occur in nature. In some embodiments, a TyrRS variant or TyrRS N- or C-terminal domain variant is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring TyrRS (or corresponding TyrRS domain) from an organism.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* ($4^{th}$ ed., Cold Spring Harbor Laboratory Press, Cold Spring Harbor, N.Y. (2012)).

The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ed., Cold Spring Harbor Laboratory Press, Cold Spring Harbor, N.Y. (2012)), the entire contents of which are incorporated herein by reference.

The term "chimeric protein" refers to a fusion protein in which the first protein portion and the second protein portion are derived from different species. For example, in some embodiments, a chimeric PylRS protein comprises an N-terminal domain of a MbPylRS (e.g., MbPylRS amino acids 1-149 as set forth in SEQ ID NO: 20) and a C-terminal domain from a MmPylRS (e.g., MmPylRS amino acids 185-454 as set forth in SEQ ID NO: 21).

The term "host cell," as used herein, refers to a cell that can host, replicate, and transfer a phage vector useful for a continuous evolution process as provided herein. In embodiments where the vector is a viral vector, a suitable host cell is a cell that can be infected by the viral vector, can replicate it, and can package it into viral particles that can infect fresh host cells. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the disclosure is not limited in this respect.

The term "stop codon", as used herein, refers to a three-nucleotide sequence that is present within messenger RNA (mRNA) and typically functions to terminate protein translation. Examples of stop codons include the DNA sequences "TAG" or "UAG" (also referred to as an "amber codon"), "TAA" or "UAA" (also referred to as an "ochre" codon), and "TGA" or "UGA" (also referred to as an "opal" or "umber" codon). In some embodiments, a tRNA synthetase protein variant, for example a PylRS protein variant, is evolved to recognize one or more stop codons and allow protein translation to read through the codon to produce a full-length protein. In some embodiments, a PylRS protein variant is evolved to enable a tRNA to insert a pyrrolyine amino acid at protein position encoded a canonical stop codon (e.g., an amber stop codon) of an mRNA. In some embodiments, a TyrRS protein variant is evolved to enable a tRNA to insert a p-iodo-L-phenylalanine amino acid at protein position encoded a canonical stop codon (e.g., an amber stop codon) of an mRNA.

DETAILED DESCRIPTION OF CERTAIN EMBODIMENTS

Some aspects of this disclosure provide tRNA synthetase variants (e.g., PylRS protein variants, TyrRS protein variants, etc.) and methods, compositions, and systems for producing the same. In some embodiments, the disclosure relates to the use of phage-assisted continuous evolution (PACE) to produce tRNA synthetase protein variants. In some embodiments, tRNA synthetase protein variants described by the disclosure exhibit improved activity (e.g., improved incorporation of target non-canonical amino acids (ncAAs) into tRNAs) or amino acid specificity (e.g., charging of preferred ncAAs) relative to the wild-type or variant tRNA synthetase protein from which they are derived. Some aspects of this disclosure provide fusion proteins, such as chimeric PylRS protein variants comprising an N-terminal domain of a MbPylRS protein or MbPylRS protein variant and a C-terminal domain of a MmPylRS protein or MmPylRS protein variant.

PylRS Protein Variants

Some aspects of the disclosure relate to tRNA synthetase protein variants. The disclosure is based, in part, on certain tRNA synthetase protein variants (e.g., PylRS variants, etc.) that are orthogonal (e.g., with respect to a non-archaebacterial cell, for example an *E. coli* cell) and are characterized by increased activity and amino acid specificity relative to wild-type tRNA synthetase proteins (e.g., the PylRS protein from which the variant was evolved). In some embodiments, tRNA synthetase protein variants described by the disclosure are characterized by improved (e.g., increased) charging activity (e.g., binding of a non-canonical amino acid to a tRNA via aminoacylation) relative to wild-type tRNA synthetase proteins (e.g., the PylRS protein from which the variant was evolved).

The tRNA synthetase protein variants described by the disclosure are typically derived from a wild-type PylRS protein and have at least one variation in the amino acid sequence of the variant protein as compared to the amino acid sequence of the cognate wild-type tRNA synthetase protein. In some embodiments, a tRNA synthetase protein variant has at least one variation in its encoding nucleic acid sequence that results in a change in the amino acid sequence present within a cognate wild-type tRNA synthetase protein. The variation in amino acid sequence generally results from a mutation, insertion, or deletion in a DNA coding sequence. Mutation of a DNA sequence can result in a nonsense mutation (e.g., a transcription termination codon (TAA, TAG, or TGA) that produces a truncated protein), a missense mutation (e.g., an insertion or deletion mutation that shifts the reading frame of the coding sequence), or a silent mutation (e.g., a change in the coding sequence that results in a codon that codes for the same amino acid normally present in the cognate protein, also referred to sometimes as a synonymous mutation). In some embodiments, mutation of a DNA sequence results in a non-synonymous (i.e., conservative, semi-conservative, or radical) amino acid substitution.

The tRNA synthetase protein can be any tRNA synthetase protein known in the art. In some embodiments, a tRNA synthetase protein variant is a pyrrolysyl-tRNA synthetase (PylRS) protein variant. In some embodiments, a wild-type PylRS protein is a *M. bakeri* PylRS (MbPylRS) protein. In some embodiments, a MbPylRS is represented by the amino acid sequence set forth in NCBI Accession Number WP_011305865.1 or SEQ ID NO: 20. Additional PylRS proteins are described, for example, in Wan et al. (2014) *Biochim Biophys Acta* 1844(6):1059-1070.

In some aspects, the disclosure relates to chimeric tRNA synthetase proteins. In some embodiments, a chimeric PylRS protein or chimeric PylRS protein variant (e.g., a chimeric PylRS protein that has been subjected to PACE) comprises an N-terminal domain from a first PylRS protein and a C-terminal domain from a second PylRS protein. In some embodiments, an N-terminal domain comprises amino acids 1-149 of a PylRS protein, for example MbPylRS (amino acids 1-149 of SEQ ID NO: 20). In some embodiments, a C-terminal domain comprises amino acids 185-454 of a PylRS protein, for example MmPylRS (amino acids 185-454 of SEQ ID NO: 21). Examples of chimeric PylRS proteins and chimeric PylRS protein variants are described by the nucleic acid sequences set forth in SEQ ID NOs: 5, 8, and 11-17.

In some embodiments, a PylRS protein variant and a wild-type PylRS protein (e.g., MbPylRS or MmPylRS) are from about 50% to about 99.9% identical, about 55% to about 95% identical, about 60% to about 90% identical, about 65% to about 85% identical, or about 70% to about 80% identical at the amino acid sequence level. In some embodiments, a PylRS protein variant comprises an amino acid sequence that is at least 50%, at least 60%, at least 70%, at least 80%, at least 90%, at least 95%, at least 99%, or at least 99.9% identical to the amino acid sequence of a wild-type PylRS protein (e.g., MbPylRS or MmPylRS). In some embodiments, amino acid sequence identity is based on an alignment against a reference sequence (e.g., a wild-type PylRS protein, for example, SEQ ID NO: 20 or 21) by NCBI Constraint-based Multiple Alignment Tool (COBALT), using the following parameters; Alignment Parameters: Gap penalties-11,-1 and End-Gap penalties-5,-1, CDD Parameters: Use RPS BLAST on; Blast E-value 0.003; Find Conserved columns and Recompute on, and Query Clustering Parameters: Use query clusters on; Word Size 4; Max cluster distance 0.8; Alphabet Regular.

In some embodiments, a PylRS protein variant is about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% identical to a wild-type PylRS protein (e.g., MbPylRS, MmPylRS, or a chimeric PylRS).

The amount or level of variation between a wild-type PylRS protein and a PylRS protein variant can also be expressed as the number of mutations present in the amino acid sequence encoding the PylRS protein variant relative to the amino acid sequence encoding the wild-type PylRS protein. In some embodiments, an amino acid sequence encoding a PylRS protein variant comprises between about 1 mutation and about 100 mutations, about 10 mutations and about 90 mutations, about 20 mutations and about 80 mutations, about 30 mutations and about 70 mutations, or about 40 and about 60 mutations relative to an amino acid sequence encoding a wild-type PylRS protein (e.g., MbPylRS, MmPylRS, or a chimeric PylRS). In some embodiments, an amino acid sequence encoding a PylRS protein variant comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mutations relative to an amino acid sequence encoding a wild-type PylRS protein (e.g., MbPylRS, MmPylRS, or a chimeric PylRS protein). In some embodiments, an amino acid sequence of a PylRS protein variant comprises more than 100 mutations relative to an amino acid sequence of a wild-type PylRS protein.

Particular combinations of mutations present in an amino acid sequence encoding a PylRS protein variant can be referred to as the "genotype" of the PylRS protein variant. For example, a PylRS protein variant genotype may comprise the mutations V31I, T56P, H62Y, and A100E, relative to a wild-type PylRS protein (e.g., SEQ ID NO: 20 or 21).

TyrRS Protein Variants

In some aspects, the disclosure relates to tyrosyl-tRNA synthetase (TyrRS) protein variants. The disclosure is based, in part, on certain tRNA synthetase protein variants (e.g., TyrRS variants, etc.) that are orthogonal (e.g., with respect to a non-archaebacterial cell, for example an *E. coli* cell) and are characterized by increased activity and amino acid specificity relative to wild-type tRNA synthetase proteins (e.g., the TyrRS protein from which the variant was evolved). In some embodiments, tRNA synthetase protein variants described by the disclosure are characterized by improved (e.g., increased) charging activity (e.g., binding of a non-canonical amino acid to a tRNA via aminoacylation) relative to wild-type tRNA synthetase proteins (e.g., the TyrRS protein from which the variant was evolved).

The tRNA synthetase protein variants described by the disclosure are typically derived from a wild-type TyrRS protein and have at least one variation in the amino acid sequence of the variant protein as compared to the amino acid sequence of the cognate wild-type tRNA synthetase protein. In some embodiments, a tRNA synthetase protein variant has at least one variation in its encoding nucleic acid sequence that results in a change in the amino acid sequence present within a cognate wild-type tRNA synthetase protein. The variation in amino acid sequence generally results from a mutation, insertion, or deletion in a DNA coding sequence. Mutation of a DNA sequence can result in a nonsense mutation (e.g., a transcription termination codon (TAA, TAG, or TGA) that produces a truncated protein), a missense mutation (e.g., an insertion or deletion mutation that shifts the reading frame of the coding sequence), or a silent mutation (e.g., a change in the coding sequence that results in a codon that codes for the same amino acid normally present in the cognate protein, also referred to sometimes as a synonymous mutation). In some embodiments, mutation of a DNA sequence results in a non-synonymous (i.e., conservative, semi-conservative, or radical) amino acid substitution.

The TyrRS protein can be any TyrRS protein known in the art. In some embodiments, a tRNA synthetase protein variant is tyrosyl-tRNA synthetase (TyrRS) protein variant. In some embodiments, a wild-type TyrRS protein is a *M. jannaschii* TyrRS (MjTyrRS) protein. In some embodiments, a MjTyrRS is represented by the amino acid sequence set forth in SEQ ID NO: 24 or NCBI Accession Number WP_010869888.1. Additional TyrRS proteins are described, for example, in Bedouelle H. Tyrosyl-tRNA Synthetases. In: Madame Curie Bioscience Database [Internet]. Austin, Tex.: Landes Bioscience; 2000-2013.

In some embodiments, a TyrRS protein variant and a wild-type TyrRS protein (e.g., MjTyrRS) are from about 50% to about 99.9% identical, about 55% to about 95% identical, about 60% to about 90% identical, about 65% to about 85% identical, or about 70% to about 80% identical at the amino acid sequence level. In some embodiments, a TyrRS protein variant comprises an amino acid sequence that is at least 50%, at least 60%, at least 70%, at least 80%, at least 90%, at least 95%, at least 99%, or at least 99.9% identical to the amino acid sequence of a wild-type TyrRS protein (e.g., MjTyrRS). In some embodiments, amino acid sequence identity is based on an alignment against a reference sequence (e.g., a wild-type TyrRS protein, for example, SEQ ID NO: 24) by NCBI Constraint-based Multiple Alignment Tool (COBALT), using the following parameters; Alignment Parameters: Gap penalties-11,-1 and End-Gap penalties-5,-1, CDD Parameters: Use RPS BLAST on; Blast E-value 0.003; Find Conserved columns and Recompute on, and Query Clustering Parameters: Use query clusters on; Word Size 4; Max cluster distance 0.8; Alphabet Regular.

In some embodiments, a TyrRS protein variant is about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% identical to a wild-type TyrRS protein (e.g., MjTyrRS).

The amount or level of variation between a wild-type TyrRS protein and a TyrRS protein variant can also be expressed as the number of mutations present in the amino acid sequence encoding the TyrRS protein variant relative to the amino acid sequence encoding the wild-type TyrRS protein. In some embodiments, an amino acid sequence encoding a TyrRS protein variant comprises between about 1 mutation and about 100 mutations, about 10 mutations and about 90 mutations, about 20 mutations and about 80 mutations, about 30 mutations and about 70 mutations, or about 40 and about 60 mutations relative to an amino acid sequence encoding a wild-type TyrRS protein (e.g., MjTyrRS). In some embodiments, an amino acid sequence encoding a TyrRS protein variant comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mutations relative to an amino acid sequence encoding a wild-type TyrRS protein (e.g., MjTyrRS). In some embodiments, an amino acid sequence of a TyrRS protein variant comprises more than 100 mutations relative to an amino acid sequence of a wild-type TyrRS protein.

Particular combinations of mutations present in an amino acid sequence encoding a PylRS protein variant can be referred to as the "genotype" of the PylRS protein variant. For example, a TyrRS protein variant genotype may comprise the mutations L69F and V235I, relative to a wild-type TyrRS protein (e.g., SEQ ID NO: 24).

Methods of Use

Some aspects of this disclosure provide methods of using the tRNA synthetase protein variants provided herein. For example, some aspects of this disclosure provide methods comprising contacting a tRNA with a tRNA synthetase protein variant as described by the disclosure (e.g., a PylRS protein variant or a TyrRS protein variant), in the presence of a cognate non-canonical amino acid, for example pyrolysine (in the case of PylRS) or p-iodo-L-phenylalanine (in the case of TyrRS), under conditions under which the tRNA synthetase protein variant "charges" (binds) the non-canonical amino acid to the tRNA.

In some embodiments, the tRNA, tRNA synthetase protein variant, and the non-canonical amino acid are contacted to one another in a cell, for example a bacterial cell. In some embodiments, the cell in which the tRNA, tRNA synthetase protein variant, and the non-canonical amino acid are contacted to one another does not naturally express the tRNA synthetase protein variant or the tRNA synthetase protein from which the variant is derived (e.g., the tRNA synthetase protein variant is orthogonal to the cell). In some embodiments, the cell is a non-archaebacteria cell, for example an *E. coli* cell.

Methods described by the disclosure are useful, in some embodiments, for charging (e.g., binding) a transfer RNA (tRNA) with a non-canonical amino acid by an aminoacylation reaction. In some embodiments, the activity (e.g., catalytic efficiency of aminoacylation) of a tRNA synthetase protein variant described by the disclosure is between about 2-fold and about 50-fold increased relative to a wild-type tRNA synthetase enzyme. In some embodiments, the activity of a tRNA synthetase protein variant is increased about 2-fold, 3-fold, 4-fold, 5-fold, 6-fold, 7-fold, 8-fold, 9-fold, 10-fold, 15-fold, 20-fold, 25-fold, 30-fold, 40-fold, or 50-fold relative to the activity of a wild-type tRNA synthetase protein. In some embodiments, the activity of a tRNA synthetase protein variant is increased more than 50-fold relative to a wild-type tRNA synthetase protein.

In some embodiments, tRNA synthetase protein variants described by the disclosure are characterized by improved substrate specificity (e.g., reduced incorporation of off-target or undesirable amino acids into a tRNA) relative to a wild-type tRNA synthetase protein. In some embodiments, substrate specificity of a tRNA synthetase protein variant described by the disclosure is increased about 2-fold, 3-fold, 4-fold, 5-fold, 6-fold, 7-fold, 8-fold, 9-fold, 10-fold, 15-fold, 20-fold, 25-fold, 30-fold, 40-fold, or 50-fold relative to the activity of a wild-type tRNA synthetase protein.

In some aspects, the disclosure relates to orthogonal translation systems (OTSs) that allow non-canonical amino acids (ncAAs) to be site-specifically incorporated into recombinant proteins, for example during translation of the recombinant protein in a cell or in vitro. Accordingly, in some embodiments, the disclosure provides a method for incorporating a non-canonical amino acid (ncAA) into a peptide, the method comprising expressing in a cell containing an ncAA: 1) a tRNA synthetase protein variant (e.g., PylRS or TyrRS protein variant); 2) a tRNA capable of incorporating the ncAA; and 3) a nucleic acid sequence encoding a protein, wherein the nucleic acid sequence comprises a codon that is recognized (e.g., bound) by the tRNA.

In some embodiments, the tRNA synthetase protein variant is orthogonal to the cell in which it is being expressed. In some embodiments, the cell is an *E. coli* cell. In some embodiments, the nucleic acid sequence is an mRNA sequence. In some embodiments, the nucleic acid sequence (e.g., mRNA sequence) comprises an amber codon (UAG) that is recognized by the tRNA synthetase.

In some embodiments, the ncAA is a pyrolysine or a p-iodo-L-phenylalanine. In some embodiments, the ncAA is introduced into the culture media surrounding the cell prior to being contained by the cell. In some embodiments, the tRNA synthetase protein variant, tRNA, and the nucleic acid sequence are expressed in the cell prior to the cell containing the ncAA (e.g., the ncAA is added to the cell after expression of the tRNA synthetase protein variant and the nucleic acid sequence).

Vectors and Systems

Some aspects of this disclosure provide expression constructs encoding gene products that select for a desired physiochemical characteristic or desired function of an evolved tRNA synthetase protein, such as PylRS or TyrRS in a host cell, e.g., in a bacterial host cell. In some embodiments, a PACE selection system comprises one or more gene products encoded by a nucleic acid (e.g., an isolated nucleic acid). In some embodiments, one or more nucleic acids that are operably linked comprise an expression construct. Expression constructs are sometimes also referred to as vectors. In some embodiments, the expression constructs are plasmids.

Figure 2A:
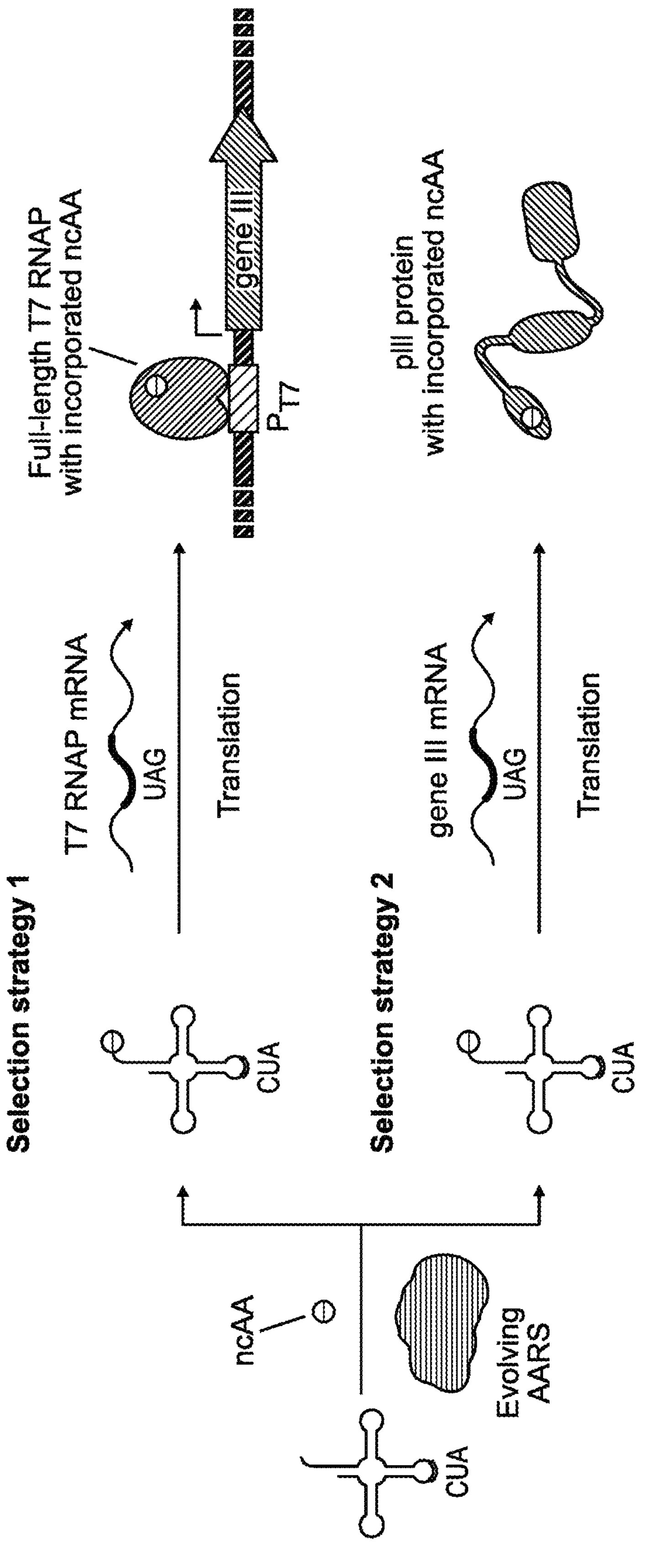
FIGS. 2A-2C show an overview of PACE positive selections for the continuous evolution of AARS activity.
Figure 2B:
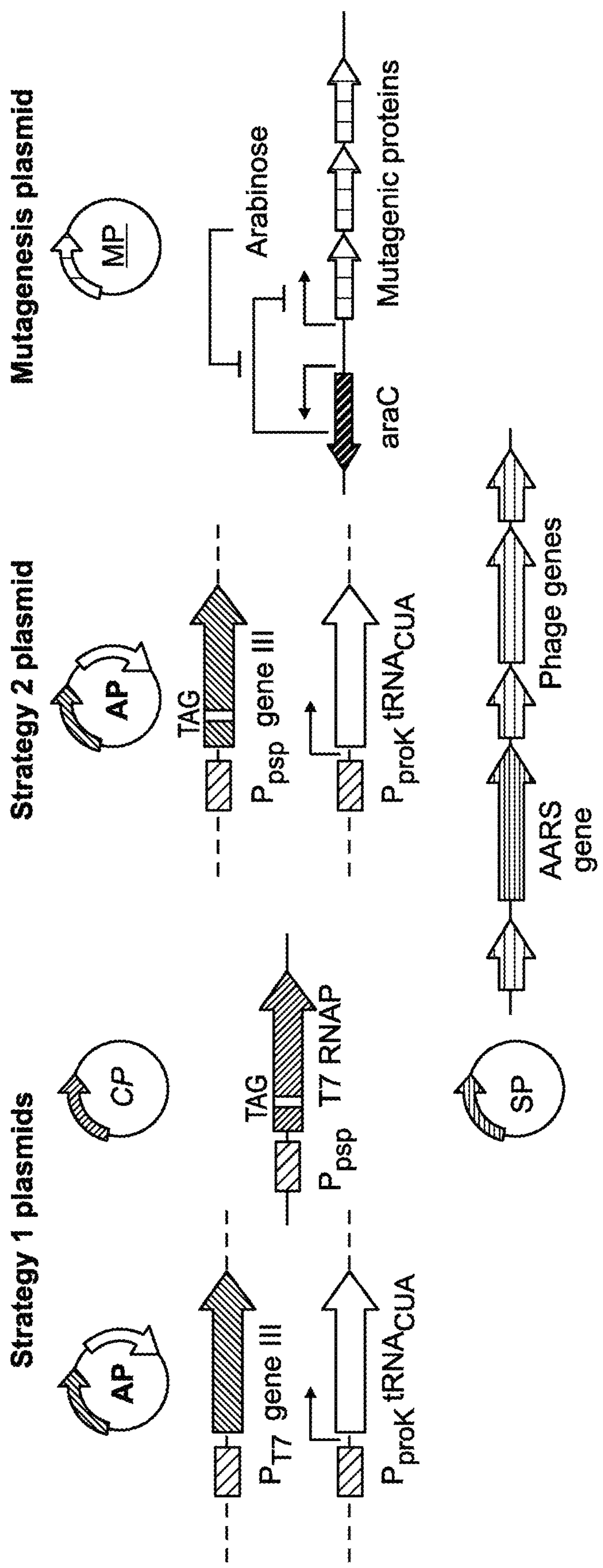
Figure 2C:
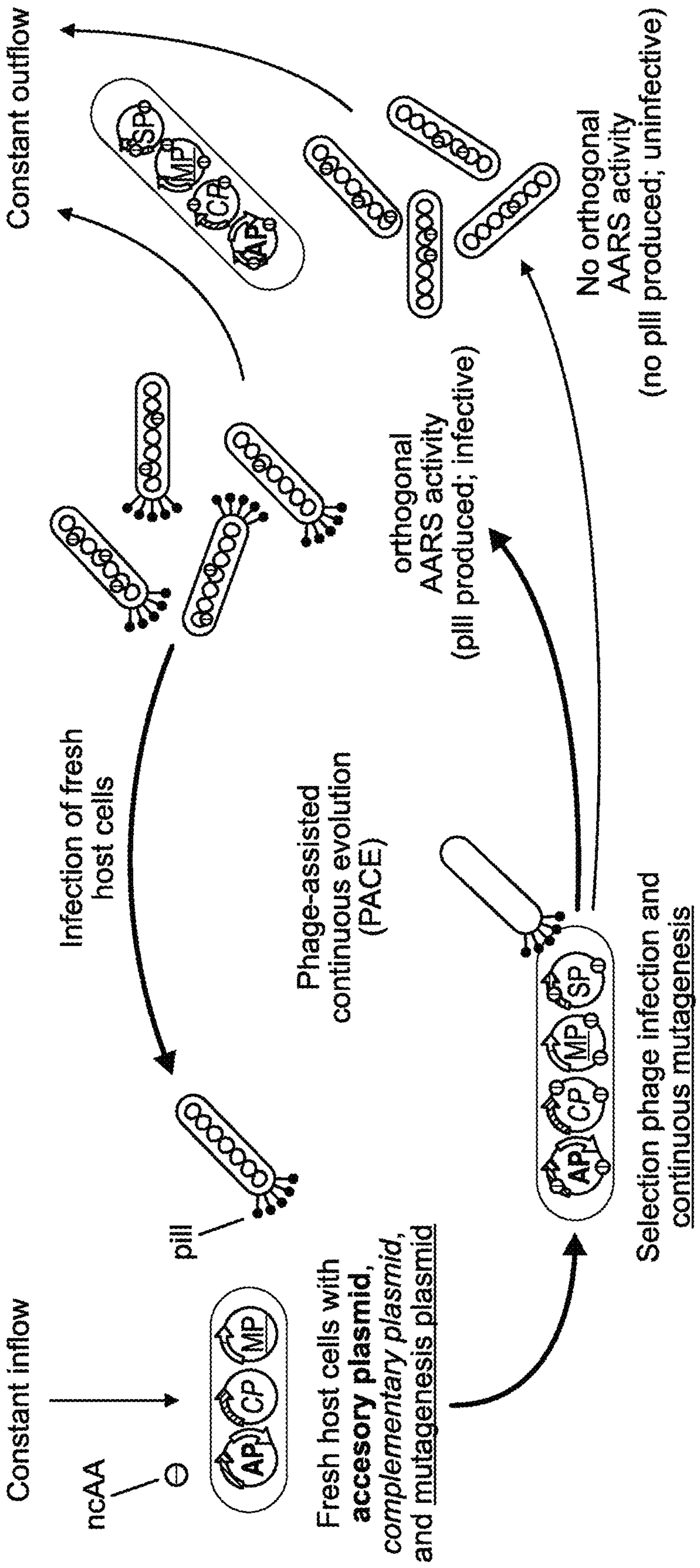

In some embodiments, a PACE selection system for production of an evolved tRNA synthetase protein comprises one or more positive selection plasmids. In some embodiments, at least one of the positive selection plasmids is an accessory plasmid (AP). In some embodiments, a positive selection AP comprises a nucleic acid sequence encoding an amber suppressor tRNA and a gene III (e.g., pIII protein). In some embodiments, a positive selection system comprises a complementary plasmid (CP) that encodes T7 RNAP controlled by the phage-shock promoter ($P_{psp}$), which is induced only upon phage infection. In some embodiments, a positive selection system comprises a mutagenesis plasmid (MP) that increases the rate of evolution during PACE through arabinose-induced production of mutagenic proteins. In some embodiments, the selection phage (SP) encodes all phage genes except gene III, which is replaced by the evolving AARS gene (e.g., gene encoding the tRNA synthetase protein to be evolved). FIGS. 2A-2C provide schematics of positive selection systems described by the disclosure.

In some embodiments, a PACE selection system for production of an evolved tRNA synthetase protein comprises one or more negative selection plasmids. In some embodiments, one or more of the negative selection plasmids is a negative accessory plasmid (AP−) and a negative complementary plasmid (CP−). In some embodiments, a negative accessory plasmid comprises one or more nucleic acid sequences encoding gene III under the control of a $P_{PSP}$ promoter, an amber suppressor tRNA, and a T7RNA polymerase that comprises amber stop codons and is under the control of a Tet promoter. In some embodiments, a negative complementary plasmid comprises a nucleic acid sequence encoding a dominant-negative variant of gene III (e.g., pIII-neg) under the control of a T7 promoter.

Figure 18A:
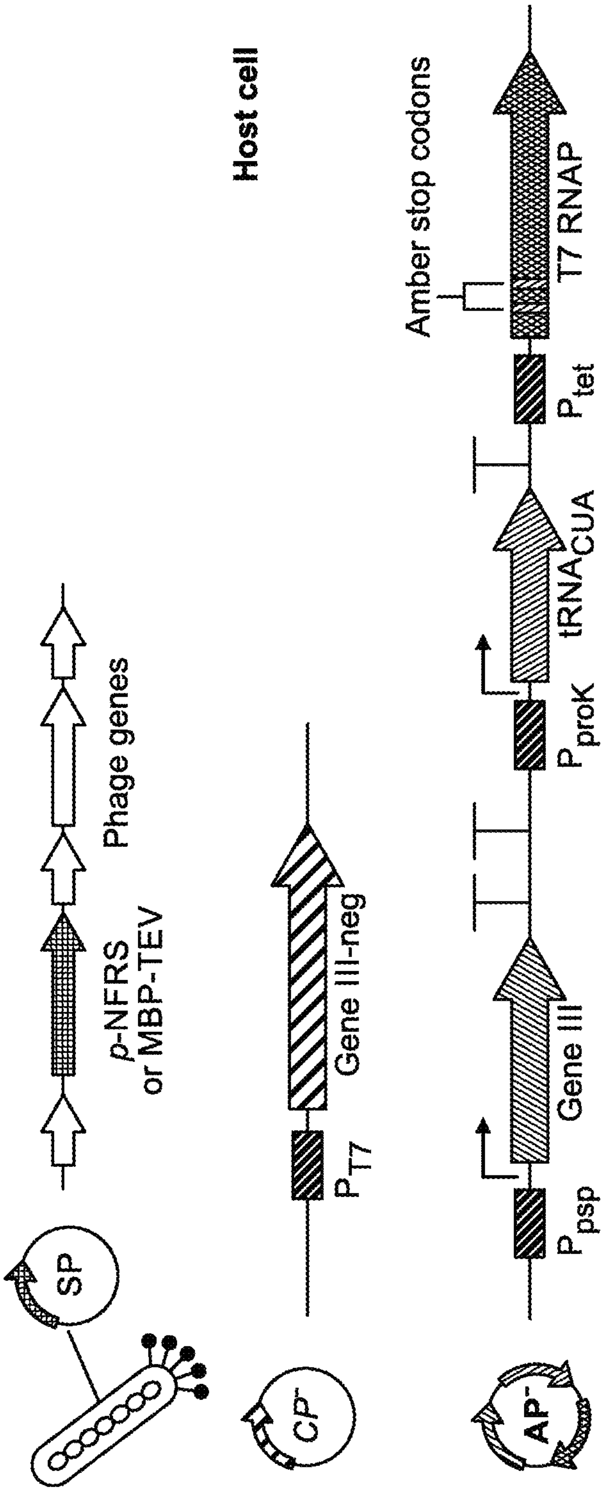
FIGS. 18A-18B show an overview of the PACE negative selection for AARS activity using the dominant-negative variant of pIII (pIII-neg).
Figure 18B:
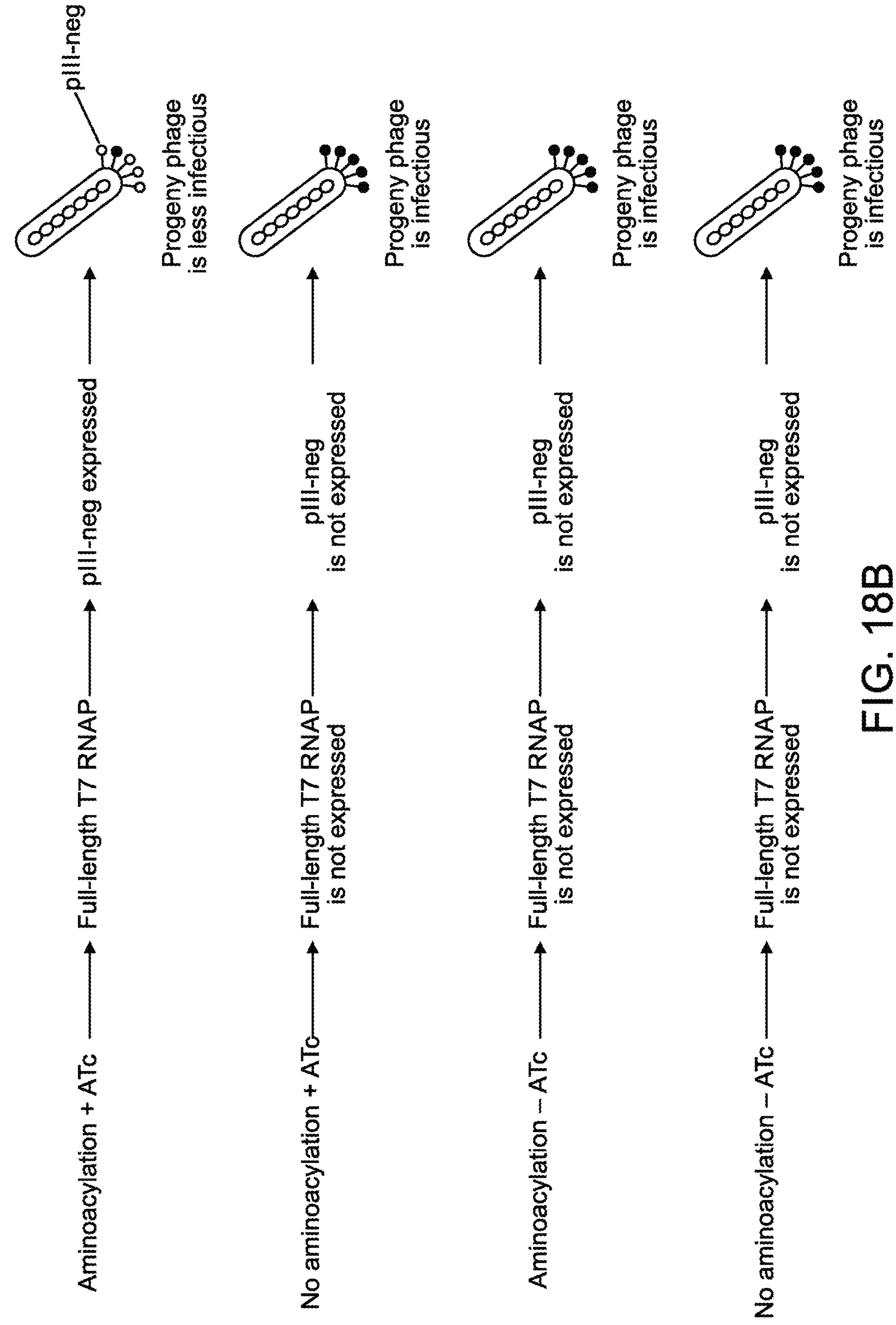

Without wishing to be bound by any theory, when an SP infects the negative selection host, production of pIII protein from gene III is induced from the phage shock promoter ($P_{PSP}$) of the AP−. If the AARS encoded by the SP (e.g., tRNA synthetase protein to be evolved) can catalyze aminoacylation under the conditions of the negative selection (e.g., in the absence of ncAA), full-length T7 RNAP is produced from the AP− through amber suppression of amber stop codons at position 12 and 203 of the T7 RNAP gene. When full-length T7 RNAP is produced, expression of gene III-neg is induced from the T7 promoter (PT7) of the CP− resulting in production of the dominant-negative pIII-neg protein. The infectivity of progeny phage decreases with the amount of pIII-neg in the host cell. Expression levels of the T7 RNAP gene on the AP− are also controlled by an ATc-inducible promoter (Ptet), allowing the negative selection to be turned on or off during PACE. Non-limiting examples of negative selection PACE systems are described in FIGS. 18A-18B.

Figure 17A:
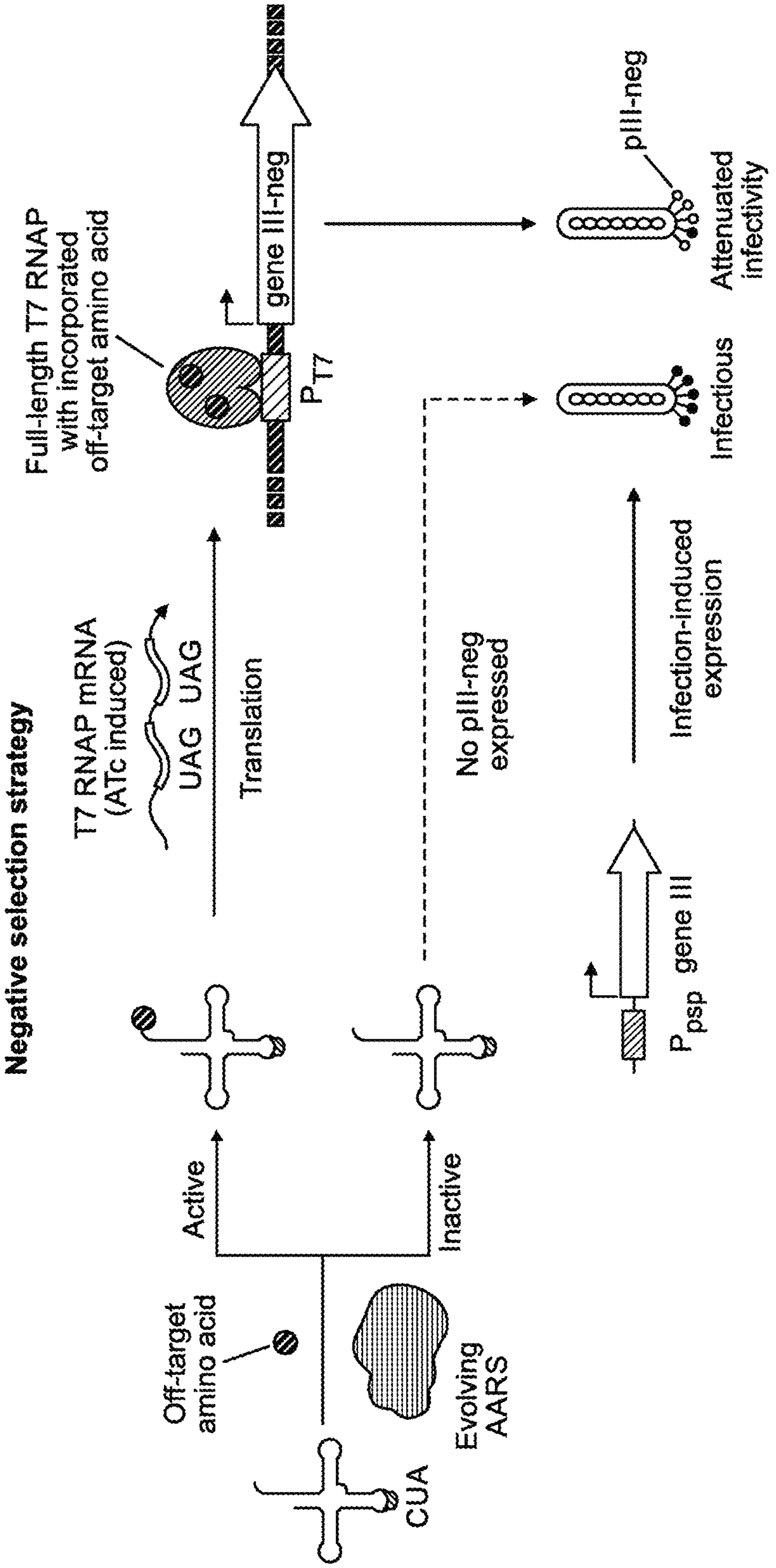
FIGS. 17A-17E show evolution of AARS variants from dual positive- and negative-selection PACE with greatly improved amino acid specificity.
Figure 17B:
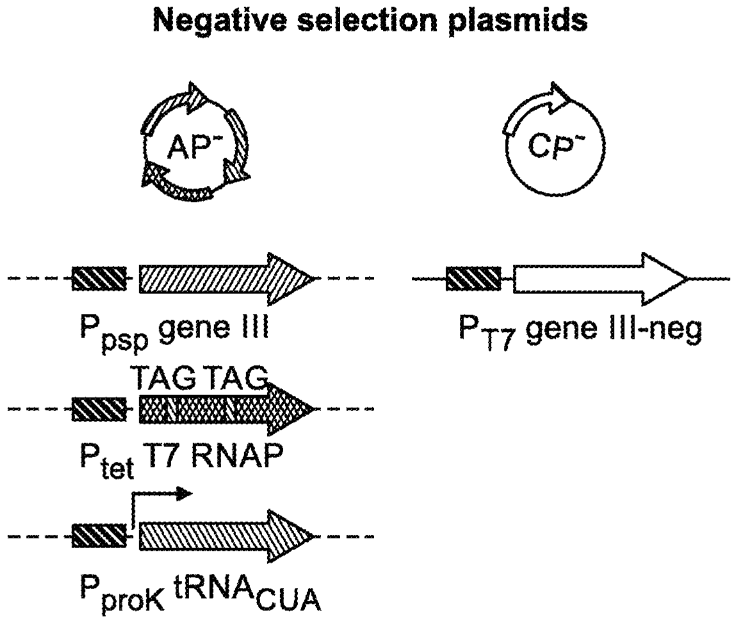

In some embodiments, a selection system for production of an evolved tRNA synthetase protein comprises one or more positive selection plasmids and one or more negative selection plasmids as described herein, and also may be referred to as a "dual-selection system". In some embodiments, a dual-selection system is described by FIGS. 17A-17C and further in the Examples section below.

In some aspects, the disclosure relates to methods of evolving a tRNA synthetase protein variant. In some embodiments, the methods comprise the steps of (i) introducing a selection phagemid comprising a gene encoding a tRNA synthetase to be evolved into a flow of bacterial host cells through a lagoon, the host cells comprise phage genes required to package the selection phagemid into infectious phage particles, wherein at least one gene required to package the selection phagemid into infectious phage particles is expressed in response to expression of the gene to be evolved in the host cell, and wherein the flow rate of the host cells through the lagoon permits replication of the phagemid, but not of the host cells, in the lagoon; (ii) replicating and mutating the phagemid within the flow of host cells; and (iii) isolating a phagemid comprising a mutated gene encoding an evolved tRNA synthetase protein variant from the flow of cells.

EXAMPLES

Example 1

General Methods.

PCR and all cloning steps were performed in HyClone water (GE Healthcare Life Sciences). In all other experiments, water was purified by a MilliQ purification system (EMD Millipore). PCR was performed with Q5 Hot Start High-Fidelity DNA polymerase (New England Biolabs) when unmodified primers were used, and Phusion U Hot Start DNA polymerase (Thermo Fisher Scientific) was used when deoxyuridine-containing primers were required for USER cloning. Plasmids and selection phage were prepared using isothermal assembly with Gibson Assembly 2× Master Mix (New England Biolabs), USER cloning with USER enzyme (New England Biolabs), or ligation cycling reaction with Ampligase (Epicentre). Genes were either synthesized from gBlock gene fragments (Integrated DNA Technologies) or PCR amplified from native sources. Chimeric PylRS, MbPylRS, and MmPylRS were obtained from pTECH plasmid sources. Premature stop codons and single point mutations were placed into genes using the Q5 Site-Directed Mutagenesis kit (New England Biolabs). The gene encoding p-NFRS was PCR amplified from the pEVOL plasmid, which was generously provided to us by P. Schultz of the Scripps Research Institute. DNA vector amplification was performed using TOP10, Mach1 (Thermo Fisher Scientific) or NEB 5-alpha F' Iq (New England Biolabs) cells. All Sanger sequencing of plasmids and SPs was performed from DNA samples that had been amplified using the Illustra Templiphi 100 Amplification Kit (GE Healthcare Life Sciences). All ncAAs were purchased from Chem-Impex International except for 4-nitro-L-phenylalanine (Nanjing Pharmatechs) and 4-iodo-L-phenylalanine (Astatech, Inc.).

Non-Continuous Phage Propagation.

S1030 cells (25 μL) were electroporated with the accessory plasmid of interest and a complementary plasmid, when required (Table 1). Transformed cells recovered 1 h in SOC media (New England Biolabs) at 37° C. while shaking. Recovered cells were plated on LB agar (United States Biologicals) containing the antibiotics required for plasmid maintenance and grew 20 h at 37° C. Single colonies of the transformed cells were picked and grown for 16 h in a 37° C. shaker at 230 rpm using 3 mL of Davis rich media (DRM) containing antibiotics. The saturated cultures were diluted 1,000-fold into 3 mL of identical media or media supplemented with 1 mM ncAA where noted. The diluted cultures were grown at 37° C. while shaking to mid-log phase (absorbance at 600 nm ($A_{600}$)=0.5-0.7). Once the desired cell density was reached, the cultures were inoculated with selection plasmid (SP) to provide a desired starting titer of ~$1\times10^5$ pfu/mL. A dilution reference was also prepared by diluting an identical volume of SP into media containing no cells. All cultures and dilution references were shaken for 16 h at 37° C. The resulting saturated cultures were centrifuged 8 min at 3,000 g, and the supernatant was filtered using a 0.22 μm cellulose acetate, Spin-X centrifuge tube filter (Costar), and the samples were stored at 4° C.

TABLE 1

| Plasmids | | | | | | | | | |
|---|---|---|---|---|---|---|---|---|---|
| | | | ORF1 | | | | ORF3 | | |
| Plasmid | Class | | | [RBS][2] | ORF2 | | | [RBS] | PACE |
| Name | (resistance) | Origin | Prom | Genes | Prom | Genes | Prom | Genes | Experiments |
| pDB007(+) | AP (carb$^R$) | SC101 | $P_{T7}$ | [SD8] gIII, luxAB | $P_{ProK}$ | tyr$T^{Opt}_{CUA}$ | — | — | p-NFRS |
| pDB021CH(+) | AP (carb$^R$) | SC101 | $P_{T7}$ | [SD8] gIII, luxAB | $P_{ProK}$ | pylT | — | — | Pyl-1, Pyl-2 |
| pDB026a | AP (carb$^R$) | SC101 | $P_{psp}$ | [SD8] gIII(P29*), luxAB | $P_{ProK}$ | tyr$T^{Opt}_{CUA}$ | — | — | |
| pDB026b | AP (carb$^R$) | SC101 | $P_{psp}$ | [SD8] gIII(P83*), luxAB | $P_{ProK}$ | tyr$T^{Opt}_{CUA}$ | — | — | |
| pDB026c | AP (carb$^R$) | SC101 | $P_{psp}$ | [SD8] gIII(T177*), luxAB | $P_{ProK}$ | tyr$T^{Opt}_{CUA}$ | — | — | |
| pDB026d | AP (carb$^R$) | SC101 | $P_{psp}$ | [SD8] gIII(Y184*), luxAB | $P_{ProK}$ | tyr$T^{Opt}_{CUA}$ | — | — | |
| pDB026e | AP (carb$^R$) | SC101 | $P_{psp}$ | [SD8] gIII(P29*, Y184*), luxAB | $P_{ProK}$ | tyr$T^{Opt}_{CUA}$ | — | — | |
| pDB026f | AP (carb$^R$) | SC101 | $P_{psp}$ | [SD8] gIII(P29*, P83*, Y184*), luxAB | $P_{ProK}$ | tyr$T^{Opt}_{CUA}$ | — | — | |
| pDB026g | AP (carb$^R$) | SC101 | $P_{psp}$ | [SD8] gIII(P29*, P83*, T177*, Y184*), luxAB | $P_{ProK}$ | tyr$T^{Opt}_{CUA}$ | — | — | |
| pJC175e | AP (carb$^R$) | SC101 | $P_{psp}$ | [SD8] gIII, luxAB | — | — | — | — | |
| pDB038 | AP (spec$^R$) | ColE1 | $P_{psp}$ | [SD8] gIII(P29*), luxAB | $P_{ProK}$ | pylT | — | — | Pyl-3 |
| pDB038a | AP (spec$^R$) | ColE1 | $P_{psp}$ | [SD8] gIII(P29*, Y184*), luxAB | $P_{ProK}$ | pylT | — | — | Pyl-3 |
| pDB038b | AP (spec$^R$) | ColE1 | $P_{psp}$ | [SD8] gIII(P29*, P83*, Y184*), luxAB | $P_{ProK}$ | pylT | — | — | Pyl-3 |
| pDB007ns2a | AP$^-$ (carb$^R$) | SC101 | $P_{psp}$ | [SD8] gIII | $P_{ProK}$ | tyr$T^{Opt}_{CUA}$ | $P_{tet}$ | [SD4] T7RNAP(S12*, S203*) | p-NFRS |
| pDB036a | AP$^-$ (carb$^R$) | SC101 | $P_{psp}$ | [SD8] gIII | $P_{ProK}$ | tyr$T^{Opt}_{CUA}$ | $P_{proD}$ | [SD4] T7RNAP(S12*, S203*) | Countersel. |
| pDB036d | AP$^-$ (carb$^R$) | SC101 | $P_{psp}$ | [SD8] gIII | $P_{ProK}$ | tyr$T^{Opt}_{CUA}$ | $P_{proA}$ | [SD4] T7RNAP(S12*, S203*) | Countersel. |
| pDB023f | CP (spec$^R$) | ColE1 | $P_{psp}$ | [SD8] T7RNAP(S12*, S203*) | — | — | — | — | Pyl-1, Pyl-2 |
| pDB023f1 | CP (spec$^R$) | ColE1 | $P_{psp}$ | [SD4] T7RNAP(S12*, S203*) | — | — | — | — | p-NFRS |
| pDB023k | CP (spec$^R$) | ColE1 | $P_{psp}$ | [SD8] T7RNAP(S12*, S203*, S527*) | — | — | — | — | |
| pDB016 | CP$^-$ (spec$^R$) | ColE1 | $P_{T7}$ | [SD8] gIII-neg | — | — | — | — | p-NFRS, Countersel. |
| DP4 | DP (chlor$^R$) | cloDF13 | $P_{psp}$ | dnaQ926, dam, seqA | $P_C$ | araC | $P_{psp\text{-}tet}$ | [sd8] gIII | Pyl-1, Pyl-2, p-NFRS |
| DP6 | DP (chlor$^R$) | cloDF13 | $P_{psp}$ | dnaQ926, dam, seqA, emrR, ugi, cda1 | $P_C$ | araC | $P_{psp\text{-}tet}$ | [sd8] gIII | Pyl-3 |
| pBAD-sfGFP | EP (carb$^R$) | pBR322 | $P_{BAD}$ | sfGFP-6xHis variant | $P_C$ | araC | — | — | |
| pDB005x(−) | EP (carb$^R$) | SC101 | $P_{lacZ}$ | [SD8] chPylRS | $P_{ProK}$ | pylT | $P_{T7}$ | [SD8] luxAB | |
| pDB007xb(−) | EP (carb$^R$) | SC101 | $P_{lacZ}$ | [SD8] p-NFRS | $P_{ProK}$ | tyr$T^{Opt}_{CUA}$ | $P_{T7}$ | [SD8] luxAB | |
| pDB027c | EP (carb$^R$) | SC101 | $P_{BAD}$ | [SD8] luxAB(Y361*), [SD8] MjTyrRS variant | $P_{ProK}$ | tyr$T^{Opt}_{CUA}$ | $P_C$ | araC | |
| pDB032c | EP (carb$^R$) | SC101 | $P_{BAD}$ | [SD8] luxAB(Y361*), [SD8] PylRS variant | $P_{ProK}$ | pylT | $P_C$ | araC | |
| pDB059c | EP (carb$^R$) | SC101 | $P_{BAD}$ | [SD8] luxAB(Y361*) | $P_C$ | araC | — | — | |
| pDB070 | EP (chlor$^R$) | p15A | $P_{tet}$ | MjTyrRS variant | $P_{ProK}$ | tyr$T^{Opt}_{CUA}$ | $P_{PN25}$ | TetR | |
| pTECH-AcK3RS | EP (chlor$^R$) | p15A | $P_{lpp}$ | AcK3RS variant | $P_{ProK}$ | pylT | — | — | |
| pTECH-PylRS | EP (chlor$^R$) | p15A | $P_{lpp}$ | PylRS variant | $P_{ProK}$ | pylT | — | — | |
| pET28b(+)-sfGFP | EP (Kan$^R$) | pBR322 | $P_{T7}$ | sfGFP-6xHis variant | $P_I$ | LacI | — | — | |
| pDB009a | EP (spec$^R$) | ColE1 | $P_{tet}$ | [SD8] wt T7 RNAP | — | — | — | — | |
| pDB009b | EP (spec$^R$) | ColE1 | $P_{tet}$ | [SD8] T7 RNAP(S12*) | — | — | — | — | |
| pDB009c | EP (spec$^R$) | ColE1 | $P_{tet}$ | [SD8] T7 RNAP(S203*) | — | — | — | — | |
| pDB009d | EP (spec$^R$) | ColE1 | $P_{tet}$ | [SD8] T7 RNAP(S527*) | — | — | — | — | |
| pDB009f | EP (spec$^R$) | ColE1 | $P_{tet}$ | [SD8] T7 RNAP(S12*, S203*) | — | — | — | — | |
| pDB009g | EP (spec$^R$) | ColE1 | $P_{tet}$ | [SD8] T7 RNAP(Y250*) | — | — | — | — | |
| pDB009h | EP (spec$^R$) | ColE1 | $P_{tet}$ | [SD8] T7 RNAP(Y312*) | — | — | — | — | |
| pDB009i | EP (spec$^R$) | ColE1 | $P_{tet}$ | [SD8] T7 RNAP(Y250*, Y312*) | — | — | — | — | |
| pDB009j | EP (spec$^R$) | ColE1 | $P_{tet}$ | [SD8] T7 RNAP(S12*, S527*) | — | — | — | — | |

TABLE 1-continued

| Plasmids | | | | | | | | | |
|---|---|---|---|---|---|---|---|---|---|
| | | | ORF1 | | | | ORF3 | | |
| Plasmid | Class | | [RBS][2] | | ORF2 | | [RBS] | | PACE |
| Name | (resistance) | Origin | Prom | Genes | Prom | Genes | Prom | Genes | Experiments |
| pDB060-AcK3RS | EP ($spec^R$) | ColE1 | $P_{lpp}$ | AcK3RS variant | $P_{ProK}$ | pylT | — | — | |
| pDB060-IFRS | EP ($spec^R$) | ColE1 | $P_{lpp}$ | IFRS variant | $P_{ProK}$ | pylT | — | — | |
| pDB060-PylRS | EP ($spec^R$) | ColE1 | $P_{lpp}$ | PylRS variant | $P_{ProK}$ | pylT | — | — | |
| MP4 | MP ($chlor^R$) | cloDF13 | $P_{psp}$ | dnaQ926, dam, seqA | $P_C$ | araC | — | — | Pyl-2, p-NFRS |
| SP-Kan | SP ($kan^R$) | M13 f1 | $P_{gIII}$ | Kan | — | — | — | — | |
| SP-chPylRS | SP (none) | M13 f1 | $P_{gIII}$ | [SD4] chPyl | — | — | — | — | Pyl-1 |
| SP-MBP-TEV | SP (none) | M13 f1 | $P_{gIII}$ | [SD8] MBP-TEV | — | — | — | — | |
| SP-p-NFRS | SP (none) | M13 f1 | $P_{gIII}$ | [SD4] p-NFRS | — | — | — | — | p-NFRS |

Plaque Assay.

S1030 cells transformed with the appropriate plasmids were grown in 2×YT liquid media (United States Biologicals) supplemented with antibiotics required for plasmid maintenance to $A_{600}$=0.6-0.8. Phage supernatant was serially diluted at 10-fold or 100-fold increments yielding either eight or four total samples, respectively, including undiluted sample. For each phage sample, 100 μL of cells were combined with 10 μL of phage. Within 2 min from phage infection, 950 μL of 55° C. top agar (7 g/L bacteriological agar in 2×YT; no antibiotics) was added and mixed with the phage-infected cells by gentle pipetting once up and down while avoiding formation of bubbles. The final mixtures were plated onto quartered Petri plates that had been previously poured with 1.5 mL of bottom agar (15 g/L bacteriological agar in 2×YT; no antibiotics). Once the overlaid agar congealed, the plates were incubated 16 h at 37° C. to allow plaque formation. When plaque formation was dependent on orthogonal AARS activity, 1 mM ncAA was also added to all liquid and solid media when denoted. When clonal-phage isolates were required, well separated plaques were picked from plates and grown individually at 37° C. while shaking in 3 mL of DRM supplemented with 1 mM ncAA of interest where required. The resulting saturated cultures were pelleted at 3,000 g for 8 min, and the phage supernatant was sterile filtered and stored at 4° C. for further analysis.

Phage-Assisted Continuous Evolution of Aminoacyl-tRNA Synthetases.

In general, the PACE apparatus—including host-cell strains, lagoons, chemostats, and media—was used as previously described, for example in WO2010/028347. All liquid and solid media contained antibiotics required for plasmid maintenance unless indicated otherwise. To prepare each PACE strain, the accessory plasmid (AP), complementary plasmid (CP), and MP or drift plasmid (DP) of interest were cotransformed into electrocompetent S1030 cells, which recovered for 1 h in SOC medium without antibiotics (New England Biolabs). The recovered transformants were plated onto 2×YT agar containing 0.4% glucose to prevent induction of mutagenesis prior to PACE, and colonies were grown for 16-20 h in a 37° C. incubator. Three colonies were picked and resuspended in DRM. A portion of each suspension was tested for arabinose sensitivity as previously described, and the remainder was used to inoculate liquid cultures in DRM, which were subsequently grown for 16 h in a 230 rpm shaker at 37° C.

Each PACE chemostat was prepared by diluting an arabinose-sensitive overnight culture into 40 mL or 80 mL of DRM, which was supplemented with ncAA where noted, and the chemostats grew at 37° C. while stirring with a magnetic stir bar. Once the culture reached an approximate cell density of $A_{600}$=1.0, fresh DRM (supplemented with ncAA where noted) was used to continuously dilute the chemostat culture at a dilution rate of 1.6 chemostat volumes per h while maintaining a constant culture volume as previously described.

Lagoons flowing from the chemostats were continuously diluted using the indicated flow rates while maintaining a 25-mL constant volume by adjusting the height of the needle drawing waste out of each lagoon. All lagoons were supplemented with 25 mM arabinose from a syringe pump to induce mutagenesis from the MP or DP, unless otherwise indicated. Arabinose supplementation began at least two hours prior to phage infection to insure cells were maximally induced at the start of each experiment. Lagoons were also supplemented with anhydrotetracycline (ATc), where noted, to induce either genetic drift (mutagenesis under weak or no selective pressure) or negative selection depending on the nature of the host-cell plasmids.

Samples of evolving SP pools were taken periodically at indicated time points from the waste line of each lagoon. Collected samples were centrifuged at 10,000 g for 2 min, and the supernatant was passed through a 0.22 μm filter and stored at 4° C. for subsequent analysis. Phage titers were determined by plaque assays using S1059 cells (containing the phage-responsive pJC175e plasmid to report total phage titer) and untransformed S1030 cells (reporting cheaters from unwanted recombination of gene III into the SP) for all collected samples. Activity-dependent plaque assays were performed for mock selection PACE experiments, using S1030 cells cotransformed with the AP and CP used in the host cells of the corresponding experiment. Mock selections were also monitored by PCR performed on phage aliquots using primers DB212 (5'-CAAGCCTCAGCGACCGAATA; SEQ ID NO: 1) and DB213 (5'-GGAAACCGAG-GAAACGCAA; SEQ ID NO: 2), which anneal to regions of the phage backbone flanking the gene of interest.

Evolution of chPylRS (Pyl-1).

Host cells cotransformed with pDB021CH(+), pDB023f, and DP4 were maintained in an 80 mL chemostat using media containing 1 mM BocK. At the beginning of PACE, genetic drift was induced (200 ng/mL ATc) in a lagoon that was flowing from the chemostat at 1 lagoon volume per h. The lagoon was infected with $10^8$ pfu of SP-chPylRS to start the experiment. ATc supplementation was adjusted to 20 ng/mL at 16 h of PACE to slowly reduce the amount of genetic drift, and ATc supplementation was stopped at 24 h. The lagoon flow rate was increased to 2 volumes per h at 40 h of PACE to increase selection stringency for the remainder of the experiment, which ended at 120 h.

Continuation of chPylRS Evolution (Pyl-2).

Three preparations of media were used, which contained different concentrations of Nε-(tert-butoxycarbonyl)-L-lysine (BocK) (DRM-A: 1 mM BocK; DRM-B: 0.5 mM BocK; DRM-C: 0.25 mM BocK). Host cells cotransformed with pDB021CH(+), pDB023f, and MP4 were maintained in a 40 mL chemostat containing DRM-A at the start of the experiment. A single lagoon was flowed from the chemostat at 1 lagoon volume per h, and the experiment was initiated by infecting the lagoon with 100 μL ($2\times10^4$ pfu) of the evolved pool of SP collected from the 120-h end point of Pyl-1. To increase the selection stringency during the experiment, the media being pumped into the chemostat was changed to DRM-B at 42 h of PACE and was changed to DRM-C at 69 h. The experiment ended at 168 h.

Continuation of chPylRS Evolution (Pyl-3).

PACE was conducted in two separate lagoons, L1 and L2, and a concentration of 1 mM BocK was maintained throughout the experiment. Selection stringency was increased during the experiment by modulating the lagoon flow rate and altering the ratio of host cells in the lagoons to increase the number of amber suppression events required to produce full-length pIII during translation (Host-A: pDB038 and DP6; Host-B: pDB038a and DP6; Host-C: pDB038b and DP6). Host cells were maintained separately in three, 40 mL chemostats (C1-C3, respectively), and each chemostat was individually prepared and coupled to both lagoons, as needed, over the course of the experiment to minimize media waste and to minimize the total growth time of each chemostat culture.

At the start of the experiment L1 and L2 were continuously diluted with Host-A from C1 at a rate of 0.5 lagoon volumes per h, and genetic drift was induced only in L1 (100 ng/mL ATc). Each lagoon was infected with $10^8$ pfu of clonal-phage isolate SP-Pyl2.288-2, which was isolated from the Pyl-2 segment (Table 2; bold residues responsible for enhancing activity of chPylRS). The flow rate from C1 through each lagoon was increased to 1 lagoon volume per h at 41 h of PACE. At the 91-h mark of the experiment, L1 and L2 were fed a 1:1 mixture of Host-A:Host-B supplied from C1 and C2, respectively, and the flow through each lagoon was maintained at 1 lagoon volume per h. At the 120-h mark, 100% Host-B was flowed to each lagoon at 0.5 lagoon volumes per h, and the flow rate was later doubled to 1 lagoon volume per h at 136 h of PACE. At the 162 h mark, L1 and L2 were fed a 1:1 mixture of Host-B:Host-C supplied from C2 and C3, respectively, and the flow through each lagoon was maintained at 1 lagoon volume per h. ATc supplementation to L1 was stopped at 184 h of PACE to end genetic drift. At the 190-h time point of PACE, 100% Host-C was flowed to each lagoon at 0.5 lagoon volumes per h for the remainder of the experiment, which was stopped at 209 h.

TABLE 2

| chPylRS | Pyl-2.162.1-5 | | | | | Pyl-2.189.1-5 | | | | | Pyl-2.288.1-5 | | | | |
|---|---|---|---|---|---|---|---|---|---|---|---|---|---|---|---|
| Residue | 1 | 2 | 3 | 4 | 5 | 1 | 2 | 3 | 4 | 5 | 1 | 2 | 3 | 4 | 5 |
| D2 | | | | | | | | | | | | | | | E |
| D7 | E | | | | | | | | | | | | | | |
| A12 | | | | | | G | | | | | | | | | |
| V31 | | I | I | I | I | I | I | I | I | I | I | I | I | I | I |
| T56 | | P | P | P | P | P | P | P | P | P | P | P | P | P | P |
| H62 | | | | | | | Y | | | | | | | | |
| E77 | | | | | | K | | | | | | | | | |
| T91 | S | | | | | | | | | | | | | | |
| A100 | | | | | | | | | | | E | E | E | E | E |
| K104 | | | | | | | | | | | | | | E | |
| R113 | | H | | | | | | | | | | | | | |
| L118 | | | | | | M | | | | | | | | | |
| A150 | | V | | | | | | | | | | | | | |
| R217 | | | | | | | | | S | | | | | | |
| D257 | | G | G | G | G | | G | G | G | G | G | G | G | G | G |
| N259 | | | | S | | | | S | | | | | | | |
| L266 | | | | | | | | I | | | | | I | | |
| P282 | | | | | | | | S | | | | | | | |
| I327 | | | | | M | | M | | | | | | | | |
| G336 | | | | | | | | | | | E | | | | |
| D338 | | | | | | | E | | | | | | | | |

Evolution of p-NFRS with Dual Selection.

The media of the positive selection contained 1 mM p-IF, and media of the negative selection contained 4 mM p-NF. Three host-cell strains (Host-A: pDB007(+), pDB023f1, and DP4; Host-B: pDB007(+), pDB023f1, and MP4; Host-C: pDB007(+)ns2a, pDB016, and MP4) were used, and were maintained separately in three, 80 mL chemostats (C1-C3), respectively. Host-A was pumped into a positive-selection lagoon (L1-pos) at a flow rate of 1 lagoon volume per h, and genetic drift was induced by supplementation with 200 ng/mL ATc to the lagoon. L1-pos was infected with $10^8$ pfu of SP-p-NFRS to initiate the experiment, and supplementation of ATc was stopped at 24 h to end genetic drift. Concomitant with the end of genetic drift, C1 was disconnected from L1-pos, and the lagoon was connected to C2 (containing Host-B), which was pumped into L1-pos at 1 lagoon volume per h. Also at this time, L1-pos was cross coupled to a second lagoon (L2-neg), which was being continuously flowed with negative-selection Host-C from C3. The maximum level of negative-selection stringency from Host-C was maintained by supplementing L2-neg with 30 ng/mL ATc. Cross coupling of the opposing selection lagoons was accomplished using two lines of Masterflex Microbore two-stop tubes (silicone; platinum cured; 0.89 mm ID) (Cole-Parmer), which each had a dead volume of 1 mL. One of the tubes was used to transfer small volumes of culture from L1-pos into L2-neg, and the second tube transferred material in the opposing direction. Material was peristaltically pumped through the cross-coupling lines with a Masterflex L/S Standard Digital Drive (Cole-Parmer)

equipped with a Masterflex L/S 8-channel multichannel pump head for microbore tubing (Cole-Parmer). The flow rate through each cross-coupling line was initially set to 0.5 mL/h to maintain a 50-fold dilution of the transferred material into the opposing lagoons. The flow rate through L1-pos and L2-neg was doubled to 2 lagoon volumes per h at 28 h, and flow through the cross-coupling lines was adjusted to 1 mL/h to maintain 50-fold dilution of transferred material in each direction. The experiment ended at 48 h.

Luciferase Assay.

S1030 cells (25 μL) were electroporated with the appropriate plasmid(s) and recovered in SOC media (New England Biolabs) for 1 h while shaking at 37° C. Transformed cells were plated and grown overnight at 37° C. on LB agar containing the antibiotics required for plasmid maintenance. Single colonies were used to inoculate 2-3 mL of DRM containing antibiotics and were grown overnight at 37° C. while shaking at 230 rpm. The saturated overnight cultures were diluted 100-fold in a 96-well deep well plate using 1 mL of DRM containing the required antibiotic and supplemented with 1 mM ncAA where denoted. The plate was shaken at 37° C. for 2 h at 230 rpm and then supplemented with the indicated concentration of isopropyl-β-D-thiogalactosidase (IPTG), anhydrotetracycline (ATc), or 1 mM arabinose—depending on the nature of the plasmids—to induce protein expression. The plate continued to incubate with shaking at 37° C. for an additional 2-3 h until maximum luminescence signal was observed. Each luminescence measurement was taken on 150 μL of each culture, which had been transferred to a 96-well black wall, clear bottom plate (Costar). The $A_{600}$ and luminescence measurements from each well were taken using an Infinite M1000 Pro microplate reader (Tecan). Background $A_{600}$ measurements were taken on wells containing media only. The raw luminescence value from each well was divided by the background-subtracted $A_{600}$ value of the corresponding well to provide the luminescence value normalized to cell density. All variants were assayed in at least biological triplicate, and error bars represent the standard deviation of the independent measurements.

sfGFP Assay.

In assays of MjTyrRS variants (p-NFRS, p-IFRS, and PACE-evolved), a pDB070 plasmid containing the AARS of interest and a pET28b(+) containing the superfolder GFP (sfGFP) of interest were cotransformed into chemically competent BL21 Star (DE3) cells (Thermo Fisher Scientific). The transformed cells recovered in SOC (New England Biolabs) for 1 h while shaking at 37° C. and were then plated and grown overnight at 37° C. on LB agar containing 50 μg/mL kanamycin and 25 μg/mL chloramphenicol. Single colonies were used to inoculate 2 mL of LB media (United States Biologicals) containing antibiotics and were grown overnight at 37° C. while shaking at 230 rpm. The saturated overnight cultures were diluted 100-fold in a 96-well deep well plate using 600 μL of LB media containing the required antibiotic and were grown at 37° C. to a cell density of $A_{600}$=0.3 while shaking at 230 rpm. AARS expression was induced by addition of LB media (200 μL) containing antibiotics and the additional components to provide each well with a final concentration of 200 ng/mL anhydrotetracycline (ATc) and 1 mM ncAA where indicated. Incubation continued until cultures reached a cell density of $A_{600}$=0.5. Each well was then supplemented with 1 mM isopropyl-β-D-thiogalactosidase (IPTG) to induce sfGFP expression.

In assays of PylRS variants (including AcK3RS variants), a pTECH plasmid containing the AARS of interest and a pBAD plasmid containing the sfGFP of interest were cotransformed into chemically competent TOP10 cells (Thermo Fisher Scientific). The transformed cells recovered in SOC (New England Biolabs) for 1 h while shaking at 37° C. and were then plated and grown overnight at 37° C. on LB agar containing 100 μg/mL carbenicillin and 25 μg/mL chloramphenicol. Single colonies were used to inoculate 2-3 mL of LB media (United States Biologicals) containing antibiotics and were grown overnight at 37° C. while shaking at 230 rpm. The saturated overnight cultures were diluted 100-fold in a 96-well deep well plate using 500 μL of LB media containing the required antibiotic. The plate was shaken at 37° C. for 3 h at 230 rpm and an additional 500 μL of LB was added containing antibiotics and additional components to provide each well with a final concentration of 1 mM ncAA where denoted and 1.5 mM arabinose to induce expression of sfGFP.

For all experiments, the cultures incubated with shaking at 37° C. for an additional 16 h after induction of sfGFP, and 150 μL of each culture was transferred to a 96-well black wall, clear bottom plate (Costar). The $A_{600}$ and fluorescence (excitation=485 nm; emission=510 nm; bandwidth of excitation and emission=5 nm) readings from each well were taken using an Infinite M1000 Pro microplate reader (Tecan). Background $A_{600}$ and background fluorescence measurements were taken on wells containing LB media only. The background-subtracted fluorescence value from each well was divided by the background-subtracted $A_{600}$ value of the same well to provide the fluorescence value normalized to cell density. All variants were assayed in at least biological triplicate, and error bars represent the standard deviation of the independent measurements.

Protein Expression and Purification of sfGFP.

Expression of His-tagged sfGFP was performed using the plasmids, cell strains, and antibiotic concentrations described in the methods for sfGFP assays. Saturated overnight cultures were prepared from single colonies of cotransformed cells, which were diluted 1,000-fold into 300 mL of LB media containing 1 mM ncAA where denoted and were grown while shaking at 230 rpm at 37° C. Once the cultures utilizing a pDB070 plasmid grew to a cell density of $A_{600}$=0.3, AARS expression was induced by supplementing with anhydrotetracycline (ATc) to a final concentration of 200 ng/mL, and incubation was continued. Cultures utilizing a pTECH plasmid did not require this step as the AARS was expressed constitutively. Once cultures grew to a cell density of $A_{600}$=0.5, sfGFP expression was induced by supplementation with a final concentration of 1 mM isopropyl-β-D-thiogalactosidase (IPTG) for cultures utilizing a pET28b(+) plasmid or a final concentration of 1 mM arabinose for cultures utilizing a pBAD plasmid. Incubation with shaking at 37° C. continued for an additional 16 h after induction of sfGFP expression. Cells were harvested by centrifugation at 5,000 g for 10 min at 4° C., and the resulting pellets were resuspended in B-PER II Bacterial Protein Extraction Reagent (Thermo Fisher Scientific) containing EDTA-free protease inhibitor cocktail (Roche). The soluble fraction of the cell lysates were diluted by an equal volume of equilibration buffer (20 mM Tris (pH 7.4), 10 mM imidazole, 300 mM NaCl) and were separately loaded onto a column containing 2 mL of HisPur Ni-NTA resin (Thermo Fisher Scientific) that had been pre-washed with two bed-volumes of equilibration buffer. The resin was washed with two bed-volumes of wash buffer (20 mM Tris (pH 7.4), 25 mM imidazole, 300 mM NaCl) and protein was then eluted in 3 mL of elution buffer (20 mM Tris (pH 7.4), 250 mM imidazole, 300 mM NaCl). The purified protein was dialyzed against 20 mM Tris (pH 7.4), 150 mM NaCl, 5 mM EDTA, 1 mM 2-mercaptoethanol (BME), and 10% glycerol. Purified protein was stored at −80° C. until analysis.

AARS Variant Expression and Purification for Aminoacylation Assays.

The genes of chPylRS variants and MjTyrRS variants were cloned into pET15a and transformed into BL21(DE3) (New England Biolabs) cells for expression. Cells were grown in 500 mL of LB media supplemented with 100 m/mL ampicillin at 37° C. to an $A_{600}$ of 0.6-0.8, and protein expression was induced by addition of 0.5 mM IPTG (chPylRS variants) or 1 mM IPTG (MjTyrRS variants). Cells were incubated at 30° C. for an additional 6 h (chPylRS variants) or 4 h (MjTyrRS variants) and harvested by centrifugation at 5,000 g for 10 min at 4° C. The cell pellet was resuspended in 15 mL of lysis buffer (50 mM Tris (pH 7.5), 300 mM NaCl, 20 mM imidazole), and cells were lysed by sonication. The crude extract was centrifuged at 20,000 g for 30 min at 4° C. The soluble fraction was loaded onto a column containing 2 mL of Ni-NTA resin (Qiagen) previously equilibrated with 20 mL of lysis buffer. The column was washed with 20 mL of lysis buffer. The bound protein was then eluted with 2 mL of 50 mM Tris (pH 7.5), 300 mM NaCl, 300 mM imidazole. The purified protein was dialyzed with 50 mM HEPES-KOH (pH 7.5), 50 mM KCl, 1 mM DTT and 50% glycerol and stored at −80° C. for further studies.

Purification of c-Myc-chPylRS-6×His Variants.

The chPylRS variants were cloned into the pTech plasmid using insertion primers that incorporate the N-terminal c-Myc sequence (MEQKLISEEDL-; SEQ ID NO: 3) and the C-terminal 6×His sequence (-GSHHHHHH; SEQ ID NO: 4). BL21 star (DE3) cells (Thermo Fisher Scientific) transformed with the appropriate pTech plasmids were grown in LB media (United States Biologicals) supplemented with 25 μg/mL chloramphenicol. For each variant, a saturated overnight culture was prepared from a single colony, and a 1:100 dilution of culture was made into 5 mL of fresh LB media containing chloramphenicol. The starter culture grew at 37° C. while shaking at 230 rpm until the cell density reached $A_{600}$=0.3. The starter culture was then used to inoculate a 1 L culture of LB media containing chloramphenicol, which continued to incubate while shaking for an additional 16 h. Cells were harvested by centrifugation at 5,000 g for 10 min at 4° C., and cell pellets were resuspended in lysis buffer (20 mM Tris (pH 7.4), 300 mM NaCl, 10 mM imidazole, and EDTA-free protease inhibitor cocktail (Roche)). The cells were lysed by sonication on ice, and the crude extract was centrifuged at 15,000 g for 15 min at 4° C. Lysates were loaded onto columns containing 2 mL of HisPur Ni-NTA resin (Thermo Fisher Scientific) that had been pre-washed with two bed-volumes of equilibration buffer. The resin was washed with 10 bed-volumes of wash buffer (20 mM Tris (pH 7.4), 25 mM imidazole, 300 mM NaCl) and protein was then eluted in 3 mL of elution buffer (20 mM Tris (pH 7.4), 250 mM imidazole, 300 mM NaCl). The purified protein was dialyzed against 20 mM Tris (pH 7.4), 150 mM NaCl, 5 mM EDTA, 1 mM dithiothreitol. Purified protein was stored in 20% glycerol at −80° C. until analysis.

Western Blot Analysis of c-Myc-chPylRS-6×His Variants.

Cell lysates (30 μL) of expressed protein were combined with 25 μL of XT Sample Buffer (Bio-Rad), 5 μL of 2-mercaptoethanol, and 40 μL water. The samples were heated at 70° C. for 10 min and 7.5 μL of prepared sample was loaded per well of a Bolt Bis-Tris Plus Gel (Thermo Fisher Scientific). Precision Plus Protein Dual Color Standard (4 μL) Bio-Rad was used as the reference ladder. The loaded gel was run at 200V for 22 min in 1× Bolt MES SDS running buffer (Thermo Fisher Scientific). The gel was transferred to a PVDF membrane using the iBlot 2 Gel Transfer Device (Thermo Fisher Scientific). The membrane was blocked for 1 h at room temperature in 50% Odyssey blocking buffer (PBS) (Li-Cor) and was then soaked 4 times for 5 min in PBS containing 0.1% Tween-20 (PBST). The blocked membrane was soaked with primary antibodies (rabbit anti-6×His (1:1,000 dilution) (Abcam, ab9108) and mouse anti-c-Myc (1:7,000 dilution) (Sigma-Aldrich, M4439)) in 50% Odyssey buffer (PBS) containing 0.2% Tween-20 for 4 h at room temperature. The membrane was washed four times in PBST, and then soaked for 1 h in the dark at room temperature with secondary antibodies (donkey anti-mouse 800CW (1:20,000 dilution) (Li-Cor) and goat anti-rabbit 680RD (1:20,000 dilution) (Li-Cor)) in Odyssey buffer containing 0.01% SDS, 0.2% Tween-20. The membrane was washed 4 times in PBST and finally rinsed with PBS. The membrane was scanned using an Odyssey Imaging System (Li-Cor).

LCMS Analysis of Intact Purified Proteins.

Purified protein samples were diluted to 10 μM in dialysis buffer lacking reducing agent or glycerol prior to analysis on an Agilent 6220 ESI-TOF mass spectrometer equipped with an Agilent 1260 HPLC. Separation and desalting was performed on an Agilent PLRP-S Column (1,000 A, 4.6×50 mm, 5 μm). Mobile the phase A was 0.1% formic acid in water and mobile phase B was acetonitrile with 0.1% formic acid. A constant flow rate of 0.250 mL/min was used. Ten microliters of the protein solution was injected and washed on the column for the first 3 min at 5% B, diverting non-retained materials to waste. The protein was then eluted using a linear gradient from 5% B to 100% B over 7 min. The mobile phase composition was maintained at 100% B for 5 min and then returned to 5% B over 1 minute. The column was then re-equilibrated at 5% B for the next 4 min. Data was analyzed using Agilent MassHunter Qualitative Analysis software (B.06.00, Build 6.0.633.0 with Bioconfirm). The charge state distribution for the protein produced by electrospray ionization was deconvoluted to neutral charge state using Bioconfirm's implementation of MaxEnt algorithm, giving a measurement of average molecular weight. The average molecular weight of the proteins were predicted using ExPASy Compute pI/Mw tool (http://web-.expasy.org/compute_pi/), and each calculation was adjusted for chromophore maturation in sfGFP and any ncAA substitutions.

Amber Suppressor tRNA Preparation.

Template plasmid containing the $tRNA^{Pyl}$ or $tRNA_{CUA}^{Tyr/Opt}$ gene was purified with the plasmid maxi kit (Qiagen). The plasmid containing $tRNA^{Pyl}$ (100 μg) was digested with BstNI (New England Biolabs). The $tRNA_{CUA}^{Tyr/Opt}$ gene was amplified by PCR. The BstNI digested template DNA or PCR product was purified by phenol chloroform extraction, followed by ethanol precipitation and dissolved in double distilled water. A His-tagged T7 RNA polymerase was purified over a column of Ni-NTA resin according to manufacturer's instructions (Qiagen). The transcription reaction (40 mM Tris (pH 8); 4 mM each of UTP, CTP, GTP, and ATP at pH 7.0; 22 mM $MgCl_2$; 2 mM spermidine; 10 mM DTT; 6 μg pyrophosphatase (Roche Applied Science); 60 m/mL of DNA template, approximately 0.2 mg/mL T7 RNA polymerase) was performed in 10 mL reactions overnight at 37° C. The tRNA was purified on 12% denaturing polyacrylamide gel containing 8 M urea and TBE buffer (90 mM Tris, 90 mM boric acid, 2 mM EDTA). UV shadowing was used to illuminate the pure tRNA band, which was excised and extracted three times with 1M sodium acetate pH 5.3 at 4° C. The tRNA extractions were then ethanol precipitated, dissolved in RNase-free distilled water, pooled, and finally desalted using a Biospin 30 column (BioRad). The tRNA was refolded by heating to 100° C. for 5 min and slow cooling to room temperature. At 65° C., $MgCl_2$ was added to a final concentration of 10 mM to aid folding. A His-tagged CCA adding enzyme was purified over column of Ni-NTA resin according to manufacturer's instructions (Qiagen). 16 μM refolded tRNA in 50 mM Tris (pH 8.0), 20 mM $MgCl_2$, 5 mM DTT, and 50 μM NaPPi was incubated at room temperature for 1 h with approximately 0.2 mg/mL CCA-adding enzyme and 1.6 μCi/μL of (α-$^{32}$P)-labeled ATP (PerkinElmer). The sample was phenol/chloroform extracted and then passed over a Bio-spin 30 column (Bio-Rad) to remove excess ATP.

Aminoacylation Assay.

A 20 μL aminoacylation reaction contained the following components for chPylRS variants: 50 mM HEPES-KOH (pH 7.2), 25 mM KCl, 10 mM $MgCl_2$, 5 mM DTT, 10 mM ATP, 25 μg/mL pyrophosphatase (Roche Applied Science), 10 mM amino acids, 500 nM PylRS variants, 5 μM unlabeled $tRNA^{Pyl}$, and 100 nM $^{32}$P-labeled $tRNA^{Pyl}$. A 20 μL aminoacylation reaction contained the following components for MjTyrRS variants: 50 mM Tris-HCl (pH 7.5), 1 mM DTT, 10 mM $MgCl_2$, 10 mM ATP, 20 μM unlabeled $tRNA_{CUA}^{Tyr/Opt}$, 3 μM $^{32}$P-labeled $tRNA_{CUA}^{Tyr/Opt}$, 2 μM MjTyrRS variants. Various concentrations of ATP (1-100 μM), BocK (0.1-10 mM), Pyl (5-500 Phe (0.1-3.2 mM), p-NF (1-32 mM), p-IF (1-32 mM), and tRNA (0.05-5 μM) were used to determine $K_M$ values for corresponding substrates. Time points were taken at 5 min, 20 min and 60 min by removing 2 μL aliquots from the reaction and immediately quenching the reaction into an ice-cold 3 μL quench solution (0.66 μg/μL nuclease P1 (Sigma) in 100 mM sodium citrate (pH 5.0)). For each reaction, 2 μL of blank reaction mixture (containing no enzyme) was added to the quench solution as the start time point. The nuclease P1 mixture was then incubated at room temperature for 30 min and 1 μL aliquots were spotted on PEI-cellulose plates (Merck) and developed in running buffer containing 5% acetic acid and 100 mM ammonium acetate. Radioactive spots for AMP and AA-AMP (representing free tRNA and aminoacyl-tRNA, respectively) were separated and then visualized and quantified by phosphorimaging using a Molecular Dynamics Storm 860 phosphorimager (Amersham Biosciences). The ratio of aminoacylated tRNA to total tRNA was determined to monitor reaction progress.

Example 2

The development of orthogonal translation systems (OTSs) that allow non-canonical amino acids (ncAAs) to be site-specifically incorporated into recombinant proteins has enabled researchers to dramatically expand the genetic code. More than 200 ncAAs have been installed into designer proteins using OTSs in prokaryotes, eukaryotic cells, and even in whole animals. The most common strategy for genetic code expansion in vivo requires three key components. An unused or rarely used codon (typically the TAG nonsense codon) is placed into a gene's coding sequence at the position(s) of desired ncAA incorporation. An orthogonal tRNA (o-tRNA) that is not recognized by host endogenous aminoacyl-tRNA synthetases (AARSs) decodes the nonsense codon during translation. Lastly, an orthogonal AARS is required, which is typically a variant that researchers have evolved to selectively aminoacylate the o-tRNA, but not endogenous tRNAs, with the target ncAA (FIG. 1). This third component must be generated for each different ncAA of interest, and evolving a tailor-made orthogonal AARS is by far the most challenging and labor-intensive requirement of this strategy.

Although researchers have evolved many AARSs to incorporate ncAAs into proteins, several outstanding challenges limit their utility and generality. Laboratory evolution of AARSs with altered amino acid specificity typically relies on three to five rounds of sequential positive and negative selections from an AARS library containing either partially or fully randomized residues in the amino acid-binding pocket. The limited number of rounds of selection typically conducted in AARS evolution campaigns reflects the effort required to complete each round of evolution, which is on the order of one week or longer. A consequence of conducting relatively few rounds of selection on libraries that focus mutagenesis on and around the amino acid-binding pocket is that laboratory-evolved AARSs routinely emerge with sub-optimal properties, for example ~1,000-fold reduced activity ($k_{cat}/K_M$) compared to their wild-type counterparts, and modest selectivity for the target ncAA over endogenous amino acids that can require compensation with high concentrations of ncAA and expression in minimal media, lowering protein yields. The modest enzymatic efficiency and selectivity of many laboratory-evolved AARSs are longstanding challenges that limit the production and purity of expressed proteins containing ncAAs.

This example describes phage-assisted continuous evolution (PACE) selections that enable the laboratory evolution of orthogonal AARSs over hundreds of generations of mutation, selection, and replication on practical time scales. AARS PACE was performed over 268 generations to evolve pyrrolysyl-tRNA synthetase (PylRS) variants that acquired up to a 45-fold improvement in enzymatic efficiency ($k_{cat}/K_M^{tRNA}$) compared to the parent PylRS. The enabling mutations from PACE were also successfully transplanted into other PylRS variants without requiring further evolution, resulting in up to 9.7-fold higher expression of ncAA-containing protein when introduced into a previously reported PylRS-derived synthetase, AcK3RS. Interestingly, PACE also gave rise to unexpected mutations that split PylRS into mutually dependent N- and C-terminal fragments that maintained high activity and specificity when co-expressed, mimicking naturally occurring split PylRS homologs. In addition, a promiscuous mutant *Methanocaldococcus jannaschii* tyrosyl-tRNA synthetase (MjTyrRS) was evolved into a variant with >23-fold higher selectivity for the desired amino acid, p-iodo-L-phenylalanine, over the undesired substrate, p-nitro-L-phenylalanine, in 48 h of PACE. Together, these results establish a rapid and effective approach to improve the catalytic efficiency and alter the amino acid specificity of AARS enzymes.

Development of a positive PACE selection for AARS activity. PACE has enabled the rapid laboratory evolution of diverse classes of proteins including polymerases, proteases, genome-editing agents, and insecticidal proteins. Two strategies by which aminoacylation of an orthogonal amber suppressor tRNA would induce pIII production through amber suppression are described. In the first strategy, amber suppression of premature stop codons in the T7 RNA polymerase (T7 RNAP) gene allows translation of full-length T7 RNAP, which transcribes gene III from an upstream T7 promoter. This approach results in pIII production in an amplified manner since each amber suppression event can give rise to many gene III transcripts. In the second, more stringent strategy, amber suppression of premature stop codons in gene III results in direct translation of full-length pIII without amplification (FIGS. 2A-2C).

Figure 4A:
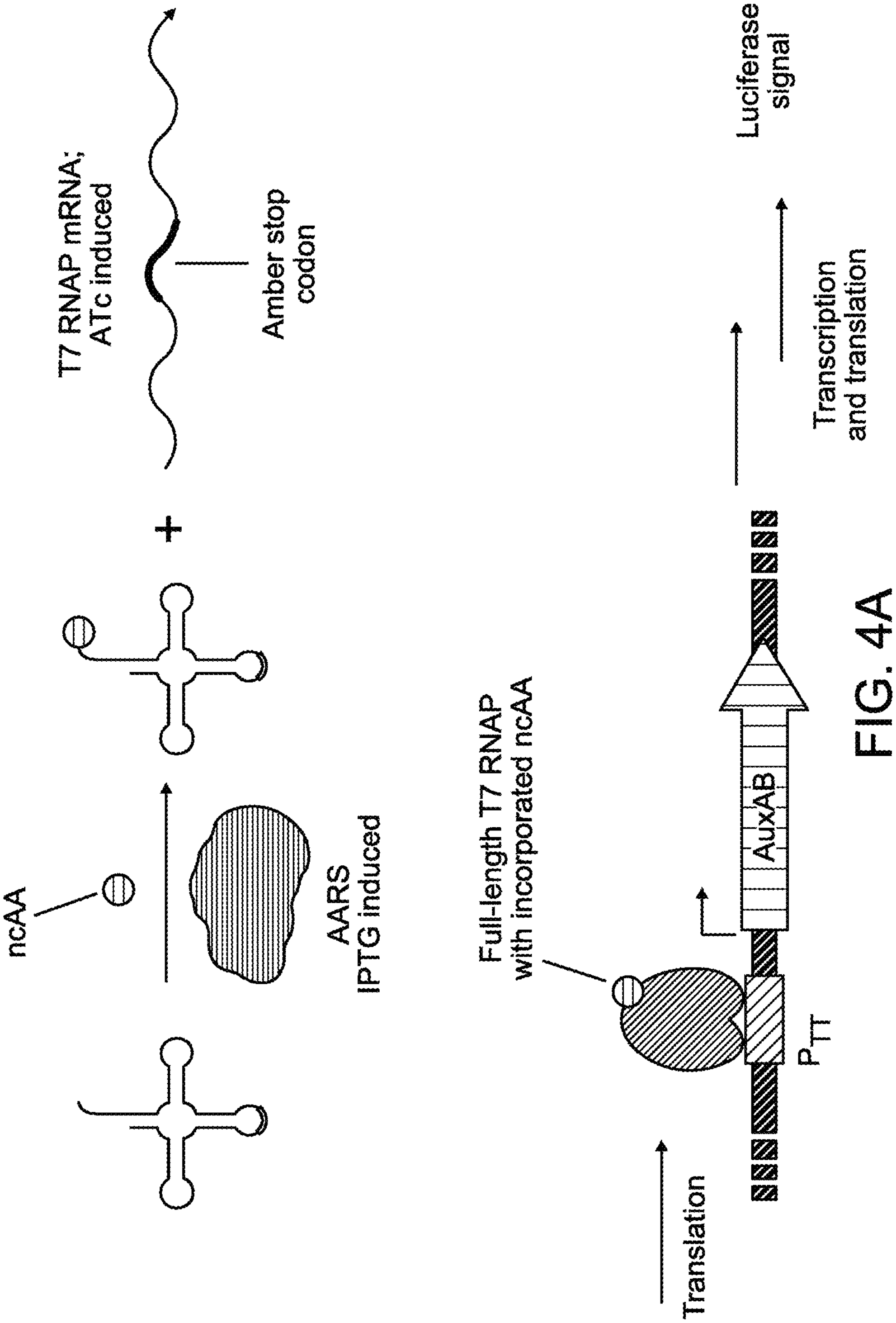
FIGS. 4A-4C show optimization of the T7 RNAP-mediated PACE positive selection for aminoacylation. Two amber stop codons in T7 RNAP are required to make reporter expression completely dependent on orthogonal translation of full-length T7 RNAP.
Figure 4B:
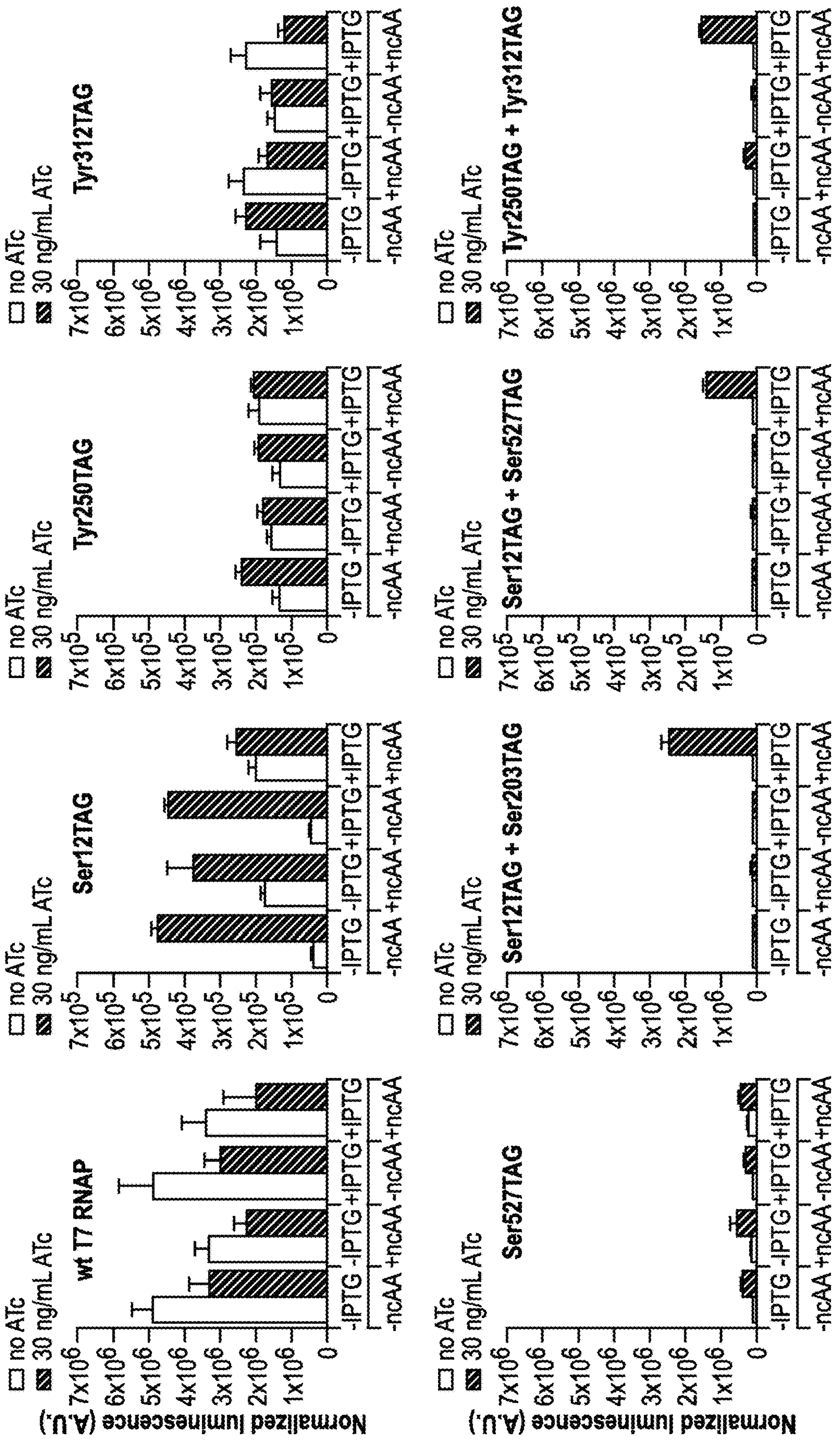
Figure 4C:
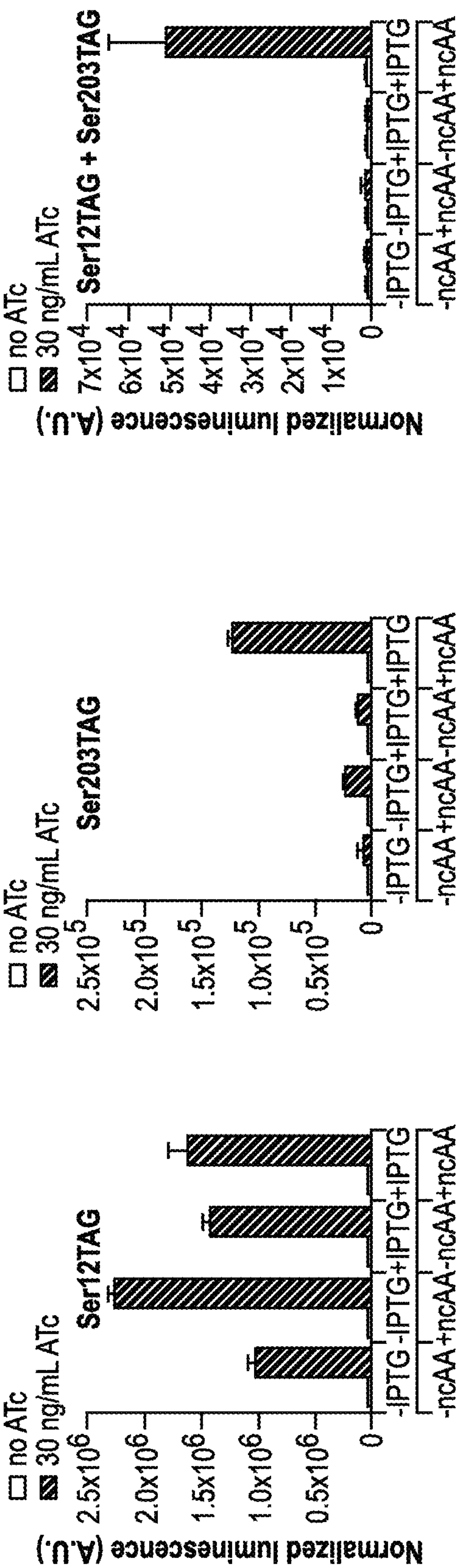

To implement the first selection strategy, permissive residues in T7 RNAP that would not inhibit enzymatic activity when mutated to a wide variety of amino acids were identified. The number of amber codons are needed in the T7 RNAP gene to make full-length translation of the polymerase completely dependent on orthogonal translation was also identified. Amber mutations were installed in the T7 RNAP gene at Ser-12, Ser-203, Tyr-250, Tyr-312, and Ser-527, positions predicted from the crystal structure that avoid perturbation of RNA polymerization or DNA binding. Suppression with p-nitro-L-phenylalanine (p-NF) (FIG. 3) at combinations of these sites using a previously evolved MjTyrRS variant (p-NFRS) revealed that a minimum of two amber stop codons were required for transcriptional activation by T7 RNAP to become fully dependent on both the AARS and the ncAA substrate (FIGS. 4A-4B). Similar results were observed with site-specific installation of Nε-(tert-butoxycarbonyl)-L-lysine (BocK) using a chimeric PylRS (chPylRS), comprising residues 1-149 of *Methanosarcina barkeri* PylRS (MbPylRS) and residues 185-454 of *Methanosarcina mazei* PylRS (MmPylRS) (FIG. 4C).

Figure 5A:
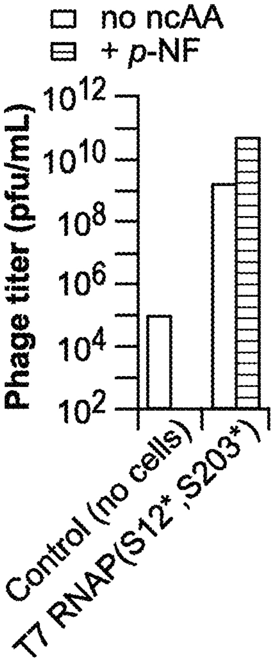
FIGS. 5A-5D show non-continuous propagation of SP in positive selections designed for PACE. To confirm activity dependence of phage propagation for each of the two positive selections (suppression of stop codons in T7 RNAP or in gene III), phage titers resulting from 16 h of propagation in batch culture were compared for SP expressing p-NFRS (FIG. 5A, FIG. 5C) or chPylRS (FIG. 5B, FIG. 5D). In each experiment, equal amounts of SP encoding the AARS of interest were used to infect cultures of S1030 host cells harboring the required PACE AP and CP plasmids in the presence or absence of the ncAA. Controls representing the starting titers for each set of experiments were prepared by diluting the same amount of SP into media lacking cells. Results indicate that selection stringency increases as the number of stop codons is increased in T7 RNAP (FIGS. 5A-5B) or gIII (FIGS. 5C-5D).
Figure 5B:
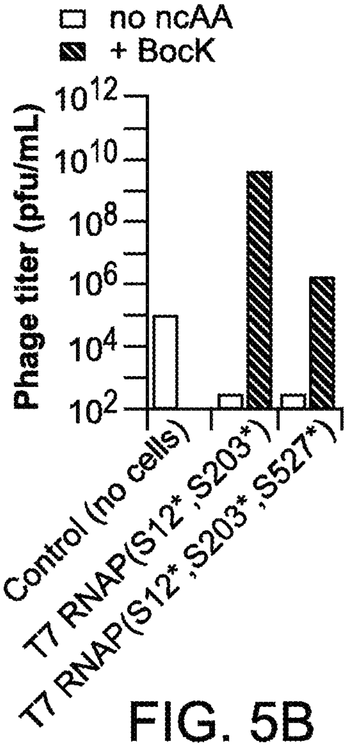

To test the ability of this selection to support phage propagation, selection phage (SP) expressing either p-NFRS (SP-p-NFRS) or chPylRS (SP-chPylRS) were propagated non-continuously in cultures of host *E. coli* cells harboring an accessory plasmid (AP) and complementary plasmid (CP) that together expressed the requisite amber suppressor tRNA, T7 RNAP(S12TAG, S203TAG), and gene III downstream of a T7 promoter. It was observed that SP propagation in these cultures was dependent on the presence of a matched ncAA substrate (FIGS. 5A-5B). Together, these results validate the PACE selection strategy based on amplified expression of gene III through amber suppression of two or more stop codons in T7 RNAP.

Figure 5C:
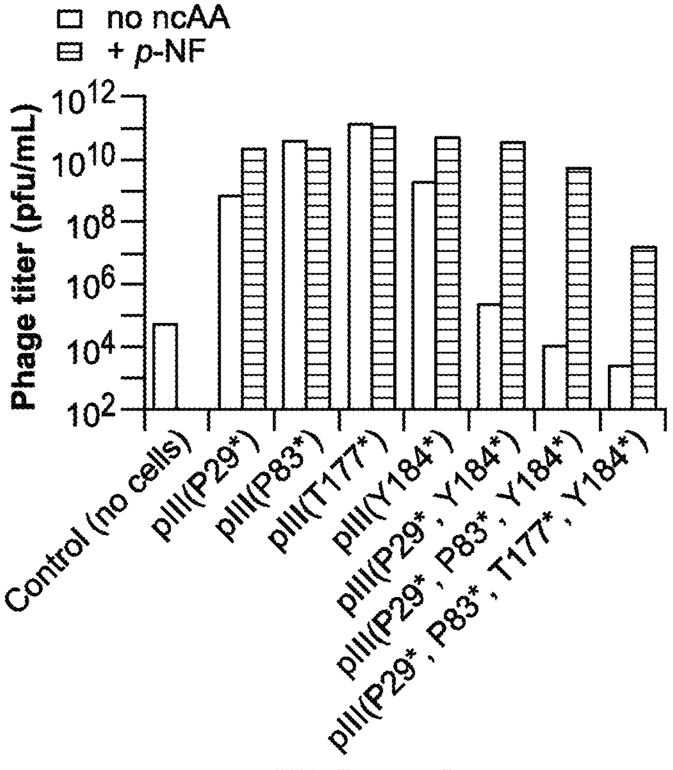
Figure 5D:
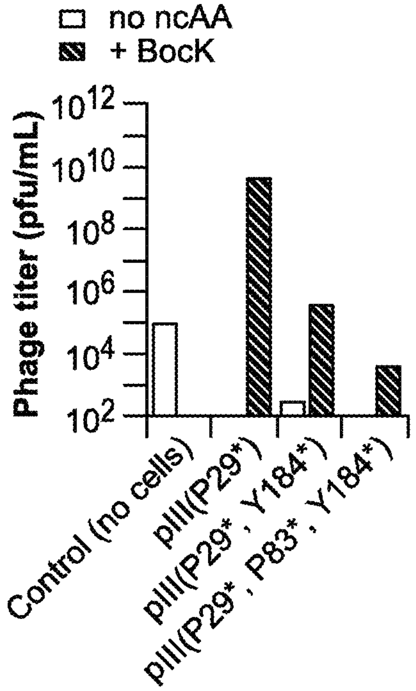

To implement the second, more stringent selection strategy based on direct amber suppression of premature stop codons in gene III, amber mutations were installed at positions Pro-29, Pro-83, Thr-177, or Tyr-184 of gene III. These residues were chosen because they are predicted to be uninvolved in pIII binding to the host cell TolA protein or to the host cell F pilus. The N-terminal signal peptide of pIII, which spans residues 1-18, was not targeted for amber suppression as this region is required for insertion of pIII into the host inner membrane. The ability of this selection to support phage propagation was investigated by challenging selection phage expressing either p-NFRS (SP-p-NFRS) or chPylRS (SP-chPylRS) to propagate non-continuously in cultures of host *E. coli* cells harboring an accessory plasmid that expressed the requisite amber suppressor tRNA and gene III containing one or more premature stop codons. It was observed that each of the mutated positions in pIII were permissive to ncAA incorporation, and the presence of a single premature stop codon in the coding sequence of pIII was sufficient to make robust phage propagation dependent on AARS activity from SP-p-NFRS or SP-chPylRS (FIGS. 5C-5D). Collectively, these developments identify positions in T7 RNAP and pIII that tolerate a range of amino acid side chains, and thereby establish two strategies to link AARS activity to phage infectivity through amber suppression of premature stop codons in T7 RNAP or in gene III.

Figure 6A:
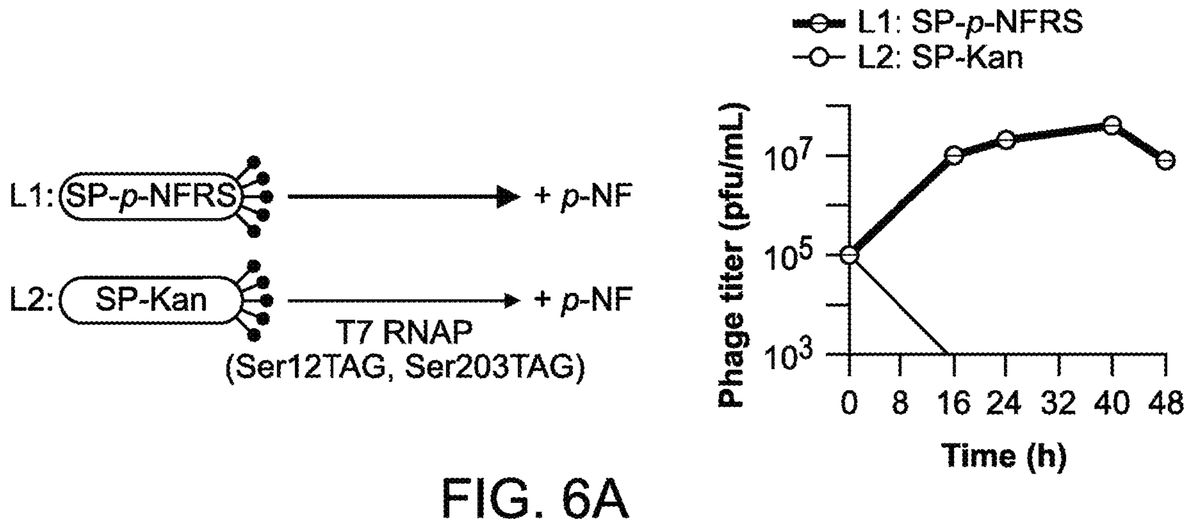
FIGS. 6A-6B show positive selections for aminoacylation support activity-dependent, continuous propagation in PACE.
Figure 6B:
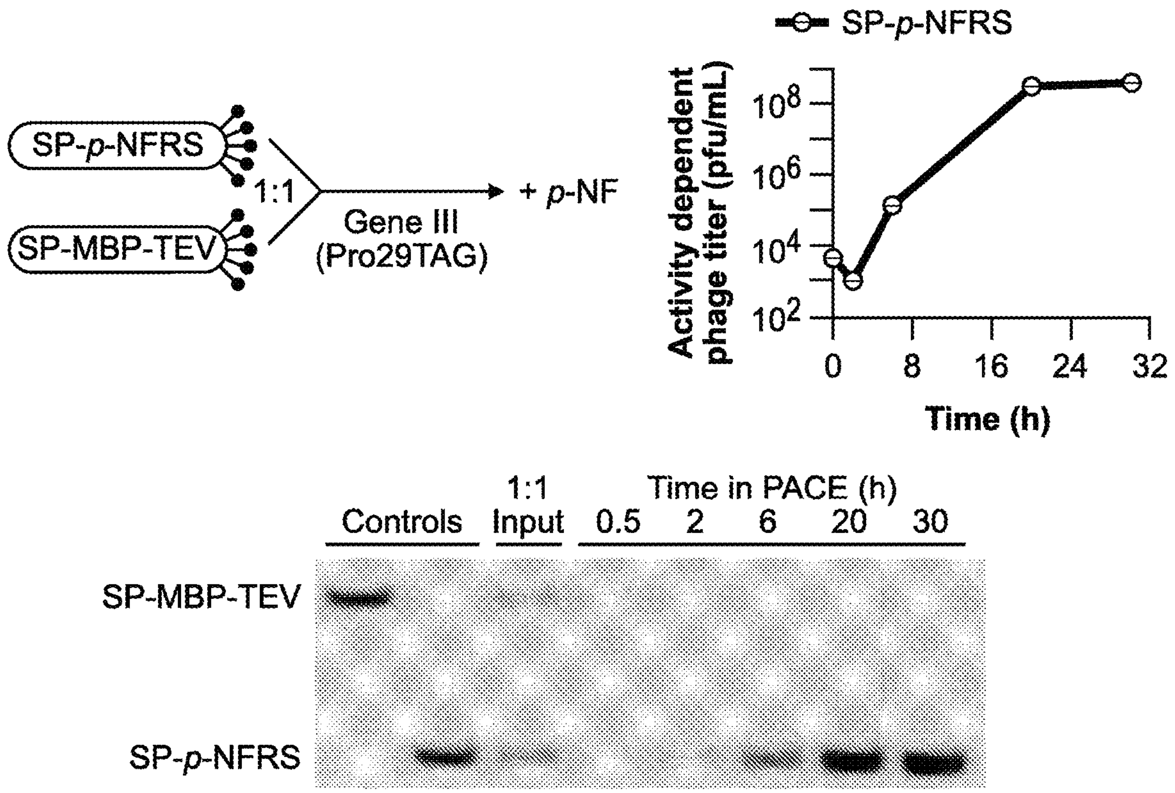

Next, whether PACE positive selection for aminoacylation based on amber suppression of stop codons in T7 RNAP could support activity-dependent phage propagation in the continuous flow format of PACE was investigated. 48-h mock PACE selections were conducted. It was observed that SP-p-NFRS propagated at high phage titer levels in a lagoon supplemented with p-NF substrate without further adaptation. In a separate control lagoon, SP expressing a kanamycin resistance gene rather than an AARS were unable to propagate in the positive selection and rapidly washed out (FIG. 6A). It was also observed that the PACE positive selection based on direct amber suppression of stop codons in gene III supported activity-dependent phage propagation in continuous flow. In a single, 30-h mock PACE using this selection strategy, active SP-p-NFRS was highly enriched starting from a 1:1 input-mixture of SP-p-NFRS and an SP expressing an unrelated gene (FIG. 6B). Together, these results confirmed that both selection strategies were capable of supporting phage propagation in PACE in a manner dependent on orthogonal AARS activity.

Figure 7A:
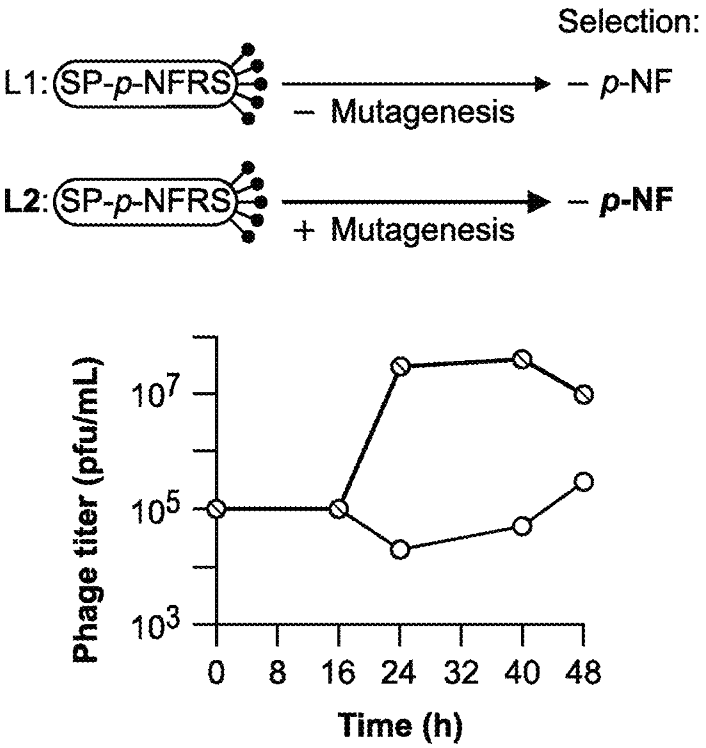
FIGS. 7A-7B show evolution of AARS activity during mock PACE.
Figure 7B:
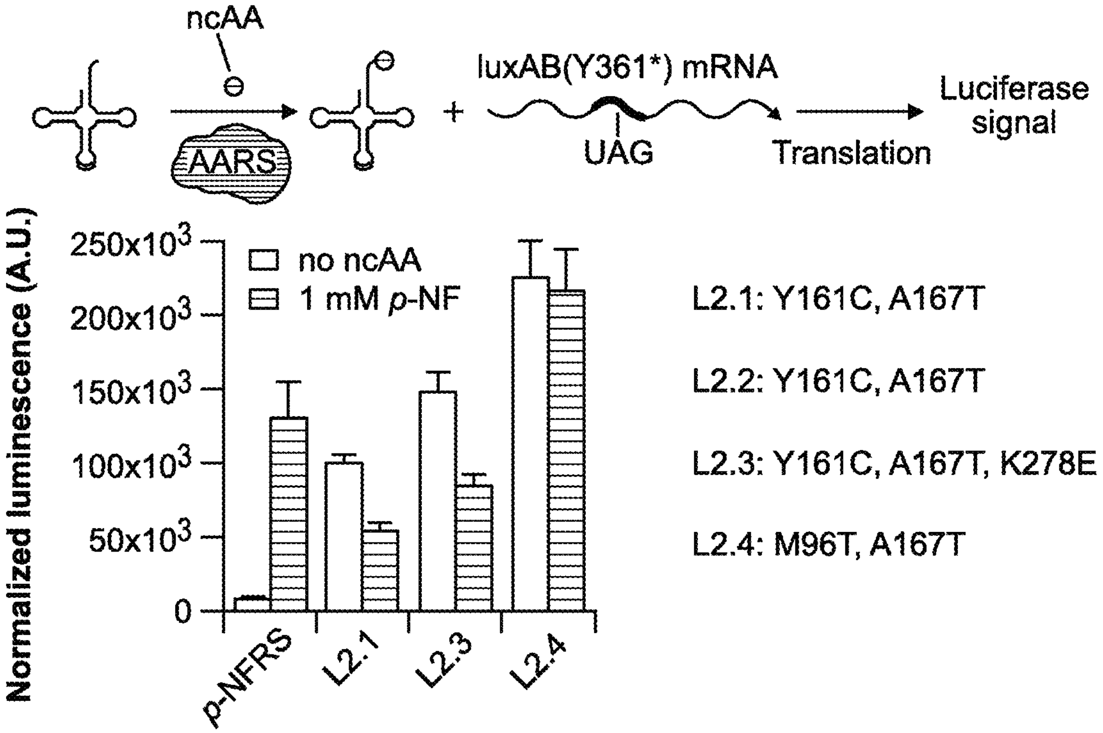

To demonstrate that an AARS with little or no starting activity on a target amino acid could evolve new activity to propagate in the positive selection, an additional mock PACE experiment in which SP-p-NFRS was challenged to evolve acceptance of endogenous amino acids was performed by propagating the phage in Davis rich media (DRM) that was not supplemented with p-NF using the selection requiring amber suppression of stop codons in T7 RNAP. Under these conditions, high titers of SP-p-NFRS were dependent on induction of a mutagenesis plasmid (MP), MP4, that enhances the rate of mutagenesis in the host *E. coli* (FIG. 7A). This observation indicates that mutation of the AARS was required in order for SP to propagate when the cognate amino acid substrate was unavailable. Sanger sequencing analysis of clonal phage from the experiments confirmed that more mutations accumulated in the gene encoding p-NFRS when MP4 was induced. Additionally, the evolved mutants, but not the starting p-NFRS, displayed strong aminoacylation activity in the absence of p-NF using a luciferase reporter of amber suppression (FIG. 7B), confirming that the AARS evolved to accept one or more canonical amino acids during PACE. Together, results of these experiments validated the positive selection for continuously evolving an orthogonal AARS.

Figure 8A:
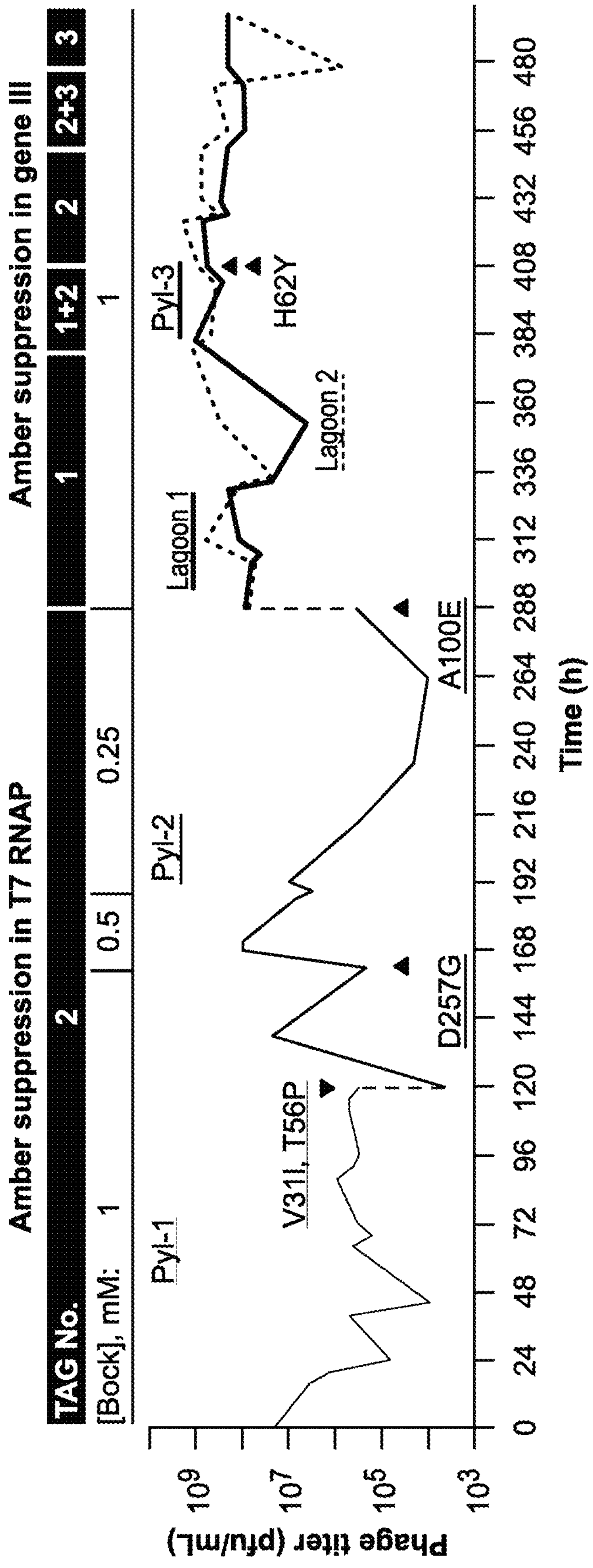
FIGS. 8A-8E show continuous evolution and characterization of chimeric pyrrolysyl-tRNA synthetase (chPylRS) variants with enhanced aminoacylation activity.

Continuous evolution of catalytically enhanced PylRS variants. PylRS from archaebacteria are preferred evolutionary starting points for genetic code expansion efforts due to their tRNA orthogonality in a range of hosts. Wild-type PylRS variants, however, are generally hampered by poor catalytic efficiency, which is typically further diminished as an undesired consequence of traditional laboratory evolution.

chPylRS—the chimera of residues 1-149 of MbPylRS and residues 185-454 of MmPylRS—was evolved to have improved aminoacylation activity over 497 h of PACE in three segments (FIG. 8A). The PylRS substrate analog, BocK, was used in the evolution of PylRS rather than the natural cognate substrate, L-pyrrolysine, which is not readily available. In the first two segments of PACE (Pyl-1 and Pyl-2), SP-chPylRS was evolved using the less stringent selection requiring amber suppression of T7 RNAP. During Pyl-1, the flow rate was modulated to increase selection stringency. The pool of phage surviving Pyl-1 was further evolved in Pyl-2, which challenged SP-chPylRS to propagate as the ncAA substrate concentration was incrementally reduced. The final PACE segment, Pyl-3, was conducted in two lagoons using the more stringent selection strategy, and the number of amber stop codons in gene III was incrementally increased from one to three to increase demands on PylRS efficiency. This approach gradually increased selection stringency over the 497-h evolution of chPylRS, and emerging variants had survived on average 268 generations of mutation, selection, and replication.

Clonal SP isolates from the 120-h endpoint of Pyl-1 were sequenced and revealed mutations throughout the PylRS gene with strong convergence toward a pair of mutations in PylRS: V31I and T56P. Sequencing of clonal isolates from the second PACE segment (Pyl-2) revealed strong convergence toward D257G at 162 h, and full convergence on A100E by the end of Pyl-2 (288 h). The additionally stringent conditions of the Pyl-3 segment selected for complete convergence toward mutation H62Y in all sequenced clones from 408 h of PACE (Tables 3-6).

TABLE 3

Summary of mutations observed in PACE segment Pyl-1

| chPylRS | Pyl-1.120.1-8 | | | | | | | |
|---|---|---|---|---|---|---|---|---|
| Residue | 1 | 2 | 3 | 4 | 5 | 6 | 7 | 8 |
| D7 | | | A | | | | | |
| V31 | I | I | I | I | F | I | I | I |

TABLE 3-continued

Summary of mutations observed in PACE segment Pyl-1

| chPylRS | Pyl-1.120.1-8 | | | | | | | |
|---|---|---|---|---|---|---|---|---|
| Residue | 1 | 2 | 3 | 4 | 5 | 6 | 7 | 8 |
| 41A | | | | | | E | | |
| T56 | P | P | P | P | | | P | P |
| A100 | | T | | | | | | |
| S127 | P | | | P | | | | |
| A152 | V | | | | | | | |
| D257 | | G | | | | | | |
| G343 | | D | | | | | | |

Mutations in chPylRS from the Pyl-1 segment were determined by Sanger sequencing of eight clonal SP isolates from 120 h of total PACE. Only coding mutations are shown. Shaded mutations were shown to be responsible for enhancing the activity of chPylRS.

TABLE 4

Summary of mutations observed in PACE segment Pyl-2

| chPylRS | Pyl-2.162.1-5 | | | | | Pyl-2.189.1-5 | | | | | Pyl-2.288.1-5 | | | | |
|---|---|---|---|---|---|---|---|---|---|---|---|---|---|---|---|
| Residue | 1 | 2 | 3 | 4 | 5 | 1 | 2 | 3 | 4 | 5 | 1 | 2 | 3 | 4 | 5 |
| D2 | | | | | | | | | | | | | | | E |
| D7 | E | | | | | | | | | | | | | | |
| A12 | | | | | | G | | | | | | | | | |
| V31 | | I | I | I | I | I | I | I | I | I | I | I | I | I | I |
| T56 | | P | P | P | P | P | P | P | P | P | P | P | P | P | P |
| H62 | | | | | | | Y | | | | | | | | |
| E77 | | | | | | K | | | | | | | | | |
| T91 | S | | | | | | | | | | | | | | |
| A100 | | | | | | | | | | | E | E | E | E | E |
| K104 | | | | | | | | | | | | | | E | |
| R113 | | H | | | | | | | | | | | | | |
| L118 | | | | | | M | | | | | | | | | |
| A150 | | V | | | | | | | | | | | | | |
| R217 | | | | | | | | | S | | | | | | |
| D257 | | G | G | G | G | | G | G | G | G | G | G | G | G | G |
| N259 | | | | S | | | | S | | | | | | | |
| L266 | | | | | | | | I | | | | | I | | |
| P282 | | | | | | | | S | | | | | | | |
| I327 | | | | | M | | M | | | | | | | | |
| G336 | | | | | | | | | | | E | | | | |
| D338 | | | | | | | E | | | | | | | | |

Mutations in chPylRS from the Pyl-2 segment were determined by Sanger sequencing of five clonal SP isolates from 162 h, 189 h, and 288 h of total PACE. Only coding mutations are shown. Shaded mutations were shown to be responsible for enhancing the activity of chPylRS.

TABLE 5

Summary of mutations observed in lagoon 1 of PACE segment Pyl-3

| chPylRS | Pyl-3-L1.408.1-8 | | | | | | | | Pyl-3-L1.450.1-8 | | | | | | | | Pyl-3-L1.497.1-8 | | | | | | | |
|---|---|---|---|---|---|---|---|---|---|---|---|---|---|---|---|---|---|---|---|---|---|---|---|---|
| Residue | 1 | 2 | 3 | 4 | 5 | 6 | 7 | 8 | 1 | 2 | 3 | 4 | 5 | 6 | 7 | 8 | 1 | 2 | 3 | 4 | 5 | 6 | 7 | 8 |
| V31 | I | I | I | I | I | I | I | I | I | I | I | I | I | I | I | I | I | I | I | I | I | I | I | I |
| T56 | P | P | P | P | P | P | P | P | P | P | P | P | P | P | P | P | P | P | P | P | P | P | P | P |
| H62 | Y | Y | Y | Y | Y | Y | Y | Y | Y | Y | Y | Y | Y | Y | Y | Y | Y | Y | Y | Y | Y | Y | Y | Y |
| K90 | | | | | | | | | | | | | | | | | | | | | | | | |
| V97 | | | | | | | | | | | | | | | | | | A | | | A | | | A |
| S99 | | | | | | | | | | | | L | | L | | | | L | L | L | L | | L | L |
| A100 | E | E | E | E | E | E | E | E | E | E | E | S | E | S | E | E | E | S | S | S | S | | S | S |
| P101 | | | | | | | | | | | | R | | R | | | | R | R | R | R | | R | R |
| V103 | | | | | | | | | | | | * | | * | | | | * | * | * | * | | * | * |
| K104 | | E | | | | | | | | | | | | | | | | | | | | | | |
| A106 | | | T | | | | | | | | | | | | | | | | | | | | | |
| M107 | | | | | | | | | | | | M' | | M' | | | | M' | M' | M' | M' | | M' | M' |
| V111 | | | | | | | | | | | | | | | | | I | | | | | G | | |
| A114 | | | | | | | | | | | | | | | | | | | T | | | | | |
| V122 | | | | | | | | | | | | | | | | | | | | | | G | | |
| V134 | I | | | | | | | | | | | | | | | | | | | | | | | |
| K157 | | R | | | | | | | | | | | | | | | | | | | | | | |

TABLE 5-continued

Summary of mutations observed in lagoon 1 of PACE segment Pyl-3

| chPylRS | Pyl-3-L1.408.1-8 | | | | | | | | Pyl-3-L1.450.1-8 | | | | | | | | Pyl-3-L1.497.1-8 | | | | | | | |
|---|---|---|---|---|---|---|---|---|---|---|---|---|---|---|---|---|---|---|---|---|---|---|---|---|
| Residue | 1 | 2 | 3 | 4 | 5 | 6 | 7 | 8 | 1 | 2 | 3 | 4 | 5 | 6 | 7 | 8 | 1 | 2 | 3 | 4 | 5 | 6 | 7 | 8 |
| S156 | | | | | | | | | | | | | | | | | | | | | | R | | |
| E203 | | | | | | D | | | | | | | | | | | | | | | | | | |
| Y207 | | S | | | | | | | | | | | | | | | | | F | | | | | |
| K251 | | | | | | | | | | | | | | | | R | | | | | | | | |
| D257 | G | G | G | G | G | G | G | G | G | G | G | G | G | G | G | G | G | G | G | G | G | G | G | G |
| N259 | | S | | | | | | | | | | | | | | | | | | | | | | |
| F260 | | | S | | | | | | | | | | | | | | | | | | | | | |
| L266 | | | | | | | | | | | | | | | | | | | | | | | I | |
| N323 | | | | | | | | | | | | | | | | S | | | | | | | | |
| S326 | | | | | | | | | | | | I | | I | | | | I | I | I | V | I | I | I |
| H334 | | T | | | | | | | | | | | | | | | | | | | | | | |
| L335 | | W | | | | | | | | | | | | | | | | | | | | | | |
| D351 | | | | | E | | | | | | | | | | | | | | | | | | | |
| K396 | | | | | | | | | | | Q | | | | | | | | | | | | | |
| K403 | | | | | | | | | | | | | | | R | | | | | | | | | |
| A405 | | | | | | | | | | | | | | | | V | | | | | | | | |
| A406 | | | | | | | | | | | | | | | | | | | S | | | | | |

Mutations in chPylRS from lagoon 1 (L1) of the Pyl-3 segment were determined by Sanger sequencing of eight clonal SP isolates from 408 h, 450 h, and 497 h of total PACE. Only coding mutations are shown. Shaded mutations were shown to be responsible for enhancing the activity of chPylRS. Mutations denoted by a star indicate stop codons that resulted in split-protein variants in which translation reinitiates at the position corresponding to Met-107 of chPylRS (M').

TABLE 6

Summary of mutations observed in lagoon 2 of PACE segment Pyl-3

| chPylRS | Pyl3-L2.408.1-8 | | | | | | | | Pyl3-L2.450.1-8 | | | | | | | | Pyl3-L2.497.1-8 | | | | | | | |
|---|---|---|---|---|---|---|---|---|---|---|---|---|---|---|---|---|---|---|---|---|---|---|---|---|
| Residue | 1 | 2 | 3 | 4 | 5 | 6 | 7 | 8 | 1 | 2 | 3 | 4 | 5 | 6 | 7 | 8 | 1 | 2 | 3 | 4 | 5 | 6 | 7 | 8 |
| V8 | | | | | | | | | G | | | | | | | G | | | | | | | | |
| T20 | | | | | | | P | | | P | | | | | | | | | | | P | | P | |
| I26 | | | | V | | | | | | | | | | | | | | | | | | | | |
| H28 | | | | | | | | | | | | | | | | Y | | | | | | | | |
| V31 | I | I | I | I | I | I | I | I | I | I | I | I | I | I | I | I | I | I | I | I | I | I | I | I |
| D44 | | | | | | | | | | | | | | | | | | | | | | G | | |
| H45 | | | | | | | | | R | | | | | | | | | | | | | | | |
| S53 | | | | | | F | | | | | | | | | | | | | | | | | | |
| T56 | P | P | P | P | P | P | P | P | P | P | P | P | P | P | P | P | P | P | P | P | P | P | P | P |
| A59 | | | | | T | | | | | | | | | | | | | | | | | | | |
| H62 | Y | Y | Y | Y | Y | Y | Y | Y | Y | Y | Y | Y | Y | Y | Y | Y | Y | Y | Y | Y | Y | Y | Y | Y |
| R73 | | | | | | | | | | | | | | | | | H | | | | | | | |
| D78 | | | | | | | | | | | | | | | | | | | | E | | | | |
| N80 | | | | | | | | | | | | | | | D | | | | | | | | | |
| T91 | | | | | | | | | A | | | | | | | | | | | | | | | |
| S92 | | | | | | | | | | | | | | | | | L | | | | | | | |
| V93 | | | | | | | | | | | | | | | | | C | | | | | | | |
| K94 | | | | | | | | | | | | | | | | | * | | | | | | | |
| S99 | | | | | | | | | | | | | F | | | | | L | F | | L | | | L |
| A100 | E | E | E | E | E | E | E | E | E | E | E | E | * | E | E | E | | S | * | E | E | S | E | S |
| P101 | | | | | | | | R | | | | | | | | | | R | | | R | R | R | R |
| V103 | | | | | | | | * | | | | | | | | | | * | | | * | * | * | * |
| M107 | | | | | | | | M' | | | | | M' | | | | M' | M' | M' | | M' | M' | M' | M' |
| S112 | | | | | | | | | | | | P | | | | | | | | | | | | |
| E119 | | | | | | | | | | | | | | | | | | | | G | | | | |
| N120 | | | | | | | | | | | | | | | | | | | | | Y | | Y | |
| A126 | | | | | | | | T | | | | | | | | | | | | | T | | T | |
| T130 | | | | | | | | | | P | | | | | | | | | | | | | | |
| N143 | | | K | | | | | | | | | | | | | | | | | | | | | |
| P147 | | | | | | | | | | | | | | | | | | L | | | | | | L |
| P153 | | | | | | | | | | | | | | | | | | V | | | | | | V |
| P234 | | | | | | | | | | | | | | | | | | S | | | | | | S |
| E236 | | | | | | | | G | | | | | | | | | | | | | G | | G | |
| D257 | G | G | G | G | G | G | G | G | G | G | G | G | G | G | G | G | G | G | G | G | G | G | G | G |
| K258 | | | | | | | | | | | | | | E | | | | | | | | | | |
| R321 | | | | | | | | | | | | | | | | | W | | | | | | | |
| S326 | | | | | | | | | | | N | | | | | | | | | | | | | |
| G343 | | | | | | D | | | | | | | | | | | | | | | | | | |
| V367 | | | | | | | | | | | | | | | | | | | I | | | | | |
| I378 | | | | | | | | | | | | | | | | | | | V | | | | | |

TABLE 6-continued

| Summary of mutations observed in lagoon 2 of PACE segment Pyl-3 | | | | | | | | | | | | | | | | | | | | | | | | |
|---|---|---|---|---|---|---|---|---|---|---|---|---|---|---|---|---|---|---|---|---|---|---|---|---|
| chPylRS | Pyl3-L2.408.1-8 | | | | | | | | Pyl3-L2.450.1-8 | | | | | | | | Pyl3-L2.497.1-8 | | | | | | | |
| Residue | 1 | 2 | 3 | 4 | 5 | 6 | 7 | 8 | 1 | 2 | 3 | 4 | 5 | 6 | 7 | 8 | 1 | 2 | 3 | 4 | 5 | 6 | 7 | 8 |
| D379 | | | | | | | | | | | | | N | | | | | | N | | | | | |
| A406 | | | | | | | | | | | | | | | | | | | | | | S | | |

Mutations in chPylRS from lagoon 2 (L2) of the Pyl-3 segment were determined by Sanger sequencing of eight clonal SP isolates from 408 h, 450 h, and 497 h of total PACE. Only coding mutations are shown. Shaded mutations were shown to be responsible for enhancing the activity of chPylRS. Mutations denoted by a star indicate stop codons that resulted in split-protein variants in which translation reinitiates at the position corresponding to Met-107 of chPylRS (M').

Figure 8B:
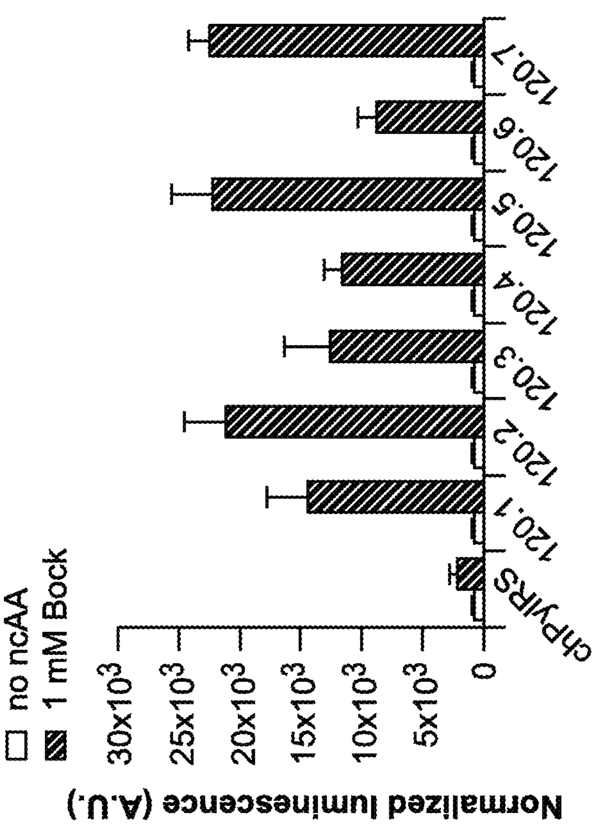
Figure 8C:
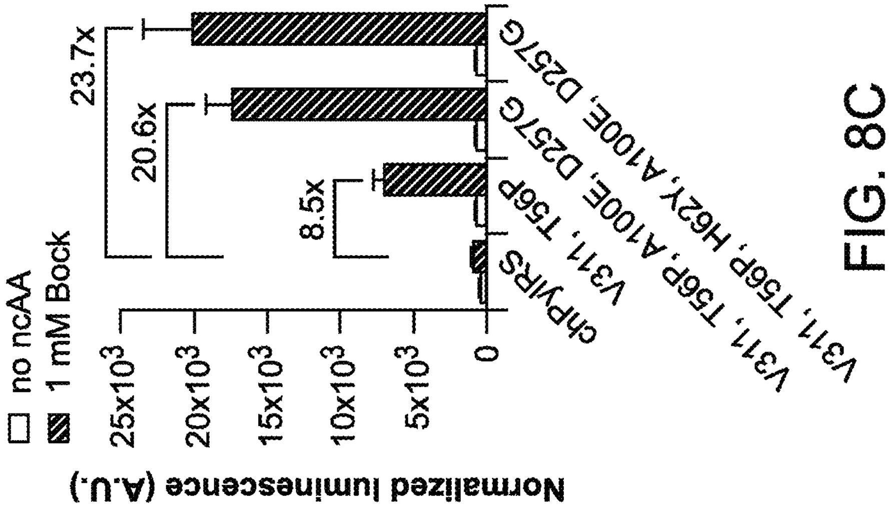
Figure 9A:
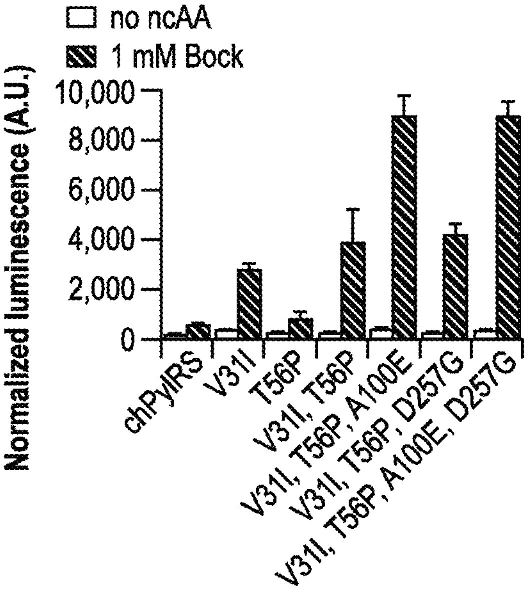
FIGS. 9A-9F show mutations emerging from PACE enhance the activity of PylRS variants on their target ncAA.

Each of the Pyl-1 variants exhibited improved aminoacylation activity in a luciferase reporter of amber suppression with BocK (FIG. 8B). Comparison of the consensus mutations acquired in each segment of PACE showed that the two combined mutations from Pyl-1 increased luciferase signal 8.5-fold compared to the progenitor chPylRS, and the additional two mutations from Pyl-2 improved amber suppression signal 21-fold. The variant containing all consensus mutations from the three segments of PACE provided 24-fold improved amber suppression signal compared to chPylRS while maintaining substrate specificity (FIG. 8C). Further analysis of the consensus mutations acquired in the first two segments of PACE demonstrated that D257G did not significantly contribute to enhance the activity of chPylRS (FIG. 9A). Therefore, the tetramutant comprising V31I, T56P, H62Y, and A100E was responsible for the large improvement in apparent activity.

BocK was incorporated at up to three positions in sfGFP to compare the relative activity of chPylRS to the tetramutant variant, chPylRS(IPYE), containing the activity-enhancing mutations from PACE (FIG. 8D and FIGS. 10A-10D). Expression of sfGFP containing three BocK residues was improved nearly 4-fold by chPylRS(IPYE) compared to chPylRS. Biochemical characterization of chPylRS(IPYE) using BocK confirmed that the $k_{cat}$ improved 8.7-fold, and the $K_M$ for $tRNA^{Pyl}$ substrate improved 5.7-fold, such that the catalytic efficiency ($k_{cat}/K_M^{tRNA}$) of the evolved variant was enhanced 45-fold compared to chPylRS (Table 7). These findings indicate that the increased apparent activity of the tetramutant results from catalytic enhancement of chPylRS, rather than solely from non-catalytic improvements such as enhanced protein expression or stability. The outcome of these experiments demonstrates that PACE positive selection is highly effective at improving the activity of an AARS commonly used for genetic code expansion.

TABLE 7

| Kinetic parameters of chPylRS variants containing mutations from PACE. | | | | | | |
|---|---|---|---|---|---|---|
| PylRS variant | $k_{cat}$, $s^{-1}$ × $10^{-3}$ | $K_M^{ATP}$, μM | $K_M^{tRNA}$, μM | $K_M^{bocK}$, mM | $k_{cat}/K_M^{tRNA}$, $\mu M^{-1} \cdot s^{-1}$ × $10^{-3}$ | Relative catalytic efficiency |
| chPylRS | 11.88 ± 0.18 | 2.54 ± 0.16 | 0.26 ± 0.07 | 1.03 ± 0.05 | 45.69 | 1 |
| V31I, T56P | 73.15 ± 1.01 | 5.74 ± 0.20 | 0.10 ± 0.02 | 0.82 ± 0.18 | 731.50 | 15.9 |
| V31P, T56P, A100E | 110.23 ± 4.65 | 3.45 ± 1.19 | 0.13 ± 0.03 | 0.91 ± 0.08 | 847.92 | 18.4 |
| V31P, T56P, H62Y, A100E | 103.87 ± 2.37 | 3.96 ± 0.52 | 0.05 ± 0.01 | 1.13 ± 0.23 | 2,077.40 | 45.2 |

Figure 8E:
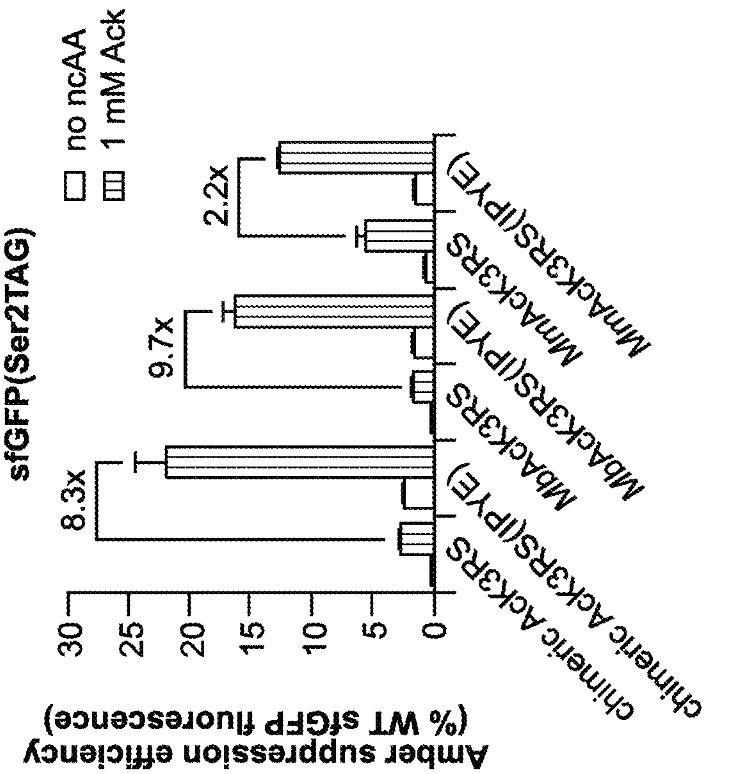
Figure 8D:
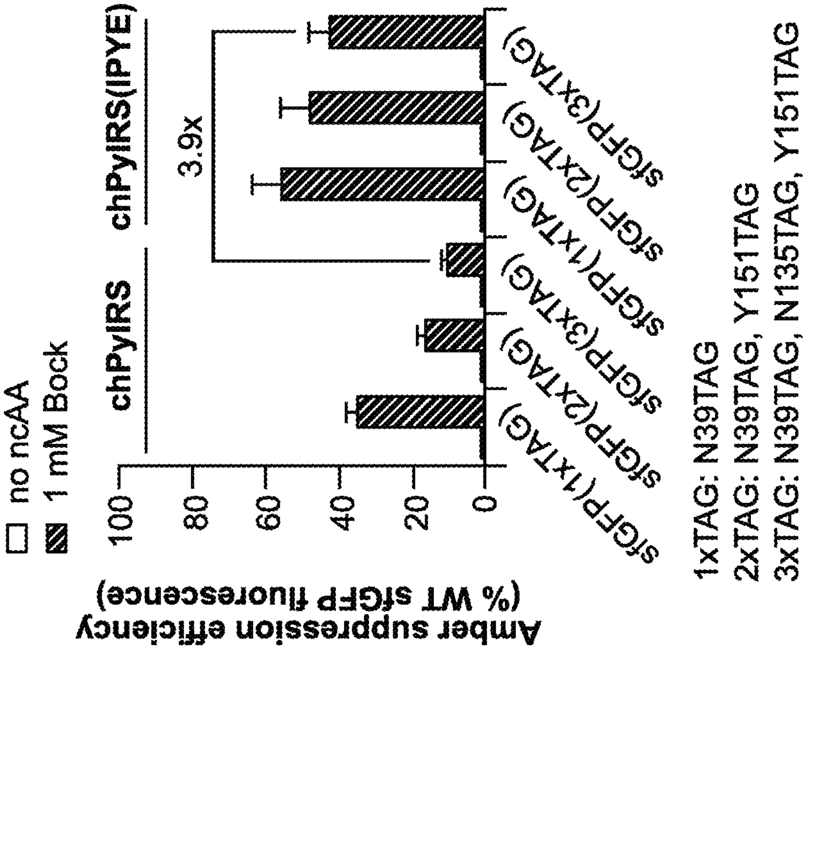
Figure 9B:
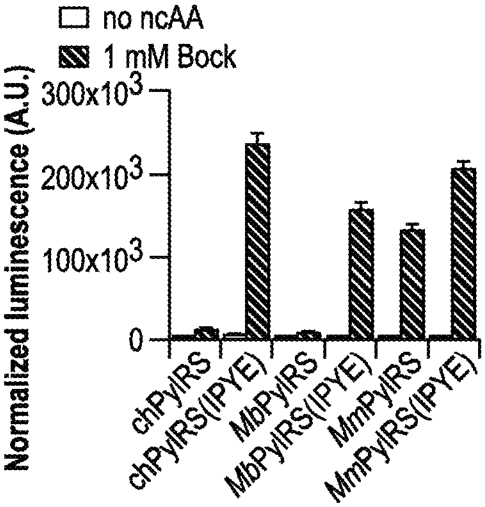
Figure 9C:
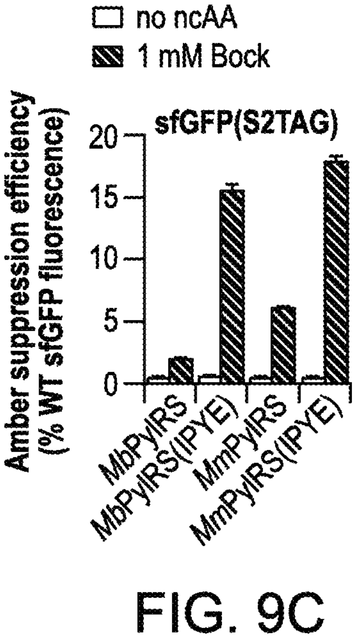
Figure 9D:
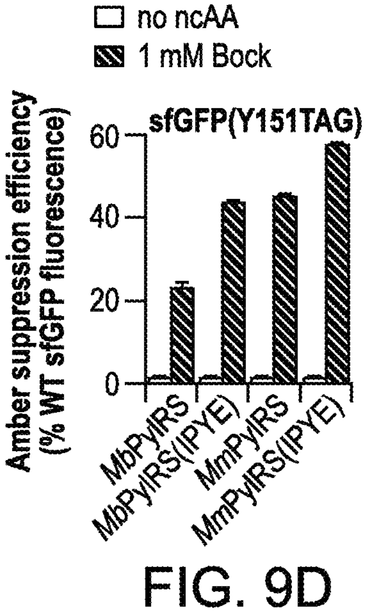
Figure 9E:
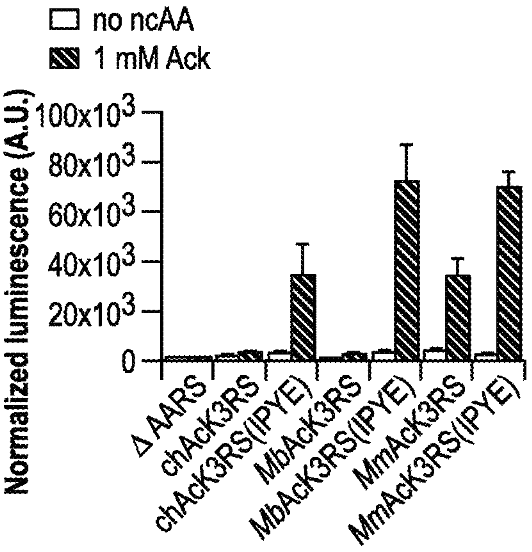
Figure 9F:
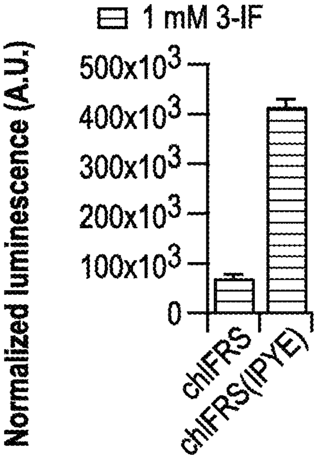
Figure 10A:
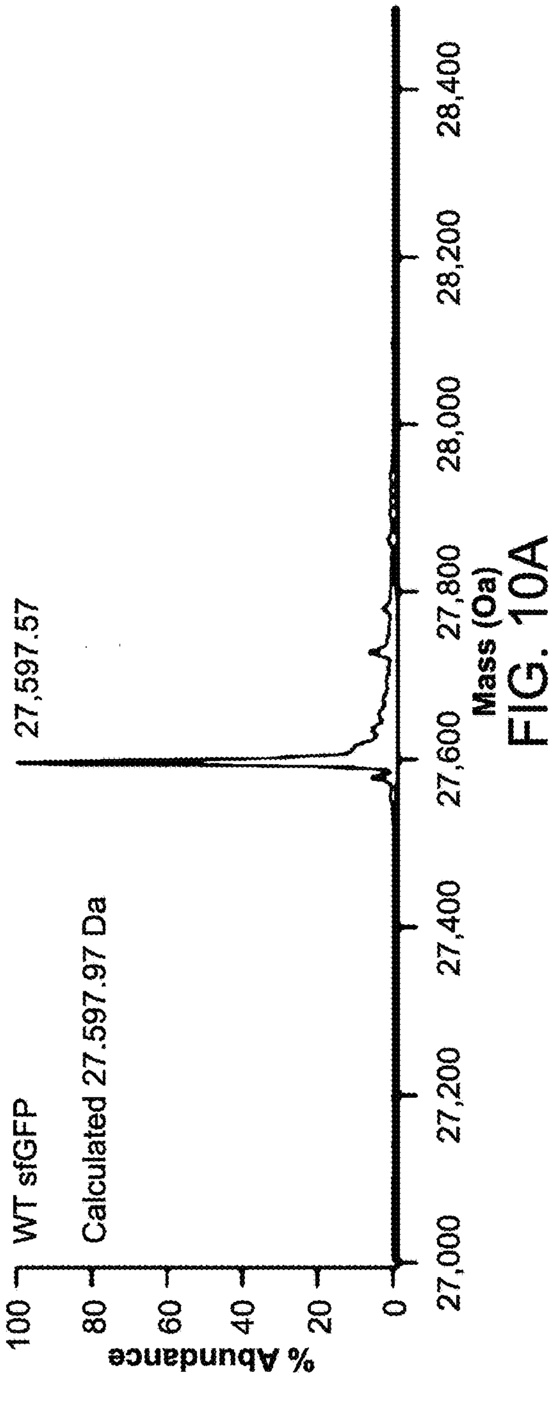
FIGS. 10A-10D show ESI-MS analysis of purified sfGFP containing up to three BocK residues produced by chPylRS (IPYE). Analysis of purified wild type sfGFP (FIG. 10A) or sfGFP containing one (FIG. 10B), two (FIG. 10C) or three (FIG. 10D) BocK residues produced by chPylRS(IPYE) in the presence of 1 mM ncAA. BocK substitutions in sfGFP were made in response to premature amber stop codons at positions 39 (1×TAG), 39 and 151 (2×TAG), or 39, 135, and 151 (3×TAG). Protein was expressed in TOP10 cells in LB media. The major peak in each of the spectra was in agreement with the calculated mass of BocK incorporation. In each of the spectra containing BocK, a minor peak corresponding to an unclipped N-terminal methionine was also observed (calculated mass+131.19 Da).
Figure 10B:
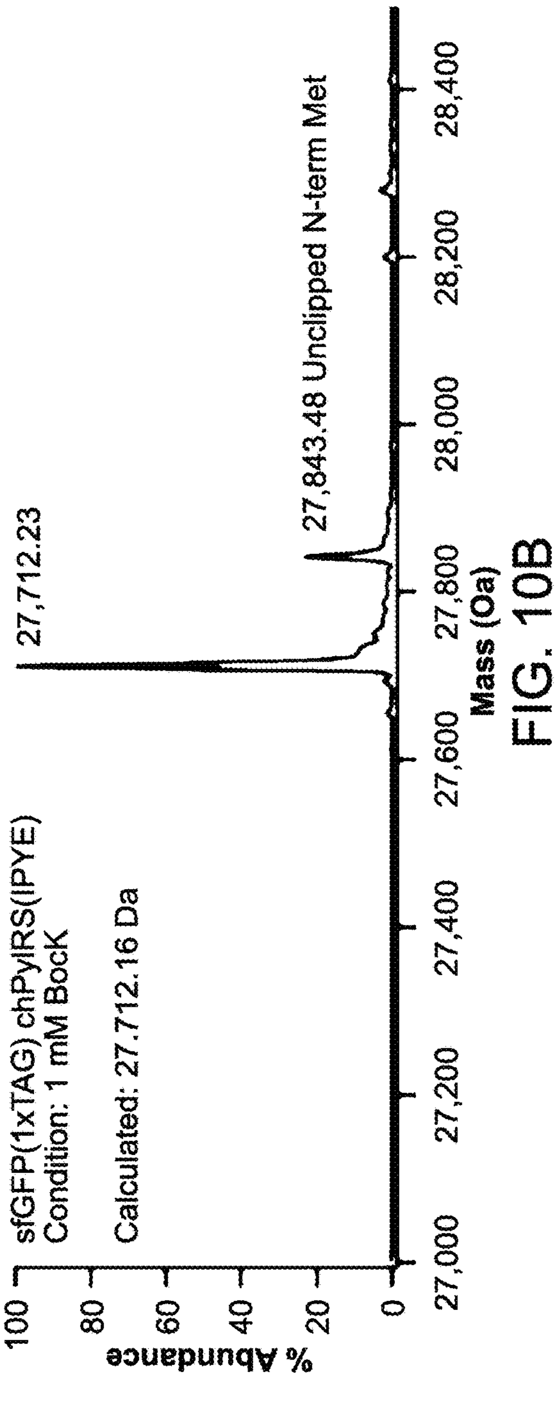
Figure 10C:
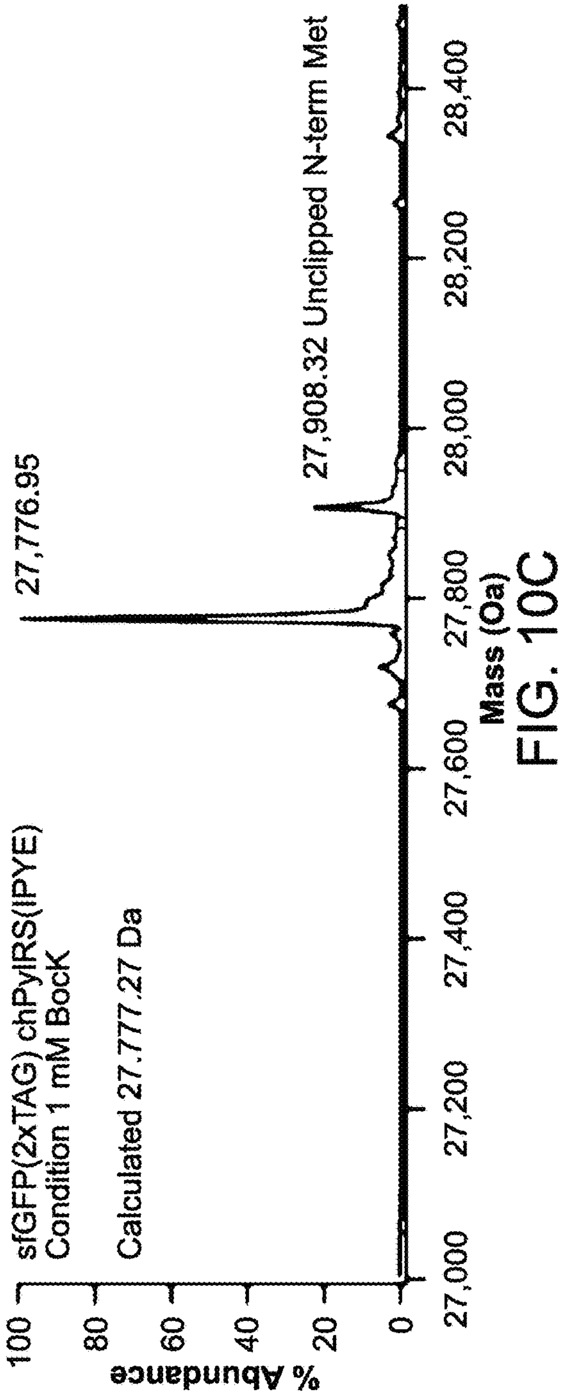
Figure 10D:
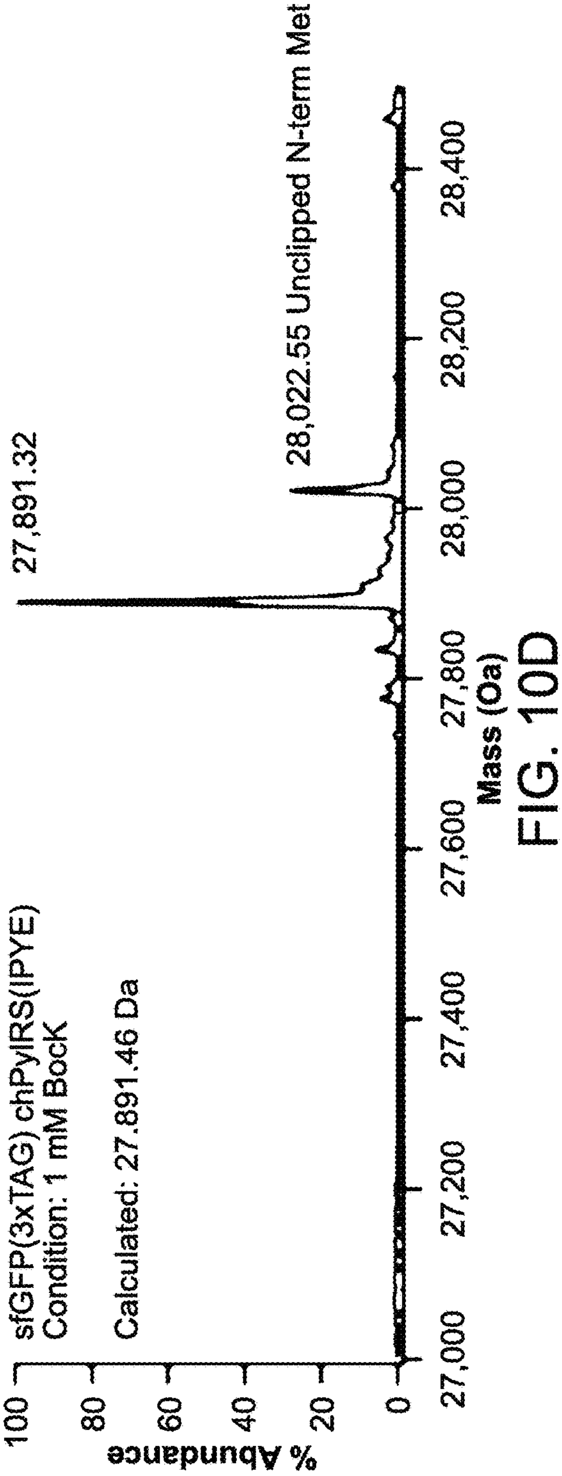
Figure 11:
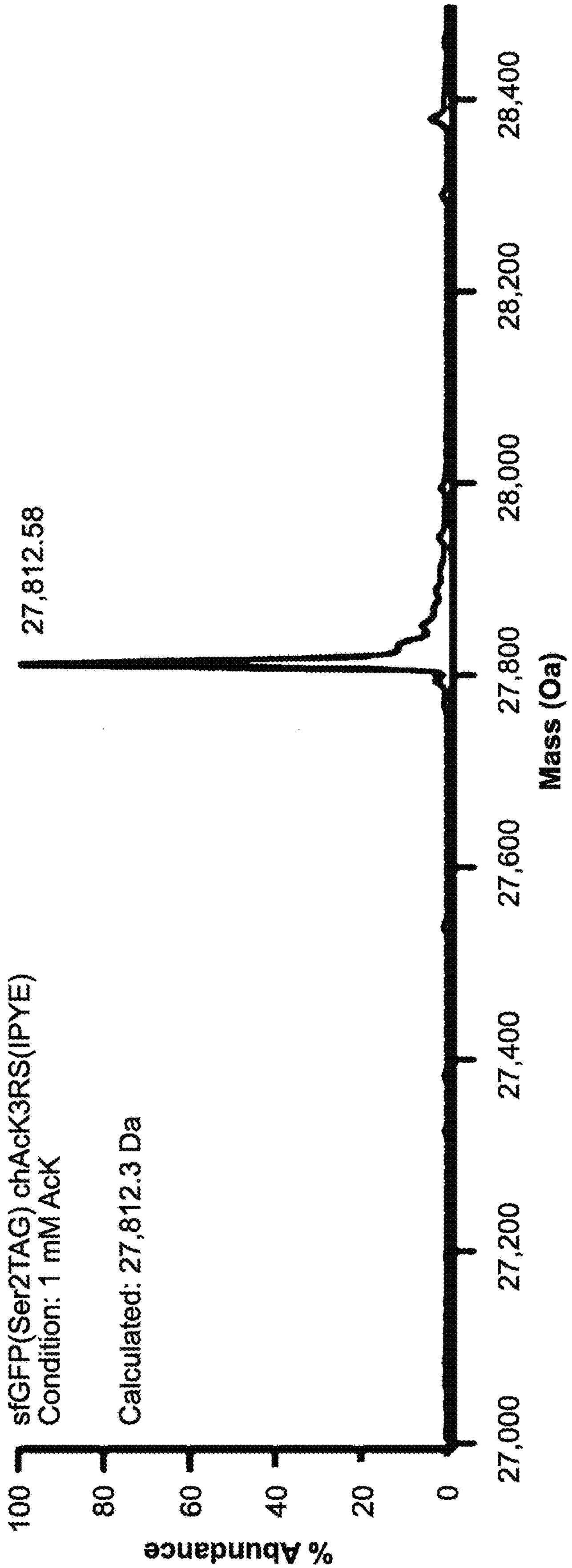
FIG. 11 shows ESI-MS analysis of purified sfGFP containing an AcK residue at position 2 produced by chAcK3RS (IPYE) in the presence of 1 mM AcK. Protein was expressed in TOP10 cells in LB media, and the major peak at found at 27,812.58 Da was in agreement with the calculated value (27,812.3 Da).

The activity-enhancing coding mutations discovered through PACE were localized exclusively in the N-terminal domain of chPylRS, which is involved in tRNA binding and is typically not targeted for mutagenesis in traditional laboratory evolution efforts. These changes occur at positions conserved in MbPylRS and MmPylRS, and in some embodiments, the PACE mutations may generally improve the activity of other natural and engineered PylRS homologs. Amber suppression assays using several different reporters demonstrated that the activity of the MbPylRS(IPYE) variant was dramatically enhanced while the MmPylRS(IPYE) variant was also improved, albeit more modestly (FIGS. 9B-9D). To test whether the beneficial mutations also enhance evolved PylRS enzymes, the four PACE-derived mutations were transplanted into AcK3RS, which was previously evolved to accept Nε-acetyl-L-lysine (AcK). MbAcK3RS, MmAcK3RS, and chimeric AcK3RS (chAcK3RS) variants containing the four mutations each exhibited increased expression of reporter proteins up to 9.7-fold compared to their unmodified PylRS counterparts, without sacrificing amino acid selectivity (FIG. 8E and FIGS. 9E and 11). Reporter expression was also enhanced more than 5-fold when the mutations were transplanted into the PylRS-derived IFRS, which was previously evolved to charge 3-iodo-L-phenylalanine (3-IF) (FIG. 9F). Collectively, these results show that the beneficial mutations discovered exclusively in the N-terminal domain of chPylRS substantially enhance activity in all six additional PylRS variants tested.

Unexpected Evolution of Split PylRS Enzymes

Figure 12A:
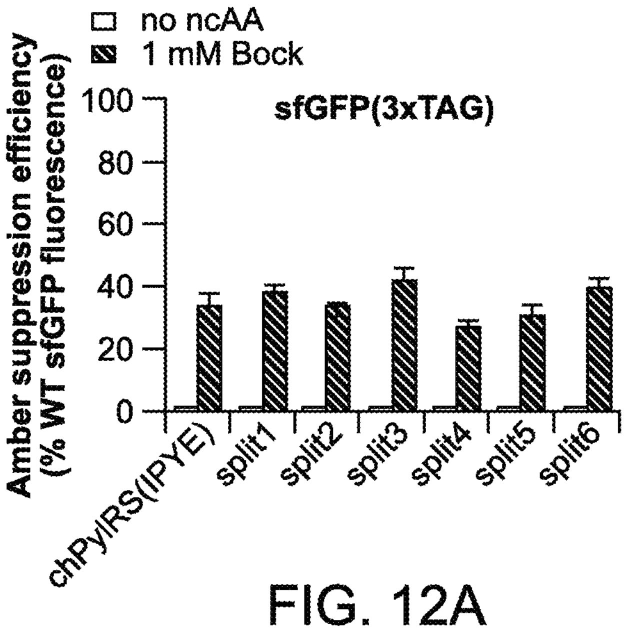
FIGS. 12A-12C show characterization of split variants of chPylRS emerging from PACE. Evolved split variants of chPylRS require the 'IPYE' tetramutation to retain high activity. Aminoacylation is dependent on both the N- and C-terminal fragments of the chPylRS variants shown.
Figure 12B:
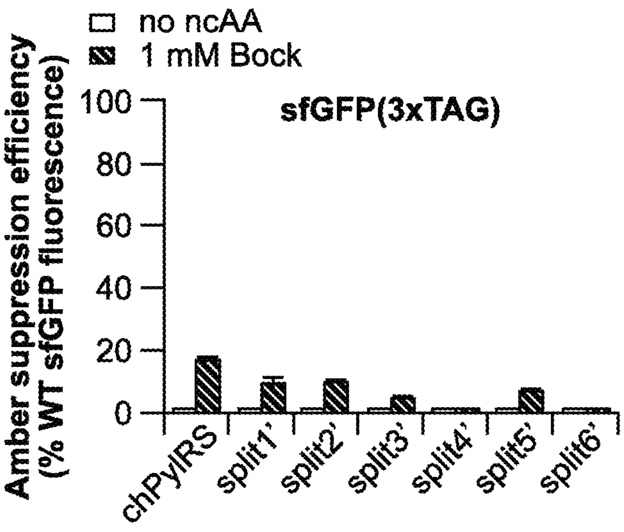
Figure 12C:
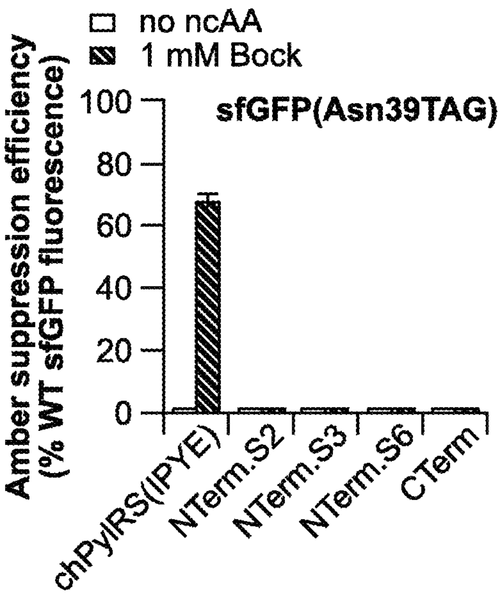
Figure 13:
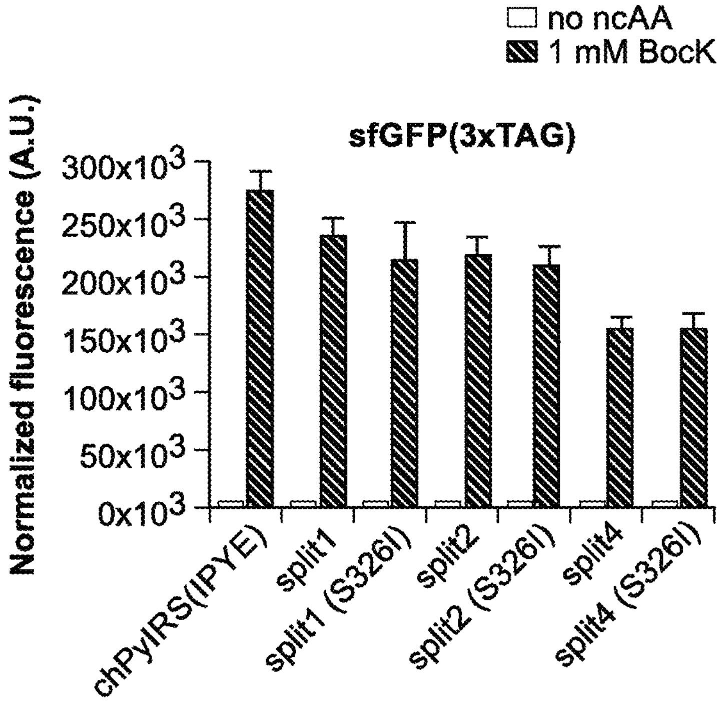
FIG. 13 shows characterization of the S326I mutation emerging from lagoon 2 during the Pyl-3 segment of PACE. The relative activity of split1, split2, and split3 containing the additional mutation, S326I, were compared to variants lacking the mutation and to the full-length chPylRS(IPYE). Each variant was used to produce sfGFP(3×TAG) containing three premature stop codons at positions 39, 135, and 151. Each value and error bar represents the s.d. of four independent biological replicates.
Figure 14A:
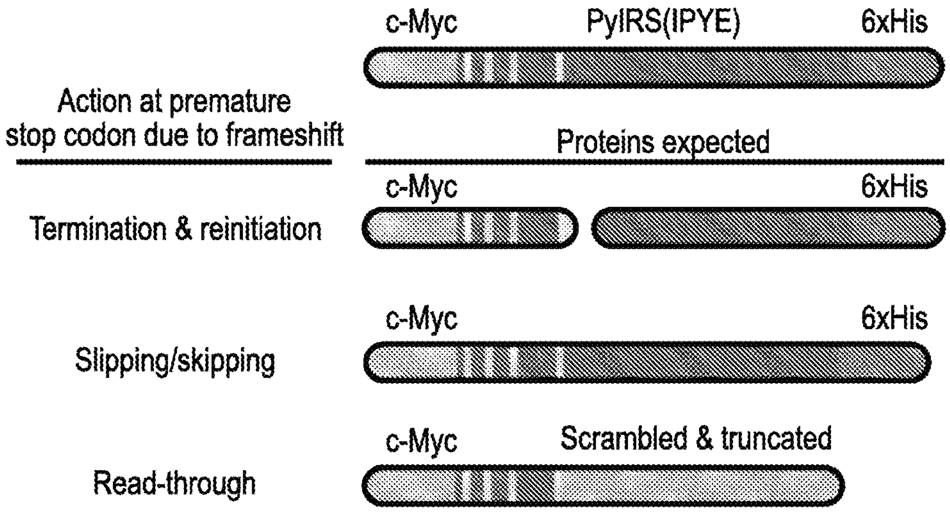
FIGS. 14A-14B show Western blot analysis of full-length and split chPylRS variants from PACE.
Figure 14B:
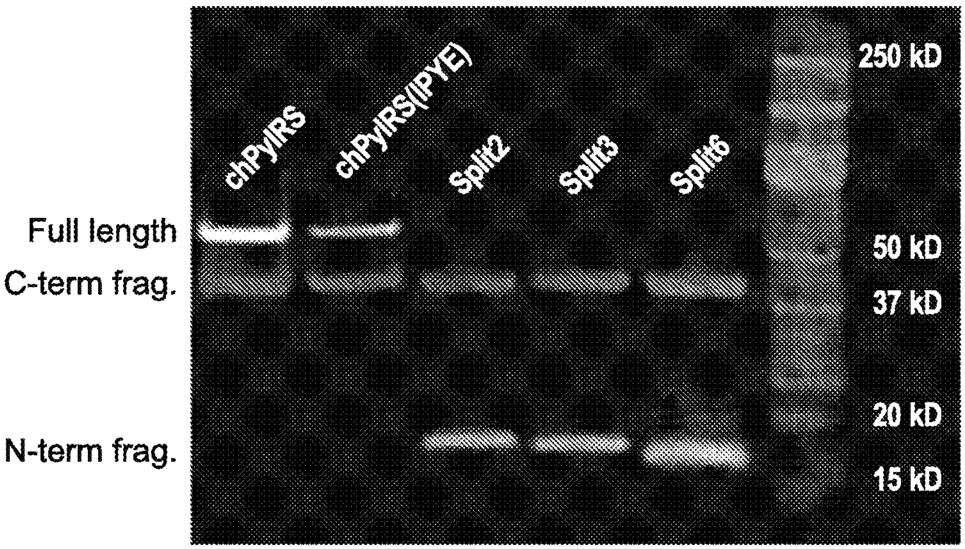
Figure 15A:
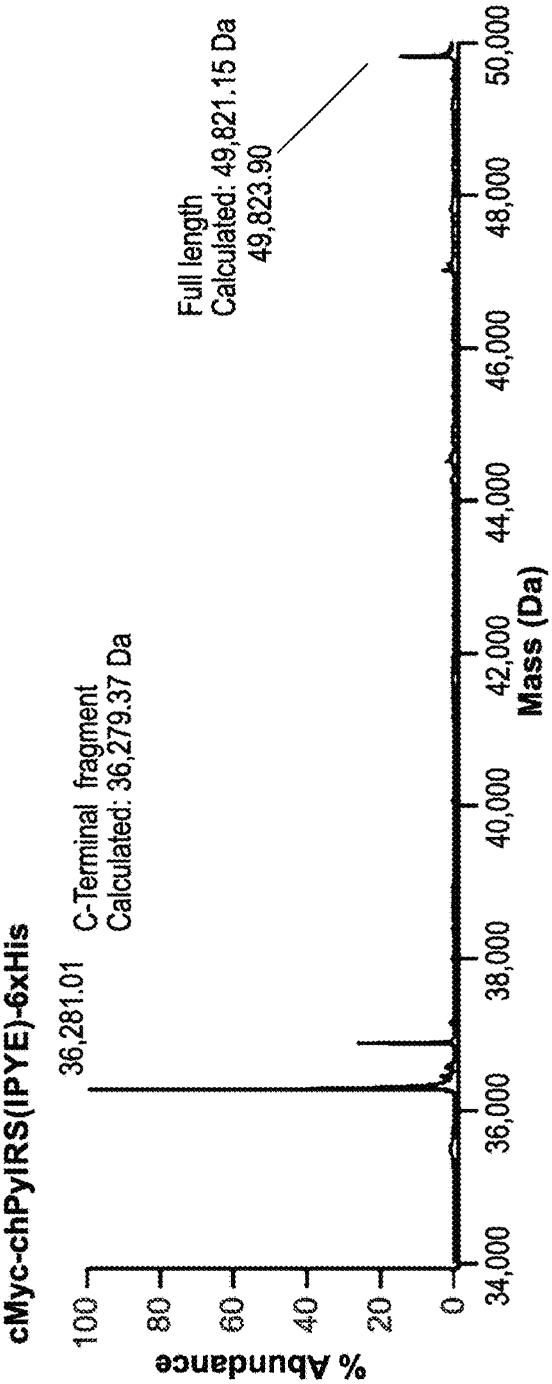
FIGS. 15A-15D show ESI-MS analysis of affinity-tagged Ni-NTA-purified chPylRS variants from PACE. The evolved synthetases, chPylRS(IPYE) (FIG. 15A), Spit2 (FIG. 15B), Split3 (FIG. 15C), and Split6 (FIG. 15D) were labeled with an N-terminal c-Myc-tag and a C-terminal 6×His-tag and purified over Ni-NTA resin prior to ESI-MS analysis. In the split variants of chPylRS, the N-terminal fragment is lost upon affinity purification. Protein was expressed in BL21 star DE3 cells in LB media. The major peaks in each spectra were in agreement with the calculated mass of the full-length enzyme, chPylRS(IPYE) (FIG. 15A), or the C-terminal fragment resulting from reinitiation at position Met-107 (FIGS. 15A-15D).
Figure 15B:
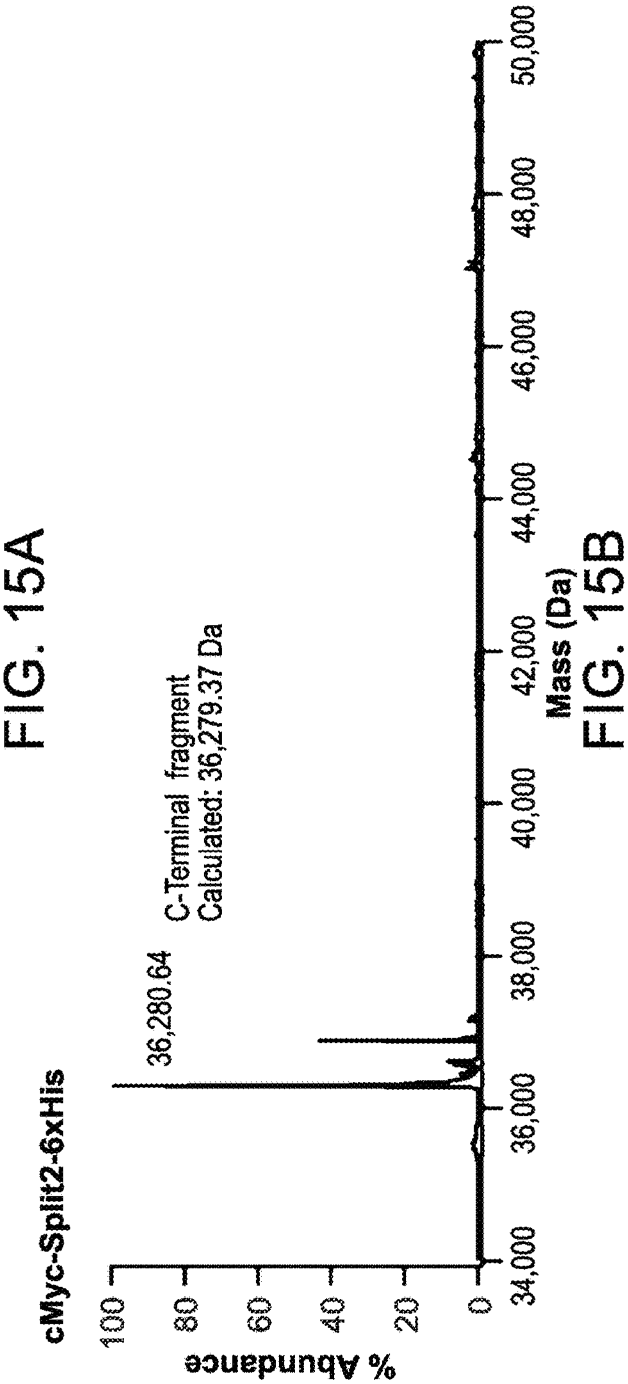
Figure 15C:
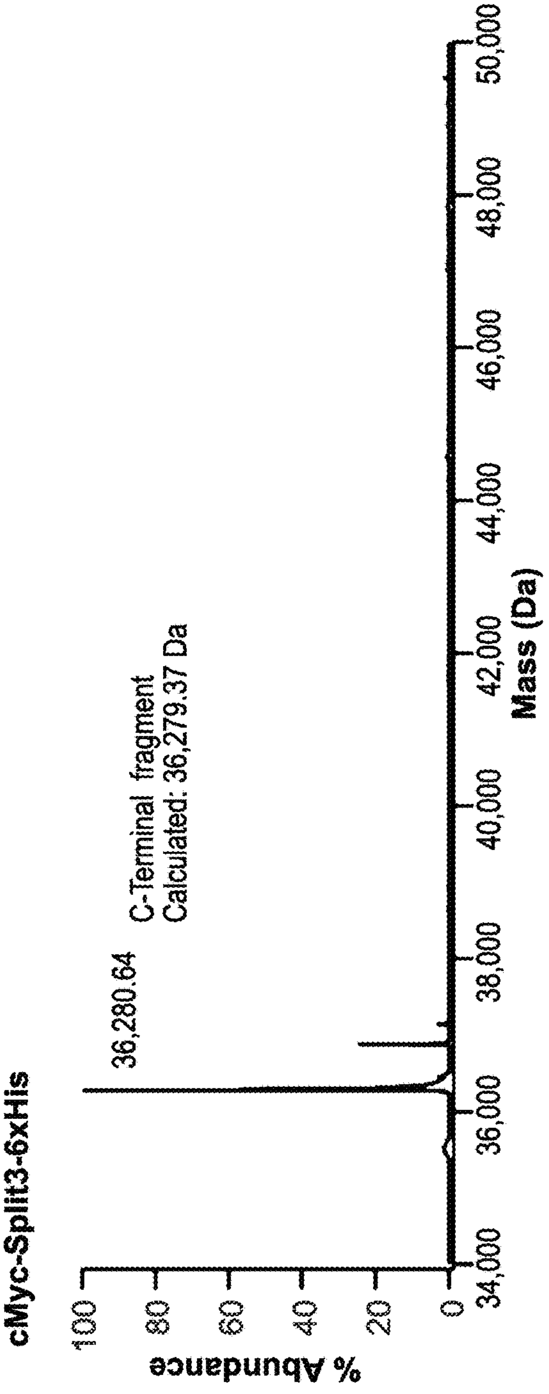
Figure 15D:
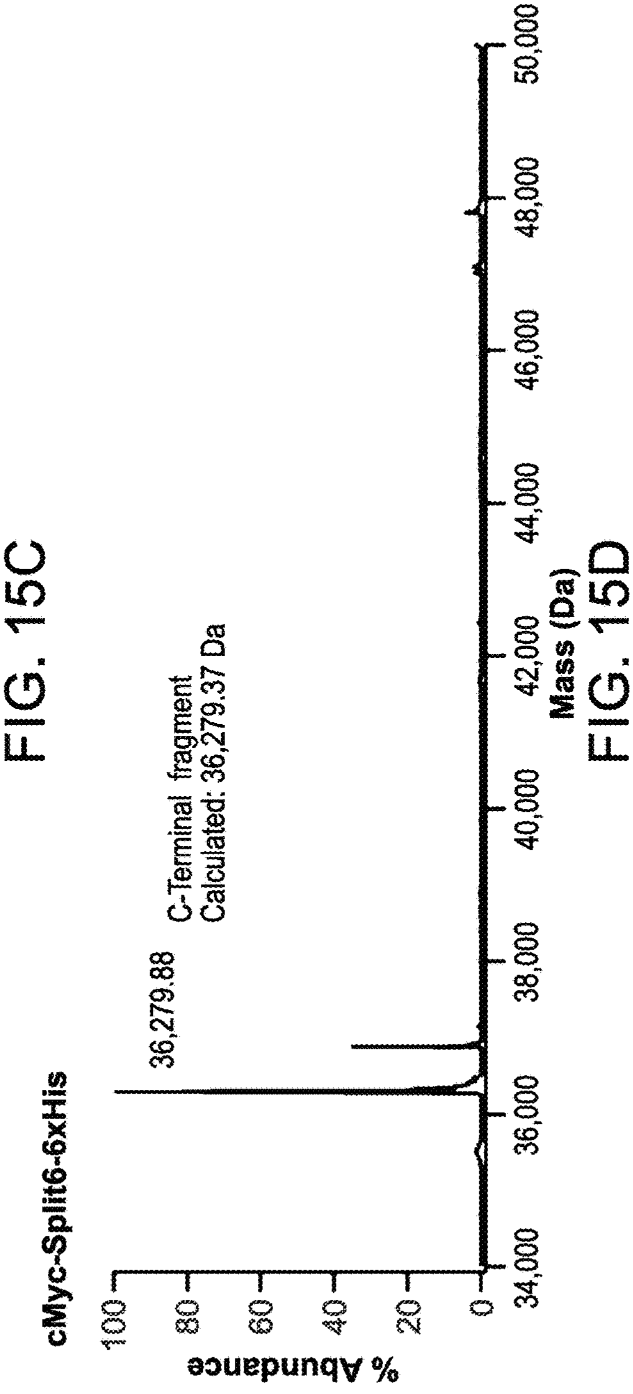

Although there was no strong convergence toward new beneficial coding mutations between the 408-h and 497-h time points, 13 of 16 (81%) of the sequenced SP isolates from the two lagoons of Pyl-3 acquired a surprising frameshift in their coding sequences by 497 h. Of the thirteen affected clones, 12 of these contained a single frameshift at one of four different locations in chPylRS (Tables 5 and 6). In each case, the shifted reading frame in the chPylRS gene produced a premature ochre (TAA) or opal (TGA) stop codon resulting in a truncated protein of 93, 99, or 102 residues. In addition, one of the 13 affected isolates from the 497-h time point contained an in-frame ochre stop codon at position Lys-90, resulting in a truncated protein of 89 residues. Downstream of the premature stop codon in every case is a Met codon at canonical position 107 of chPylRS. In some embodiments, protein synthesis reinitiates from Met-107 resulting in a split chPylRS. In assays of amber suppression, the split chPylRS(IPYE) variants exhibited comparable apparent activity as the full-length chPylRS (IPYE) enzyme. Activity of the split variants was strictly dependent on the presence of both fragments (FIG. 12A, FIG. 12C, and Tables 8-9). In contrast, split chPylRS variants lacking the PACE-evolved coding mutations in their N-terminal fragment resulted in significant loss of activity (FIG. 12B), which may explain why the split enzyme was not observed in PACE until the four activity-enhancing mutations were acquired. Results from western blot analysis and ESI-MS analysis of split variants confirmed translational reinitiation from Met-107 (FIGS. 14-15). The prevalence of the split PylRS variants suggest a fitness advantage to the split constructs during PACE, although the molecular basis of this potential advantage is currently unknown.

TABLE 8

Kinetic parameters of chPylRS variants using L-pyrrolysine substrate.

| PylRS variant | $k_{cat}$, $s^{-1} \times 10^{-3}$ | $K_M^{Pyl}$, μM |
|---|---|---|
| chPylRS | 33.24 ± 2.74 | 21.03 ± 0.15 |
| V31I, T56P, A100E | 289.16 ± 11.45 | 18.42 ± 0.69 |

TABLE 9

Kinetic parameters of the fusions of split chPylRS variants from PACE.

| AARS variant | $k_{cat}$, $s^{-1} \times 10^{-3}$ | $K_M^{BocK}$, mM | $K_M^{tRNA}$, μM |
|---|---|---|---|
| Fused Split2 | 20 ± 1 | 1.68 ± 0.19 | 3.62 ± 0.51 |
| Fused Split3 | 33 ± 3 | 4.90 ± 0.92 | 3.84 ± 0.34 |
| Fused Split6 | 19 ± 0.2 | 1.00 ± 0.05 | 3.61 ± 0.38 |

The evolution of a split PylRS variant in PACE appears to mirror the evolution of PylRS in nature, as PylRS homologs in certain bacteria are expressed from two separate genes (pylSc and pylSn). The *D. hafniense* pylSn encodes a 110-residue polypeptide that is homologous to the N-terminal region of archaeal PylRS, and an alignment of PylSn to the N-terminal split PylRS evolved in PACE shows that they terminate near the same location (FIG. 16). These observations together demonstrate the ability of PACE to evolve unexpected changes in protein topology.

Development and validation of AARS negative selections in PACE. While positive selection PACE was able to greatly increase the activity of PylRS, the evolution of AARSs to recognize non-cognate substrates requires the use of negative selections to minimize activity on endogenous amino acids. A PACE negative selection that links tRNA aminoacylation to the inhibition of phage propagation was developed. A dominant-negative variant of pIII (pIII-neg) was used as the basis of a PACE negative selection for RNA polymerase activity and DNA binding activity. Because pIII-neg poisons the infectivity of emergent phage, variants possessing undesired activity are unable to effectively propagate and are gradually washed out from the evolving pool of SP under constant dilution.

Figure 19A:
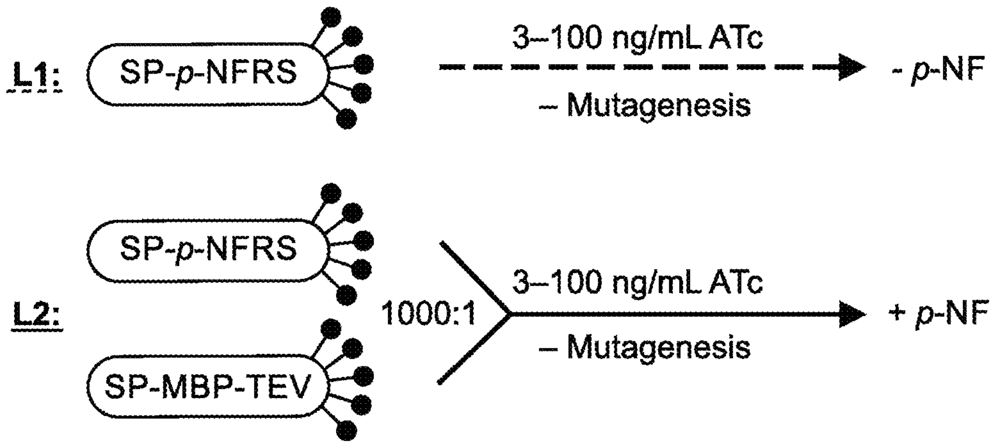
FIGS. 19A-19C show validation of the PACE negative selection.
Figure 19B:
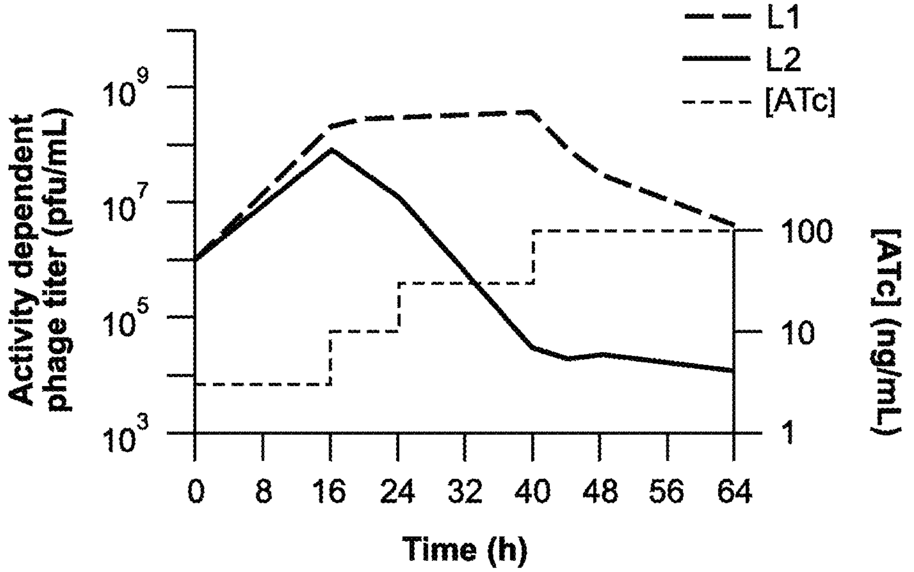
Figure 19C:
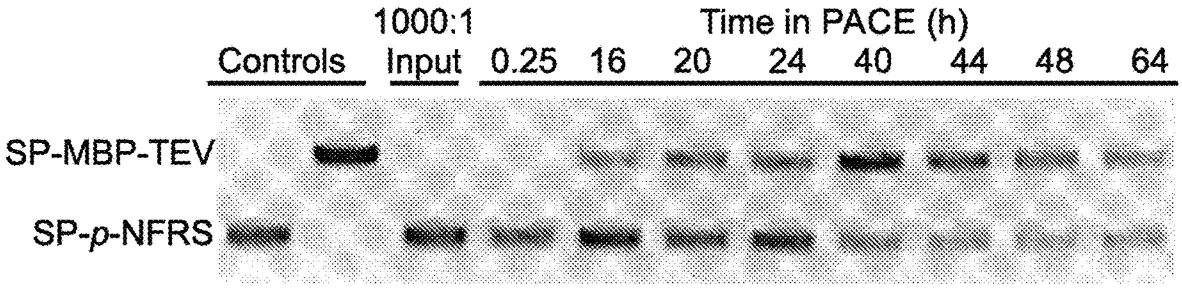

In the PACE negative selection for aminoacylation, amber suppression of two stop codons in T7 RNAP(S12TAG, S203TAG) allows transcriptional activation of the gene encoding pIII-neg. Amber suppression in this context thus results in expression of pIII-neg and reduced progeny phage infectivity (FIGS. 17A-17B, and FIGS. 18A-18B). Mock PACE negative selections with SP-p-NFRS confirmed negative selection against AARS activity. SP-p-NFRS in the presence of p-NF quickly washed out of PACE lagoons under negative selection, whereas an SP lacking any AARS activity propagated robustly under the same conditions (FIGS. 19A-19C). These findings established a PACE negative selection against undesired aminoacylation activity.

Continuous Evolution of an AARS with Greatly Improved Amino Acid Selectivity.

Figures 20A, 20B:
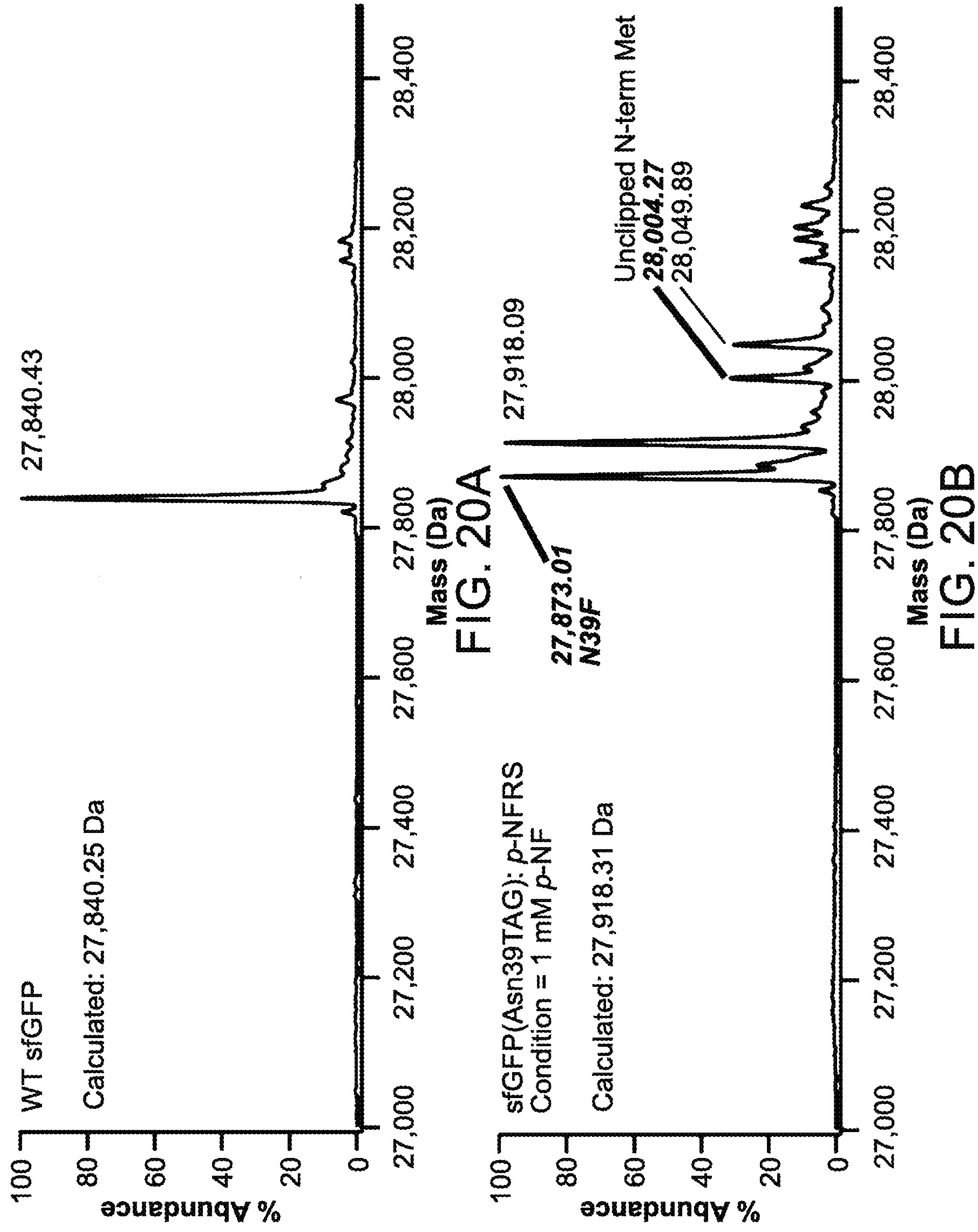
FIGS. 20A-20D show the previously evolved AARS, p-NFRS, accepts multiple amino acid substrates. ESI-MS analysis of purified wild type sfGFP (FIG. 20A) or sfGFP (Asn39TAG) expressed with p-NFRS in the presence of 1 mM p-NF (FIG. 20B), no ncAA (FIG. 20C), or 1 mM p-IF (FIG. 20D) demonstrates that p-NFRS accepts Phe, p-NF, and p-IF. Protein was expressed in BL21 star DE3 cells in LB media.
Figure 20C:
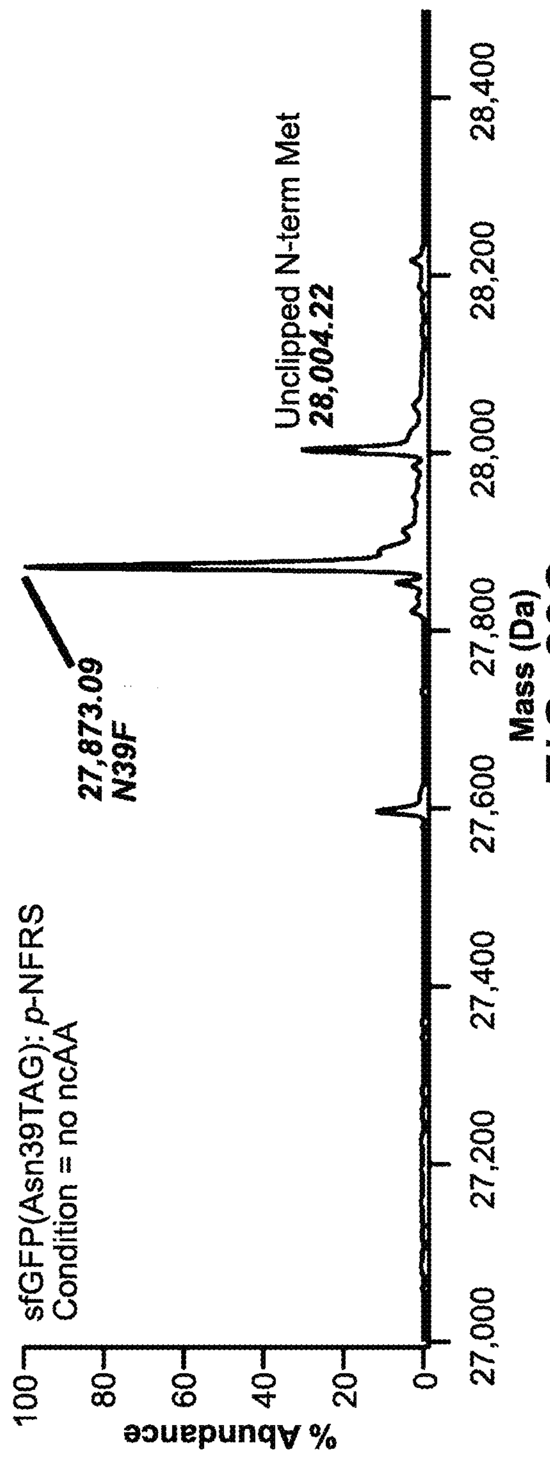
Figure 20D:
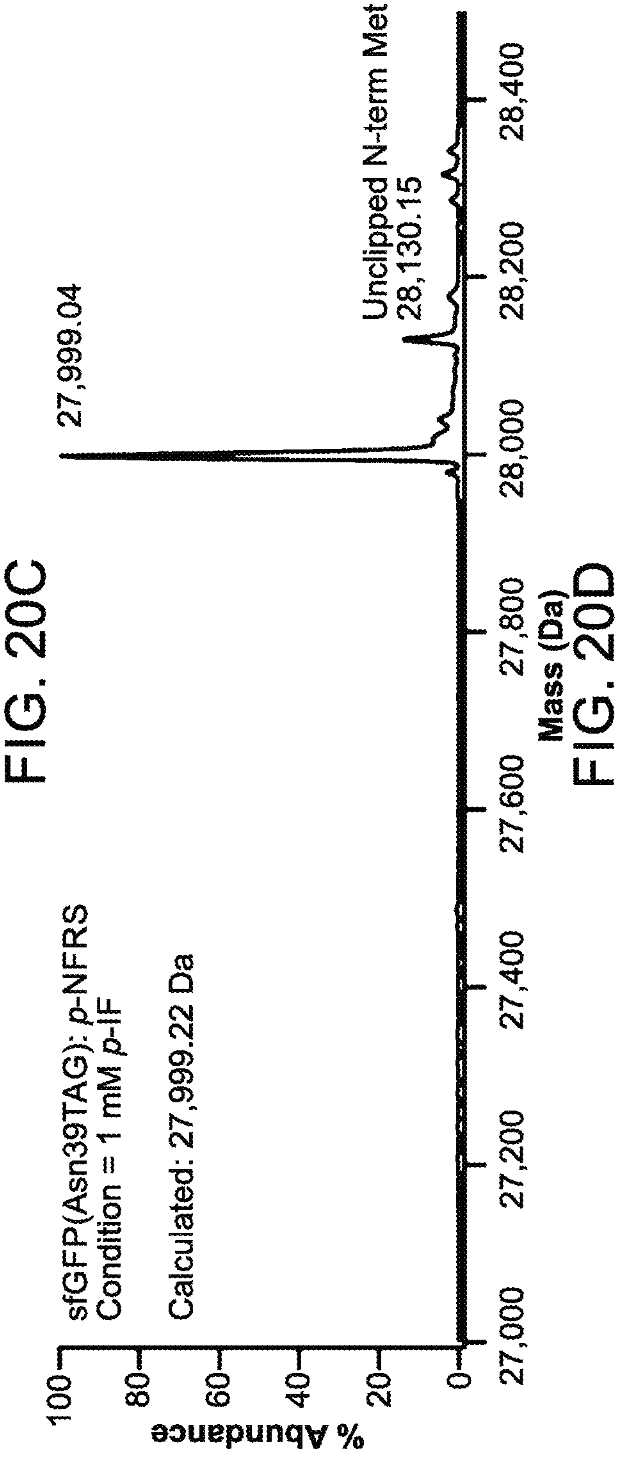

Homogeneity of ncAA incorporation is often crucial for downstream applications, as it is usually impractical or impossible to purify proteins containing the desired ncAA substitution from mixtures containing undesired amino acids at the position(s) of interest. The amino acid selectivity of evolved AARSs is therefore a critical determinant of their utility. The laboratory-evolved MjTyrRS variant, p-NFRS, selectively charges p-NF in minimal media, but overnight expression in LB media demonstrated that p-NFRS also efficiently charges Phe in the presence or in the absence of 1 mM p-NF (FIGS. 20A-20C). Additionally, p-NFRS is a polyspecific enzyme, as it efficiently charges p-iodo-L-phenylalanine (p-IF) in addition to p-NF (FIG. 20D). The ability of coupled PACE positive and negative selections to generate a highly specific AARS by evolving p-NFRS to charge p-IF selectively was investigated.

Figure 17C:
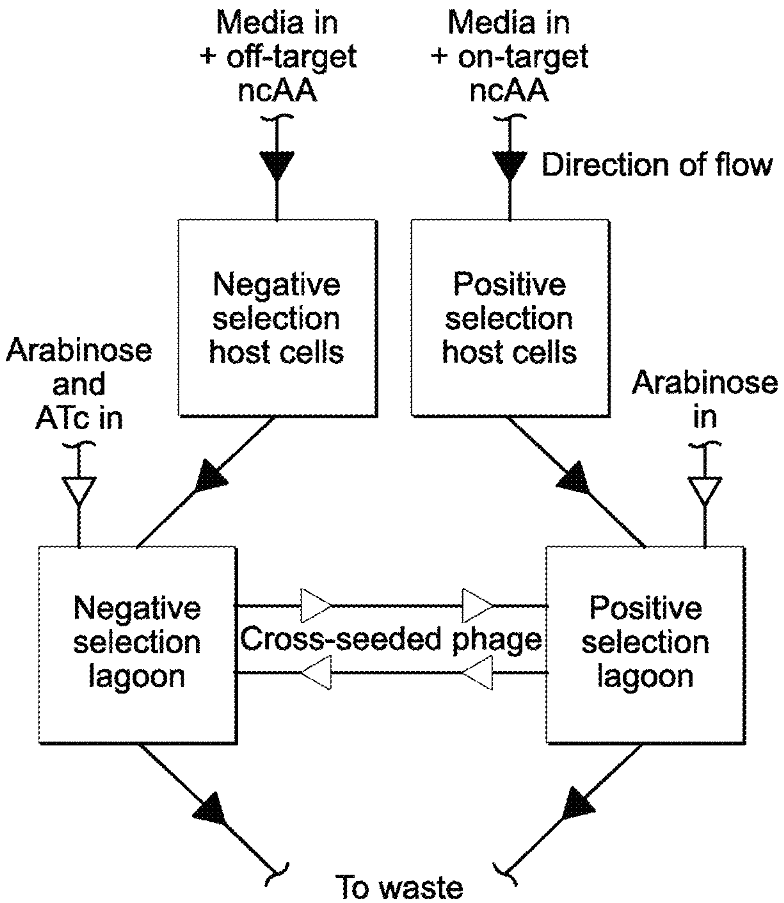

Opposing positive and negative selections were coupled continuously by constantly exchanging small volumes of material from opposing PACE lagoons, which allows the pool of AARS variants to be evolved in both selections simultaneously, rather than performing iterative counterselections (FIG. 17C). This strategy's effectiveness relies on (1) the only actively replicating element in the selection lagoons is the SP, (2) the comparatively small number of host cells that are diverted into the opposing selection should not greatly affect either selection due to the much larger population of correct host cells being continuously infused, and (3) any contaminating ncAA diverted into the opposing selection would be diluted to a very low concentration that would be insufficient to support effective aminoacylation. In some embodiments, coupling the opposing selections lagoons provides an opportunity for SP variants capable of propagating in both selections—i.e., those AARS variants that evolved high amino acid selectivity—to outcompete variants able to propagate exclusively in one of the opposing selections.

Figure 21B:
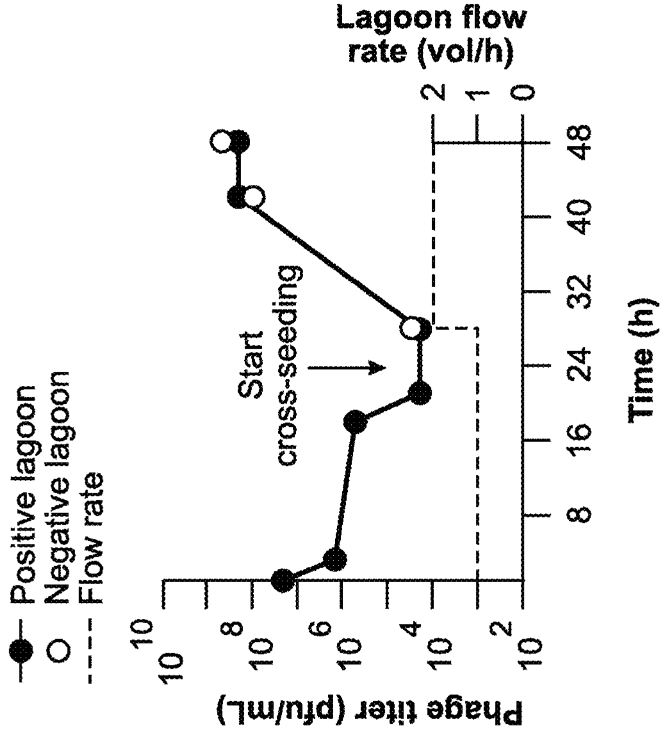
FIGS. 21A-21B show dual-selection PACE of the polyspecific MjTyrRS variant, p-NFRS, to evolve selective activity on p-IF.
Figure 21A:
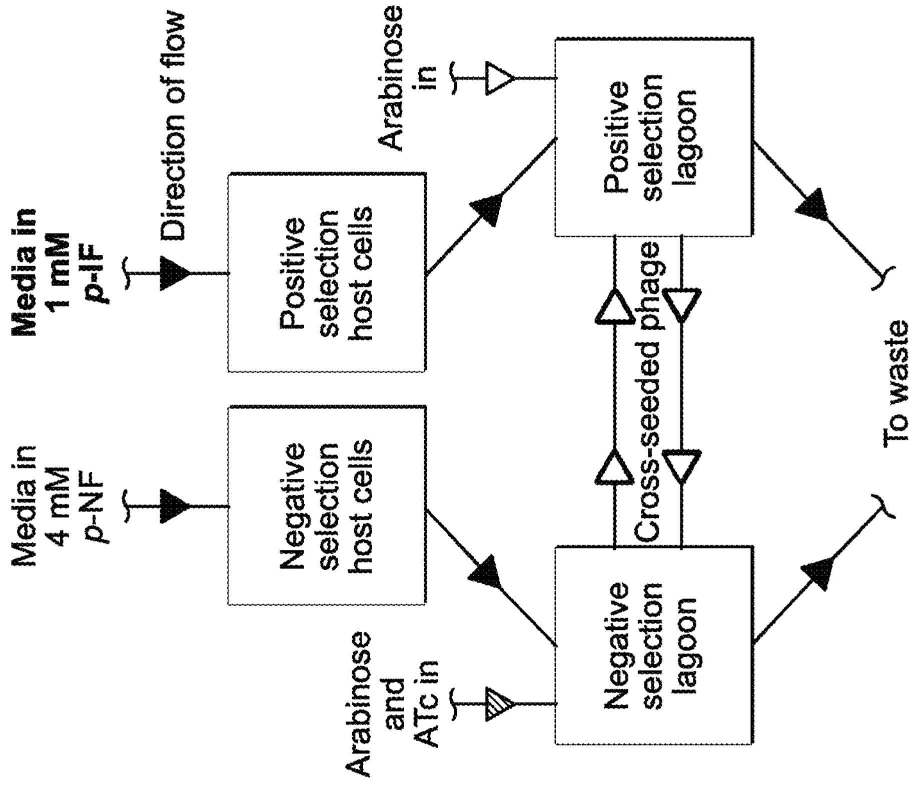
Figure 22A:
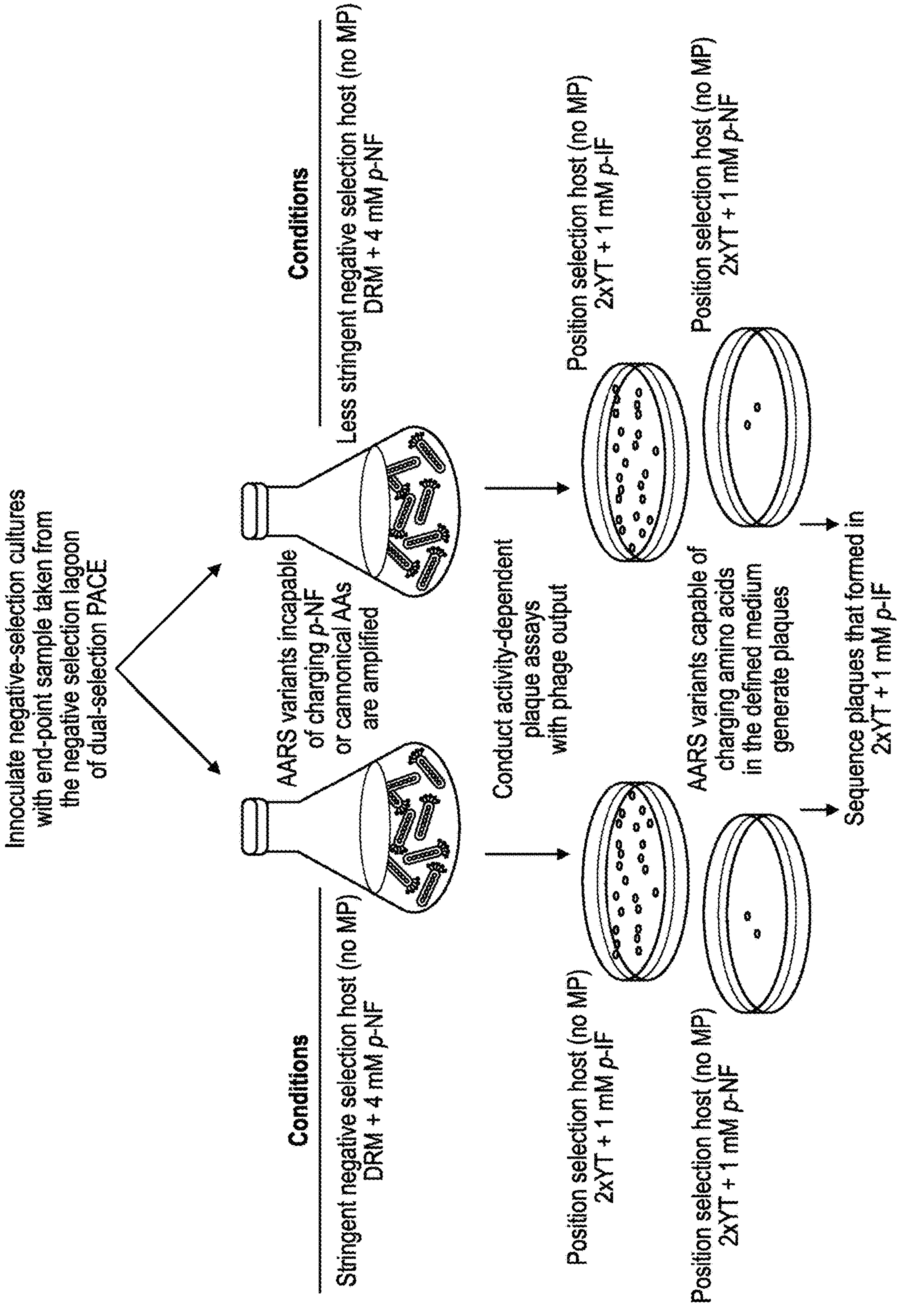

SP-p-NFRS was evolved for 24 h of positive selection PACE toward p-IF followed by 24 h of coupled positive selection with negative selection against the undesired ncAA, p-NF (FIGS. 21A-21B). SPs that acquired preferential activity toward p-IF in PACE were isolated from the evolved pool using a single round of non-continuous counterselections. To enrich variants possessing little to no activity on the undesired ncAA, endpoint SPs from the PACE negative selection were challenged to propagate non-continuously on negative-selection host cells in media containing 4 mM p-NF. The resulting SPs were then challenged with positive-selection host cells in the presence of the desired substrate, 1 mM p-IF, for their ability to promote formation of activity-dependent plaques (the result of phage propagation in semi-solid media) and eight of the resulting plaques were sequenced (FIGS. 22A-22B).

Figure 17E:
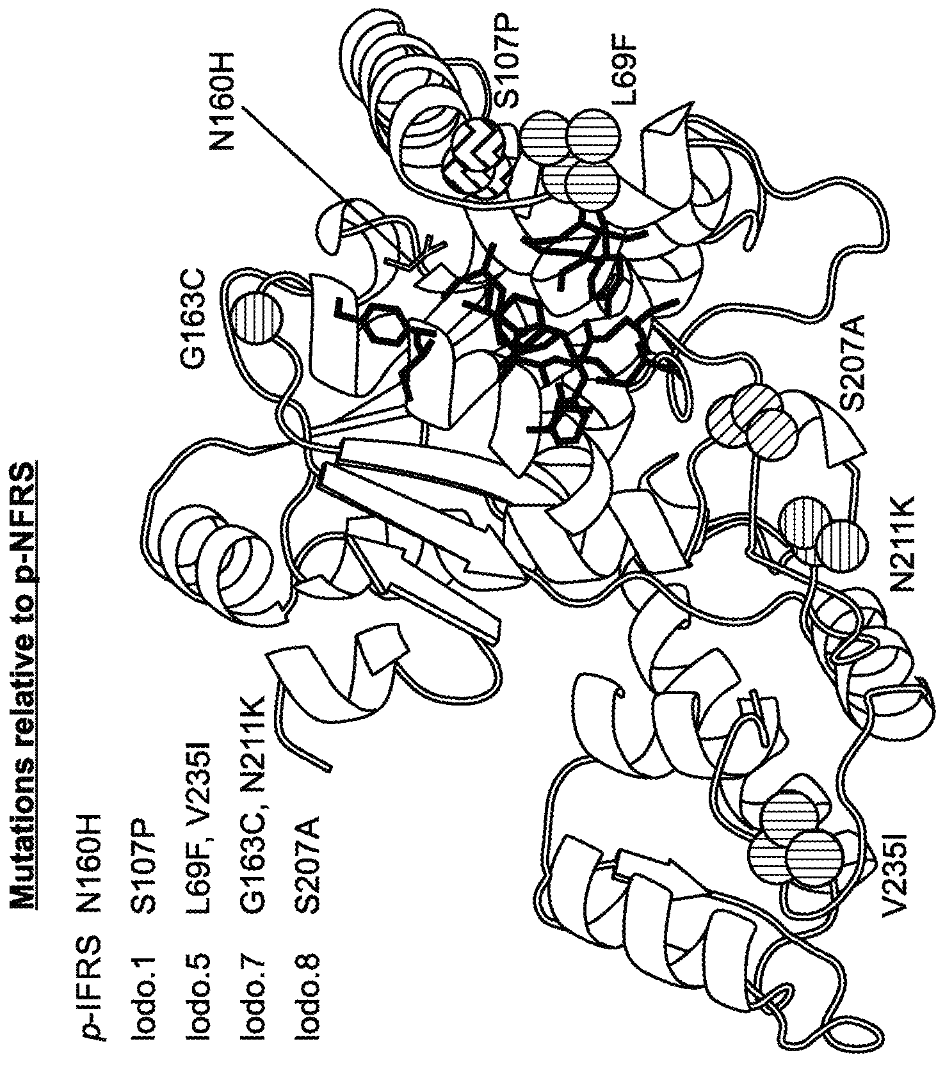
Figure 17D:
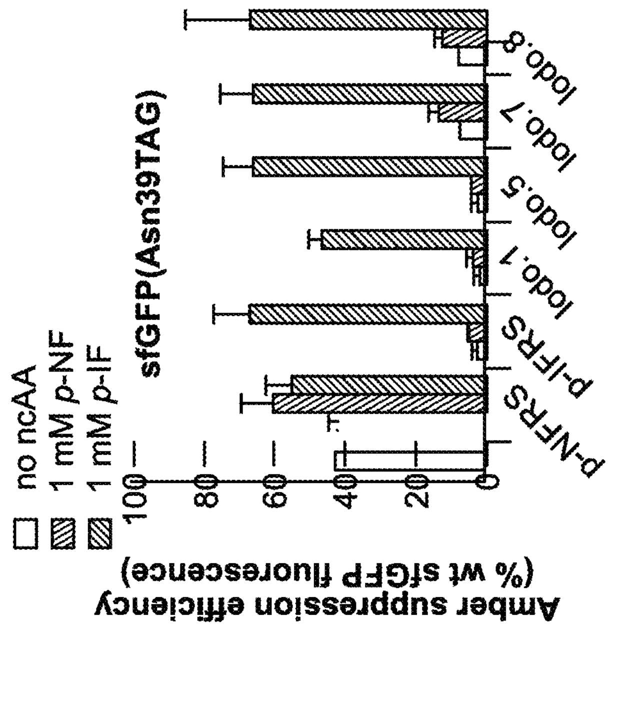

Of the eight sequenced phage isolates, four acquired no new mutations in the AARS gene, but instead emerged from PACE with weakened ribosome binding sites driving AARS expression. Each of the remaining four SP variants contained one or more coding mutations and demonstrated a strong preference for charging p-IF over p-NF (FIGS. 17D-17E and Table 10). The best performing PACE-evolved variant, Iodo.5, which contained mutations L69F and V235I with respect to p-NFRS, matched the amino acid specificity of a previously reported MjTyrRS variant, p-IFRS, that was evolved to charge p-IF through positive and negative selection on agar plates. Based on our limit of detection in the assay, expression of sfGFP(Asn39TAG) using variant Iodo.5 was >23-fold higher with p-IF than with p-NF.

TABLE 10

Kinetic parameters of MjTyrRS variants containing mutations from PACE.

| AARS variant | ncAA | $k_{cat}$, $s^{-1} \times 10^{-3}$ | $K_M^{ncAA}$, MM | kcat/$K_M^{ncAA}$, $mM^{-1} \cdot s^{-1} \times 10^{-3}$ | Relative catalytic efficiency |
|---|---|---|---|---|---|
| p-NFRS | p-NF | 1.40 ± 0.05 | 3.68 ± 0.29 | 0.38 | 1.00 |
| p-NFRS | p-IF | 0.87 ± 0.11 | 2.23 ± 0.46 | 0.39 | 1.03 |
| p-NFRS | Phe | 0.14 ± 0.003 | 0.16 ± 0.03 | 0.875 | 2.3 |
| Iodo.5 | p-NF | ND | ND | ND | ND |
| Iodo.5 | p-IF | ND | ND | ND | ND |
| Iodo.1 | p-IF | 1.60 ± 1.27 | 5.65 ± 1.82 | 0.28 | 0.74 |
| Iodo.7 | p-IF | 0.21 ± 0.03 | 0.92 ± 0.22 | 0.23 | 0.61 |
| Iodo.8 | p-IF | 1.00 ± 0.10 | 3.80 ± 0.84 | 0.26 | 0.68 |

Figure 23A:
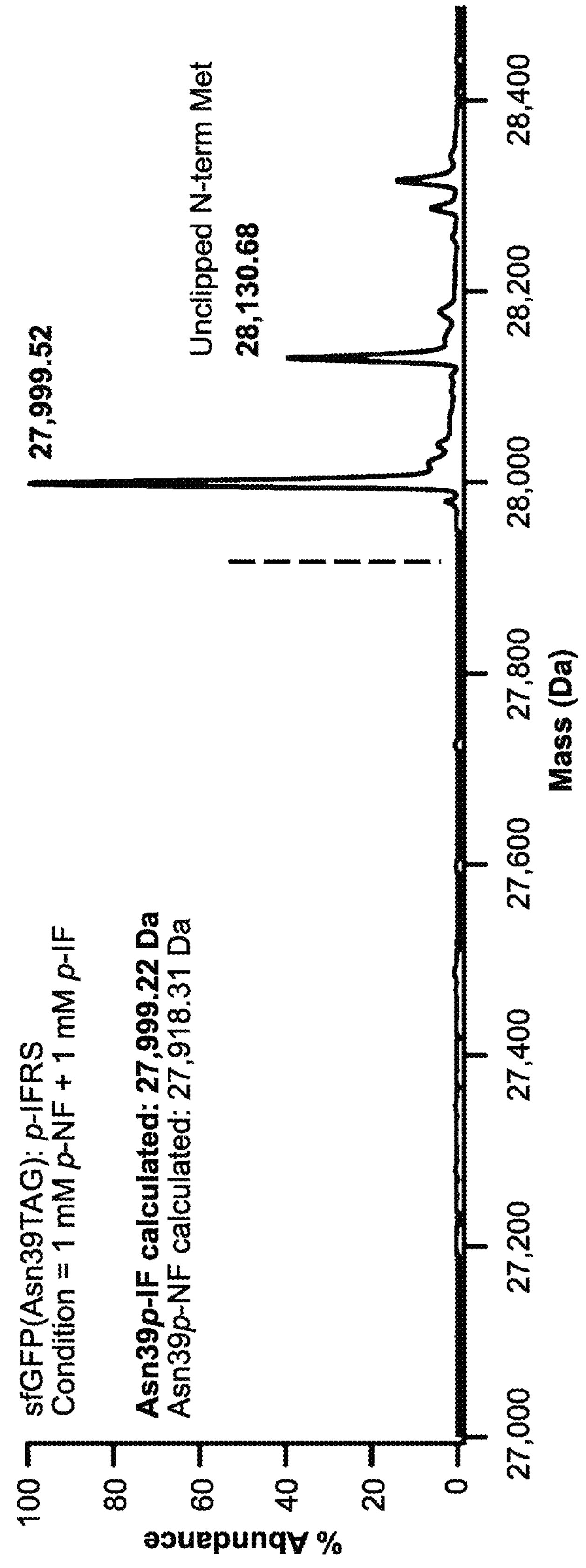
FIGS. 23A-23B show the PACE-evolved Iodo.5 variant is highly selective for the desired substrate, p-IF. ESI-MS analysis of purified sfGFP from expression of sfGFP (Asn39TAG) with p-IFRS (FIG. 23A) or Iodo.5 (FIG. 23B) in LB media supplemented with both 1 mM p-NF and 1 mM p-IF demonstrates that each AARS enzyme selectively incorporates p-IF. (a, b) A peak corresponding to incorporation of p-IF into sfGFP was found at 27,999.52 Da and 27,999.45 Da, respectively (calculated: 27,999.22 Da). Incorporation of p-NF into sfGFP was calculated to have a mass of 27,918.31 Da (dashed line).
Figure 23B:
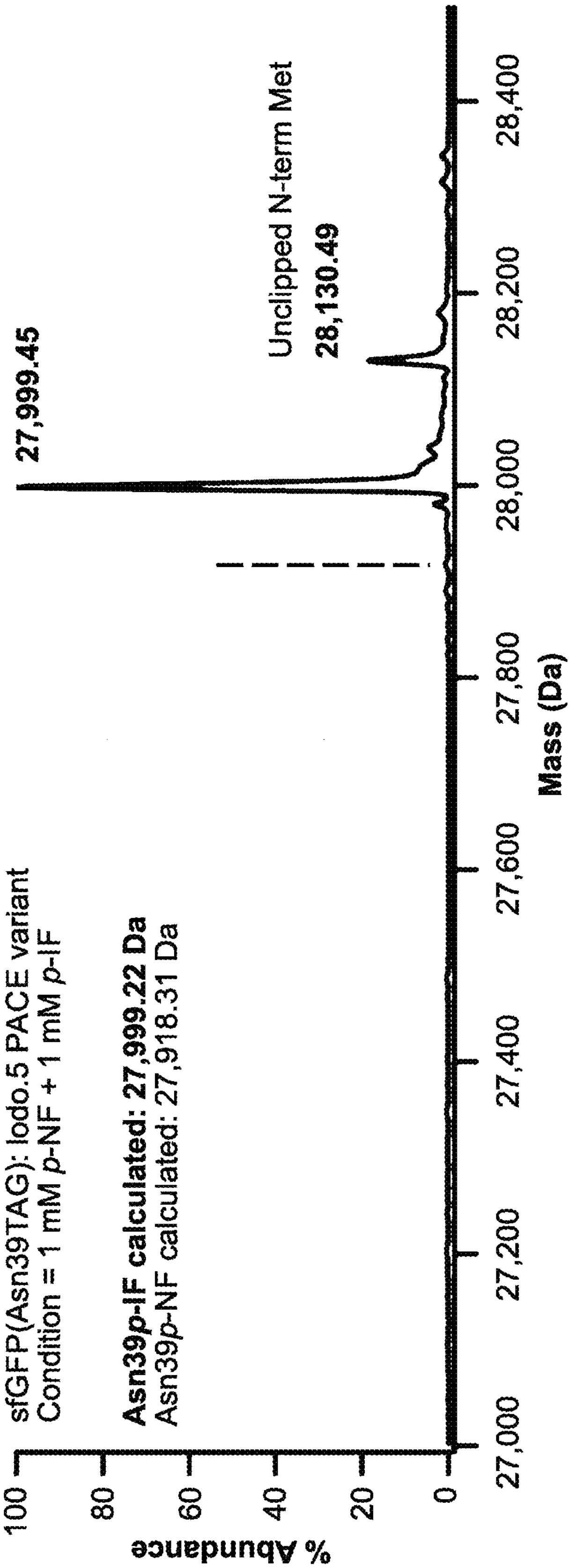

The protein sequences of p-IFRS and p-NFRS differ by only a single amino acid; p-NFRS contains Asn160 and p-IFRS contains His160. It is possible that His160 also emerged in PACE but was not isolated. We further tested Iodo.5 by expressing the sfGFP reporter in LB media containing both 1 mM p-NF and 1 mM p-IF in a single culture. Intact protein mass spectrometry of the resulting purified protein revealed the desired mass corresponding to incorporation of p-IF with only trace p-NF incorporation and no detectable incorporation of Phe at the site of interest (FIGS. 23A-23B). These results establish that PACE can rapidly evolve a highly selective AARS from a polyspecific variant in 48 h with no library cloning.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

SEQUENCES

>SEQ ID NO: 5; DNA sequence of chPylRS. Bolded codons (Val-31, Thr-56, His-62, and Ala-100) were mutated to 'ATT', 'CCC', 'TAT', and 'GAG', respectively, in the 'IPYE' variant of the enzyme (SEQ ID NO: 25, 26).

ATGGATAAGAAGCCGCTGGATGTTCTGATCTCTGCGACCGGTCTGTGGATGTCCCGTACCGGCACGCT

GCACAAGATCAAGCACTATGAGGTTTCTCGTTCTAAAATCTACATCGAAATGGCGTGTGGTGACCATC

TGGTTGTGAACAACTCTCGTTCTTGTCGTACCGCACGTGCATTCCGTCATCATAAATACCGTAAAACC

TGCAAACGTTGTCGTGTTTCTGACGAAGATATCAACAACTTCCTGACCCGTTCTACCGAAGGCAAAAC

CTCTGTTAAAGTTAAAGTTGTTTCTGCGCCGAAAGTGAAAAAAGCGATGCCGAAATCTGTTTCTCGTG

CGCCGAAACCGCTGGAAAATCCGGTTTCTGCGAAAGCGTCTACCGACACCTCTCGTTCTGTTCCGTCT

CCGGCGAAATCTACCCCGAACTCTCCGGTTCCGACCTCTGCAAGTGCCCCCGCACTTACGAAGAGCCA

GACTGACAGGCTTGAAGTCCTGTTAAACCCAAAAGATGAGATTTCCCTGAATTCCGGCAAGCCTTTCA

GGGAGCTTGAGTCCGAATTGCTCTCTCGCAGAAAAAAAGACCTGCAGCAGATCTACGCGGAAGAAAG

GGAGAATTATCTGGGGAAACTCGAGCGTGAAATTACCAGGTTCTTTGTGGACAGGGGTTTTCTGGAAA

TAAAATCCCCGATCCTGATCCCTCTTGAGTATATCGAAAGGATGGGCATTGATAATGATACCGAACTT

TCAAAACAGATCTTCAGGGTTGACAAGAACTTCTGCCTGAGACCCATGCTTGCTCCAAACCTTTACAA

CTACCTGCGCAAGCTTGACAGGGCCCTGCCTGATCCAATAAAAATTTTTGAAATAGGCCCATGCTACA

GAAAAGAGTCCGACGGCAAAGAACACCTCGAAGAGTTTACCATGCTGAACTTCTGCCAGATGGGATC

GGGATGCACACGGGAAAATCTTGAAAGCATAATTACGGACTTCCTGAACCACCTGGGAATTGATTTCA

AGATCGTAGGCGATTCCTGCATGGTCTATGGGGATACCCTTGATGTAATGCACGGAGACCTGGAACTT

TCCTCTGCAGTAGTCGGACCCATACCGCTTGACCGGGAATGGGGTATTGATAAACCCTGGATAGGGGC

AGGTTTCGGACTCGAACGCCTTCTAAAGGTTAAACACGACTTTAAAAATATCAAGAGAGCTGCAAGG

TCCGAGTCTTACTATAACGGGATTTCTACCAACCTGTAA

>SEQ ID NO: 6; DNA sequence of MbPylRS. Bolded codons (Val-31, Thr-56, His-62, and Ala-100) were mutated to 'ATT', 'CCC', 'TAT', and 'GAG', respectively, in the 'IPYE' variant of the enzyme (SEQ ID NO: 27, 28).

ATGGATAAGAAGCCGCTGGATGTTCTGATCTCTGCGACCGGTCTGTGGATGTCCCGTACCGGCACGCT

GCACAAGATCAAGCACTATGAGGTTTCTCGTTCTAAAATCTACATCGAAATGGCGTGTGGTGACCATC

TGGTTGTGAACAACTCTCGTTCTTGTCGTACCGCACGTGCATTCCGTCATCATAAATACCGTAAAACC

TGCAAACGTTGTCGTGTTTCTGACGAAGATATCAACAACTTCCTGACCCGTTCTACCGAAGGCAAAAC

CTCTGTTAAAGTTAAAGTTGTTTCTGCGCCGAAAGTGAAAAAAGCGATGCCGAAATCTGTTTCTCGTG

CGCCGAAACCGCTGGAAAATCCGGTTTCTGCGAAAGCGTCTACCGACACCTCTCGTTCTGTTCCGTCT

CCGGCGAAATCTACCCCGAACTCTCCGGTTCCGACCTCTGCGCCGGCGCCGTCTCTGACCCGTTCTCA

GCTGGATCGTGTTGAAGCGCTGCTGTCTCCGGAAGATAAAATCTCTCTGAACATCGCGAAACCGTTCC

GTGAACTGGAATCTGAACTGGTTACCCGTCGTAAAAACGATTTCCAGCGTCTGTACACCAACGATCGT

GAAGACTACCTGGGTAAACTGGAACGTGACATCACCAAATTCTTCGTTGACCGTGATTTCCTGGAAAT

CAAATCTCCGATCCTGATCCCGGCGGAATACGTTGAACGTATGGGTATCAACAACGATACCGAACTGT

CTAAACAGATCTTCCGTGTTGATAAAAACCTGTGCCTGCGTCCGATGCTGGCGCCGACCCTGTACAAC

TATCTGCGTAAACTGGATCGTATCCTGCCGGACCCGATCAAAATCTTCGAAGTTGGTCCGTGCTACCG

TAAAGAATCTGACGGTAAAGAACACCTGGAAGAGTTCACCATGGTGAACTTCTGCCAGATGGGTTCT

GGTTGCACCCGTGAGAACCTGGAATCTCTGATCAAAGAATTTCTGGACTACCTGGAAATCGACTTCGA

AATCGTTGGTGACTCCTGCATGGTGTACGGTGATACCCTGGACATCATGCACGGTGACCTGGAACTGT

CTTCTGCGGTTGTTGGTCCGGTTCCGCTGGATCGTGAATGGGGTATCGACAAACCGTGGATCGGTGCG

-continued

GGTTTCGGTCTGGAACGTCTGCTGAAAGTTATGCACGGTTTCAAAAACATCAAACGTGCGTCTCGTTC

TGAATCTTACTACAACGGTATCTCTACCAACCTGTAA

>SEQ ID NO: 7; DNA sequence of MmPylRS. Bolded codons (Val-31, Thr-56, His-62, and Ala-100) were mutated to ‘ATT’, ‘CCC’, ‘TAT’, and ‘GAG’, respectively, in the ‘IPYE’ variant of the enzyme (SEQ ID NO: 29, 30).

ATGGATAAAAAACCACTAAACACTCTGATATCTGCAACCGGGCTCTGGATGTCCAGGACCGGAACAA

TTCATAAAATAAAACACCACGAAGTCTCTCGAAGCAAAATCTATATTGAAATGGCATGCGGAGACCA

CCTTGTTGTAAACAACTCCAGGAGCAGCAGGACTGCAAGAGCGCTCAGGCACCACAAATACAGGAA

GACCTGCAAACGCTGCAGGGTTTCGGATGAGGATCTCAATAAGTTCCTCACAAAGGCAAACGAAGAC

CAGACAAGCGTAAAAGTCAAGGTCGTTTCTGCCCCTACCAGAACGAAAAAGGCAATGCCAAAATCCG

TTGCGAGAGCCCCGAAACCTCTTGAGAATACAGAAGCGGCACAGGCTCAACCTTCTGGATCTAAATTT

TCACCTGCGATACCGGTTTCCACCCAAGAGTCAGTTTCTGTCCCGGCATCTGTTTCAACATCAATATCA

AGCATTTCTACAGGAGCAACTGCATCCGCACTGGTAAAAGGGAATACGAATCCCATTACATCCATGTC

TGCCCCTGTTCAGGCAAGTGCCCCCGCACTTACGAAGAGCCAGACTGACAGGCTTGAAGTCCTGTTAA

ACCCAAAAGATGAGATTTCCCTGAATTCCGGCAAGCCTTTCAGGGAGCTTGAGTCCGAATTGCTCTCT

CGCAGAAAAAAAGACCTGCAGCAGATCTACGCGGAAGAAAGGGAGAATTATCTGGGGAAACTCGAG

CGTGAAATTACCAGGTTCTTTGTGGACAGGGGTTTTCTGGAAATAAAATCCCCGATCCTGATCCCTCTT

GAGTATATCGAAAGGATGGGCATTGATAATGATACCGAACTTTCAAAACAGATCTTCAGGGTTGACA

AGAACTTCTGCCTGAGACCCATGCTTGCTCCAAACCTTTACAACTACCTGCGCAAGCTTGACAGGGCC

CTGCCTGATCCAATAAAAATTTTTGAAATAGGCCCATGCTACAGAAAAGAGTCCGACGGCAAAGAAC

ACCTCGAAGAGTTTACCATGCTGAACTTCTGCCAGATGGGATCGGGATGCACACGGGAAAATCTTGA

AAGCATAATTACGGACTTCCTGAACCACCTGGGAATTGATTTCAAGATCGTAGGCGATTCCTGCATGG

TCTATGGGGATACCCTTGATGTAATGCACGGAGACCTGGAACTTTCCTCTGCAGTAGTCGGACCCATA

CCGCTTGACCGGGAATGGGGTATTGATAAACCCTGGATAGGGGCAGGTTTCGGGCTCGAACGCCTTCT

AAAGGTTAAACACGACTTTAAAAATATCAAGAGAGCTGCAAGGTCCGAGTCTTACTATAACGGGATT

TCTACCAACCTGTAA

>SEQ ID NO: 8; DNA sequence of chAcK3RS. Bolded codons (Val-31, Thr-56, His-62, and Ala-100) were mutated to ‘ATT’, ‘CCC’, ‘TAT’, and ‘GAG’, respectively, in the ‘IPYE’ variant of the enzyme (SEQ ID NO: 31, 32).

ATGGATAAGAAGCCGCTGGATGTTCTGATCTCTGCGACCGGTCTGTGGATGTCCCGTACCGGCACGCT

GCACAAGATCAAGCACTATGAGGTTTTCTCGTTCTAAAATCTACATCGAAATGGCGTGTGGTGACCATC

TGGTTGTGAACAACTCTCGTTCTTGTCGTACCGCACGTGCATTCCGTCATCATAAATACCGTAAAACC

TGCAAACGTTGTCGTGTTTCTGGTGAAGATATCAACAACTTCCTGACCCGTTCTACCGAAGGCAAAAC

CTCTGTTAAAGTTAAAGTTGTTTCTGCGCCGAAAGTGAAAAAAGCGATGCCGAAATCTGTTTCTCGTG

CGCCGAAACCGCTGGAAAATCCGGTTTCTGCGAAAGCGTCTACCGACACCTCTCGTTCTGTTCCGTCT

CCGGCGAAATCTACCCCGAACTCTCCGGTTCCGACCTCTGCAAGTGCCCCCGCACTTACGAAGAGCCA

GACTGACAGGCTTGAAGTCCTGTTAAACCCAAAAGATGAGATTTCCCTGAATTCCGGCAAGCCTTTCA

GGGAGCTTGAGTCCGAATTGCTCTCTCGCAGAAAAAAAGACCTGCAGCAGATCTACGCGGAAGAAAG

GGAGAATTATCTGGGGAAACTCGAGCGTGAAATTACCAGGTTCTTTGTGGACAGGGGTTTTCTGGAAA

TAAAATCCCCGATCCTGATCCCTCTTGAGTATATCGAAAGGATGGGCATTGATAATGATACCGAACTT

TCAAAACAGATCTTCAGGGTTGACAAGAACTTCTGCCTGAGACCCATGATGGCTCCAAACATTTTTAA

CTACGCTCGCAAGCTTGACAGGGCCCTGCCTGATCCAATAAAAATTTTTGAAATAGGCCCATGCTACA

GAAAAGAGTCCGACGGCAAAGAACACCTCGAAGAGTTTACCATGCTGAACTTCTTTCAGATGGGATC

-continued

GGGATGCACACGGGAAAATCTTGAAAGCATAATTACGGACTTCCTGAACCACCTGGGAATTGATTTCA

AGATCGTAGGCGATTCCTGCATGGTCTATGGGGATACCCTTGATGTAATGCACGGAGACCTGGAACTT

TCCTCTGCAGTAGTCGGACCCATACCGCTTGACCGGGAATGGGGTATTGATAAACCCTGGATAGGGGC

AGGTTTCGGACTCGAACGCCTTCTAAAGGTTAAACACGACTTTAAAAATATCAAGAGAGCTGCAAGG

TCCGAGTCTTACTATAACGGGATTTCTACCAACCTGTAA

>SEQ ID NO: 9; DNA sequence of MbAcK3RS. Bolded codons (Val-31, Thr-56, His-62, and Ala-100) were mutated to 'ATT', 'CCC', 'TAT', and 'GAG', respectively, in the 'IPYE' variant of the enzyme (SEQ ID NO: 33, 34).

ATGGATAAGAAGCCGCTGGATGTTCTGATCTCTGCGACCGGTCTGTGGATGTCCCGTACCGGCACGCT

GCACAAGATCAAGCACTATGAGGTTTCTCGTTCTAAAATCTACATCGAAATGGCGTGTGGTGACCATC

TGGTTGTGAACAACTCTCGTTCTTGTCGTACCGCACGTGCATTCCGTCATCATAAATACCGTAAAACC

TGCAAACGTTGTCGTGTTTCTGGTGAAGATATCAACAACTTCCTGACCCGTTCTACCGAAGGCAAAAC

CTCTGTTAAAGTTAAAGTTGTTTCTGCGCCGAAAGTGAAAAAAGCGATGCCGAAATCTGTTTCTCGTG

CGCCGAAACCGCTGGAAAATCCGGTTTCTGCGAAAGCGTCTACCGACACCTCTCGTTCTGTTCCGTCT

CCGGCGAAATCTACCCCGAACTCTCCGGTTCCGACCTCTGCGCCGGCGCCGTCTCTGACCCGTTCTCA

GCTGGATCGTGTTGAAGCGCTGCTGTCTCCGGAAGATAAAATCTCTCTGAACATCGCGAAACCGTTCC

GTGAACTGGAATCTGAACTGGTTACCCGTCGTAAAAACGATTTCCAGCGTCTGTACACCAACGATCGT

GAAGACTACCTGGGTAAACTGGAACGTGACATCACCAAATTCTTCGTTGACCGTGATTTCCTGGAAAT

CAAATCTCCGATCCTGATCCCGGCGGAATACGTTGAACGTATGGGTATCAACAACGATACCGAACTGT

CTAAACAGATCTTCCGTGTTGATAAAAACCTGTGCCTGCGTCCGATGATGGCGCCGACCATTTTTAAC

TATGCTCGTAAACTGGATCGTATCCTGCCGGACCCGATCAAAATCTTCGAAGTTGGTCCGTGCTACCG

TAAAGAATCTGACGGTAAAGAACACCTGGAAGAGTTCACCATGGTGAACTTCTTTCAGATGGGTTCTG

GTTGCACCCGTGAGAACCTGGAATCTCTGATCAAAGAATTTCTGGACTACCTGGAAATCGACTTCGAA

ATCGTTGGTGACTCCTGCATGGTGTACGGTGATACCCTGGACATCATGCACGGTGACCTGGAACTGTC

TTCTGCGGTTGTTGGTCCGGTTCCGCTGGATCGTGAATGGGGTATCGACAAACCGTGGATCGGTGCGG

GTTTCGGTCTGGAACGTCTGCTGAAAGTTATGCACGGTTTCAAAAACATCAAACGTGCGTCTCGTTCT

GAATCTTACTACAACGGTATCTCTACCAACCTGTAA

>SEQ ID NO: 10; DNA sequence of MmAcK3RS. Bolded codons (Val-31, Thr-56, His-62, and Ala-100) were mutated to 'ATT', 'CCC', 'TAT', and 'GAG', respectively, in the 'IPYE' variant of the enzyme (SEQ ID NO: 35, 36).

ATGGATAAAAAACCACTAAACACTCTGATATCTGCAACCGGGCTCTGGATGTCCAGGACCGGAACAA

TTCATAAAATAAAACACCACGAAGTCTCTCGAAGCAAAATCTATATTGAAATGGCATGCGGAGACCA

CCTTGTTGTAAACAACTCCAGGAGCAGCAGGACTGCAAGAGCGCTCAGGCACCACAAATACAGGAA

GACCTGCAAACGCTGCAGGGTTTCGGGTGAGGATCTCAATAAGTTCCTCACAAAGGCAAACGAAGAC

CAGACAAGCGTAAAAGTCAAGGTCGTTTCTGCCCCTACCAGAACGAAAAAGGCAATGCCAAAATCCG

TTGCGAGAGCCCCGAAACCTCTTGAGAATACAGAAGCGGCACAGGCTCAACCTTCTGGATCTAAATTT

TCACCTGCGATACCGGTTTCCACCCAAGAGTCAGTTTCTGTCCCGGCATCTGTTTCAACATCAATATCA

AGCATTTCTACAGGAGCAACTGCATCCGCACTGGTAAAAGGGAATACGAATCCCATTACATCCATGTC

TGCCCCTGTTCAGGCAAGTGCCCCCGCACTTACGAAGAGCCAGACTGACAGGCTTGAAGTCCTGTTAA

ACCCAAAAGATGAGATTTCCCTGAATTCCGGCAAGCCTTTCAGGGAGCTTGAGTCCGAATTGCTCTCT

CGCAGAAAAAAAGACCTGCAGCAGATCTACGCGGAAGAAAGGGAGAATTATCTGGGGAAACTCGAG

CGTGAAATTACCAGGTTCTTTGTGGACAGGGGTTTTCTGGAAATAAAATCCCCGATCCTGATCCCTCTT

GAGTATATCGAAAGGATGGGCATTGATAATGATACCGAACTTTCAAAACAGATCTTCAGGGTTGACA

-continued

AGAACTTCTGCCTGAGACCCATGATGGCTCCAAACATTTTTAACTACGCTCGCAAGCTTGACAGGGCC

CTGCCTGATCCAATAAAAATTTTTGAAATAGGCCCATGCTACAGAAAAGAGTCCGACGGCAAAGAAC

ACCTCGAAGAGTTTACCATGCTGAACTTCTTTCAGATGGGATCGGGATGCACACGGGAAAATCTTGAA

AGCATAATTACGGACTTCCTGAACCACCTGGGAATTGATTTCAAGATCGTAGGCGATTCCTGCATGGT

CTATGGGGATACCCTTGATGTAATGCACGGAGACCTGGAACTTTCCTCTGCAGTAGTCGGACCCATAC

CGCTTGACCGGGAATGGGGTATTGATAAACCCTGGATAGGGGCAGGTTTCGGGCTCGAACGCCTTCTA

AAGGTTAAACACGACTTTAAAAATATCAAGAGAGCTGCAAGGTCCGAGTCTTACTATAACGGGATTTC

TACCAACCTGTAA

>SEQ ID NO: 11; DNA sequence of chIFRS. Bolded codons (Val-31, Thr-56, His-62, and Ala-100) were mutated to 'ATT', 'CCC', 'TAT', and 'GAG', respectively, in the 'IPYE' variant of the enzyme (SEQ ID NO: 37, 38).

ATGGATAAGAAGCCGCTGGATGTTCTGATCTCTGCGACCGGTCTGTGGATGTCCCGTACCGGCACGCT

GCACAAGATCAAGCACTATGAGGTTTCTCGTTCTAAAATCTACATCGAAATGGCGTGTGGTGACCATC

TGGTTGTGAACAACTCTCGTTCTTGTCGTACCGCACGTGCATTCCGTCATCATAAATACCGTAAAACC

TGCAAACGTTGTCGTGTTTCTGACGAAGATATCAACAACTTCCTGACCCGTTCTACCGAAGGCAAAAC

CTCTGTTAAAGTTAAAGTTGTTTCTGCGCCGAAAGTGAAAAAAGCGATGCCGAAATCTGTTTCTCGTG

CGCCGAAACCGCTGGAAAATCCGGTTTCTGCGAAAGCGTCTACCGACACCTCTCGTTCTGTTCCGTCT

CCGGCGAAATCTACCCCGAACTCTCCGGTTCCGACCTCTGCAAGTGCCCCCGCACTTACGAAGAGCCA

GACTGACAGGCTTGAAGTCCTGTTAAACCCAAAAGATGAGATTTCCCTGAATTCCGGCAAGCCTTTCA

GGGAGCTTGAGTCCGAATTGCTCTCTCGCAGAAAAAAAGACCTGCAGCAGATCTACGCGGAAGAAAG

GGAGAATTATCTGGGGAAACTCGAGCGTGAAATTACCAGGTTCTTTGTGGACAGGGGTTTTCTGGAAA

TAAAATCCCCGATCCTGATCCCTCTTGAGTATATCGAAAGGATGGGCATTGATAATGATACCGAACTT

TCAAAACAGATCTTCAGGGTTGACAAGAACTTCTGCCTGAGACCCATGCTTGCTCCAAACCTTTACAA

CTACCTGCGCAAGCTTGACAGGGCCCTGCCTGATCCAATAAAAATTTTTGAAATAGGCCCATGCTACA

GAAAAGAGTCCGACGGCAAAGAACACCTCGAAGAGTTTACCATGCTGTCGTTCATTCAGATGGGATC

GGGATGTACACGGGAAAATCTTGAAAGCATAATTACGGACTTCCTGAACCACCTGGGAATTGATTTCA

AGATCGTAGGCGATTCCTGCATGGTCTATGGGGATACCCTTGATGTAATGCACGGAGACCTGGAACTT

TCCTCTGCAGTAGTCGGACCCATACCGCTTGACCGGGAATGGGGTATTGATAAACCCTGGATAGGGGC

AGGTTTCGGGCTCGAACGCCTTCTAAAGGTTAAACACGACTTTAAAAATATCAAGAGAGCTGCAAGG

TCCGAGTCTTACTATAACGGGATTTCTACCAACCTGTAA

>SEQ ID NO: 12; DNA sequence of PACE-evolved chPylRS variant, Split1. The in-frame,
premature stop codon of the split enzyme is underlined, and the position of translational reinitiation, corresponding to Met-107 of chPylRS, is italicized.
In the Spit1' variant, bolded codons were reverted back to 'GTT', 'ACC', 'CAT', and 'GCG', respectively.

ATGGATAAGAAGCCGCTGGATGTTCTGATCTCTGCGACCGGTCTGTGGATGTCCCGTACCGGCACGCT

GCACAAGATCAAGCACTATGAGATTTCTCGTTCTAAAATCTACATCGAAATGGCGTGTGGTGACCATC

TGGTTGTGAACAACTCTCGTTCTTGTCGTCCCGCACGTGCATTCCGTTATCATAAATACCGTAAAACC

TGCAAACGTTGTCGTGTTTCTGACGAAGATATCAACAACTTCCTGACCCGTTCTACCGAAGGCAAAAC

CTCTGTTAAAGTTAAAGCTGTTCTGAGCCGAAAGTGAAAAAAGCG*ATG*CCGAAATCTGTTTCTCGTG

CGCCGAAACCGCTGGAAAATCCGGTTTCTGCGAAAGCGTCTACCGACACCTCTCGTTCTGTTCCGTCT

CCGGCGAAATCTACCCCGAACTCTCCGGTTCCGACCTCTGCAAGTGCCCCCGCACTTACGAAGAGCCA

GACTGACAGGCTTGAAGTCCTGTTAAACCCAAAAGATGAGATTTCCCTGAATTCCGGCAAGCCTTTCA

GGGAGCTTGAGTCCGAATTGCTCTCTCGCAGAAAAAAAGACCTGCAGCAGATCTACGCGGAAGAAAG

GGAGAATTATCTGGGGAAACTCGAGCGTGAAATTACCAGGTTCTTTGTGGACAGGGGTTTTCTGGAAA

-continued

TAAAATCCCCGATCCTGATCCCTCTTGAGTATATCGAAAGGATGGGCATTGATAATGATACCGAACTT

TCAAAACAGATCTTCAGGGTTGACAAGAACTTCTGCCTGAGACCCATGCTTGCTCCAAACCTTTACAA

CTACCTGCGCAAGCTTGACAGGGCCCTGCCTGATCCAATAAAAATTTTTGAAATAGGCCCATGCTACA

GAAAAGAGTCCGACGGCAAAGAACACCTCGAAGAGTTTACCATGCTGAACTTCTGCCAGATGGGATC

GGGATGCACACGGGAAAATCTTGAAAGCATAATTACGGACTTCCTGAACCACCTGGGAATTGATTTCA

AGATCGTAGGCGATTCCTGCATGGTCTATGGGGATACCCTTGATGTAATGCACGGAGACCTGGAACTT

TCCTCTGCAGTAGTCGGACCCATACCGCTTGACCGGGAATGGGGTATTGATAAACCCTGGATAGGGGC

AGGTTTCGGGCTCGAACGCCTTCTAAAGGTTAAACACGACTTTAAAAATATCAAGAGAGCTGCAAGG

TCCGAGTCTTACTATAACGGGATTTCTACCAACCTGTAA

>SEQ ID NO: 13; DNA sequence of PACE-evolved chPylRS variant, Split2. The in-frame,
premature stop codono f the split enzyme is underlined, and the position of translational reinitiation, corresponding to Met-107 of chPylRS, is italicized. In the Spit2′ variant, bolded codons were reverted back to ‘GTT’, ‘ACC’, ‘CAT’, and ‘GCG’, respectively.

ATGGATAAGAAGCCGCTGGATGTTCTGATCTCTGCGACCGGTCTGTGGATGTCCCGTACCGGCACGCT

GCACAAGATCAAGCACTATGAGATTTCTCGTTCTAAAATCTACATCGAAATGGCGTGTGGTGACCATC

TGGTTGTGAACAACTCTCGTTCTTGTCGTCCCGCACGTGCATTCCGTTATCATAAATACCGTAAAACC

TGCAAACGTTGTCGTGTTTCTGACGAAGATATCAACAACTTCCTGACCCGTTCTACCGAAGGCAAAAC

CTCTGTTAAAGTTAAAGTTGTTCTGAGCCGAAAGTGAAAAAAGCG*ATG*CCGAAATCTGTTTCTCGTGC

GCCGAAACCGCTGGAAAATCCGGTTTCTGCGAAAGCGTCTACCGACACCTCTCGTTCTGTTCCGTCTC

CGGCGAAATCTACCCCGAACTCTCCGGTTCCGACCTCTGCAAGTGCCCCCGCACTTACGAAGAGCCAG

ACTGACAGGCTTGAAGTCCTGTTAAACCCAAAAGATGAGATTTCCCTGAATTCCGGCAAGCCTTTCAG

GGAGCTTGAGTCCGAATTGCTCTCTCGCAGAAAAAAAGACCTGCAGCAGATCTACGCGGAAGAAAGG

GAGAATTATCTGGGGAAACTCGAGCGTGAAATTACCAGGTTCTTTGTGGACAGGGGTTTTCTGGAAAT

AAAATCCCCGATCCTGATCCCTCTTGAGTATATCGAAAGGATGGGCATTGATAATGATACCGAACTTT

CAAAACAGATCTTCAGGGTTGACAAGAACTTCTGCCTGAGACCCATGCTTGCTCCAAACCTTTACAAC

TACCTGCGCAAGCTTGACAGGGCCCTGCCTGATCCAATAAAAATTTTTGAAATAGGCCCATGCTACAG

AAAAGAGTCCGACGGCAAAGAACACCTCGAAGAGTTTACCATGCTGAACTTCTGCCAGATGGGATCG

GGATGCACACGGGAAAATCTTGAAAGCATAATTACGGACTTCCTGAACCACCTGGGAATTGATTTCAA

GATCGTAGGCGATTCCTGCATGGTCTATGGGGATACCCTTGATGTAATGCACGGAGACCTGGAACTTT

CCTCTGCAGTAGTCGGACCCATACCGCTTGACCGGGAATGGGGTATTGATAAACCCTGGATAGGGGC

AGGTTTCGGGCTCGAACGCCTTCTAAAGGTTAAACACGACTTTAAAAATATCAAGAGAGCTGCAAGG

TCCGAGTCTTACTATAACGGGATTTCTACCAACCTGTAA

>SEQ ID NO: 14; DNA sequence of PACE-evolved chPylRS variant, Split3. The in-frame,
premature stop codono f the split enzyme is underlined, and the position of translational reinitiation, corresponding to Met-107 of chPylRS, is italicized. In the Spit3′ variant, bolded codons were reverted back to ‘GTT’, ‘ACC’, ‘CAT’, and ‘GCG’, respectively.

ATGGATAAGAAGCCGCTGGATGTTCTGATCTCTGCGACCGGTCTGTGGATGTCCCGTACCGGCACGCT

GCACAAGATCAAGCACTATGAGATTTCTCGTTCTAAAATCTACATCGAAATGGCGTGTGGTGACCATC

TGGTTGTGAACAACTCTCGTTCTTGTCGTCCCGCACGTGCATTCCGTTATCATAAATACCGTAAAACC

TGCAAACGTTGTCGTGTTTCTGACGAAGATATCAACAACTTCCTGACCCGTTCTACCGAAGGCAAAAC

CTCTGTTAAAGTTAAAGTTGTTTTCTGAGCCGAAAGTGAAAAAAGCG*ATG*CCGAAATCTGTTTCTCGT

GCGCCGAAACCGCTGGAAAATCCGGTTTCTGCGAAAGCGTCTACCGACACCTCTCGTTCTGTTCCGTC

-continued

TCCGGCGAAATCTACCCCGAACTCTCCGGTTCCGACCTCTGCAAGTGCCCCCGCACTTACGAAGAGCC

AGACTGACAGGCTTGAAGTCCTGTTAAACCCAAAAGATGAGATTTCCCTGAATTCCGGCAAGCCTTTC

AGGGAGCTTGAGTCCGAATTGCTCTCTCGCAGAAAAAAAGACCTGCAGCAGATCTACGCGGAAGAAA

GGGAGAATTATCTGGGGAAACTCGAGCGTGAAATTACCAGGTTCTTTGTGGACAGGGGTTTTCTGGAA

ATAAAATCCCCGATCCTGATCCCTCTTGAGTATATCGAAAGGATGGGCATTGATAATGATACCGAACT

TTCAAAACAGATCTTCAGGGTTGACAAGAACTTCTGCCTGAGACCCATGCTTGCTCCAAACCTTTACA

ACTACCTGCGCAAGCTTGACAGGGCCCTGCCTGATCCAATAAAAATTTTTGAAATAGGCCCATGCTAC

AGAAAAGAGTCCGACGGCAAAGAACACCTCGAAGAGTTTACCATGCTGAACTTCTGCCAGATGGGAT

CGGGATGCACACGGGAAAATCTTGAAAGCATAATTACGGACTTCCTGAACCACCTGGGAATTGATTTC

AAGATCGTAGGCGATTCCTGCATGGTCTATGGGGATACCCTTGATGTAATGCACGGAGACCTGGAACT

TTCCTCTGCAGTAGTCGGACCCATACCGCTTGACCGGGAATGGGGTATTGATAAACCCTGGATAGGGG

CAGGTTTCGGGCTCGAACGCCTTCTAAAGGTTAAACACGACTTTAAAAATATCAAGAGAGCTGCAAG

GTCCGAGTCTTACTATAACGGGATTTCTACCAACCTGTAA

>SEQ ID NO: 15; DNA sequence of PACE-evolved chPylRS variant, Split4. The in-frame,
premature stop codon of the split enzyme is underlined, and the position of ranslational reinitiation, corresponding to Met-107 of chPylRS, is italicized. In the Spit4′ variant, bolded codons were reverted back to ‘GTT’, ‘ACC’, ‘CAT’, and ‘GCG’, respectively.

ATGGATAAGAAGCCGCTGGATGTTCTGATCTCTGCGACCGGTCTGTGGATGTCCCGTACCGGCACGCT

GCACAAGATCAAGCACTATGAGATTTCTCGTTCTAAAATCTACATCGAAATGGCGTGTGGTGACCATC

TGGTTGTGAACAACTCTCGTTCTTGTCGTCCCGCACGTGCATTCCGTTATCATAAATACCGTAAAACC

TGCAAACGTTGTCGTGTTTCTGACGAAGATATCAACAACTTCCTGACCCGTTCTACCGAAGGCTAAAC

CTCTGTTAAAGTTAAAGTTGTTTCTGAGCCGAAAGTGAAAAAAGCG*ATG*CCGAAATCTGTTTCTCGTG

CGCCGAAACCGCTGGAAAATCCGGTTTCTGCGAAAGCGTCTACCGACACCTCTCGTTCTGTTCCGTCT

CCGGCGAAATCTACCCCGAACTCTCCGGTTCCGACCTCTGCAAGTGCCCCCGCACTTACGAAGAGCCA

GACTGACAGGCTTGAAGTCCTGTTAAACCCAAAAGATGAGATTTCCCTGAATTCCGGCAAGCCTTTCA

GGGAGCTTGAGTCCGAATTGCTCTCTCGCAGAAAAAAAGACCTGCAGCAGATCTACGCGGAAGAAAG

GGAGAATTATCTGGGGAAACTCGAGCGTGAAATTACCAGGTTCTTTGTGGACAGGGGTTTTCTGGAAA

TAAAATCCCCGATCCTGATCCCTCTTGAGTATATCGAAAGGATGGGCATTGATAATGATACCGAACTT

TCAAAACAGATCTTCAGGGTTGACAAGAACTTCTGCCTGAGACCCATGCTTGCTCCAAACCTTTACAA

CTACCTGCGCAAGCTTGACAGGGCCCTGCCTGATCCAATAAAAATTTTTGAAATAGGCCCATGCTACA

GAAAAGAGTCCGACGGCAAAGAACACCTCGAAGAGTTTACCATGCTGAACTTCTGCCAGATGGGATC

GGGATGCACACGGGAAAATCTTGAAAGCATAATTACGGACTTCCTGAACCACCTGGGAATTGATTTCA

AGATCGTAGGCGATTCCTGCATGGTCTATGGGGATACCCTTGATGTAATGCACGGAGACCTGGAACTT

TCCTCTGCAGTAGTCGGACCCATACCGCTTGACCGGGAATGGGGTATTGATAAACCCTGGATAGGGGC

AGGTTTCGGGCTCGAACGCCTTCTAAAGGTTAAACACGACTTTAAAAATATCAAGAGAGCTGCAAGG

TCCGAGTCTTACTATAACGGGATTTCTACCAACCTGTAA

>SEQ ID NO: 16; DNA sequence of PACE-evolved chPylRS variant, Split5. The in-frame,
premature stop codon of the split enzyme is underlined, and the position of translational reinitiation, corresponding to Met-107 of chPylRS, is italicized. In the Spit5′ variant, bolded codons were reverted back to ‘GTT’, ‘ACC’, ‘CAT’, and ‘GCG’, respectively.

ATGGATAAGAAGCCGCTGGATGTTCTGATCTCTGCGACCGGTCTGTGGATGTCCCGTACCGGCACGCT
GCACAAGATCAAGCACTATGAGATTTCTCGTTCTAAAATCTACATCGAAATGGCGTGTGGTGACCATC

TGGTTGTGAACAACTCTCGTTCTTGTCGTCCCGCACGTGCATTCCGTTATCATAAATACCGTAAAACC

-continued

TGCAAACGTTGTCGTGTTTCTGACGAAGATATCAACAACTTCCTGACCCGTTCTACCGAAGGCAAAAC

CTCTGTTAAAGTTAAAGTTGTTTCTGAGCGAAAGTGAAAAAAGCG*ATG*CCGAAATCTGTTTCTCGTGC

GCCGAAACCGCTGGAAAATCCGGTTTCTGCGAAAGCGTCTACCGACACCTCTCGTTCTGTTCCGTCTC

CGGCGAAATCTACCCCGAACTCTCCGGTTCCGACCTCTGCAAGTGCCCCCGCACTTACGAAGAGCCAG

ACTGACAGGCTTGAAGTCCTGTTAAACCCAAAAGATGAGATTTCCCTGAATTCCGGCAAGCCTTTCAG

GGAGCTTGAGTCCGAATTGCTCTCTCGCAGAAAAAAAGACCTGCAGCAGATCTACGCGGAAGAAAGG

GAGAATTATCTGGGGAAACTCGAGCGTGAAATTACCAGGTTCTTTGTGGACAGGGGTTTTCTGGAAAT

AAAATCCCCGATCCTGATCCCTCTTGAGTATATCGAAAGGATGGGCATTGATAATGATACCGAACTTT

CAAAACAGATCTTCAGGGTTGACAAGAACTTCTGCCTGAGACCCATGCTTGCTCCAAACCTTTACAAC

TACCTGCGCAAGCTTGACAGGGCCCTGCCTGATCCAATAAAAATTTTTGAAATAGGCCCATGCTACAG

AAAAGAGTCCGACGGCAAAGAACACCTCGAAGAGTTTACCATGCTGAACTTCTGCCAGATGGGATCG

GGATGCACACGGGAAAATCTTGAAAGCATAATTACGGACTTCCTGAACCACCTGGGAATTGATTTCAA

GATCGTAGGCGATTCCTGCATGGTCTATGGGGATACCCTTGATGTAATGCACGGAGACCTGGAACTTT

CCTCTGCAGTAGTCGGACCCATACCGCTTGACCGGGAATGGGGTATTGATAAACCCTGGATAGGGGC

AGGTTTCGGGCTCGAACGCCTTCTAAAGGTTAAACACGACTTTAAAAATATCAAGAGAGCTGCAAGG

TCCGAGTCTTACTATAACGGGATTTCTACCAACCTGTAA

>SEQ ID NO: 17; DNA sequence of PACE-evolved chPylRS variant, Split6. This split enzyme contained several in-frame, premature stop codons (underlined) between the frameshift and the position of translational reinitiation, corresponding to Met-107 of chPylRS italicized. In the Spit6′ variant, bp; ded codons were reverted back to ‘GTT’, ’ACC’, ‘CAT’, and ‘GCG’, respectively.

ATGGATAAGAAGCCGCTGGATGTTCTGATCTCTGCGACCGGTCTGTGGATGTCCCGTACCGGCACGCT

GCACAAGATCAAGCACTATGAGATTTCTCGTTCTAAAATCTACATCGAAATGGCGTGTGGTGACCATC

TGGTTGTGAACAACTCTCGTTCTTGTCGTCCCGCACGTGCATTCCGTTATCATAAATACCGTAAAACC

TGCAAACGTTGTCGTGTTTCTGACGAAGATATCAACAACTTCCTGACCCGTTCTACCGAAGGCAAAAC

CCTCTGTTAAAGTTAAAGTTGTTTCTGAGCCGAAAGTGAAAAAAGCG*ATG*CCGAAATCTGTTTCTCGT

GCGCCGAAACCGCTGGAAAATCCGGTTTCTGCGAAAGCGTCTACCGACACCTCTCGTTCTGTTCCGTC

TCCGGCGAAATCTACCCCGAACTCTCCGGTTCCGACCTCTGCAAGTGCCCCCGCACTTACGAAGAGCC

AGACTGACAGGCTTGAAGTCCTGTTAAACCCAAAAGATGAGATTTCCCTGAATTCCGGCAAGCCTTTC

AGGGAGCTTGAGTCCGAATTGCTCTCTCGCAGAAAAAAAGACCTGCAGCAGATCTACGCGGAAGAAA

GGGAGAATTATCTGGGGAAACTCGAGCGTGAAATTACCAGGTTCTTTGTGGACAGGGGTTTTCTGGAA

ATAAAATCCCCGATCCTGATCCCTCTTGAGTATATCGAAAGGATGGGCATTGATAATGATACCGAACT

TTCAAAACAGATCTTCAGGGTTGACAAGAACTTCTGCCTGAGACCCATGCTTGCTCCAAACCTTTACA

ACTACCTGCGCAAGCTTGACAGGGCCCTGCCTGATCCAATAAAAATTTTTGAAATAGGCCCATGCTAC

AGAAAAGAGTCCGACGGCAAAGAACACCTCGAAGAGTTTACCATGCTGAACTTCTGCCAGATGGGAT

CGGGATGCACACGGGAAAATCTTGAAAGCATAATTACGGACTTCCTGAACCACCTGGGAATTGATTTC

AAGATCGTAGGCGATTCCTGCATGGTCTATGGGGATACCCTTGATGTAATGCACGGAGACCTGGAACT

TTCCTCTGCAGTAGTCGGACCCATACCGCTTGACCGGGAATGGGGTATTGATAAACCCTGGATAGGGG

CAGGTTTCGGGCTCGAACGCCTTCTAAAGGTTAAACACGACTTTAAAAATATCAAGAGAGCTGCAAG

GTCCGAGTCTTACTATAACGGGATTTCTACCAACCTGTAA

>SEQ ID NO: 18; DNA sequence of p-NFRS (amino acid sequence SEQ ID NO: 39).

ATGGACGAATTTGAAATGATAAAGAGAAACACATCTGAAATTATCAGCGAGGAAGAGTTAAGAGAG

GTTTTAAAAAAAGATGAAAAATCTGCTCTGATAGGTTTTGAACCAAGTGGTAAAATACATTTAGGGCA

-continued

TTATCTCCAAATAAAAAAGATGATTGATTTACAAAATGCTGGATTTGATATAATTATATTGTTGGCTG

ATTTACACGCCTATTTAAACCAGAAAGGAGAGTTGGATGAGATTAGAAAAATAGGAGATTATAACAA

AAAAGTTTTTGAAGCAATGGGGTTAAAGGCAAAATATGTTTATGGAAGTTCGTTCCAGCTTGATAAGG

ATTATACACTGAATGTCTATAGATTGGCTTTAAAAACTACCTTAAAAAGAGCAAGAAGGAGTATGGA

ACTTATAGCAAGAGAGGATGAAAATCCAAAGGTTGCTGAAGTTATCTATCCAATAATGCAGGTTAATC

CTCTTAATTATGAGGGCGTTGATGTTGCAGTTGGAGGGATGGAGCAGAGAAAAATACACATGTTAGC

AAGGGAGCTTTTACCAAAAAAGGTTGTTTGTATTCACAACCCTGTCTTAACGGGTTTGGATGGAGAAG

GAAAGATGAGTTCTTCAAAAGGGAATTTTATAGCTGTTGATGACTCTCCAGAAGAGATTAGGGCTAAG

ATAAAGAAAGCATACTGCCCAGCTGGAGTTGTTGAAGGAAATCCAATAATGGAGATAGCTAAATACT

TCCTTGAATATCCTTTAACCATAAAAAGGCCAGAAAAATTTGGTGGAGATTTGACAGTTAATAGCTAT

GAGGAGTTAGAGAGTTTATTTAAAAATAAGGAATTGCATCCAATGCGCTTAAAAAATGCTGTAGCTG

AAGAACTTATAAAGATTTTAGAGCCAATTAGAAAGAGATTATAA

>SEQ ID NO: 19; DNA sequence of p-IFRS (amino acid sequence SEQ ID NO: 40).
ATGGACGAATTTGAAATGATAAAGAGAAACACATCTGAAATTATCAGCGAGGAAGAGTTAAGAGAG

GTTTTAAAAAAAGATGAAAAATCTGCTCTGATAGGTTTTGAACCAAGTGGTAAAATACATTTAGGGCA

TTATCTCCAAATAAAAAAGATGATTGATTTACAAAATGCTGGATTTGATATAATTATATTGTTGGCTG

ATTTACACGCCTATTTAAACCAGAAAGGAGAGTTGGATGAGATTAGAAAAATAGGAGATTATAACAA

AAAAGTTTTTGAAGCAATGGGGTTAAAGGCAAAATATGTTTATGGAAGTTCGTTCCAGCTTGATAAGG

ATTATACACTGAATGTCTATAGATTGGCTTTAAAAACTACCTTAAAAAGAGCAAGAAGGAGTATGGA

ACTTATAGCAAGAGAGGATGAAAATCCAAAGGTTGCTGAAGTTATCTATCCAATAATGCAGGTTAATC

CTCTTCATTATGAGGGCGTTGATGTTGCAGTTGGAGGGATGGAGCAGAGAAAAATACACATGTTAGC

AAGGGAGCTTTTACCAAAAAAGGTTGTTTGTATTCACAACCCTGTCTTAACGGGTTTGGATGGAGAAG

GAAAGATGAGTTCTTCAAAAGGGAATTTTATAGCTGTTGATGACTCTCCAGAAGAGATTAGGGCTAAG

ATAAAGAAAGCATACTGCCCAGCTGGAGTTGTTGAAGGAAATCCAATAATGGAGATAGCTAAATACT

TCCTTGAATATCCTTTAACCATAAAAAGGCCAGAAAAATTTGGTGGAGATTTGACAGTTAATAGCTAT

GAGGAGTTAGAGAGTTTATTTAAAAATAAGGAATTGCATCCAATGCGCTTAAAAAATGCTGTAGCTG

AAGAACTTATAAAGATTTTAGAGCCAATTAGAAAGAGATTATAA

>SEQ ID NO: 20; Amino acid sequence of MbPylRS
MDKKPLDVLISATGLWMSRTGTLHKIKHYEVSRSKIYIEMACGDHLVVNNSRSCRTARAFRHHKYRKTCK

RCRVSDEDINNFLTRSTEGKTSVKVKVVSAPKVKKAMPKSVSRAPKPLENPVSAKASTDTSRSVPSPAKST

PNSPVPTSAPAPSLTRSQLDRVEALLSPEDKISLNIAKPFRELESELVTRRKNDFQRLYTNDREDYLGKLERD

ITKFFVDRDFLEIKSPILIPAEYVERMGINNDTELSKQIFRVDKNLCLRPMLAPTLYNYLRKLDRILPDPIKIFE

VGPCYRKESDGKEHLEEFTMVNFCQMGSGCTRENLESLIKEFLDYLEIDFEIVGDSCMVYGDTLDIMHGDL

ELSSAVVGPVPLDREWGIDKPWIGAGFGLERLLKVMHGFKNIKRASRSESYYNGISTNL

>SEQ ID NO: 21; Amino acid sequence of MmPylRS
MDKKPLNTLISATGLWMSRTGTIHKIKHHEVSRSKIYIEMACGDHLVVNNSRSSRTARALRHHKYRKTCK

RCRVSDEDLNKFLTKANEDQTSVKVKVVSAPTRTKKAMPKSVARAPKPLENTEAAQAQPSGSKFSPAIPV

STQESVSVPASVSTSISSISTGATASALVKGNTNPITSMSAPVQASAPALTKSQTDRLEVLLNPKDEISLNSG

KPFRELESELLSRRKKDLQQIYAEERENYLGKLEREITRFFVDRGFLEIKSPILIPLEYIERMGIDNDTELSKQI

FRVDKNFCLRPMLAPNLYNYLRKLDRALPDPIKIFEIGPCYRKESDGKEHLEEFTMLNFCQMGSGCTRENL

ESIITDFLNHLGIDFKIVGDSCMVYGDTLDVMHGDLELSSAVVGPIPLDREWGIDKPWIGAGFGLERLLKVK

HDFKNIKRAARSESYYNGISTNL

-continued

>SEQ ID NO: 22; Amino acid sequence of p-NFRS
MDEFEMIKRNTSEIISEEELREVLKKDEKSALIGFEPSGKIHLGHYLQIKKMIDLQNAGFDIIILLADLHAYLN

QKGELDEIRKIGDYNKKVFEAMGLKAKYVYGSSFQLDKDYTLNVYRLALKTTLKRARRSMELIAREDENP

KVAEVIYPIMQVNPLNYEGVDVAVGGMEQRKIHMLARELLPKKVVCIHNPVLTGLDGEGKMSSSKGNFIA

VDDSPEEIRAKIKKAYCPAGVVEGNPIMEIAKYFLEYPLTIKRPEKFGGDLTVNSYEELESLFKNKELHPMR

LKNAVAEELIKILEPIRKRL

SEQ ID NO: 23; Amino acid sequence p-IFRS
MDEFEMIKRNTSEIISEEELREVLKKDEKSALIGFEPSGKIHLGHYLQIKKMIDLQNAGFDIIILLADLHAYLN

QKGELDEIRKIGDYNKKVFEAMGLKAKYVYGSSFQLDKDYTLNVYRLALKTTLKRARRSMELIAREDENP

KVAEVIYPIMQVNPLHYEGVDVAVGGMEQRKIHMLARELLPKKVVCIHNPVLTGLDGEGKMSSSKGNFIA

VDDSPEEIRAKIKKAYCPAGVVEGNPIMEIAKYFLEYPLTIKRPEKFGGDLTVNSYEELESLFKNKELHPMR

LKNAVAEELIKILEPIRKRL

SEQ ID NO: 24; Amino acid sequence of *M. jannaschii TyrRS*
MDEFEMIKRNTSEIISEEELREVLKKDEKSAYIGFEPSGKIHLGHYLQIKKMIDLQNAGFDIIILLADLHAYLN

QKGELDEIRKIGDYNKKVFEAMGLKAKYVYGSEFQLDKDYTLNVYRLALKTTLKRARRSMELIAREDENP

KVAEVIYPIMQVNDIHYLGVDVAVGGMEQRKIHMLARELLPKKVVCIHNPVLTGLDGEGKMSSSKGNFIA

VDDSPEEIRAKIKKAYCPAGVVEGNPIMEIAKYFLEYPLTIKRPEKFGGDLTVNSYEELESLFKNKELHPMD

LKNAVAEELIKILEPIRKR

---

What is claimed is:

1. A tRNA synthetase protein variant comprising an amino acid sequence that is at least 85% identical to SEQ ID NO: 20 or SEQ ID NO: 21, and includes at least one mutation at a position selected from V31, T56, H62, and A100.

2. The tRNA synthetase protein variant of claim 1, wherein the at least one mutation is V31I, T56P, H62Y, A100E, or A100S.

3. The tRNA synthetase protein variant of claim 1 comprising mutations at V31, T56, H62, and A100.

4. The tRNA synthetase protein variant of claim 3, wherein the mutations are V31I, T56P, H62Y, and A100E.

5. The tRNA synthetase protein variant of claim 1, wherein the nucleic acid sequence encoding the amino acid sequence comprises one or more premature stop codons.

6. A chimeric pyrrolysyl-tRNA synthetase (PylRS) protein variant comprising:

(i) a first portion comprising amino acid residues 1-149 of *Methanosarcina barkeri* PylRS (SEQ ID NO: 20); and (ii) a second portion comprising amino acid residues 185-454 of *Methanosarcina mazei* PylRS (SEQ ID NO: 21), wherein the first portion or the second portion comprises at least one of the amino acid substitutions set forth in Tables 2-6.

7. The chimeric PylRS protein variant of claim 6, wherein the chimeric PylRS protein variant comprises an amino acid substitution at at least one of the following positions: V31, T56, H62, or A100.

8. The chimeric PylRS protein variant of claim 7, wherein the amino acid substitution is V31I, T56P, H62Y, A100E, or any combination thereof.

* * * * *

UNITED STATES PATENT AND TRADEMARK OFFICE

CERTIFICATE OF CORRECTION

PATENT NO. : 11,447,809 B2
APPLICATION NO. : 16/628456
DATED : September 20, 2022
INVENTOR(S) : David R. Liu et al.

It is certified that error appears in the above-identified patent and that said Letters Patent is hereby corrected as shown below:

On the Title Page

At item (72), the place of residence of Inventor David R. Liu, "Lexington, MA (US)" should be replaced with --Cambridge, MA (US)--.

At item (72), the place of residence of Inventor David Irby Bryson Jr., "Dorchester, MA (US)" should be replaced with --Cambridge, MA (US)--.

Signed and Sealed this
Thirteenth Day of December, 2022

Katherine Kelly Vidal

Katherine Kelly Vidal
*Director of the United States Patent and Trademark Office*